United States Patent
Bair et al.

(10) Patent No.: US 11,479,564 B2
(45) Date of Patent: Oct. 25, 2022

(54) PIPERIDINE DERIVATIVES AND COMPOSITIONS FOR THE INHIBITION OF NICOTINAMIDE PHOSPHORIBOSYLTRANSFERASE (NAMPT)

(71) Applicant: Valo Health, Inc., Boston, MA (US)

(72) Inventors: Kenneth W. Bair, Wellesley, MA (US); Timm R. Baumeister, Cambridge, MA (US); Alexandre J. Buckmelter, Acton, MA (US); Karl H. Clodfelter, Brighton, MA (US); Bingsong Han, Westwood, MA (US); Judith D. Kuntz, Watertown, MA (US); Jian Lin, Acton, MA (US); Dominic J. Reynolds, Stoneham, MA (US); Chase C. Smith, Rutland, MA (US); Zhongguo Wang, Lexington, MA (US); Xiaozhang Zheng, Lexington, MA (US)

(73) Assignee: Valo Health, Inc., Boston, MA (US)

( * ) Notice: Subject to any disclaimer, the term of this patent is extended or adjusted under 35 U.S.C. 154(b) by 0 days.

(21) Appl. No.: 17/022,906

(22) Filed: Sep. 16, 2020

(65) Prior Publication Data
US 2021/0246147 A1    Aug. 12, 2021

Related U.S. Application Data

(63) Continuation of application No. 16/002,651, filed on Jun. 7, 2018, now abandoned, which is a continuation of application No. 15/419,727, filed on Jan. 30, 2017, now abandoned, which is a continuation of application No. 14/115,849, filed as application No. PCT/US2011/050303 on Sep. 2, 2011, now Pat. No. 9,555,039.

(60) Provisional application No. 61/512,546, filed on Jul. 28, 2011, provisional application No. 61/483,937, filed on May 9, 2011.

(51) Int. Cl.
| | |
|---|---|
| *C07D 519/00* | (2006.01) |
| *C07D 215/48* | (2006.01) |
| *C07D 471/04* | (2006.01) |
| *C07D 513/04* | (2006.01) |
| *A61K 31/4545* | (2006.01) |
| *A61K 31/5377* | (2006.01) |
| *A61K 45/06* | (2006.01) |
| *A61K 31/437* | (2006.01) |
| *A61K 31/4709* | (2006.01) |
| *A61K 31/497* | (2006.01) |
| *C07D 495/04* | (2006.01) |

(52) U.S. Cl.
CPC .......... *C07D 519/00* (2013.01); *A61K 31/437* (2013.01); *A61K 31/4545* (2013.01); *A61K 31/4709* (2013.01); *A61K 31/497* (2013.01); *A61K 31/5377* (2013.01); *A61K 45/06* (2013.01); *C07D 215/48* (2013.01); *C07D 471/04* (2013.01); *C07D 495/04* (2013.01); *C07D 513/04* (2013.01)

(58) Field of Classification Search
None
See application file for complete search history.

(56) References Cited

U.S. PATENT DOCUMENTS

| | | |
|---|---|---|
| 6,506,901 B2 | 1/2003 | Steffan et al. |
| 8,450,348 B2 | 5/2013 | Murthi et al. |
| 9,169,209 B2 | 10/2015 | Bair et al. |
| 9,458,172 B2 | 10/2016 | Bair et al. |
| 9,555,039 B2 | 1/2017 | Bair et al. |
| 9,676,721 B2 | 6/2017 | Bair et al. |
| 9,822,129 B2 | 11/2017 | Bair et al. |
| 10,272,072 B2 | 4/2019 | Bair et al. |
| 10,329,275 B2 | 6/2019 | Bair et al. |
| 10,456,382 B2 | 10/2019 | Bair et al. |

(Continued)

FOREIGN PATENT DOCUMENTS

| | | |
|---|---|---|
| CN | 1671662 A | 9/2005 |
| JP | 2013/542265 A | 11/2013 |

(Continued)

OTHER PUBLICATIONS

Tanuma et al., "Structural Basis of Beneficial Design for Effective Nicotinamide Phosphoribosyltransferase Inhibitors", 2020, Molecules, 25(16), pp. 1-15. (doi:10.3390/molecules25163633) (Year: 2020).*

(Continued)

*Primary Examiner* — My-Chau T. Tran
(74) *Attorney, Agent, or Firm* — Choate, Hall & Stewart LLP; Michael A. Shinall; Erica M. D'Amato

(57) ABSTRACT

The present invention relates to compounds and compositions for the inhibition of NAMPT, their synthesis, applications and antidotes. An illustrative compound of the invention is shown below: Formula (I)

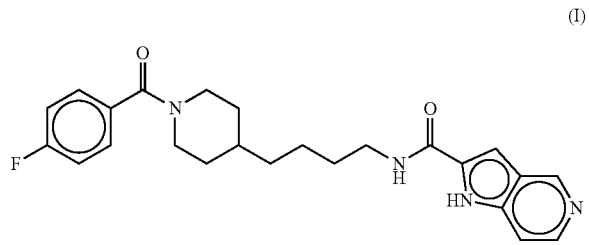

7 Claims, No Drawings

(56) References Cited

U.S. PATENT DOCUMENTS

| | | |
|---|---|---|
| 10,647,695 B2 | 5/2020 | Bair et al. |
| 10,696,692 B2 | 6/2020 | Bair et al. |
| 10,730,889 B2 | 8/2020 | Bair et al. |
| 10,772,874 B2 | 9/2020 | Bair et al. |
| 11,279,687 B2 | 3/2022 | Bair et al. |
| 2003/0229053 A1 | 12/2003 | Chan Chun Kong et al. |
| 2009/0275556 A1 | 11/2009 | Dai et al. |
| 2013/0273034 A1 | 10/2013 | Bair et al. |
| 2013/0295051 A1 | 11/2013 | Bair et al. |
| 2014/0248240 A1 | 9/2014 | Bair et al. |
| 2014/0275057 A1 | 9/2014 | Bair et al. |
| 2014/0294805 A1 | 10/2014 | Bair et al. |
| 2015/0104384 A1 | 4/2015 | Bair et al. |
| 2016/0355514 A1 | 12/2016 | Bair et al. |
| 2017/0137441 A1 | 5/2017 | Bair et al. |
| 2017/0216262 A1 | 8/2017 | Bair et al. |
| 2018/0291000 A1 | 10/2018 | Bair et al. |
| 2018/0339998 A1 | 11/2018 | Bair et al. |
| 2019/0031686 A1 | 1/2019 | Bair et al. |
| 2019/0105307 A1 | 4/2019 | Bair et al. |
| 2019/0270721 A1 | 9/2019 | Bair et al. |
| 2020/0283403 A1 | 9/2020 | Bair et al. |
| 2021/0171545 A1 | 6/2021 | Bair et al. |
| 2021/0244717 A1 | 8/2021 | Bair et al. |

FOREIGN PATENT DOCUMENTS

| | | |
|---|---|---|
| WO | WO-02/06255 A2 | 1/2002 |
| WO | WO-03/035644 A1 | 5/2003 |
| WO | WO-2007/056155 A1 | 5/2007 |
| WO | WO-2008/025857 A2 | 3/2008 |
| WO | WO-2010/142735 A1 | 12/2010 |
| WO | WO-2012/067965 A1 | 5/2012 |
| WO | WO-2012/154194 A1 | 11/2012 |

OTHER PUBLICATIONS

U.S. Appl. No. 17/018,196, Bair et al.
U.S. Appl. No. 16/944,581, Bair et al.
Beauparlant, P. et al., Predinical development of the nicotinamide phosphoribosyl transferase inhibitor prodrug GMX1777, Anti-Cancer Drugs, 20(5):346-354 (2009).
Colombano, G. et al., A Novel Potent Nicotinamide Phosphoribosyltransferase Inhibitor Synthesized via Click Chemistry, J. Med. Chem., 53:616-623 (2010).
Drevs, J. et al., Antiangiogenic potency of FK866/K22.175, a new inhibitor of intracellular NAD biosynthesis, in murine renal cell carcinoma, Anticancer Research, 23:4853-4858 (2003) (Abstract only).
Galli, M. et al., The Nicotinamide Phosphoribosyltransferase: A Molecular Link between Metabolism, Inflammation, and Cancer, Cancer Research, 70(1):8-11 (2010).
Galli, U. et al., Synthesis and biological evaluation of isosteric analogues of FK866, an inhibitor of NAD salvage, ChemMedChem, 3:771-779 (2008).
Garten, A. et al., Nampt Linking NAD biology, metabolism, and cancer, Trends Endocrinol Metab, 20(3):130-138 (2009).
Hasmann, M. and Schemainda, I., FK866, a Highly Specific Non-competitive Inhibitor of Nicotinamide phosphoribosyltransferase, Represents a Novel Mechanism for Induction of Tumor Cell Apoptosis, Cancer Research, 63:7436-7442 (2003).
Holen, K. et al., The pharmacokinetics, toxicities, and biologic effects of FK866, a nicotinamide adenine dinucleotide Biosynthesis inhibitor, Invest New Drugs, 26:45-51 (2008).
Hovstadius, P. et al., A Phase I study of CHS 828 in patients with solid tumor malignancy, Clinical Cancer Research, 8:2843-2850 (2002).
Imai, S. et al., "Clocks" in the NAD World: NAD as a metabolic oscillator for the regulation of metabolism and aging, Biochimica et Biophysica Acta, 1804(8):1584-1590 (2010).
International Search Report for PCT/US11/050303, 3 pages (dated Oct. 20, 2011).
Khan, J.A. et al., Nicotinamide adenine dinucleotide metabolism as an attractive target for drug discovery, Expert Opin. Ther. Targets, 11(5):695-705 (2007).
Lovborg, H. et al., Structure-activity relationship analysis of cytotoxic cyanoguanidines: selection of CHS 828 as andidate drug, BMC Research Notes, 2:114-121 (2009).
Olesen, U.H. et al., Anticancer agent CHS-828 inhibits cellular synthesis of NAD, Biochemical and Biophysical Research Communications, 367:799-804 (2008).
Pogrebniak, A, et al. Chemopotentiating effects of a novel NAD biosynthesis inhibitor, FK866, in combination with antineoplastic agents, Eur J Med Res., 11: 313-321 (2006).
Ravaud, A. et al., Phase I study and guanidine kinetics of CHS-828, a guanidine-containing compound, administered brally as a single dose every 3 weeks in solid tumors: an ECSG/EORTC study, European Journal of Cancer, 41:702-707 (2005).
Rongvaux, A., et al. Nicotinamide Phosphoribosyl Transferase/Pre-B Cell Colony-Enhancing Factor/Visfatin Is Required for Lymphocyte Development and Cellular Resistance to Genotoxic Stress, The Journal of Immunology, 181:4685-4695 (2008).
Sampath, D. et al., Inhibition of nicotinamide phosphoribosyltransferase (NAMPT) as a therapeutic strategy in cancer, Pharmacology & Therapeutics, 151:16-31 (2015).
You, H. et al., Design, synthesis and X-ray crystallographic study of NAmPRTase inhibitors as anti-cancer agents, European Journal of Medicinal Chemistry, 46(4):1153-1164 (2011).

* cited by examiner

PIPERIDINE DERIVATIVES AND COMPOSITIONS FOR THE INHIBITION OF NICOTINAMIDE PHOSPHORIBOSYLTRANSFERASE (NAMPT)

PRIORITY CLAIM

This application is a continuation of U.S. application Ser. No. 16/002,651 filed on Jun. 7, 2018, which is a continuation of U.S. application Ser. No. 15/419,727 filed on Jan. 30, 2017, which is a continuation of U.S. application Ser. No. 14/115,849 filed on Apr. 8, 2014, now U.S. Pat. No. 9,555,039, which is a National Application under 35 U.S.C. § 371 of International Patent Application No. PCT/US2011/050303, which claims priority from U.S. Provisional Application 61/483,937 filed on May 9, 2011, and U.S. Provisional Application 61/512,546 filed on Jul. 28, 2011, the contents of each of which are fully incorporated herein by reference.

FIELD OF THE INVENTION

The present invention relates to compounds and composition for inhibition of Nicotinamide phosphoribosyltransferase ("NAMPT"), their synthesis, applications and antidote.

BACKGROUND OF THE INVENTION

Nicotinamide adenine dinucleotide (NAD) plays fundamental roles in both cellular energy metabolism and cellular signaling. In energy metabolism, the chemistry of the pyridine ring allows NAD to readily accept mid donate electrons in hydride transfer reactions catalyzed by numerous dehydrogenases.

The preparation of a class of compounds, comprising several subclasses, which act as inhibitors of the formation of nicotinamide adenyl nucleotide, and their use thereof as anti-tumour agents, is already described in the patent applications WO00/50399, WO97/48695, WO97/48696, WO97/48397, WO99/31063, WO99/31060, WO99/31087, WO99/31064, WO00/50399, and WO03/80054.

One of these inhibitors, (E)-N-[4-(1-benzoylpiperidin-4-yl)butyl]-3-(pyridine-3-yl)-acrylamide also known as APO866, FK866, WK175, or WK22.175 and hereinafter referred to as FK866 [International Non-proprietary Name], is especially described in the literature as an anticancer agent. FK866 may be used for treatment of diseases implicating deregulated apoptosis such as cancer. It has been demonstrated in the prior art that FK866 interferes with nicotinamide adenine dinucleotide (also known and hereinafter referred to as NAD) biosynthesis and induces apoptotic cell death without any DNA damaging effects.

Additionally, FK866 ((E)-N-[4-(1-benzoylpiperidin-4-yl)butyl]-3-(pyridin-3-yl) acrylamide) induces apoptosis in HepG2 cells without having primary effects on cellular energy metabolism. (Hasmann M, Schemainda I. FK866, a Highly Specific Noncompetitive Inhibitor of Nicotinamide Phosphoribosyltransferase, Represents a Novel Mechanism for Induction of Tumor Cell Apoptosis. Cancer Res 2003; 63:7436-7442. [PubMed: 14612543]). Instead of causing immediate cytotoxicity, it inhibits NAMPT and depletes the cells of NAD, suggesting that FK866 could be a promising agent against cancer cells that rely on nicotinamide to synthesize NAD. The crystal structure of the NAMPT-FK866 complex reveals that the compound binds at the nicotinamide-binding site of NAMPT to inhibit its activity. FK866 has been tested in a murine renal cell carcinoma model and shown to display anti-tumor, antimetastatic, and anti-angiogenic activities (Drevs J, et al. Antiangiogenic potency of FK866/K22.175, a new inhibitor of intracellular NAD biosynthesis, in murine renal cell carcinoma. Anticancer Res 2003; 23:4853-4858. [PubMed: 14981935]).

In a mouse mammary carcinoma model, FK866 also induces a delay in tumor growth and an enhancement in tumor radiosensitivity accompanied with dose-dependent decreases in NAD levels, pH, and energy status. A chemo-sensitizing effect of FK866 has also been observed on anti-neoplastic 1-methyl-3-nitro-1-nitrosoguanidinium (MNNG)-induced cell death in THP-1 and K562 leukemia cell lines (Pogrebniak A, et al. Chemopotentiating effects of a novel NAD biosynthesis inhibitor, FK866, in combination with antineoplastic agents. Eur J Med Res 2006; 11:313-321. [PubMed: 17052966]).

The efficacy of GMX1777 was evaluated in xenograft models and the pharmacokinetic profile of GMX1778 and its effect on nicotinamide adenine dinucleotide cellular levels was measured by liquid chromatography/mass spectrometry. (Beauparlant P., et al. Preclinical development of the nicotinamide phosphoribosyl transferase inhibitor prodrug GMX1777. Anticancer Drugs. 2009 Jun. 20(5):346-54).

GMX1777 is a water-soluble intravenously administered prodrug of GMX1778 that Gemin X in-licensed from LEO Pharma (LEO numbers: EB1627 and CHS828, respectively). These compounds and other substituted cyanoguanidines have the structures of Table 1. None of the compounds of the present invention are cyanoguanidines.

TABLE 1

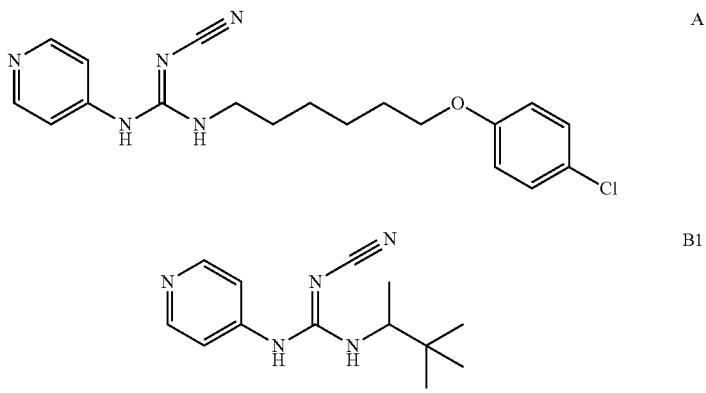

TABLE 1-continued

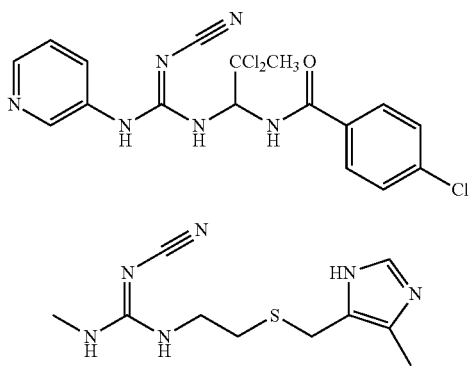

Substituted Cyanoguanidines with Defined Pharmacological Effects:

A Cytotoxic CHS 828;

B Potassium channel openers pinacidil (B1) and 12 g of compound as described in Perez-Medrano et al (B2); and C Histamine-II receptor antagonist cimetidine. (from Lövborg et al. *BMC Research Notes* 2009 2:114 doi: 10.1186/1756-0500-2-114)

More recently, CHS-828 has been identified as a NAMPT inhibitor (Olesen U H, et al. Anticancer agent CHS-828 inhibits cellular synthesis of NAD. Biochem Biophys Res Commun 2008; 367:799-804. [PubMed: 18201551]). CHS-828 has been shown that this compound potently inhibits cell growth in a broad range of tumor cell lines, although the detailed mechanism for this inhibitory effect of CHS-828 remains undetermined (Ravaud A, et al. Phase I study and guanidine kinetics of CHS-828, a guanidine-containing compound, administered orally as a single dose every 3 weeks in solid tumors: an ECSG/EORTC study. Eur J Cancer 2005; 41:702-707. [PubMed: 15763645]). Both FK866 and CHS-828 are currently in clinical trials for cancer treatments.

There are numerous uses for drugs which inhibit NAMPT.

Lack of NAMPT expression strongly affects development of both T and B lymphocytes. By using mutant forms of this protein and a well-characterized pharmacological inhibitor (FK866), authors demonstrated that the ability of the NAMPT to regulate cell viability during genotoxic stress requires its enzymatic activity. Collectively, these data demonstrate that NAMPT participates in cellular resistance to genotoxic/oxidative stress, and it may confer to cells of the immune system the ability to survive during stressful situations such as inflammation. (Rongvaux, A., et al. *The Journal of Immunology*, 2008, 181: 4685-4695).

NAMPT may also have effects on endothelium (EC) in relation to high glucose levels, oxidative stress and on aging. It is also believed that NAMPT may enable proliferating human EC to resist the oxidative stress of aging and of high glucose, and to productively use excess glucose to support replicative longevity and angiogenic activity.

SUMMARY OF THE INVENTION

One aspect of this invention is the provision of compounds, compositions, kits, and antidotes for the NAMPT pathway in mammals having a compound of the Formula I:

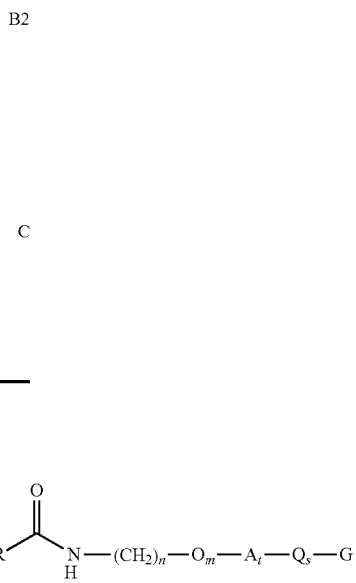

wherein

R is an aryl, heteroaryl, $C_3$-$C_8$ cycloalkyl, $C_3$-$C_8$ cycloalkenyl, heterocycloalkyl, arylalkyl-, (heteroaryl)alkyl-, ($C_3$-$C_8$ cycloalkyl)alkyl-, ($C_3$-$C_8$ cycloalkenyl)alkyl-, (heterocycloalkyl)alkyl-, (aryloxy)alkyl-, (heteroaryloxy)alkyl-, ($C_3$-$C_8$ cycloalkyloxy)alkyl-, ($C_3$-$C_8$ cycloalkenyloxy)alkyl- or (heterocycloalkyloxy)alkyl-, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with an aryl or heteroaryl, still further wherein any of said aryl, heteroaryl and heterocycloalkyl is either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, alkyl hydroxy, hydroxyl, alkyl hydroxy, or (alkoxyalkyl) amino-, —N($R^3$)—C(O)-alkyl, —N($R^3$)—C(O)-aryl, -cycloalkyl, -heterocycloalkyl, -aryl, and -heteroaryl, with the proviso that no two adjacent ring heteroatoms are both S or both O;

G is aryl, heteroaryl, cycloalkyl, heterocycloalkyl or

with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, -alkyl hydroxyl, aryloxy-, (alkoxyalkyl)amino-, —N(R³)—C(O)-alkyl, —N(R³)—C(O)-aryl, -cycloalkyl, -heterocycloalkyl, -aryl, and -heteroaryl;

R¹ and R² are the same or they are different, and are independently selected from H, a straight or branched C₁ to C₇ alkyl, straight or branched C₁ to C₇ alkoxy, straight or branched C₁ to C₄ hydroxyalkyl, aryl, heteroaryl, heterocycloalkyl and cycloalkyl, and wherein heteroatoms of said heteroaryl and heterocycloalkyl are independently selected from one or more N, O and S, with the proviso that no two adjacent ring heteroatoms are both S or both O, further wherein R¹ and R² can be either unsubstituted or optionally independently substituted with one or more substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, -alkyl, -alkenyl, -alkynyl, hydroxyalkyl-, -alkoxy, hydroxyl, alkyl hydroxy, hydroxyl, alkyl hydroxy, carboxy, (alkoxyalkyl) amino-, -alkylamine, aminocarbonyl-, —CHO, —N(R³)—C(O)-alkyl, —N(R³)—C(O)-aryl, -cycloalkyl, -heterocycloalkyl, -aryl, and heteroaryl;

R³ is H, alkyl or arylalkyl-;

A is aryl, heteroaryl, heterocycloalkyl or C₃ to C₈ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, -alkyl, -alkenyl, -alkynyl, -alkoxy, hydroxyl, -alkyl hydroxyl, aryloxy-, (alkoxyalkyl)amino-, —N(R³)—C(O)-alkyl, —N(R³)—C(O)-aryl, -cycloalkyl, -heterocycloalkyl, -aryl, and -heteroaryl;

Q is C(O), S(O), S(O)₂, —CH₂—C(O)—, —N(H)—C(O)—, —S(O₂)—NH—, or —N(H)—S(O₂)—;

n is 0, 1, 2, 3, 4, 5 or 6;

z is 0, 1 or 2;

m is 0 or 1;

s is 0 or 1; and t is 0 or 1 and pharmaceutically acceptable salts, solvates, esters, isomers and prodrugs thereof.

Another aspect of the invention is compounds of Formula II

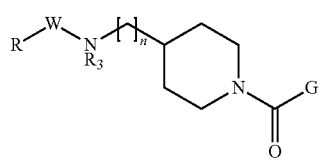

II wherein

W is —C(O)—, —S(O)— or —S(O)₂—;

R is an aryl or heteroaryl bicycle wherein the heteroatoms of each of said heteroaryl numbers 1, 2 or 3, and are independently selected from N, S or O, wherein each of said aryl, heteroaryl is optionally substituted with one or more substituents which can be the same or different and are independently selected from the group consisting of deuterium, halo, cyano, amino, aminoalkyl, (amino)alkoxy, —CONH₂, —C(O)NH(alkyl), —C(O)N(alkyl)₂, —C(O)NH(aryl), —C(O)N(aryl)₂, —CF₃, —CHF₂, —CH₂F, -alkyl, alkoxy, hydroxyl, hydroxyalkyl, (alkoxyalkyl) amino, —N(R³)—C(O)-alkyl, —N(R³)—C(O)-aryl, cycloalkyl, heterocycloalkyl, aryl, and heteroaryl, with the proviso that no two adjacent ring heteroatoms are both S or both O;

G is aryl, heteroaryl, cycloalkyl, heterocycloalkyl or —NR¹R², with each of said aryl, heteroaryl, heterocycloalkyl and cycloalkyl being either unsubstituted or independently substituted with 1, 2, 3 or 4 substituents which can be the same or different and are independently selected from the group consisting of deuterium, halo, cyano, amino, aminoalkyl, (amino)alkoxy-, —CONH₂, —C(O)NH(alkyl), —C(O)N(alkyl)₂, —C(O)NH(aryl), —C(O)N(aryl)₂, —CF₃, —CHF₂, —CH₂F, alkyl, alkenyl, alkynyl, alkoxy, hydroxyl, hydroxyalkyl, aryloxy, (alkoxyalkyl)amino-, —N(R³)—C(O)-alkyl, —N(R³)—C(O)-aryl, cycloalkyl, heterocycloalkyl, aryl, and heteroaryl;

R¹ and R² are the same or they are different, and are independently selected from H, C₁ to C₇ alkyl, C₁ to C₇ alkoxy, C₁ to C₄ hydroxyalkyl, aryl, heteroaryl, heterocycloalkyl and cycloalkyl, and wherein heteroatoms of said heteroaryl and heterocycloalkyl are independently selected from one or more N, O and S, with the proviso that no two adjacent ring heteroatoms are both S or both O, further wherein R¹ and R² can be either unsubstituted or optionally independently substituted with one or more substituents which can be the same or different and are independently selected from the group consisting of deuterium, halo, cyano, amino, aminoalkyl, (amino)alkoxy, —CONH₂, —C(O)NH(alkyl), —C(O)N(alkyl)₂, —C(O)NH(aryl), —C(O)N(aryl)₂, —CF₃, —CHF₂, —CH₂F, alkyl, hydroxyalkyl, -alkoxy, hydroxyl, hydroxyalkyl, carboxy, (alkoxyalkyl) amino, -alkylamine, aminoearbonyl, —CHO, —N(R³)—C(O)-alkyl, —N(R³)—C(O)-aryl, cycloalkyl, heterocycloalkyl, aryl, and heteroaryl;

R³ is H, alkyl or arylalkyl;

n is 4, 5 or 6;

or a pharmaceutically acceptable salt thereof.

Another aspect of this invention is the provision of methods of treating a disease via the inhibition of NAMPT in a subject (e.g., a human) in need thereof by administering to the subject an effective amount of the compound or the pharmaceutical formulation of the present invention.

Still another aspect of this invention is to provide a method for treating, preventing, inhibiting or eliminating a disease or condition in a patient by inhibiting NAMPT in said patient by administering a therapeutically effective amount of at least one compound of the disclosure, wherein said disease or condition is selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodkins' disease, viral infection, Human Immunodeficiency Virus, hepatitis virus, herpes virus, herpes simplex, inflammatory disorders, irritable bowel syndrome, inflammatory bowel disease, rheumatoid arthritis, asthma, chronic obsturcive pulmonary disease, osteroarthritis, osteoporosis, demiatitis, atptic dermatitis, psoriasis, systemic lupus erythematous, multiple sclerosis, psoriatic arthritis, ankylosing spondylitis, draft versus host disease, Alzheimer disease, cardiovascular accident, atherosclerosis, diabetes, glomerulonephritis, metabolic syndrome, non-small cell lung cancer, small cell lung cancer, multiple myeloma, leukemia, lymphomas, squamous cell cancers, kidney cancer, literal and bladder cancers, cancer of head and neck, cancers of the brain and central nervous system.

Another preferred embodiment is a pharmaceutical formulation comprising a pharmaceutically acceptable compound of the present invention, which provides, upon administration to a human, a decrease in tumor burden and/or metastases. The pharmaceutical formulation can be administered by oral means or other suitable means.

Yet another embodiment is a method of treating ovarian cancer in a subject (e.g., a human) in need thereof by administering to the subject an effective amount of the compound or the pharmaceutical formulation of the present invention.

Yet another embodiment is a method of treating colon cancer in a subject (e.g., a human) in need thereof by administering to the subject an effective amount of the compound or the pharmaceutical formulation of the present invention.

Yet another embodiment is a method of treating breast cancer in a subject (e.g., a human) in need thereof by administering to the subject an effective amount of the pharmaceutical formulation of the present invention.

Yet another embodiment is a method of treating leukemia in a subject (e.g., a human) in need thereof by administering to the subject an effective amount of the compound or the pharmaceutical formulation of the present invention.

Yet another embodiment is a method of treating colon cancer, before or after surgical resection and/or radiation therapy, in a subject (e.g., a human) in need thereof by administering to the subject an effective amount of the compound or the pharmaceutical formulation of the present invention.

Yet another embodiment is a method of treating cancer, before or after surgical resection and/or radiation therapy, in a subject (e.g., a human) in need thereof by administering to the subject an effective amount of the compound or the pharmaceutical formulation of the present invention, including adjunctive therapy to treat nausea, with or without dexamethasone.

Yet another embodiment is a method of treating cancer, before or after surgical resection and/or radiation therapy, in a subject (e.g., a human) in need thereof by administering to the subject an effective amount of the compound or the pharmaceutical formulation of the present invention, including adjunctive therapy with one or more additional therapeutic agents, or their pharmaceutically acceptable salts thereof. Non-limiting examples of such additional therapeutic agents include cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil or 5-FU); anti-metabolites (such as methoxtrexate); alkylating agents (such as temozolomide, cyclophosphamide); Farnesyl protein transferase inhibitors (such as, SARASAR™; (4-[2-[4-[(11R)-3,10-dibromo-8-chloro-6,11-dihydro-5H-benzo[5, -6]cyclohepta[1,2-b]pyridin-11-yl-]-1-piperidinyl]-2-oxoethyl]-1-piperidine-carboxamide, or SCH 66336), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (from Astra Zeneca Pharmaceuticals, England), Tarceva® (EGER kinase inhibitors), antibodies to EGFR (e.g., C225), GLEEVEC® (C-abl kinase inhibitor from Novartis Pharmaceuticals, East Hanover, N.J.); interferons such as, for example, Intron© (from Merck & Company), Peg-Intron® (from Merck & Company); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylcncmclaminc, Triethylcncthiophosphoraminc, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN® from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mitliramycin, Deoxycotormycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade®, Zevalin, Trisenox, Xeloda, Vinorelbine, Porfimer, Erbitux, Liposomal, Thiolepa, Altretamine, Melphalan, Trasluzumab, Lerozole, Fulvestrant, Exemestane, Ifosfomide, Rituximab, C225, and Campath, 5-fluorouracil and leucovorin, with or without a 5-HT$_3$ receptor inhibitor (e.g., dolansetron, granisetron, ondansetron) with or without dexamethasone.

If formulated as a fixed dose, such combination products employ the compounds of this invention within the dosage range described herein, or as known to those skilled in the art and the other pharmaceutically active agent or treatment within its dosage range. For example, the CDCl$_2$ inhibitor olomucine has been found to act synergistically with known cytotoxic agents in inducing apoptosis (J. Cell Sci., (1995) 108, 2897). The compounds of the invention may also be administered sequentially with known anticancer or cytotoxic agents when a combination formulation is inappropriate. In any combination treatment, the invention is not limited in the sequence of administration; compounds of Formula (I) may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Definitions

As used above, and throughout this disclosure, the following terms, unless otherwise indicated, shall be understood to have the following meanings. If a definition is missing, convention definition as known to one skilled in the art controls.

"Patient" includes both human and animals.

"Mammal" means humans and other mammalian animals.

The term "inhibitor" refers to a molecule such as a compound, a drug, an enzyme activator or a hormone that blocks or otherwise interferes with a particular biologic activity.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation. Thus, the expression "effective amount" generally refers to the quantity for which the active substance has therapeutic effects. In the present ease the active substance is the inhibitor of the formation of nicotinamide phosphoribosyltransferase (NAMPT).

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

By "pharmaceutically acceptable" or "pharmacologically acceptable" is meant a material which is not biologically or otherwise undesirable, i.e., the material may be administered to an individual without causing a minimum of undesirable biological effects or interacting in a deleterious manner with any of the components of the composition in which it is contained.

"Carrier materials" or what are also referred to as "excipients" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., Remington's Pharmaceutical Sciences, Mack Publishing Co., Easton, Pa. 1975.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

As used herein, "alkyl" means a straight chain or branched saturated, partially saturated or unsaturated (e.g. alkenyl and alkynyl) chain having from 1 to carbon atoms. In an embodiment, "alkyl" groups are saturated. It is understood that the term "alkyl" used in conjunction with another group, the alkyl portion of the group is saturated, partially unsaturated or unsaturated. For example, "aralkyl" includes Ph-CH=CH—. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2.2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3.3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, branched or cyclized. As used herein, "lower alkyl" means an alkyl having from 1 to 6 carbon atoms.

As used herein, an "alkenyl group" includes an unbranched or branched hydrocarbon chain having one or more double bonds therein. The double bond of an alkenyl group can be unconjugated or conjugated to another unsaturated group. Illustrative alkenyl groups include, but are not limited to, ($C_2$-$C_8$) alkenyl groups, such as ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted.

The term "hydroxyalkyl" denotes an alkyl group as defined above wherein at least one of the hydrogen atoms of the alkyl group is replaced by a hydroxy group. Examples of hydroxyalkyl include, but are not limited to, methyl, ethyl, propyl, isopropyl, isobutyl, sec-butyl, tert-butyl, pentyl or n-hexyl wherein one or more hydrogen atoms are replaced by OH, as well as those hydroxyalkyl groups specifically illustrated by the examples herein below.

The term "cyanoalkyl" denotes an alkyl group as defined above wherein at least one of the hydrogen atoms of the alkyl group is replaced by a cyano (—CN) group.

As used herein, "alkynyl group" includes an unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted. The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include, but are not limited to, methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, -ethyl or -propyl, for example 3, 3, 3-trifluoropropyl, 2-fluoroethyl, 2, 2, 2-trifluoroethyl, fluoromethyl, trifluoromethyl.

The terms "trifluoromethyl." "sulfonyl," and "carboxyl" include $CF_3$, —$SO_2$, and $CO_2H$, respectively.

The term "hydroxy" means an OH group;

The term "oxo" means =O-group.

The term "alkoxy" as used herein includes —O-(alkyl), wherein alkyl is defined above.

The term "aminoalkyl" as used herein means a group having one or more nitrogen atoms and one or more alkyl groups as defined above on the nitrogen.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Heteroarylalkyl" means a heteroaryl moiety as defined herein linked via an alkyl moiety (defined above) to a parent core. Non-limiting examples of suitable heteroaryls include 2-pyridinylmethyl, quinolinylmethyl and the like.

"Heterocyclylalkyl" means a heterocyclyl moiety as defined herein linked via an alkyl moiety (defined above) to a parent core. Non-limiting examples of suitable heterocyclylalkyls include piperidinylmethyl, piperazinylmethyl and the like.

It should also be noted that any carbon as well as heteroatom which unsatisfied valences in the text, schemes, examples and Tables herein is assumed to have the sufficient number of hydrogen atom(s) to satisfy the valences.

When any variable (e.g., aryl, heterocycle, $R^2$, etc.) occurs more than one time in any constituent or in the Formulas, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "deuterium" as used herein means a stable isotope of hydrogen having odd numbers of protons and neutrons.

The term "halo" as used herein means a substituent having at least one halogen selected from fluorine, chlorine, bromine, and iodine.

The term "cyano" as used herein means a substituent having a carbon atom joined to a nitrogen atom by a triple bond.

The term "amino" as used herein means a substituent containing at least one nitrogen atom.

The term "(amino)alkoxy" as used herein means a substituent having at least one amino group and at least one alkoxy group.

The term "aryloxy" as used herein means a substituent of the form Ar—O— where Ar is an aryl group as defined herein.

The term "methylenedioxy" as used herein means a functional group with the structural formula —O—$CH_2$—O— which is connected to the molecule by two chemical bonds via the oxygens.

As used herein, "alkoxyalkyl" means -(alkyl)-O-(alkyl), wherein each "alkyl" is independently an alkyl group defined above.

The term "(alkoxyalkyl)amino" as used herein means a substituent having at least one alkoxyalkyl group as defined above and at least one amino group as defined above.

The term "spiroheterocycloalkyl" as used herein means a spiro group (containing no heteroatom) linked in a spiro manner to a heterocycloalkyl group. A non-limiting example would be the moiety shown below:

The term "heterospiroheterocycloalkyl" as used herein means a spiro group (containing a hetero atom such O, N or S) linked in a spiro manner to a heterocycloalkyl group. A non-limiting example would be the moiety shown below:

As used herein, the term "aryl" refers to a monocyclic, or fused or spiro polycyclic, aromatic carbocycle (ring structure having ring atoms that are all carbon) having from 3 to 24 ring atoms per ring. Illustrative examples of aryl groups include, but are not limited to, the following moieties:

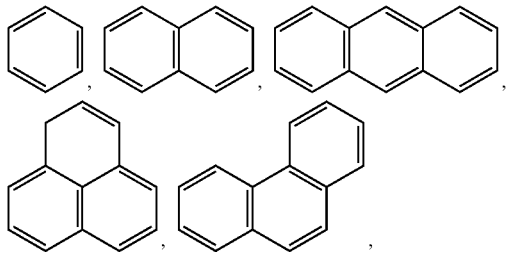

and the like.

Illustrative substituted aryls include:

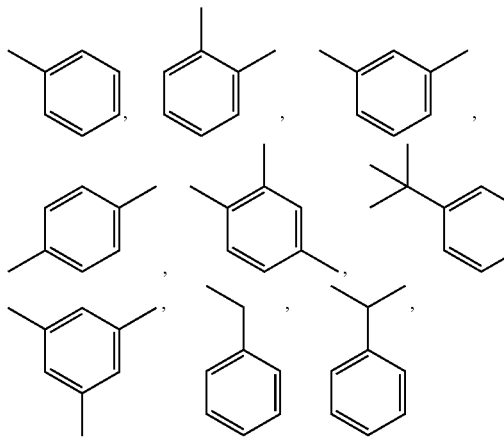

-continued

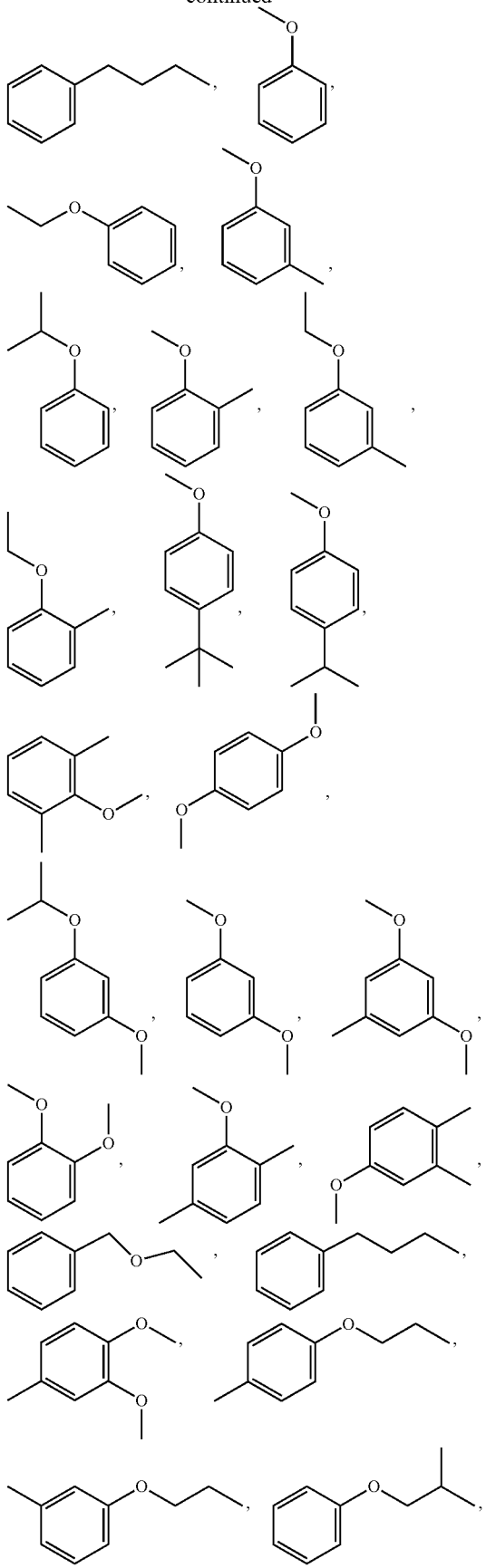

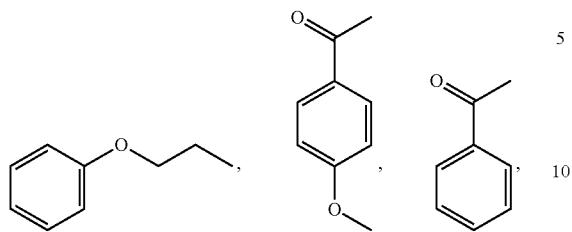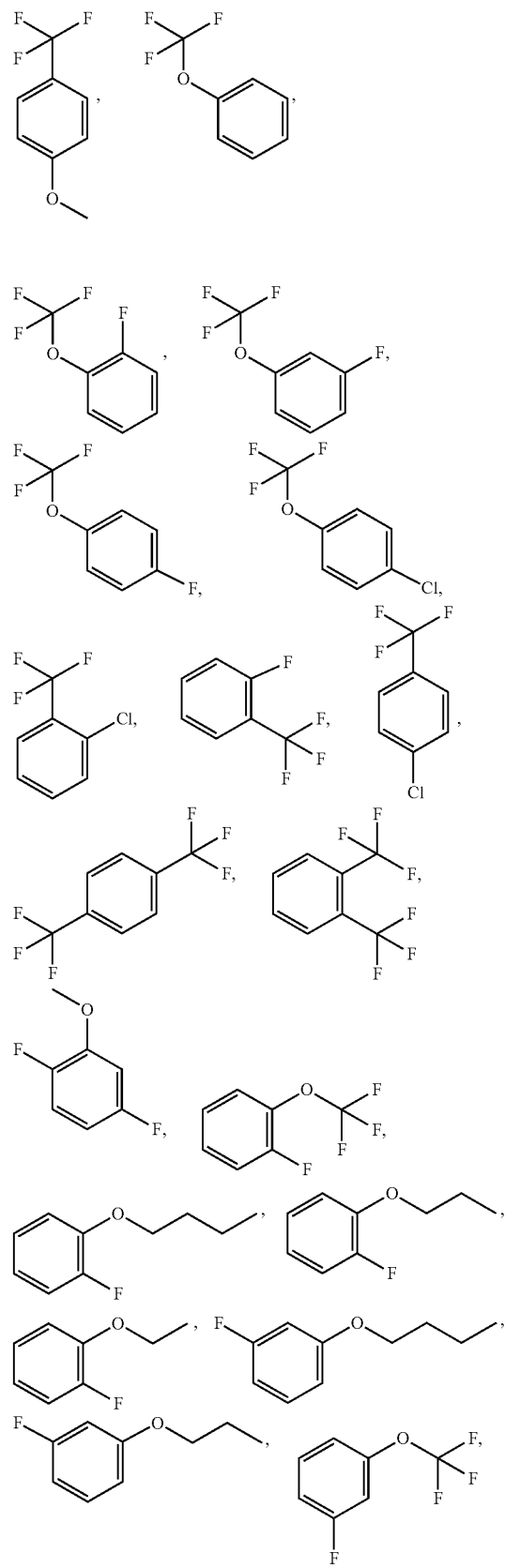

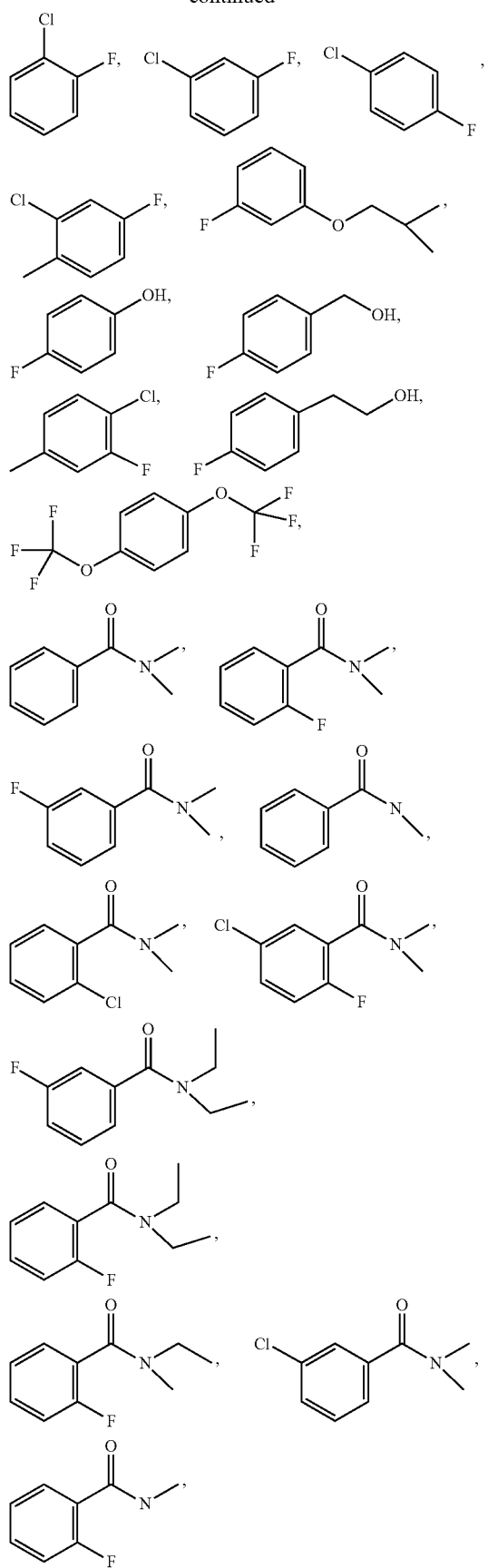
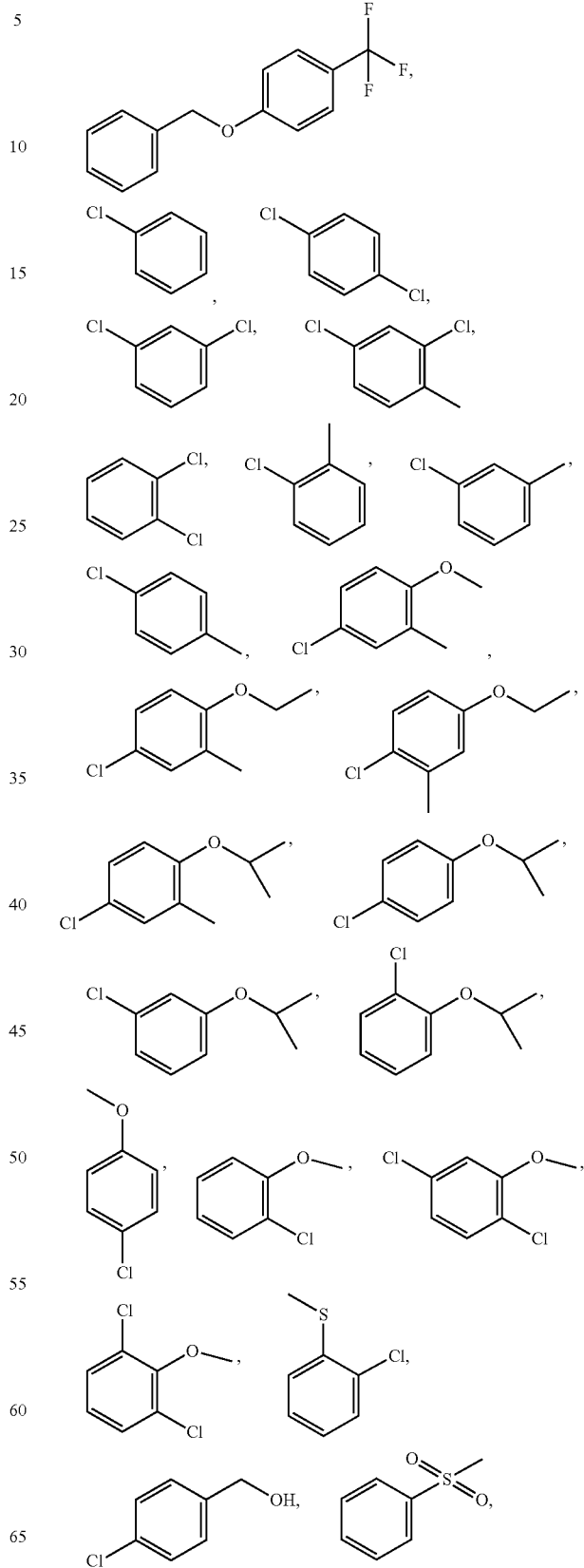

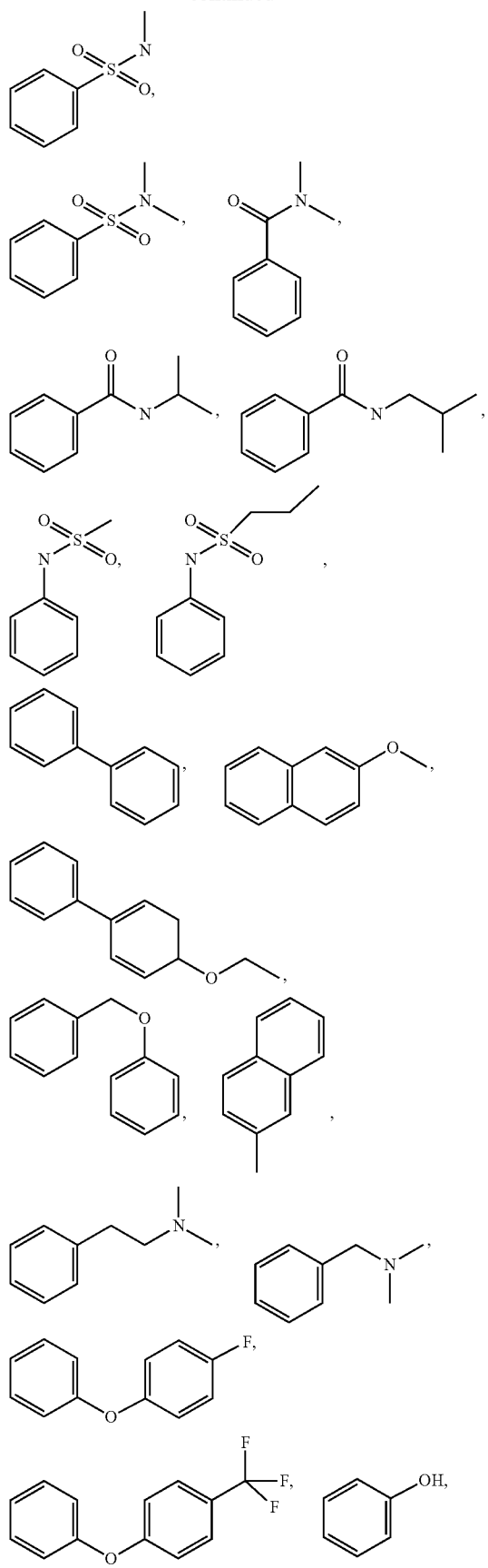

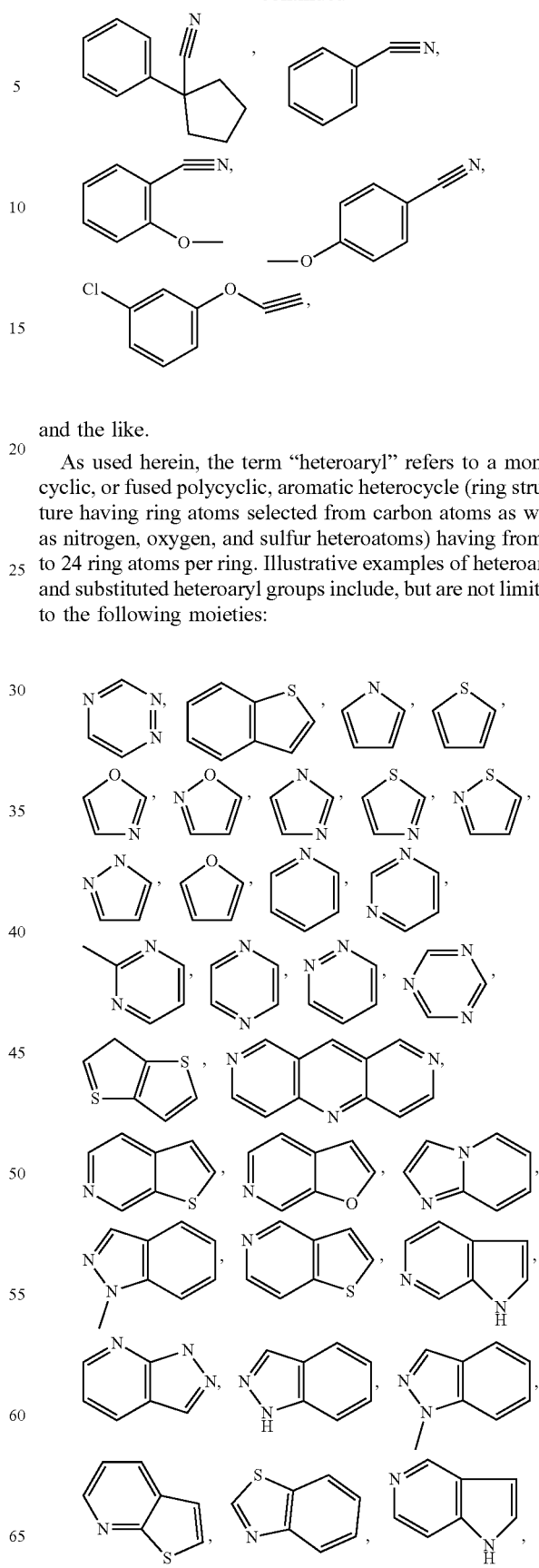

and the like.

As used herein, the term "heteroaryl" refers to a monocyclic, or fused polycyclic, aromatic heterocycle (ring structure having ring atoms selected from carbon atoms as well as nitrogen, oxygen, and sulfur heteroatoms) having from 3 to 24 ring atoms per ring. Illustrative examples of heteroaryl and substituted heteroaryl groups include, but are not limited to the following moieties:

-continued
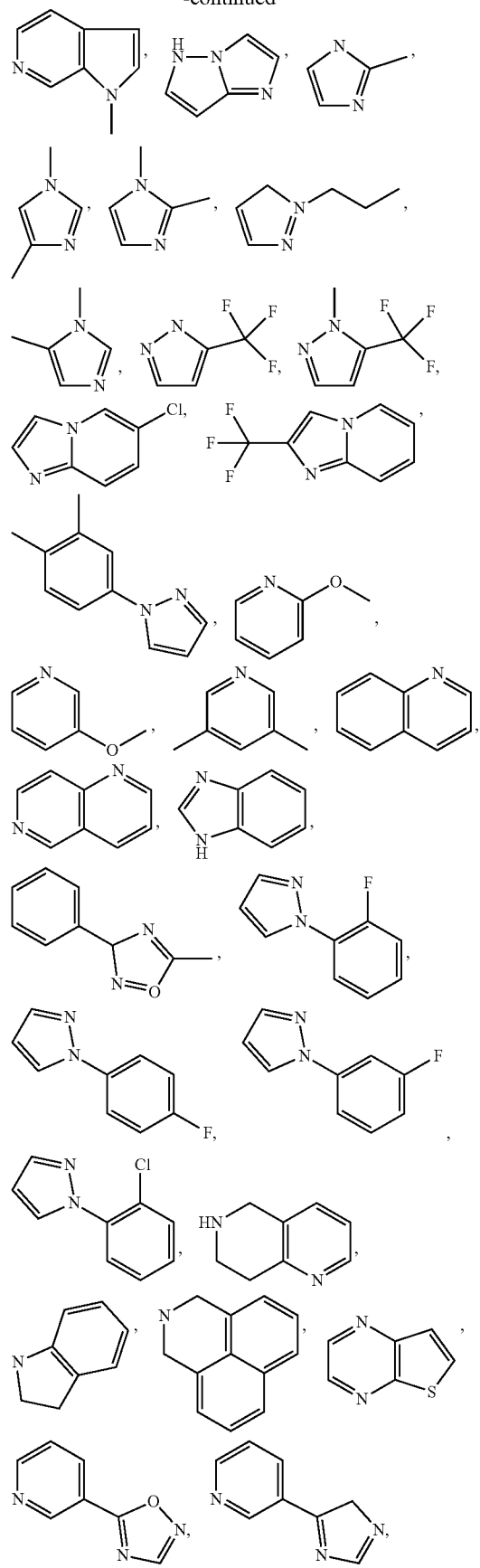
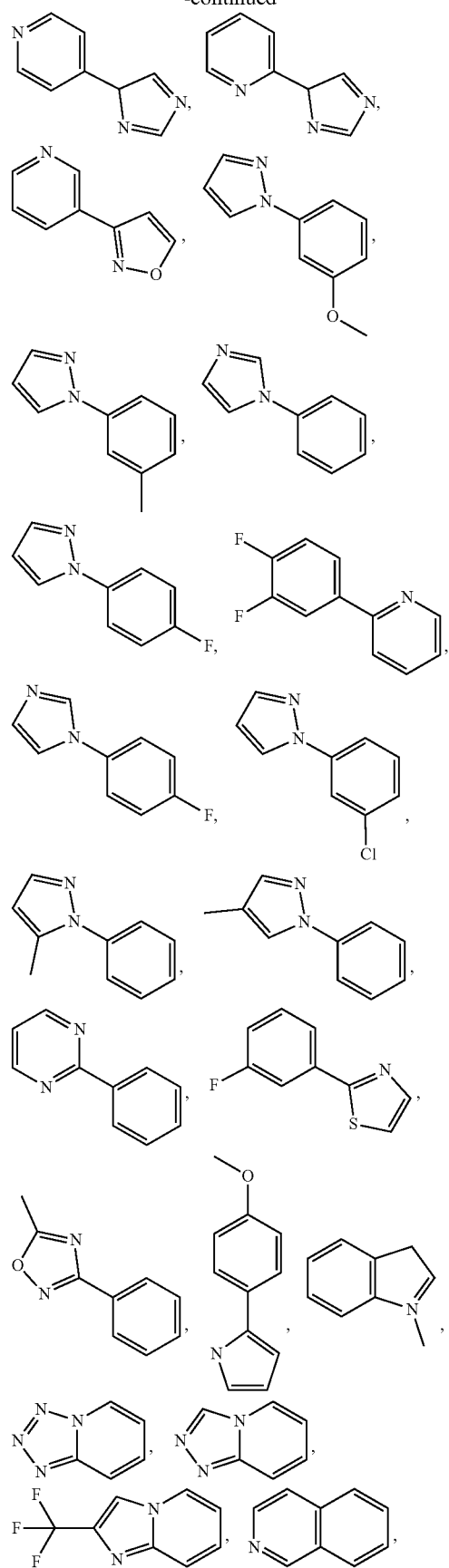

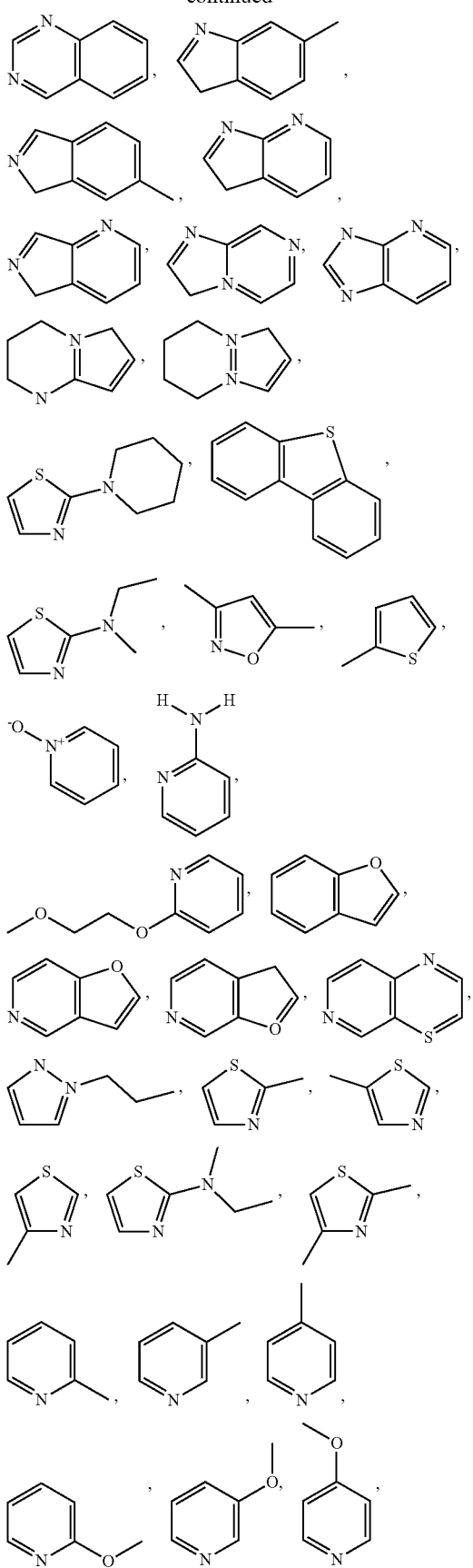

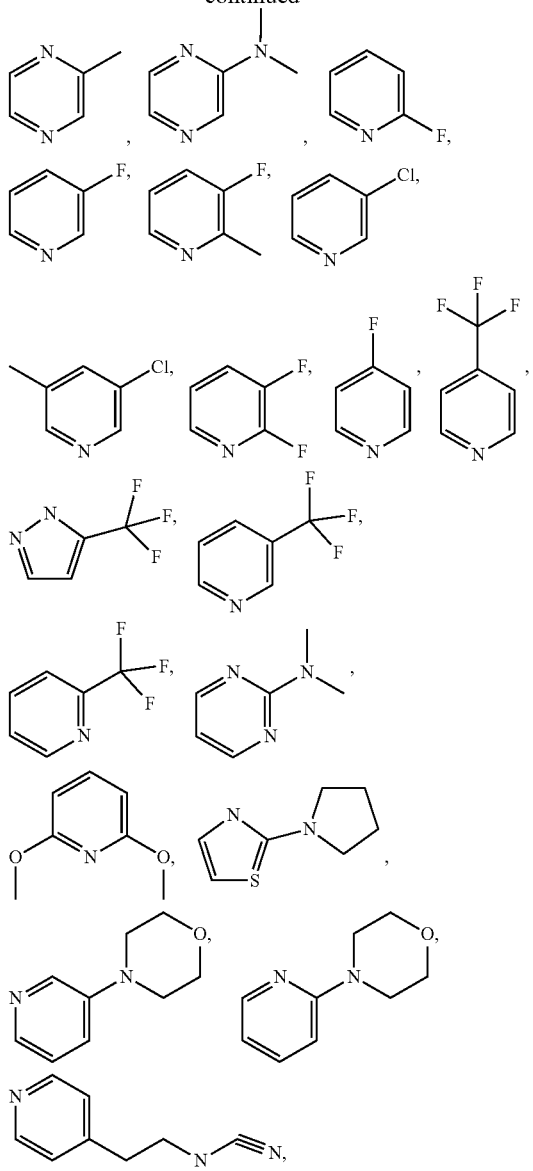

and the like.

The term "bicyclic heteroaryl" means a structure having atoms arranged in two rings fused together with at least two atoms common to each ring, and at least one of the rings being a heteroaryl ring. Non limiting examples of bicyclic heteroaryl comprise 5 to 14 membered bicyclic heteroaryl-groups comprising 1, 2, 3, or 4 heteroatoms independently selected from N, S or O. Illustrative examples of bicyclic heteroaryls include but are not limited to:

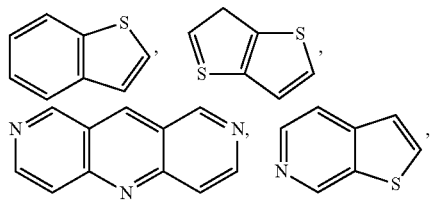

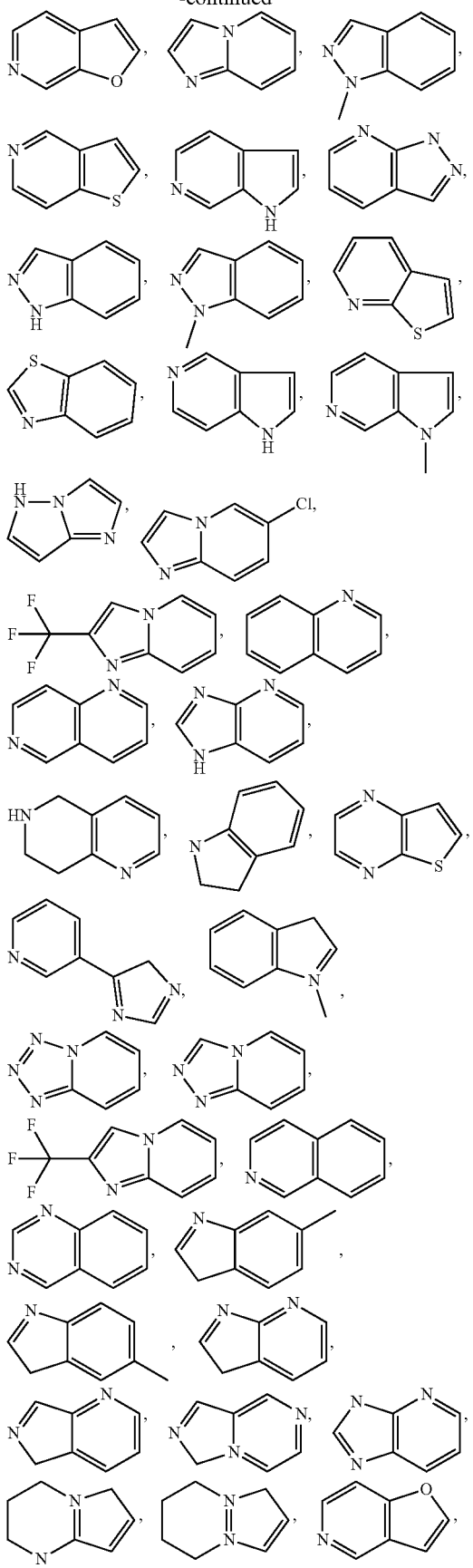

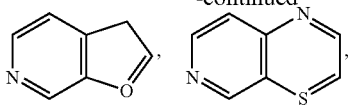

and the like.

Further examples of bicyclic heteroaryls include but are not limited to:

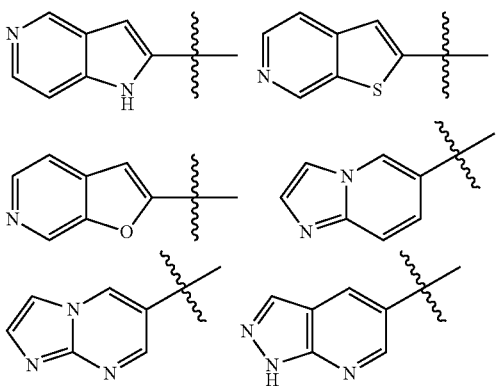

These bicyclic heteroaryl groups can be substituted as defined herein.

As used herein, the term "cycloalkyl" refers to a saturated, unsaturated or partially saturated, monocyclic or fused or spiro polycyclic, carbocycle having from 3 to 24 ring atoms per ring. Illustrative examples of cycloalkyl groups include, but are not limited to, the following moieties:

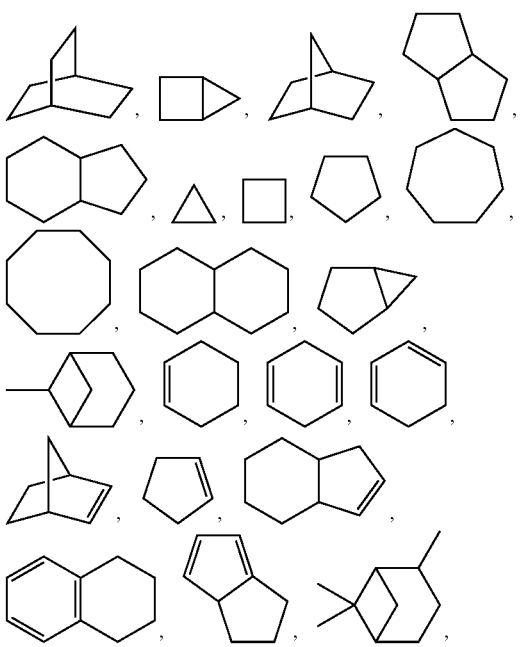

and the like.

As used herein, the term "heterocycloalkyl" refers to a monocyclic, or fused or spiro, polycyclic, ring structure that is saturated, unsaturated or partially saturated and has from 3 to 24 ring atoms per ring selected from C atoms and N, O, and S heteroatoms. Illustrative examples of heterocycloalkyl and substituted heterocycloalkyl groups include, but are not limited to:
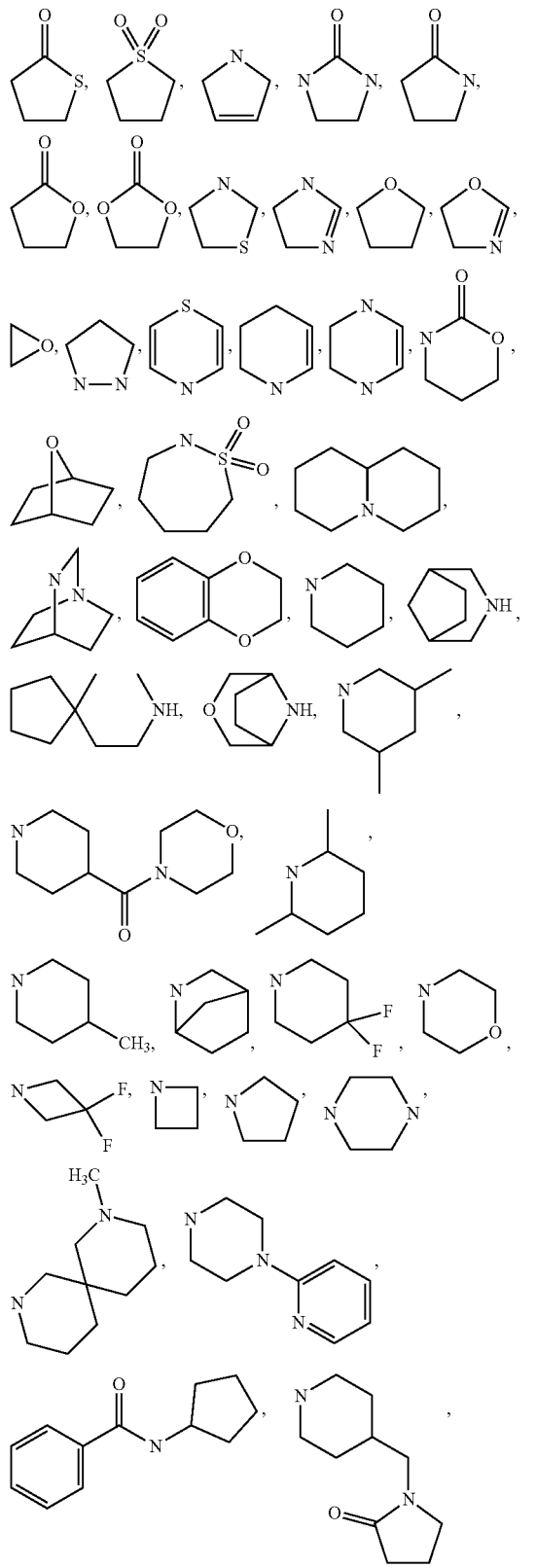
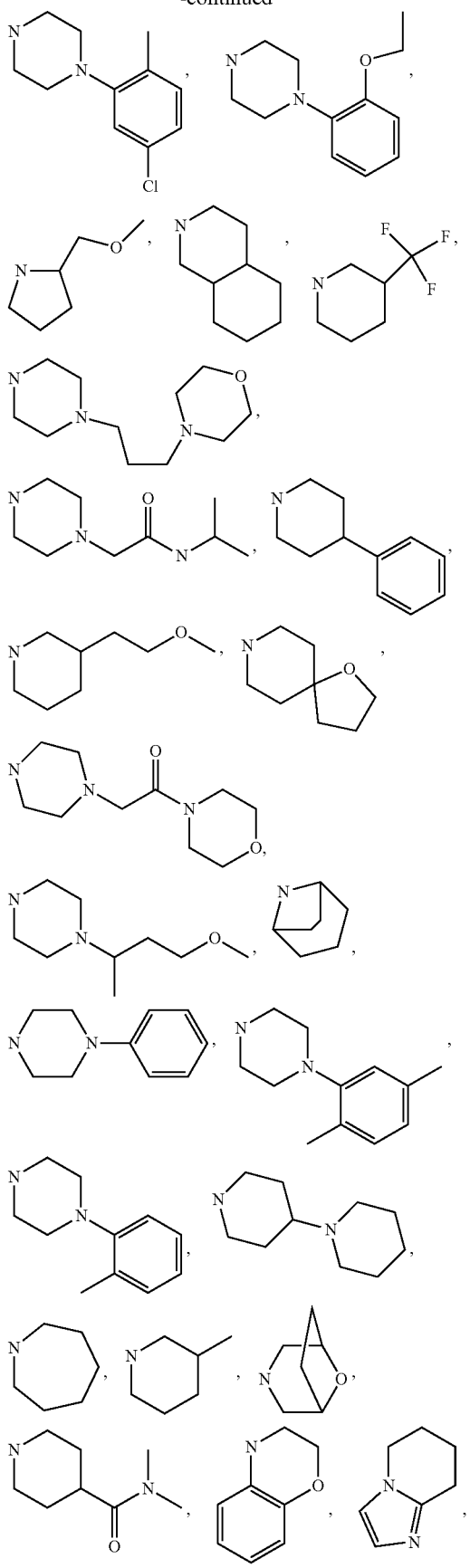

-continued
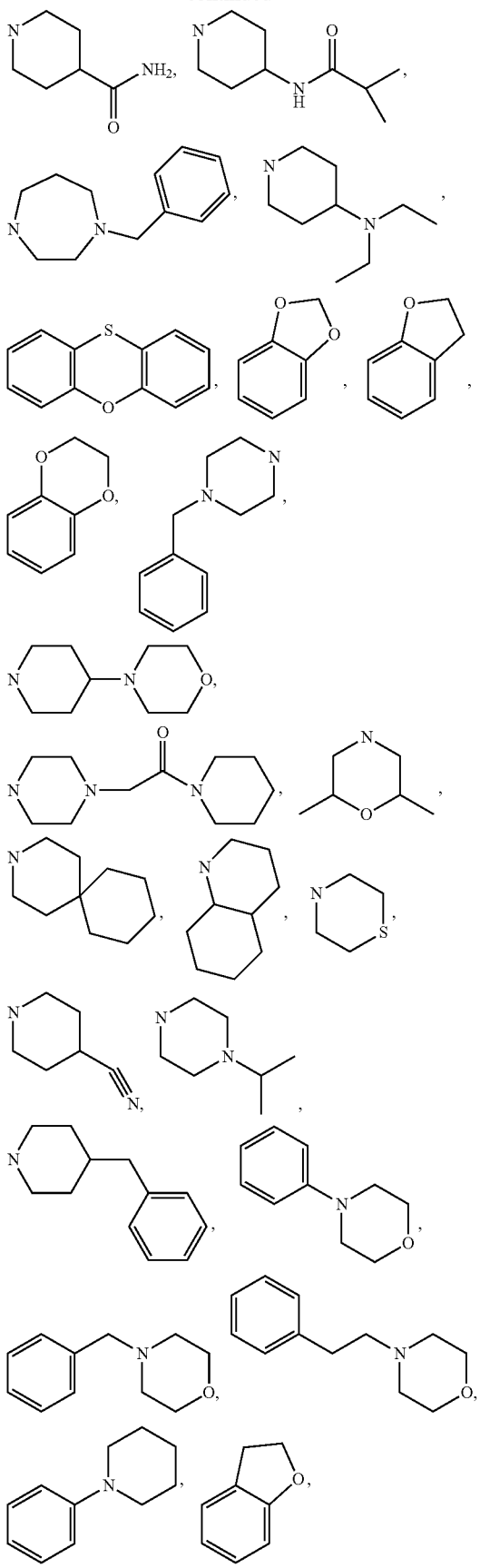
-continued
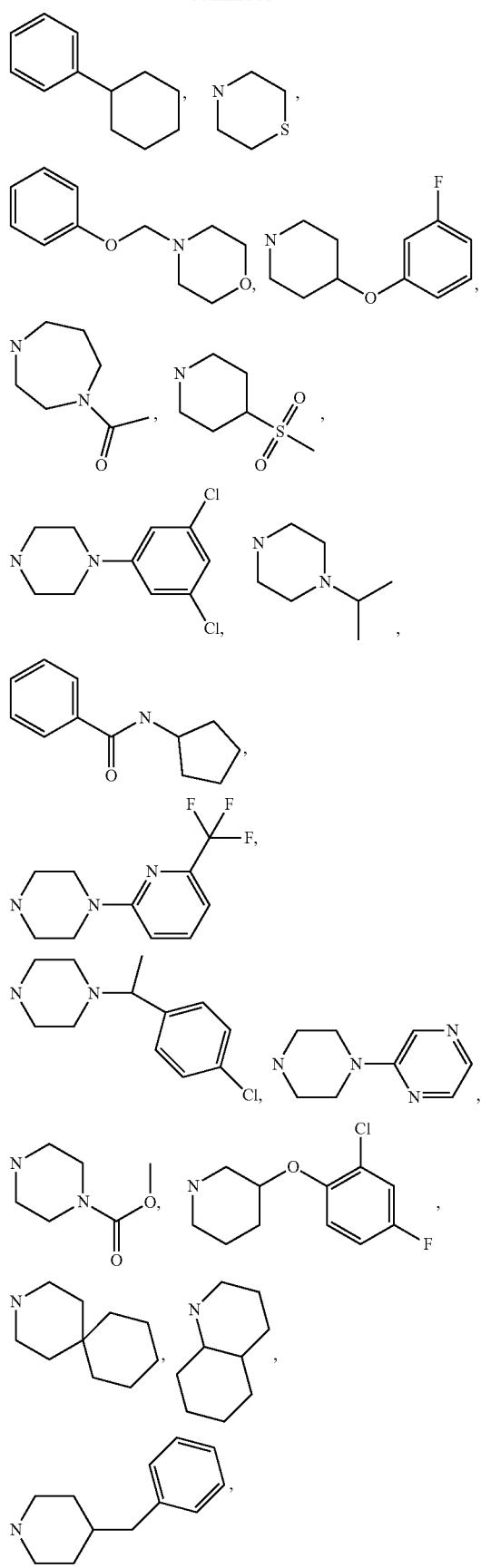

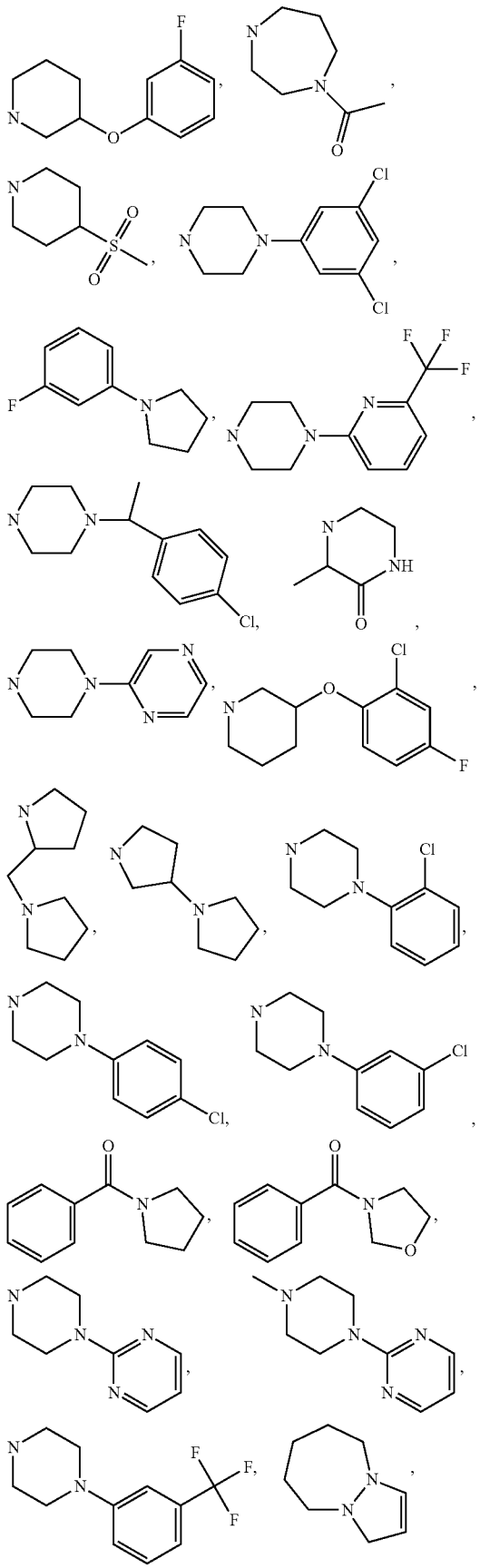
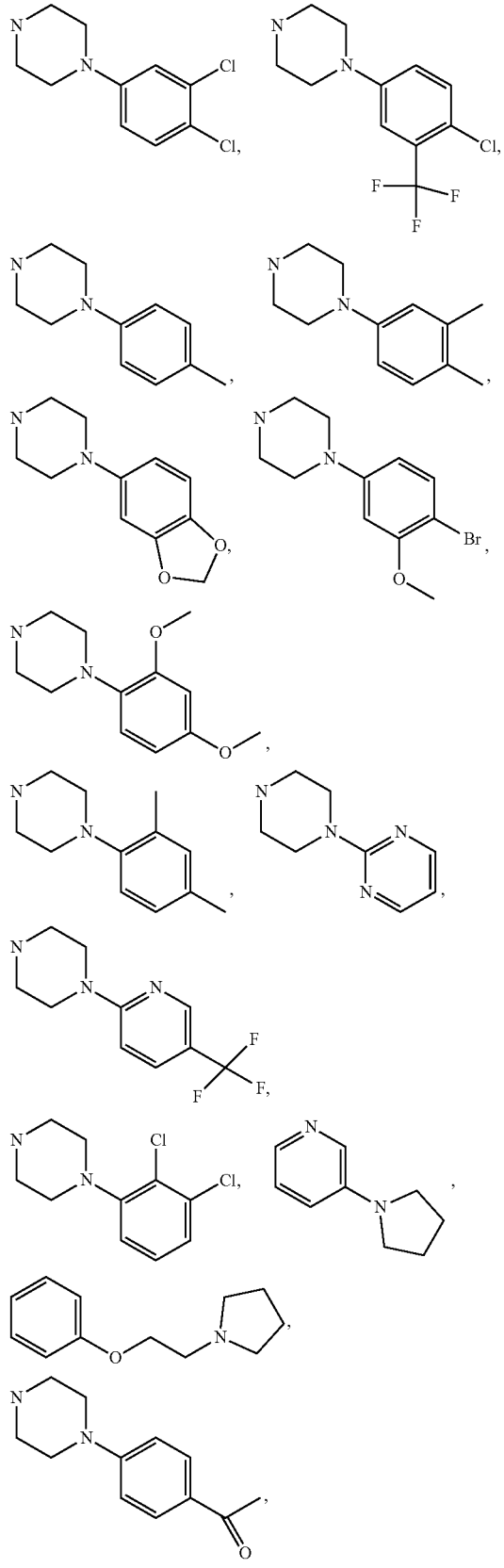

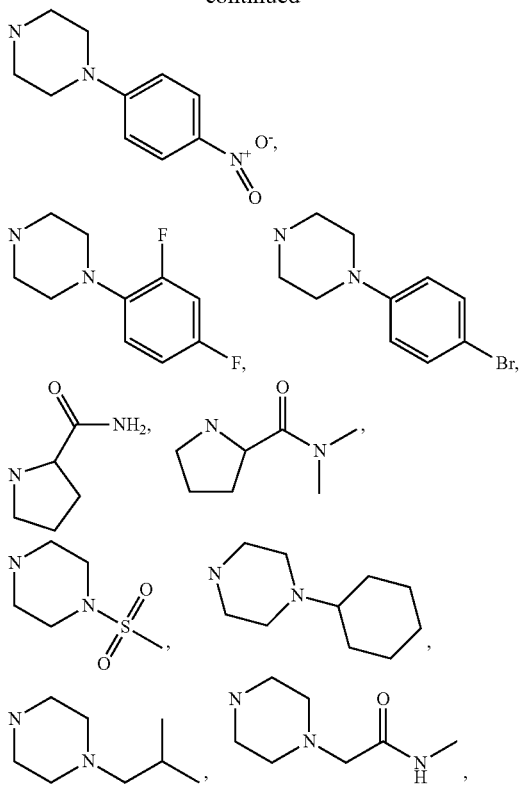

and the like.

Numerical ranges, as used herein, are intended to include sequential whole numbers. For example, a range expressed as "from 0 to 4" would include 0, 1, 2, 3 and 4.

As used herein, the term "substituted" means that the specified group or moiety bears one or more suitable substituents.

As used herein, the term "unsubstituted" means that the specified group bears no substituents.

As used herein, the term "optionally substituted" means that the specified group is unsubstituted or substituted by one or more substituents.

When a multifunctional moiety is shown, the point of attachment to the core is indicated by a line. For e.g. (cycloalkyloxy)alkyl-refers to alkyl being the point of attachment to the core while cycloalkyl is attached to alkyl via the oxy group.

The expression "adjunctive chemotherapeutic agent" generally refers to agents which treat, alleviate, relieve, or ameliorate the side effects of chemotherapeutic agents. Such agents include those which modify blood cell growth and maturation. Examples of adjunctive chemotherapeutic agents include, but are not limited to, filgrastim and erythropoietin. Other such adjunctive chemotherapeutic agents include those which inhibit nausea associated with administration of the chemotherapeutic agents, such as a 5-HT$_3$ receptor inhibitor (e.g., dolansetron, granisetron, or ondansetron), with or without dexamethasone.

The terms "chemotherapeutic agent" and "antineoplastic agent" generally refer to agents which treat, prevent, cure, heal, alleviate, relieve, alter, remedy, ameliorate, improve, or affect malignancies and their metastasis. Examples of such agents (also known as "antineoplastic agents") include, but are not limited to, prednisone, fluorouracil (e.g., 5-fluorouracil (5-EU)), anastrozole, bicalutamide, carboplatin, cisplatin, chlorambucil, cisplatin, carboplatin, docetaxel, doxorubicin, flutamide, interferon-alpha, letrozole, leuprolide, megestrol, mitomycin, oxaliplatin, paclitaxel, plicamycin (Mithracin™), tamoxifen, thiotepa, topotecan, valrubicin, vinblastine, vincristine, and any combination of any of the foregoing. Additional such agents are described later.

"Nicotinamide phosphoribosyltransferase" also named NAMPT, NMPRT, NMPRTase or NAmPRTase, (International nomenclature: E.C. 2.4.2.12) is a key enzyme in nicotinamide adenyl dinucleotide (NAD) biosynthesis from the natural precursor nicotinamide.

It must be noted that, as used in the specification and the appended claims, the singular forms "a," "an" and "the" include plural referents unless the context clearly dictates otherwise.

When used as a therapeutic agent the inhibitors of the formation of nicotinamide phosphoribosyltransferase (NAMPT) described herein may be administered with one or more physiologically acceptable excipients. A physiologically acceptable carrier or excipient is a formulation to which the compound can be added to dissolve it or otherwise facilitate its administration.

The dosage forms of the present invention, may contain a mixture of one or more compounds of this invention, and may include additional materials known to those skilled in the art as pharmaceutical excipients. Such pharmaceutical excipients include, for example, the following: Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant) Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetale, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, caranuba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celluloses, hydroxyalkylcelluloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, micro crystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (bacteriostatic water for injection, bacteriostatic sodium chloride injection); Viscosity-increasing agent; Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in dosage forms of the present invention.

The compounds of the disclosed Formulas can form salts which are also within the scope of this invention. Reference to a compound of the Formula herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the Formulas contain both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formulas may be formed, for example, by reacting a compound of a Formula with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge ct al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the compounds of the invention are also considered to be part of the invention. Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of the instant Formulas or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

Tor example, if a compound of the instant Formulas or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a compound of the instant Formulas contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacetyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of the instant Formulas incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino$(C_1-C_4)$alkyl or mono-N- or di-N,N—$(C_1-C_6)$alkylaminoalkyl, —C(Y$^4$)Y$^5$ wherein Y$^4$ is H or methyl and Y$^5$ is mono-N- or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS PharmSciTech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of the various Formulas, and salts, solvates, esters and prodrugs thereof, may exist in their tautomeric form (for example, as an amide or imino ether). All such tautomeric forms are contemplated herein as part of the present invention.

The compounds of the various Formulas may contain asymmetric or chiral centers, and, therefore, exist in different stereoisomeric forms. It is intended that all stereoisomeric forms of the compounds of the various Formulas as well as mixtures thereof, including racemic mixtures, form part of the present invention. In addition, the present invention embraces all geometric and positional isomers. For example, if a compound of the various Formulas incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulas may be atropisomers (e.g., substituted biaryls) and are considered as part of this invention. Enantiomers can also be separated by use of chiral HPLC column.

It is also possible that the compounds of the various Formulas may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulas incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the various Formulas (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of the various Formulas can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the various Formulas, and of the salts, solvates, esters and prodrugs of the compounds of the various Formulas, are intended to be included in the present invention.

Benefits of the present invention include oral administration of an optimal amount of a nicotinamide phosphoribosyltransferase biosynthesis inhibitor.

Benefits of the present invention include intravenous administration of an optimal amount of a nicotinamide phosphoribosyltransferase biosynthesis inhibitor.

Benefits of the present invention include intraperitoneal administration of an optimal amount of a nicotinamide phosphoribosyltransferase biosynthesis inhibitor.

Benefits of the present invention include intramural administration of an optimal amount of a nicotinamide phosphoribosyltransferase biosynthesis inhibitor.

Benefits of the present invention include intramuscular administration of an optimal amount of a nicotinamide phosphoribosyltransferase biosynthesis inhibitor.

Benefits of the present invention include subcutaneous administration of an optimal amount of a nicotinamide phosphoribosyltransferase biosynthesis inhibitor.

Benefits of the present invention include intra-tumor administration of an optimal amount of a nicotinamide phosphoribosyltransferase biosynthesis inhibitor.

Benefits of the present invention include intrathecal administration of an optimal amount of a nicotinamide phosphoribosyltransferase biosynthesis inhibitor.

Benefits of the present invention include subdural administration of an optimal amount of a nicotinamide phosphoribosyltransferase biosynthesis inhibitor.

Benefits of the present invention include periorbital administration of an optimal amount of a nicotinamide phosphoribosyltransferase biosynthesis inhibitor.

Based on these results, the present invention has important implications for the design of novel treatment strategies for patients with cancer, including leukemias and solid tumors, inflammatory diseases, osteoporosis, atherosclerosis; irritable bowel syndrome and other conditions disclosed herein or that are known to those skilled in the art.

DESCRIPTION OF EMBODIMENTS

An aspect of the present invention concerns compounds disclosed herein.

An aspect of the present invention concerns compounds which are or can be inhibitors of the formation of nicotinamide phosphoribosyltransferase.

An aspect of the present invention concerns the use of an inhibitor of the formation of nicotinamide phosphoribosyltransferase for the preparation of a medicament used in the treatment, prevention, inhibition or elimination of tumors.

An aspect of the present invention concerns the use of an inhibitor of the formation of nicotinamide phosphoribosyltransferase for the preparation of a medicament used in the treatment, prevention, inhibition or elimination of cancer.

An aspect of the present invention concerns the use of an inhibitor of the formation of nicotinamide phosphoribosyltransferase for the preparation of a medicament used in the treatment, prevention, inhibition or elimination of cancer, where the cancer is selected from leukemia, lymphoma, ovarian cancer, breast cancer, uterine cancer, colon cancer, cervical cancer, lung cancer, prostate cancer, skin cancer, CNS cancer, bladder cancer, pancreatic cancer and Hodgkin's disease.

The present invention also describes one or more methods of synthesizing the compounds of the present invention.

The invention also describes one or more uses of the compounds of the present invention.

The invention also describes one or more uses of the compounds of the present invention with an adjunctive agent such as use with TNF, GCSF, or other chemotherapeutic agents.

The invention also describes one or more uses of the pharmaceutical compositions of the present invention.

An aspect of the present invention concerns the use as an inhibitor of the formation of nicotinamide phosphoribosyltransferase for the preparation of a medicament used in the treatment of inflammatory diseases.

An aspect of the present invention concerns the use as an inhibitor of the formation of nicotinamide phosphoribosyltransferase for the preparation of a medicament used in the treatment of inflammatory diseases, such as Irritable Bowel Syndrome or Inflammatory Bowel Disease.

An aspect of the present invention concerns the use as an inhibitor of the formation of nicotinamide phosphoribosyltransferase for the preparation of a medicament used in the treatment of disease of the bone such as osteoporosis.

An aspect of the present invention concerns the use as an inhibitor of the formation of nicotinamide phosphoribosyltransferase for the preparation of a medicament used in the treatment of disease of the cardiovascular system, such as atherosclerosis.

An aspect of the present invention concerns the use as an inhibitor of the formation of nicotinamide phosphoribosyltransferase for the preparation of a medicament used in the treatment of disease or a condition caused by an elevated level of NAMPT.

Such disease or condition is one or more selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, ureteral and bladder cancers, cancers of head and neck, cancers of the brain and central nervous system (CNS).

The inventive compounds of can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease.

More specifically, the compounds can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of the invention may induce or inhibit apoptosis.

The compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

A further aspect of the invention is a method of inhibiting a NAMPT pathway in an animal, said method comprising administering to said animal a pharmaceutically acceptable amount of a compound of the invention to an animal in need thereof.

A further aspect of the invention is a pharmaceutical formulation comprising a compound of the invention.

Another embodiment of the invention comprises a pharmaceutical formulation of the invention, wherein the pharmaceutical formulation, upon administration to a human, results in a decrease in tumor burden.

Still another embodiment of the invention is a pharmaceutical formulation, further comprising one or more of an antineoplastic agent, a chemotherapeutic agent, or an adjunctive chemotherapeutic agent.

The pharmaceutical formulations of the invention may further comprise a therapeutic effective amount of an adjunctive chemotherapeutic agent.

The adjunctive chemotherapeutic agent may be an agent which modifies blood cell growth and maturation. Non-limiting examples of adjunctive, chemotherapeutic agent are filgrastim, pegfilgrastim and erythropoietin.

The invention is also directed to a method of treating or preventing a disorder associated with excessive rate of growth of cells in a mammal comprising administering to the mammal an effective amount of the pharmaceutical formulation of the invention. Non-limiting examples of disorder include cancer or metastasis from malignant tumors.

Another aspect of the invention is a method of inhibiting tumor cell growth and rate of division in a mammal with cancer, or other disorder associated with abnormally dividing cells comprising administering to the mammal an effective amount of the pharmaceutical formulation of this invention.

Another embodiment of the invention is a method of treating bone pain due to excessive growth of a tumor or metastasis to bone in a mammal in need thereof comprising administering to the mammal an effective amount of the pharmaceutical formulation of this invention.

Still another embodiment of the invention is a method for administering a NAMPT-inhibitor-containing compound to a mammal in need thereof comprising administering to the mammal the pharmaceutical formulation of the invention. In one embodiment, the mammal is a human.

A further embodiment of the invention is a method of preparing a pharmaceutical formulation comprising mixing at least one pharmaceutically acceptable compound of the present invention, and, optionally, one or more pharmaceutically acceptable excipients or additives.

Another aspect of the invention relates to a pharmaceutical composition comprising a compound of the invention and a cell rescuing agent. In an embodiment of the invention, the cell rescuing agent can be selected from the group consisting of nicotinamide, nicotinic acid and nicotinamide mononucleotide.

The invention is also directed to methods of synthesizing compounds of the present invention.

Compounds of the Invention

The present invention relates to particular molecules and pharmaceutically acceptable salts or isomers thereof. The invention further relates to molecules which are useful in inhibiting the enzyme nicotinamide phosphoribosyltransferase (NAMPT) and pharmaceutically acceptable salts, solvates, esters, prodrugs or isomers thereof.

The invention is directed to compounds as described herein and pharmaceutically acceptable salts, solvates, esters, prodrugs or isomers thereof, and pharmaceutical compositions comprising one or more compounds as described herein and pharmaceutically acceptable salts or isomers thereof. One aspect of this invention is the provision of compounds, compositions, kits, and antidotes for the NAMPT pathway in mammals having a compound of the Formula I:

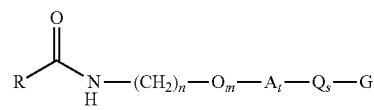

wherein

R is an aryl, heteroaryl, $C_3$-$C_8$ cycloalkyl, $C_3$-$C_8$ cycloalkenyl, heterocycloalkyl, arylalkyl-, (heteroaryl)alkyl-, ($C_3$-$C_8$ cycloalkyl)alkyl-, ($C_3$-$C_8$ cycloalkenyl)alkyl-, (heterocycloalkyl)alkyl-, (aryloxy)alkyl-, (heteroaryloxy)alkyl-, ($C_3$-$C_8$ cycloalkyloxy)alkyl-, ($C_3$-$C_8$ cycloalkenyloxy)alkyl- or (heterocycloalkyloxy)alkyl-, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with an aryl or heteroaryl, still further wherein any of said aryl, heteroaryl and heterocycloalkyl is either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, alkyl hydroxy, hydroxyl, alkyl hydroxy, or (alkoxyalkyl) amino-, —N($R^3$)—C(O)-alkyl, —N($R^3$)—C(O)-aryl, -cycloalkyl, -heterocycloalkyl, -aryl, and -heteroaryl, with the proviso that no two adjacent ring heteroatoms are both S or both O;

G is aryl, heteroaryl, cycloalkyl, heterocycloalkyl or

with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, -alkyl hydroxyl, aryloxy-, (alkoxyalkyl)amino-, —N($R^3$)—C(O)-alkyl, —N($R^3$)—C(O)-aryl, -cycloalkyl, -heterocycloalkyl, -aryl, and -heteroaryl;

$R^1$ and $R^2$ are the same or they are different, and are independently selected from H, a straight or branched $C_1$ to $C_7$ alkyl, straight or branched $C_1$ to $C_7$ alkoxy, straight or branched $C_1$ to $C_4$ hydroxyalkyl, aryl, heteroaryl, heterocycloalkyl and cycloalkyl, and wherein heteroatoms of said heteroaryl and heterocycloalkyl are independently selected from one or more N, O and S, with the proviso that no two adjacent ring heteroatoms are both S or both O, further wherein $R^1$ and $R^2$ can be either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, hydroxyalkyl-, -alkoxy, hydroxyl, alkyl hydroxy, hydroxyl, alkyl hydroxy, carboxy, (alkoxyalkyl) amino-, -alkylamine, aminocarbonyl-, —CHO, —N($R^3$)—C(O)-alkyl, —N($R^3$)—C(O)-aryl, -cycloalkyl, -heterocycloalkyl, -aryl, and heteroaryl;

$R^3$ is H, alkyl or arylalkyl-;

A is aryl, heteroaryl, heterocycloalkyl or $C_3$ to $C_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, -alkyl hydroxyl, aryloxy-, (alkoxyalkyl)amino-, —N($R^3$)—C(O)-alkyl, —N($R^3$)—C(O)-aryl, -cycloalkyl, -heterocycloalkyl, -aryl, and -heteroaryl;

Q is C(O), S(O), S(O)$_2$, —$CH_2$—C(O)—, —N(H)—C(O)—, —S(O$_2$)—NH—, or —N(H)—S(O$_2$)—;

n is 0, 1, 2, 3, 4, 5 or 6;

z is 0, 1 or 2;

m is 0 or 1;

s is 0 or 1; and t is 0 or 1;

and pharmaceutically acceptable salts, solvates, esters, prodrugs or isomers thereof.

In another embodiment, the compound of Formula I, wherein m=0 and s=1, is the compound of Formula IA:

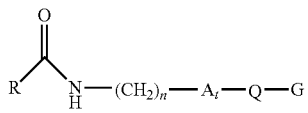

IA wherein

R is an aryl, heteroaryl, $C_3$-$C_8$ cycloalkyl, $C_3$-$C_8$ cycloalkenyl, heterocycloalkyl, arylalkyl-, (heteroaryl)alkyl-, ($C_3$-$C_8$ cycloalkyl)alkyl-, ($C_3$-$C_8$ cycloalkenyl)alkyl-, (heterocycloalkyl)alkyl-, (aryloxy)alkyl-, (heteroaryloxy)alkyl-, ($C_3$-$C_8$ cycloalkyloxy)alkyl-, ($C_3$-$C_8$ cycloalkenyloxy)alkyl- or (heterocycloalkyloxy)alkyl-, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with an aryl or heteroaryl, still further wherein any of said aryl, heteroaryl and heterocycloalkyl is either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, alkyl hydroxy, hydroxyl, alkyl hydroxy, or (alkoxyalkyl) amino-, —N($R^3$)—C(O)-alkyl, —N($R^3$)—C(O)-aryl, -cycloalkyl, -heterocycloalkyl, -aryl, and heteroaryl, with the proviso that no two adjacent ring heteroatoms are both S or both O;

G is aryl, heteroaryl, cycloalkyl, or heterocycloalkyl with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, -alkyl hydroxyl, aryloxy-, (alkoxyalkyl)amino-, —N($R^3$)—C(O)-alkyl, —N($R^3$)—C(O)-aryl, -cycloalkyl, -heterocycloalkyl, -aryl, and -heteroaryl;

$R^3$ is H, alkyl or arylalkyl-;

A is aryl, heteroaryl, heterocycloalkyl or $C_3$ to $C_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, -alkyl hydroxyl, aryloxy-, (alkoxyalkyl)amino-, —N($R^3$)—C(O)-alkyl, —N($R^3$)—C(O)-aryl, -cycloalkyl, -heterocycloalkyl, -aryl, and -heteroaryl;

Q is C(O), S(O), S(O)$_2$, —N(H)—C(O)—, —S(O$_2$)—NH—, or —N(H)—S(O$_2$)—;

n is 0, 1, 2, 3, 4, 5 or 6;

z is 0, 1 or 2; and t is 0 or 1;

and pharmaceutically acceptable salts, solvates, esters, prodrugs or isomers thereof.

Another embodiment, the compound of Formula I, wherein m=0, t=1 and s=1, is the compound of Formula IB:

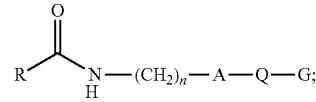

IB

Wherein

R is an aryl, heteroaryl, $C_3$-$C_8$ cycloalkyl, $C_3$-$C_8$ cycloalkenyl, heterocycloalkyl, arylalkyl-, (heteroaryl)alkyl-, ($C_3$-$C_8$ cycloalkyl)alkyl-, ($C_3$-$C_8$ cycloalkenyl)alkyl-, (heterocycloalkyl)alkyl-, (aryloxy)alkyl-, (heteroaryloxy)alkyl-, ($C_3$-$C_8$ cycloalkyloxy)alkyl-, ($C_3$-$C_8$ cycloalkenyloxy)alkyl- or (heterocycloalkyloxy)alkyl-, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with an aryl or heteroaryl, still further wherein any of said aryl, heteroaryl and heterocycloalkyl is either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N (alkyl)$_2$, —C(O)NH(aryl), —C(O)N(aryl)$_2$, —CH$_z$F$_{3-z}$, —OCH$_z$F$_{3-z}$, -alkyl, -alkenyl, -alkynyl. -alkoxy, hydroxyl, alkyl hydroxy, hydroxyl, alkyl hydroxy, or (alkoxyalkyl) amino-, —N(R$^3$)—C(O)-alkyl, —N(R$^3$)—C(O)-aryl, -cycloalkyl, -heterocycloalkyl, -aryl, and heteroaryl, with the proviso that no two adjacent ring heteroatoms are both S or both O;

n=0, 1, 2, 3, 4, 5 or 6;

A is aryl, heteroaryl, heterocycloalkyl or C$_3$ to C$_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, -alkenyl, -alkynyl, -alkoxy, hydroxyl, -alkyl hydroxyl, aryloxy-, (alkoxyalkyl)amino-, —N(R$^3$)—C(O)-alkyl, —N(R$^3$)—C(O)-aryl, -cycloalkyl, -heterocycloalkyl, -aryl, and -heteroaryl;

Q is C(O), S(O), S(O)$_2$, or —CH$_2$—C(O);

G is G is aryl, heteroaryl, cycloalkyl, or heterocycloalkyl with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, -alkenyl, -alkynyl, -alkoxy, hydroxyl, -alkyl hydroxyl, aryloxy-, (alkoxyalkyl)amino-, —N(R$^3$)—C(O)-alkyl, —N(R$^3$)—C(O)-aryl, -cycloalkyl, -heterocycloalkyl, -aryl, and -heteroaryl;

And z is 0, 1 or 2.

Yet another embodiment, the compound of Formula I, wherein n=4, m=0, t=1 and s=1, is the compound of Formula IC:

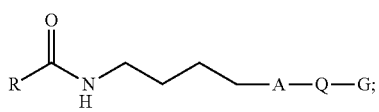

IC

Wherein

R is an aryl, heteroaryl, C$_3$-C$_8$ cycloalkyl, C$_3$-C$_8$ cycloalkenyl, heterocycloalkyl, arylalkyl-, (heteroaryl)alkyl-, (C$_3$-C$_8$ cycloalkyl)alkyl-, (C$_3$-C$_8$ cycloalkenyl)alkyl-, (heterocycloalkyl)alkyl-, (aryloxy)alkyl-, (heteroaryloxy)alkyl-, (C$_3$-C$_8$ cycloalkyloxy)alkyl-, (C$_3$-C$_8$ cycloalkenyloxy)alkyl- or (heterocycloalkyloxy)alkyl-, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with an aryl or heteroaryl, still further wherein any of said aryl, heteroaryl and heterocycloalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, -alkenyl, -alkynyl, -alkoxy, hydroxyl, alkyl hydroxy, hydroxyl, alkyl hydroxy, or (alkoxyalkyl) amino-, —N(R$^3$)—C(O)-alkyl, —N(R$^3$)—C(O)-aryl, -cycloalkyl, -heterocycloalkyl, -aryl, and heteroaryl, with the proviso that no two adjacent ring heteroatoms are both S or both O;

A is

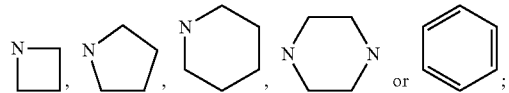

Q is C(O), S(O)$_2$, or —CH$_2$—C(O);

G is aryl, heteroaryl, cycloalkyl, or heterocycloalkyl with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, -alkenyl, -alkynyl, -alkoxy, hydroxyl, -alkyl hydroxyl, aryloxy-, (alkoxyalkyl)amino-, —N(R$^3$)—C(O)-alkyl, —N(R$^3$)—C(O)-aryl, -cycloalkyl, -heterocycloalkyl, -aryl, and -heteroaryl;

And z is 0, 1 or 2.

In a further embodiment, compounds of the invention have the general Formula II,

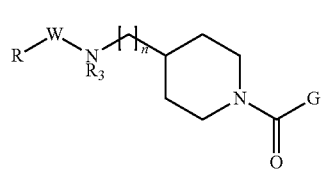

II wherein,

W is —C(O)—, —S(O)— or —S(O)$_2$—;

R is an aryl or bicyclic heteroaryl wherein the heteroatoms of each of said heteroaryl numbers 1, 2 or 3, and are independently selected from N, S or O, wherein each of said aryl, heteroaryl is optionally substituted with one or more substituents which can be the same or different and are independently selected from the group consisting of deuterium, halo, cyano, amino, aminoalkyl, (amino)alkoxy, —CONH$_2$, —C(O)NH(alkyl), —C(O)N(alkyl)$_2$, —C(O)NH(aryl), —C(O)N(aryl)$_2$, —CF$_3$, —CHF$_2$, —CH$_2$F, -alkyl, alkoxy, hydroxyl, hydroxyalkyl, (alkoxyalkyl) amino, —N(R$^3$)—C(O)-alkyl, —N(R$^3$)—C(O)-aryl, cycloalkyl, heterocycloalkyl, aryl, and heteroaryl, with the proviso that no two adjacent ring heteroatoms are both S or both O;

G is aryl, heteroaryl, cycloalkyl, heterocycloalkyl or —NR$^1$R$^2$, with each of said aryl, heteroaryl, heterocycloalkyl and cycloalkyl being either unsubstituted or independently substituted with 1, 2, 3 or 4 substituents which can be the same or different and are independently selected from the group consisting of deuterium, halo, cyano, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CF$_3$, —CHF$_2$, —CH$_2$F, alkyl, alkenyl, alkynyl, alkoxy, hydroxyl, hydroxy alkyl, aryloxy, (alkoxyalkyl)amino, —N(R$^3$)—C(O)-alkyl, —N(R$^3$)—C(O)-aryl, cycloalkyl, heterocycloalkyl, aryl, and heteroaryl;

R$^1$ and R$^2$ are the same or they are different, and are independently selected from H, C$_1$ to C$_7$ alkyl, C$_1$ to C$_7$ alkoxy, C$_1$ to C$_4$ hydroxyalkyl, aryl, heteroaryl, heterocycloalkyl and cycloalkyl, and wherein heteroatoms of said heteroaryl and heterocycloalkyl are independently selected from one or more N, O and S, with the proviso that no two adjacent ring heteroatoms are both S or both O, further wherein R$^1$ and R$^2$ can be either unsubstituted or optionally independently substituted with one or more substituents which can be the same or different and are independently selected from the group consisting of deuterium, halo, cyano, amino, aminoalkyl, (amino)alkoxy, —CONH$_2$, —C(O)NH(alkyl), —C(O)N(alkyl)$_2$, —C(O)NH(aryl), —C(O)N(aryl)$_2$, —CF$_3$, —CHF$_2$, —CH$_2$F, alkyl, hydroxyalkyl, -alkoxy, hydroxyl, hydroxyalkyl, carboxy, (alkoxyalkyl) amino, -alkylamine, aminocarbonyl, —CHO, —N(R$^3$)—C(O)-alkyl, —N(R$^3$)—C(O)-aryl, cycloalkyl, heterocycloalkyl, aryl, and heteroaryl;

R$^3$ is H, alkyl or arylalkyl;

n is 4, 5 or 6;

or a pharmaceutically acceptable salt thereof.

In an embodiment in which compounds have the general Formula II, W is —C(O)—. In another embodiment W is —S(O)$_2$—.

In an embodiment in which compounds have the general Formula II, 11 is 4. In another embodiment, n is 5. In another embodiment, n is 6. In another embodiment, n is 7.

In an embodiment in which compounds have the general Formula II, R$^3$ is H. In another embodiment, R$^3$ is Me.

In an embodiment in which compounds have the general Formula II, R is selected from the group consisting of optionally substituted thienopyridine, 1H-pyrrolopyidine, pyrrolopyidine, imidazopyridine, pyrazolopyridine, quinoline and furopyridine. In an embodiment, R is 1H-pyrrolopyidine. In an embodiment, R is 1H-pyrrolo[3,2-c]pyidin-2-yl. In an embodiment, R is pyrrolopyidine. In an embodiment, R is 1H-pyrrolo[3,2-c]pyidin-2-yl. In an embodiment, R is imidazopyridine. In an embodiment, R is thieno[2,3-c]pyridin-2-yl. In an embodiment, R is pyrazolopyridine. In an embodiment, R is pyrazolo[3,4-b]pyridin-5-yl. In an embodiment, R is quinoline. In an embodiment, R is quinolin-6-yl. In an embodiment, R is furopyridine. In an embodiment, R is furo[2,3-c]pyridin-2-yl. In an embodiment R is substituted with 1 to 3 halo, hydroxyl, amino, alkyl, haloalkyl, alkoxy or haloalkyl groups. In an embodiment, R is unsubstituted.

In an embodiment in which compounds have the general Formula II, G is selected from the group consisting of aryl, heteroaryl, cycloalkyl, heterocycloalkyl optionally substituted with 1 to 3 substituents selected from the group consisting of halo, amino, cyano, hydroxyl, alkyl, haloalkyl, alkoxy, acyl, haloalkoxy, aryl, heteroaryl, alkoxyalkyl and mercapto. In an embodiment, G is phenyl, thiazol-4-yl, pyridin-2-yl, pyridin-3-yl, pyridin-4-yl, indol-2-yl, indol-6-yl, imidazol-2-yl, imidazol-4-yl, piperidin-4-yl, furan-3-yl, oxazol-4-yl, pyridin-2-yl, cyclohexyl, benzodioxolane, benzothiophene, benzothiazole, imidazol[1,2-a]pyridin-6-yl or 1H-pyrrolo[3,2-c]pyidin-2-yl optionally substituted with 1 to 3 substituents selected from the group consisting of halo, amino, cyano, hydroxyl, alkyl, haloalkyl, alkoxy, acyl, haloalkoxy, aryl, heteroaryl, alkoxyalkyl and mercapto. In an embodiment G is imidazo[1,2-a]pyridine-6-yl. In an embodiment G is 1H-pyrrolo[3,2-c]pyidin-2-yl. In an embodiment G is thieno[2,3-c]pyridin-2-yl. In an embodiment G is furo[2,3-c]pyridin-2-yl. In an embodiment, G is phenyl substituted with 1 to 3 substituents selected from the group consisting of Cl, F, MeO, EtO, CF3O, CHF$_2$O, CF$_3$, Me, iPr-O and pyrazol-1-yl. In an embodiment, G is thiazol-4-yl substituted with 1 to 3 substituents selected from the group consisting of Me, phenyl, CF$_3$ and pyridin-3-yl. In an embodiment, G is pyridin-2-yl, pyridin-3-yl or pyridin-4-yl substituted with 1 to 3 substituents selected from the group consisting of Me, methoxymethyl, CF$_3$O— and mercapto.

In an embodiment in which compounds have the general Formula II, R is thieno[2,3-c]pyridin-2-yl, 1H-pyrrolo[3,2-c]pyidin-2-yl, 1H-pyrrolo[3,2-c]pyidin-2-yl, imidazo[1,2-a]pyridin-6-yl or pyrazolo[3,4-b]pyridin-5-yl and G is phenyl, thiazol-4-yl, pyridin-2-yl, pyridin-3-yl, pyridin-4-yl, indol-2-yl, indol-6-yl, imidazol-2-yl, imidazol-4-yl, piperidin-4-yl, furan-3-yl, oxazol-4-yl, pyridin-2-yl, cyclohexyl, benzodioxolane, benzothiophene, benzothiazole, imidazol[1,2-a]pyridin-6-yl or 1H-pyrrolo[3,2-c]pyidin-2-yl optionally substituted with 1-4 substituents selected from the group consisting of halo, amino, cyano, hydroxyl, alkyl, haloalkyl, alkoxy, acyl, haloalkoxy, aryl, heteroaryl, alkoxyalkyl and mercapto.

In the compounds of Formulas I, IA, IB, IC and II the various moieties are independently selected.

The following embodiments are directed to Formulas I, IA, IB, and IC. For any moieties that are not specifically defined, the previous definitions control. Further, the moieties aryl, heteroaryl, heterocycloalkyl, cycloalkyl, cycloalkenyl and heterocycloalkenyl in these embodiments can be independently unsubstituted or optionally substituted or optionally fused as described earlier. Any one or more embodiments listed here may be combined with other embodiments to create new embodiments.

An embodiment of the invention is the provision of a compound, where the various moieties are independently selected, R is aryl, and n, m, t, s, X, A, Q and G are as defined.

Another embodiment of the invention is the provision of a compound, where the various moieties are independently selected, R is heteroaryl, and n, m, t, s, X, A, Q and G are as defined.

Another embodiment of the invention is the provision of a compound, where the various moieties are independently selected, R is C$_3$-C$_8$ cycloalkyl, and n, m, t, s, X, A, Q and G are as defined.

Another embodiment of the invention is the provision of a compound, where the various moieties are independently selected, R is C$_4$-C$_8$ cycloalkcnyl, and n, m, t, s, X, A, Q and G are as defined.

Another embodiment of the invention is the provision of a compound, where the various moieties are independently selected, R is heterocycloalkyl, and n, m, t, s, X, A, Q and G are as defined.

Another embodiment of the invention is the provision of a compound, where the various moieties are independently selected, R is arylalkyl, and n, m, t, s, X, A, Q and G are as defined.

Another embodiment of the invention is the provision of a compound, where the various moieties are independently selected, R is (heteroaryl)alkyl, and n, m, t, s, X, A, Q and G are as defined.

Another embodiment of the invention is the provision of a compound, where the various moieties are independently selected, R is (C$_3$-C$_8$ cycloalkyl)alkyl, and n, m, t, s, X, A, Q and G are as defined.

Another embodiment of the invention is the provision of a compound, where the various moieties are independently selected, R is ($C_3$-$C_8$ cycloalkenyl)alkyl, and n, m, s, t, X, A, Q and G are as defined.

Another embodiment of the invention is the provision of a compound, where the various moieties are independently selected, R is (heterocycloalkyl)alkyl, and n, m, s, t, X, A, Q and G are as defined.

Another embodiment of the invention is the provision of a compound, where the various moieties are independently selected, R is (aryloxy)alkyl, and n, m, s, t, X, A, Q and G are as defined.

Another embodiment of the invention is the provision of a compound, where the various moieties are independently selected, R is (heteroaryloxy)alkyl, and n, m, s, t, X, A, Q and G are as defined.

Another embodiment of the invention is the provision of a compound, where the various moieties are independently selected, R is ($C_3$-$C_8$ cycloalkyloxy)alkyl, and n, m, s, t, X, A, Q and G are as defined.

Another embodiment of the invention is the provision of a compound, where the various moieties are independently selected, R is ($C_3$-$C_8$ cycloalkenyloxy)alkyl, and n, m, s, t, X, A, Q and G are as defined.

Another embodiment of the invention is the provision of a compound, where the various moieties are independently selected, R is (heterocycloalkyloxy)alkyl, and n, m, s, t, X, A, Q and G are as defined.

Another embodiment of the invention is the provision of a compound, where the various moieties are independently selected, R, n, m, s, X, Q and G are as defined, t=1 and A is aryl.

Another embodiment of the invention is the provision of a compound, where the various moieties are independently selected, R, n, m, s, X, Q and G are as defined, t=1 and A is heteroaryl.

Another embodiment of the invention is the provision of a compound, where the various moieties are independently selected, R, n, m, s, X, Q and G are as defined, t=1 and A is heterocycloalkyl.

Another embodiment of the invention is the provision of a compound, where the various moieties are independently selected, R, n, m, s, X, Q and G are as defined, t=1 and A is $C_3$-$C_8$ cycloalkyl.

Another embodiment of the invention is the provision of a compound, where the various moieties are independently selected, R, m, s, t, X, A, Q and G are as defined and n is 0.

Another embodiment of the invention is the provision of a compound, where the various moieties are independently selected, R, m, s, t, X, A, Q and G are as defined and n is 1.

Another embodiment of the invention is the provision of a compound, where the various moieties are independently selected, R, m, s, t, X, A, Q and G are as defined and n is 2.

Another embodiment of the invention is the provision of a compound, where the various moieties are independently selected, R, m, s, t, X, A, Q and G are as defined and n is 3.

Another embodiment of the invention is the provision of a compound, where the various moieties are independently selected, R, m, s, t, X, A, Q and G are as defined and n is 4.

Another embodiment of the invention is the provision of a compound, where the various moieties are independently selected, R, m, s, t, X, A, Q and G are as defined and n is 5.

Another embodiment of the invention is the provision of a compound, where the various moieties are independently selected, R, m, s, t, X, A, Q and G are as defined and n is 6.

Another embodiment of the invention is the provision of a compound, where the various moieties are independently selected, R, n, s, t, A, Q and G are as defined and m is 0.

Another embodiment of the invention is the provision of a compound, where the various moieties are independently selected, R, X, A, n, m, t and G are as defined, s=1 and Q is C(O).

Another embodiment of the invention is the provision of a compound, where the various moieties are independently selected, R, X, A, n, m, t and G are as defined, s=1 and Q is S(O).

Another embodiment of the invention is the provision of a compound, where the various moieties are independently selected, R, X, A, n, m, t and G are as defined, s=1 and Q is $S(O_2)$.

Another embodiment of the invention is the provision of a compound, where the various moieties are independently selected, R, X, A, n, m, t and G are as defined, s=1 and Q is —N(H)—$S(O_2)$—.

Another embodiment of the invention is the provision of a compound, where the various moieties are independently selected, R, X, A, n, m, t and G are as defined, s=1 and Q is —$S(O_2)$—N(H)—.

Another embodiment of the invention is the provision of a compound, where the various moieties are independently selected, R, X, A, n, m, t and G are as defined, s=1 and Q is —N(H)—C(O)—

Another embodiment of the invention is the provision of a compound, where the various moieties are independently selected, R, n, m, t, A, X and G are as defined and s is 0.

Another embodiment of the invention is the provision of a compound, where the various moieties are independently selected, R, X, A, n, m and Q are as defined and G is aryl.

Another embodiment of the invention is the provision of a compound, where the various moieties are independently selected, R, X, A, n, m, s, t and t and Q are as defined and G is heteroaryl.

Another embodiment of the invention is the provision of a compound, where the various moieties are independently selected, R, X, A, n, m, s, t and Q are as defined and G is cycloalkyl.

Another embodiment of the invention is the provision of a compound, where the various moieties are independently selected, R, X, A, n, m, s, t and Q are as defined and G is heterocycloalkyl.

Another embodiment of the invention is the provision of a compound, where the various moieties are independently selected, R, X, A, n, m, s, t and Q are as defined and G is —N($R^1R^2$).

An embodiment of the invention is the provision of a compound, where the various moieties are independently selected, R is phenyl, and n, m, s, t, X, A, Q and G are as defined.

An embodiment of the invention is the provision of a compound, where the various moieties are independently selected, R is naphthyl, and n, m, s, t, X, A, Q and G are as defined.

An embodiment of the invention is the provision of a compound, where the various moieties are independently selected, R is pyridyl, and n, m, s, t, X, A, Q and G are as defined.

An embodiment of the invention is the provision of a compound, where the various moieties are independently selected, R is a pyrrolopyridinyl group, and n, m, s, t, X, A, Q and G are as defined.

An embodiment of the invention is the provision of a compound, where the various moieties are independently selected, R is a thienopyridinyl group, and n, m, s, t, X, A, Q and G are as defined.

An embodiment of the invention is the provision of a compound, where the various moieties are independently selected, R is an indazolyl group, and n, m, s, t, X, A, Q and G are as defined.

An embodiment of the invention is the provision of a compound, where the various moieties are independently selected, R is a pyrazolopyridinyl group, and n, m, s, t, X, A, Q and G are as defined.

An embodiment of the invention is the provision of a compound, where the various moieties are independently selected, R is an imidazopyridinyl group, and n, m, s, t, X, A, Q and G are as defined.

An embodiment of the invention is the provision of a compound, where the various moieties are independently selected, R is an imidazopyrazolyl group, and n, m, s, t, X, A, Q and G are as defined.

An embodiment of the invention is the provision of a compound, where the various moieties are independently selected, R is a tetrazolopyridinyl group, and n, m, s, t, X, A, Q and G are as defined.

An embodiment of the invention is the provision of a compound, where the various moieties are independently selected, R is a naphthyridinyl group, and n, m, s, t, X, A, Q and G are as defined.

An embodiment of the invention is the provision of a compound, where the various moieties are independently selected, R is a benzodiazolyl group, and n, m, s, t, X, A, Q and G are as defined.

An embodiment of the invention is the provision of a compound, where the various moieties are independently selected, R is a benzothiazolyl group, and n, m, s, t, X, A, Q and G are as defined.

An embodiment of the invention is the provision of a compound, where the various moieties are independently selected, R is a furopyridinyl group, and n, m, s, t, X, A, Q and G are as defined.

An embodiment of the invention is the provision of a compound, where the various moieties are independently selected, R is a (pyridmyloxy)methy 1 group, and n, m, s, t, X, A, Q and G are as defined.

Another embodiment of the invention is the provision of a compound, where the various moieties are independently selected, R is (pyridinyl)alkyl, and n, m, s, t, X, A, Q and G are as defined.

Another embodiment of the invention is the provision of a compound, where the various moieties are independently selected, R is (pyridinyl)ethyl, and n, m, s, t, X, A, Q and G are as defined.

Another embodiment of the invention is the provision of a compound, where the various moieties are independently selected, R is (pyrrolopyridinyl)methyl, and n, m, s, t, X, A, Q and G are as defined.

Another embodiment of the invention is the provision of a compound, where the various moieties are independently selected, R, n, m, s, t, X, Q and G are as defined and A is phenyl.

Another embodiment of the invention is the provision of a compound, where the various moieties are independently selected, R, n, m, s, t X, Q and G are as defined and A is piperidinyl.

Another embodiment of the invention is the provision of a compound, where the various moieties are independently selected, R, n, m, s, X, Q and G are as defined and t is 0.

Another embodiment of the invention is the provision of a compound, where the various moieties are independently selected, R, X, A, n, m, t, s and Q are as defined and G is phenyl, with said phenyl being substituted or unsubstituted as defined earlier.

Another embodiment of the invention is the provision of a compound, where the various moieties are independently selected, R, X, A, n, m, t, s and Q are as defined and G is tetrahydronaphthalinyl, with said phenyl being substituted or unsubstituted as defined earlier.

Another embodiment of the invention is the provision of a compound, where the various moieties are independently selected, R, X, A, n, m, s, t, $R^2$, and Q are as defined, G is —$N(R^1R^2)$, and $R^1$ is H.

Another embodiment of the invention is the provision of a compound, where the various moieties are independently selected, R, A, n, $R^1$, and Q are as defined, G is —$N(R^1R^2)$, and —$R^2$ is piperidinyl.

Another embodiment of the invention is the provision of a compound, where the various moieties are independently selected, R, A, n, $R^1$, and Q are as defined, G is —$N(R^1R^2)$, and —$R^2$ is quinolinyl.

Another embodiment of the invention is the provision of a compound, where the various moieties are independently selected, R, A, n, $R^1$, and Q are as defined, G is —$N(R^1R^2)$, $R^1$ is H and —$R^2$ is morpholinyl.

Another embodiment of the invention is the provision of a compound, where the various moieties are independently selected, R, A, n, $R^1$, and Q are as defined, G is —$N(R^1R^2)$, $R^1$ is H and —$R^2$ is piperidinyl.

Another embodiment of the invention is the provision of a compound, where the various moieties are independently selected, R, A, n, $R^1$, and Q are as defined, G is —$N(R^1R^2)$, $R^1$ is H and —$R^2$ is quinolinyl.

Another embodiment of the invention is the provision of a compound, where the various moieties are independently selected, R, A, n, $R^1$, and Q are as defined, G is —$N(R^1R^2)$, and —$R^2$ is morpholinyl.

Another embodiment of the invention is the provision of a compound, where the various moieties are independently selected, R, X, A, n, m, s, t and Q are as defined and G is piperidinyl.

Another embodiment of the invention is the provision of a compound, where the various moieties are independently selected, R, X, A, n, m, s, t, and Q are as defined and G is 8-oxa-3-azabicyclooctanyl.

Another embodiment of the invention is the provision of a compound, where the various moieties are independently selected, R, X, A, n, m, s, t, and Q are as defined, G is dihydrobenzodioxinyl.

Another embodiment of the invention is the provision of a compound where the various moieties are independently selected, R, X, A, n, m, s, t, and Q are as defined, G is indazolyl.

Another embodiment of the invention is the provision of a compound, where the various moieties are independently selected, R, X, A, n, m, s, t, and Q are as defined, G is 1-oxo-isochromenyl.

Another embodiment of the invention is the provision of a compound, where the various moieties are independently selected, n, m, s, X, G, and Q are as defined, t=1, and both A and R are aryl.

Another embodiment of the invention is the provision of a compound, where the various moieties are independently selected, n, m, s, X, G, and Q are as defined, t=1, and both A and R are heteroaryl.

Another embodiment of the invention is the provision of a compound, where the various moieties are independently selected, n, m, s, X, G, and Q are as defined, R is heteroaryl, t=1, and A is aryl.

Another embodiment of the invention is the provision of a compound, where the various moieties are independently selected, n, m, s, X, G, and Q are as defined, R is (heteroaryl)alkyl, t=1, and A is aryl.

Another embodiment of the invention is the provision of a compound, where the various moieties are independently selected, n, m, s, X, G, and Q are as defined, R is (heteroaryloxy)alkyl t=1, and A is aryl.

Another embodiment of the invention is the provision of a compound, where the various moieties are independently selected, n, m, s, X, G, and Q are as defined, R is aryl, t=1, and A is heteroaryl.

Another embodiment of the invention is the provision of a compound, where the various moieties are independently selected, n, m, X, and G are as defined, t=1, both A and R are aryl, s=1 and Q is $S(O_2)$.

Another embodiment of the invention is the provision of a compound, where the various moieties are independently selected, n, m, X, and G are as defined, t=1, both A and R are heteroaryl, s=1 and Q is $S(O_2)$.

Another embodiment of the invention is the provision of a compound, where the various moieties are independently selected, n, m, X, and G are as defined, t=1, A is aryl, R is heteroaryl, s=1 and Q is $S(O_2)$.

Another embodiment of the invention is the provision of a compound, where the various moieties are independently selected, n, m, X, and G are as defined, t=1, A is aryl, R is (heteroaryl)alkyl, s=1 and Q is $S(O_2)$.

Another embodiment of the invention is the provision of a compound, where the various moieties are independently selected, n, m, X, and G are as defined, t=1, A is aryl, R is (heteroaryloxy)alkyl, s=1 and Q is $S(O_2)$.

Another embodiment of the invention is the provision of a compound, where the various moieties are independently selected, n, m, and X, are as defined, t=1, A is aryl, R is (heteroaryloxy)alkyl, s=1, Q is $S(O_2)$ and G is aryl.

Another embodiment of the invention is the provision of a compound, where the various moieties are independently selected, n, m, and X are as defined, t=1, A is aryl, R is (heteroaryloxy)alkyl, s=1, Q is $S(O_2)$ and G is heteroaryl.

Another embodiment of the invention is the provision of a compound, where the various moieties are independently selected, n, m, and X are as defined, t=1, A is aryl, R is (heteroaryloxy)alkyl, s=1, Q is $S(O_2)$ and G is heterocycloalkyl.

Another embodiment of the invention is the provision of a compound, where the various moieties are independently selected, n, m, and X are as defined, t=1, A is aryl, R is heteroaryl, s=1, Q is $S(O_2)$ and G is aryl.

Another embodiment of the invention is the provision of a compound, where the various moieties are independently selected, n, m, and X are as defined, t=1, A is aryl, R is heteroaryl, s=1, Q is $S(O_2)$ and G is heteroaryl.

Another embodiment of the invention is the provision of a compound, where the various moieties are independently selected, n, m, and X are as defined, t=1, A is aryl, R is heteroaryl, s=1, Q is $S(O_2)$ and G is heterocycloalkyl.

Another embodiment of the invention is the provision of a compound, where the various moieties are independently selected, n, m, and X are as defined, t=1, A is aryl, R is (heteroaryl)alkyl, s=1, Q is $S(O_2)$ and G is aryl.

Another embodiment of the invention is the provision of a compound, where the various moieties are independently selected, n, m, and X are as defined, t=1, A is aryl, R is (heteroaryl)alkyl, s=1, Q is $S(O_2)$ and G is heteroaryl. Another embodiment of the invention is the provision of a compound, where the various moieties are independently selected, n, m, and X are as defined, t=1, A is aryl, R is (heteroaryl)alkyl, s=1, Q is $S(O_2)$ and G is heterocycloalkyl.

Another embodiment of the invention is the provision of a compound, where the various moities are independently selected, s, t, R, X, A and G are as defined, m=1, and n=3.

Another embodiment of the invention is the provision of a compound, where re the various moities are independently selected, R, X, and G are as defined, and m=1, t=0, s=0 and n=6.

In another embodiment, the invention is further illustrated by the compounds shown in Table 2:

TABLE 2

| Structure | Chemical Name |
|---|---|
| 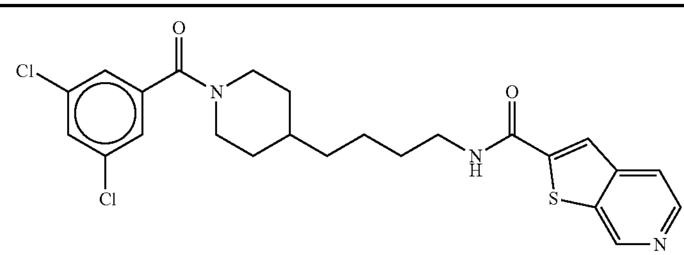 | N-(4-{1-[(3,5-dichlorophenyl)carbonyl]piperidin-4-yl}butyl)thieno[2,3-c]pyridine-2-carboxamide |
| 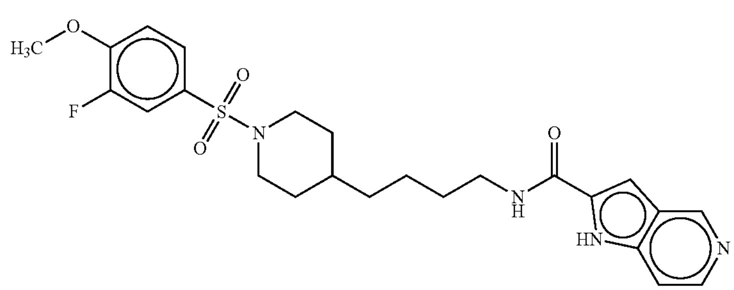 | N-(4-{1-[(3-fluoro-4-methoxybenzene)sulfonyl]piperidin-4-yl}butyl)-1H-pyrrolo[3,2-c]pyridine-2-carboxamide |

TABLE 2-continued

| Structure | Chemical Name |
|---|---|
| 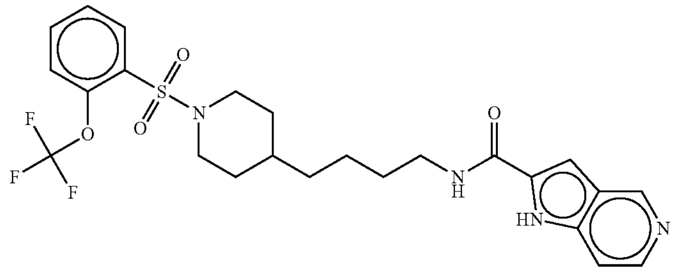 | N-[4-(1-{[2-(trifluoromethoxy)benzene]sulfonyl}piperidin-4-yl)butyl]-1H-pyrrolo[3,2-c]pyridine-2-carboxamide |
| 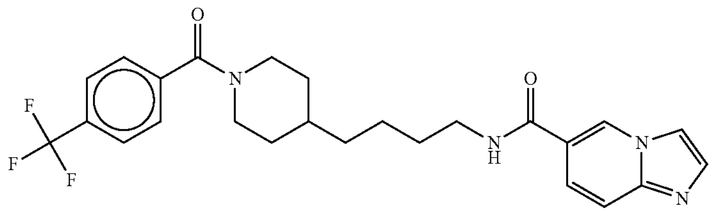 | N-[4-(1-{[4-(trifluoromethyl)phenyl]carbonyl}piperidin-4-yl)butyl]imidazo[1,2-a]pyridine-6-carboxamide |
| 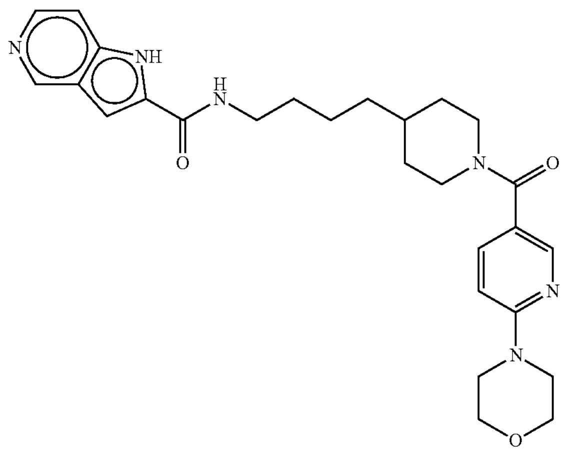 | N-[4-(1-{[6-(morpholin-4-yl)pyridin-3-yl]carbonyl}piperidin-4-yl)butyl]-1H-pyrrolo[3,2-c]pyridine-2-carboxamide |
| 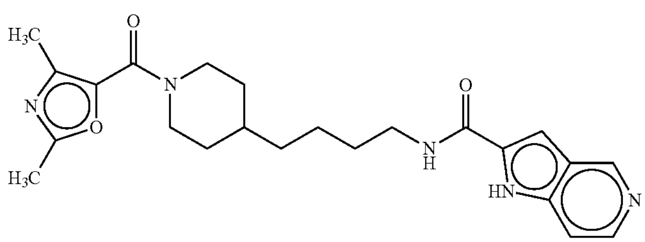 | N-(4-{1-[(dimethyl-1,3-thiazol-5-yl)carbonyl]piperidin-4-yl}butyl)-1H-pyrrolo[3,2-c]pyridine-2-carboxamide |
| 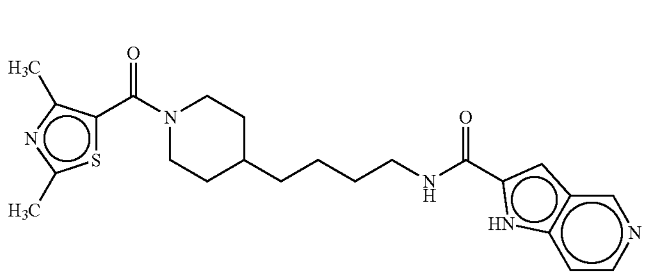 | N-[4-(1-cyclohexanecarbonylpiperidin-4-yl)butyl]-1H-pyrrolo[3,2-c]pyridine-2-carboxamide |

TABLE 2-continued

| Structure | Chemical Name |
|---|---|
| 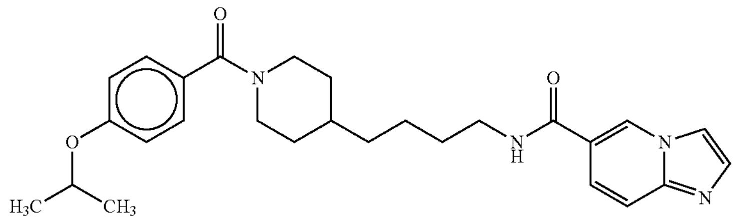 | N-[4-(1-{[4-(propan-2-yloxy)phenyl]carbonyl}piperidin-4-yl)butyl]imidazo[1,2-a]pyridine-6-carboxamide |
| 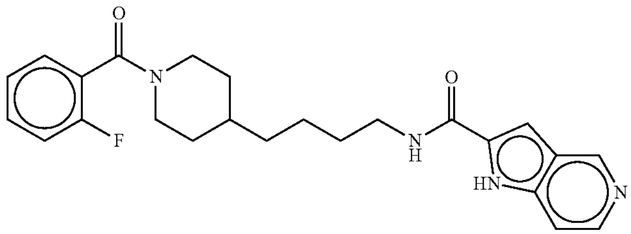 | N-(4-{1-[(2-fluorophenyl)carbonyl]piperidin-4-yl}butyl)-1H-pyrrolo[3,2-c]pyridine-2-carboxamide |
| 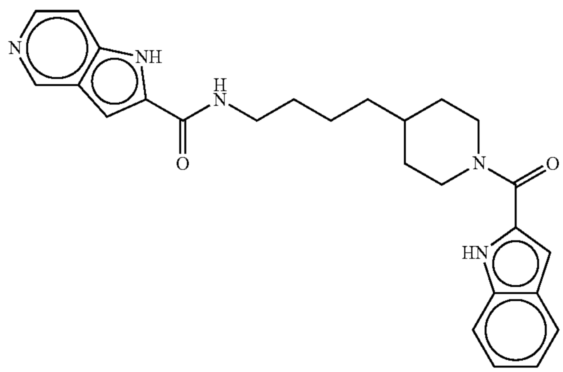 | N-(4-{1-[(1H-indol-2-yl)carbonyl]piperidin-4-yl}butyl)-1H-pyrrolo[3,2-c]pyridine-2-carboxamide |
| 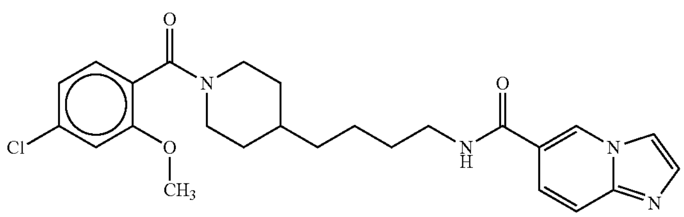 | N-(4-{1-[(4-chloro-2-methoxyphenyl)carbonyl]piperidin-4-yl}butyl)imidazo[1,2-a]pyridine-6-carboxamide |
| 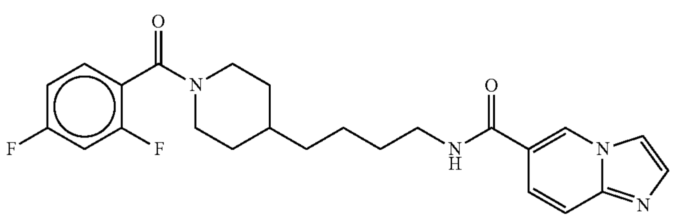 | N-(4-{1-[(2,4-difluorophenyl)carbonyl]piperidin-4-yl}butyl)imidazo[1,2-a]pyridine-6-carboxamide |
| 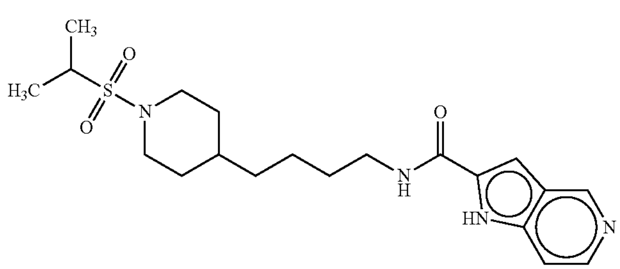 | N-{4-[1-(propane-2-sulfonyl)piperidin-4-yl]butyl}-1H-pyrrolo[3,2-c]pyridine-2-carboxamide |

TABLE 2-continued

| Structure | Chemical Name |
|---|---|
| 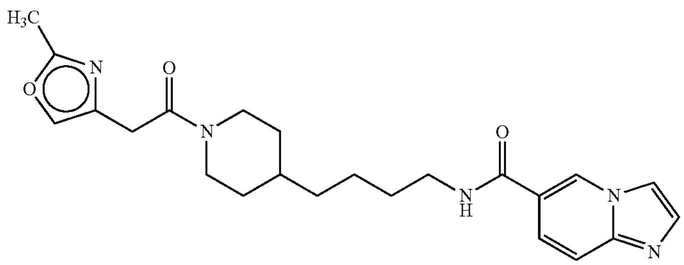 | N-(4-{1-[2-(2-methyl-1,3-thiazol-4-yl)acetyl]piperidin-4-yl}butyl)imidazo[1,2-a]pyridine-6-carboxamide |
| 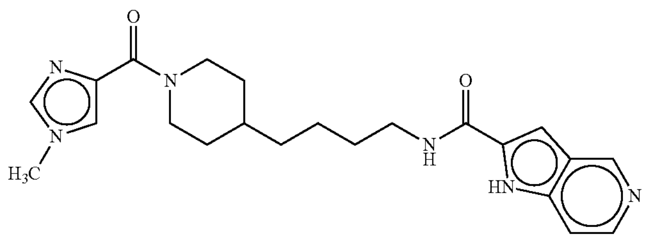 | N-(4-{1-[(1-methyl-1H-imidazol-4-yl)carbonyl]piperidin-4-yl}butyl)-1H-pyrrolo[3,2-c]pyridine-2-carboxamide |
| 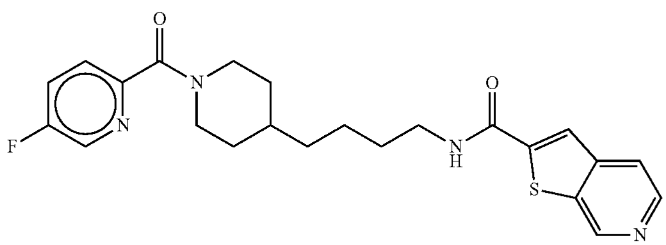 | N-(4-{1-[(5-fluoropyridin-2-yl)carbonyl]piperidin-4-yl}butyl)thieno[2,3-c]pyridine-2-carboxamide |
| 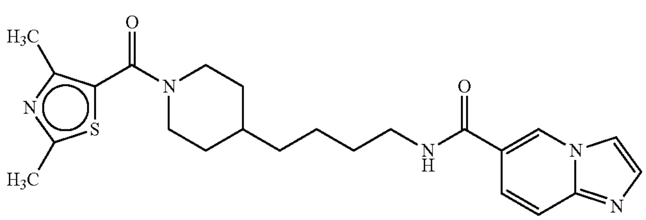 | N-(4-{1-[(dimethyl-1,3-thiazol-5-yl)carbonyl]piperidin-4-yl}butyl)imidazo[1,2-a]pyridine-6-carboxamide |
| 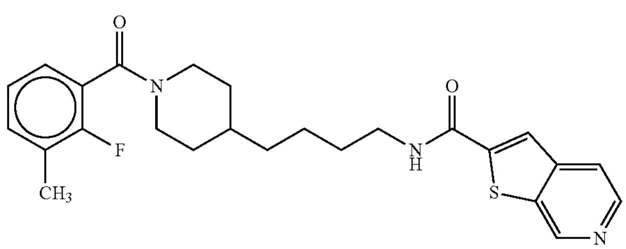 | N-(4-{1-[(2-fluoro-3-methylphenyl)carbonyl]piperidin-4-yl}butyl)thieno[2,3-c]pyridine-2-carboxamide |
| 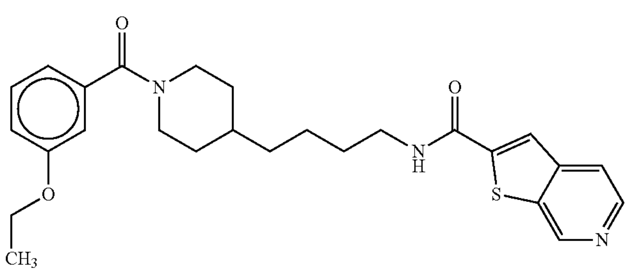 | N-(4-{1-[(3-ethoxyphenyl)carbonyl]piperidin-4-yl}butyl)thieno[2,3-c]pyridine-2-carboxamide |

TABLE 2-continued

| Structure | Chemical Name |
|---|---|
| 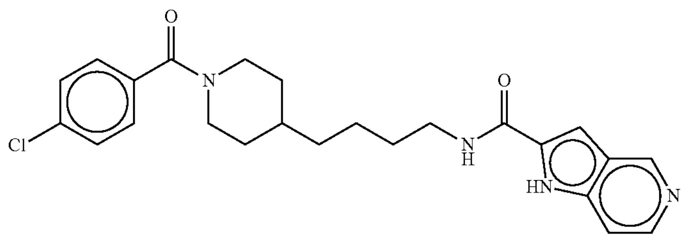 | N-(4-{1-[(4-chlorophenyl)carbonyl]piperidin-4-yl}butyl)-1H-pyrrolo[3,2-c]pyridine-2-carboxamide |
| 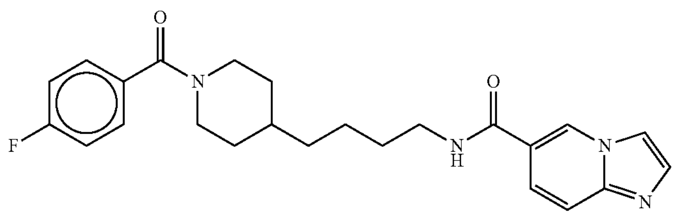 | N-(4-{1-[(4-fluorophenyl)carbonyl]piperidin-4-yl}butyl)imidazo[1,2-a]pyridine-6-carboxamide |
| 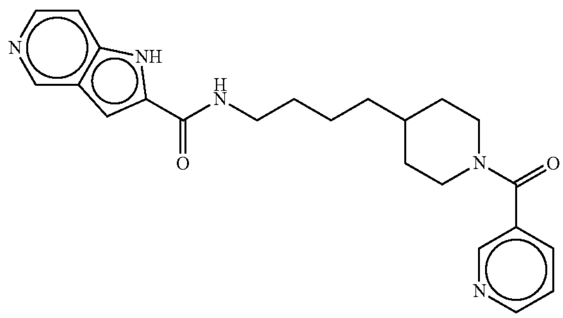 | N-(4-{1-[(pyridin-3-yl)carbonyl]piperidin-4-yl}butyl)-1H-pyrrolo[3,2-c]pyridine-2-carboxamide |
| 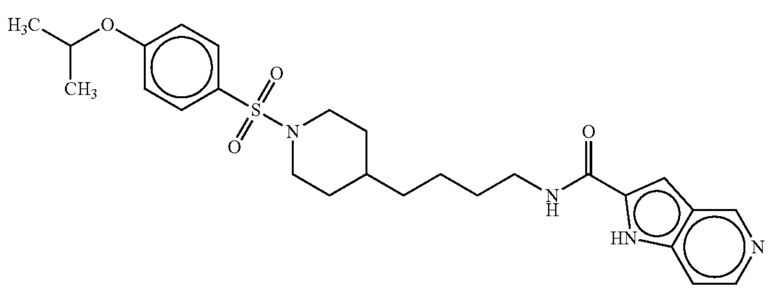 | N-[4-(1-{[4-(propan-2-yloxy)benzene]sulfonyl}piperidin-4-yl)butyl]-1H-pyrrolo[3,2-c]pyridine-2-carboxamide |
| 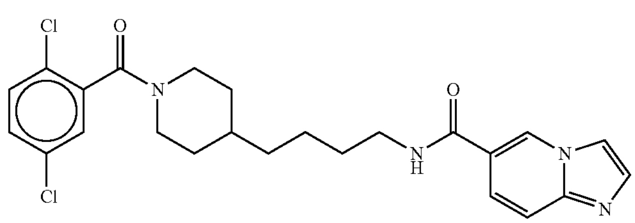 | N-(4-{1-[(2,5-dichlorophenyl)carbonyl]piperidin-4-yl}butyl)imidazo[1,2-a]pyridine-6-carboxamide |
| 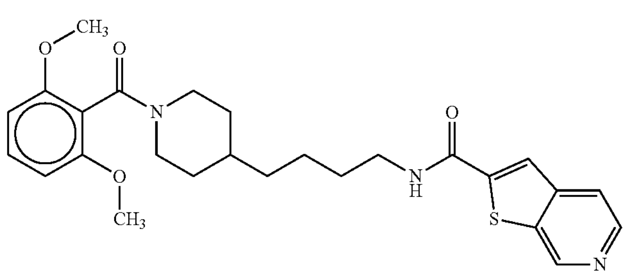 | N-(4-{1-[(2,6-dimethoxyphenyl)carbonyl]piperidin-4-yl}butyl)thieno[2,3-c]pyridine-2-carboxamide |

TABLE 2-continued

| Structure | Chemical Name |
|---|---|
| 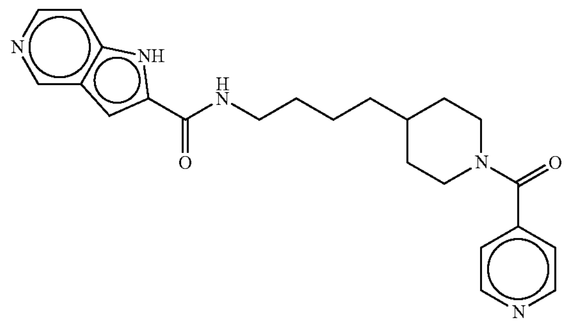 | N-(4-{1-[(pyridin-4-yl)carbonyl]piperidin-4-yl}butyl)-1H-pyrrolo[3,2-c]pyridine-2-carboxamide |
| 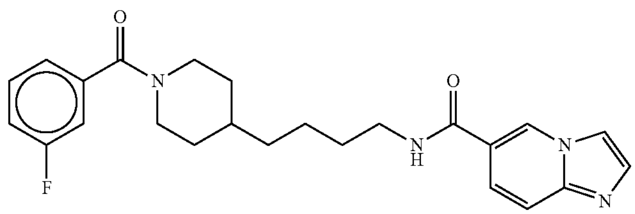 | N-(4-{1-[(3-fluorophenyl)carbonyl]piperidin-4-yl}butyl)imidazo[1,2-a]pyridine-6-carboxamide |
| 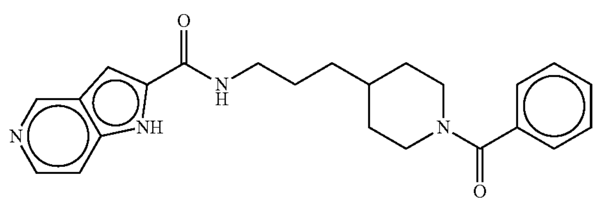 | N-(3-(1-benzoylpiperidin-4-yl)propyl)-1H-pyrrolo[3,2-c]pyridine-2-carboxamide |
| 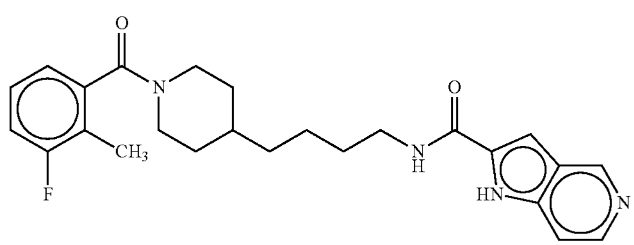 | N-(4-{1-[(3-fluoro-2-methylphenyl)carbonyl]piperidin-4-yl}butyl)-1H-pyrrolo[3,2-c]pyridine-2-carboxamide |
| 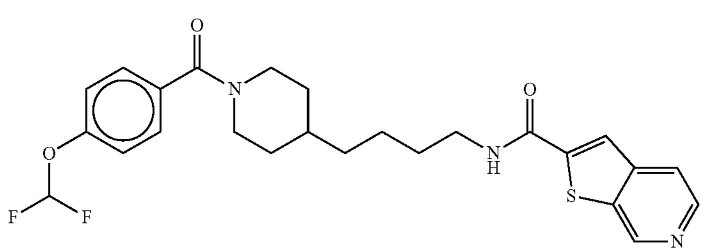 | N-[4-(1-{[4-(difluoromethoxy)phenyl]carbonyl}piperidin-4-yl)butyl]thieno[2,3-c]pyridine-2-carboxamide |
| 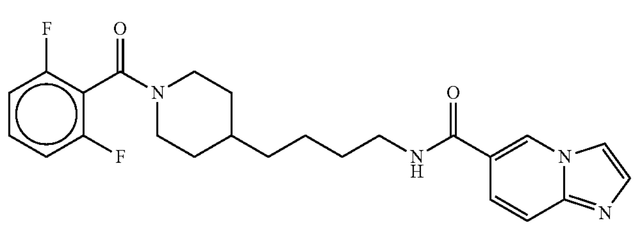 | N-(4-{1-[(2,6-difluorophenyl)carbonyl]piperidin-4-yl}butyl)imidazo[1,2-a]pyridine-6-carboxamide |

TABLE 2-continued

| Structure | Chemical Name |
|---|---|
| 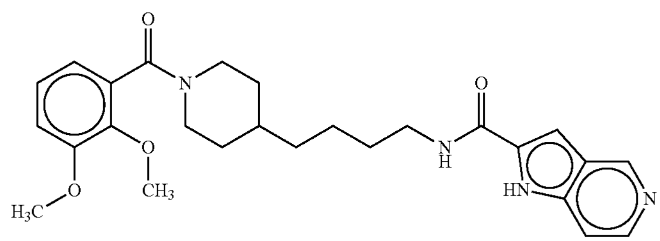 | N-(4-{1-[(2,3-dimethoxyphenyl)carbonyl]piperidin-4-yl}butyl)-1H-pyrrolo[3,2-c]pyridine-2-carboxamide |
| 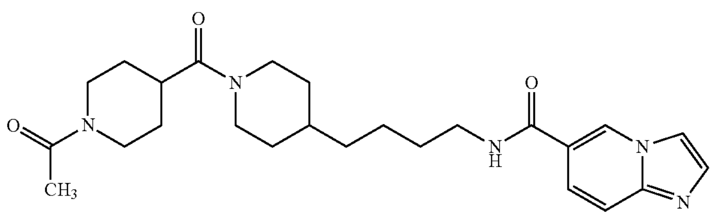 [SMILES: CC(=O)N1CCC(C(=O)N2CCC(CCCCNC(=O)c3ccc4nccn4c3)CC2)CC1] | N-(4-{1-[(1-acetylpiperidin-4-yl)carbonyl]piperidin-4-yl}butyl)imidazo[1,2-a]pyridine-6-carboxamide |
| 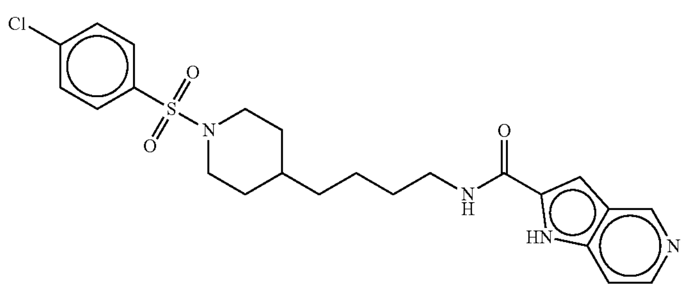 | N-(4-{1-[(4-chlorobenzene)sulfonyl]piperidin-4-yl}butyl)-1H-pyrrolo[3,2-c]pyridine-2-carboxamide |
| 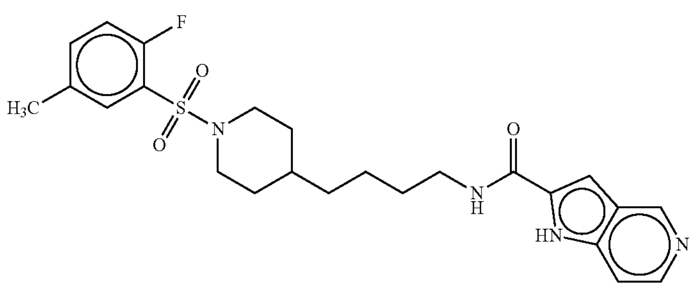 | N-(4-{1-[(2-fluoro-5-methylbenzene)sulfonyl]piperidin-4-yl}butyl)-1H-pyrrolo[3,2-c]pyridine-2-carboxamide |
| 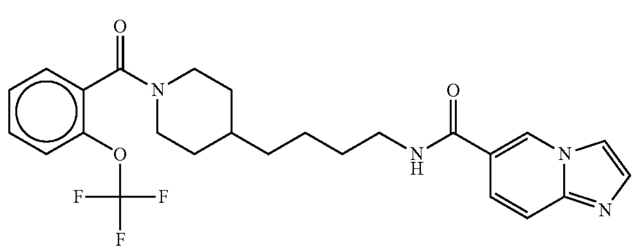 | N-[4-(1-{[2-(trifluoromethoxy)phenyl]carbonyl}piperidin-4-yl)butyl]imidazo[1,2-a]pyridine-6-carboxamide |
| 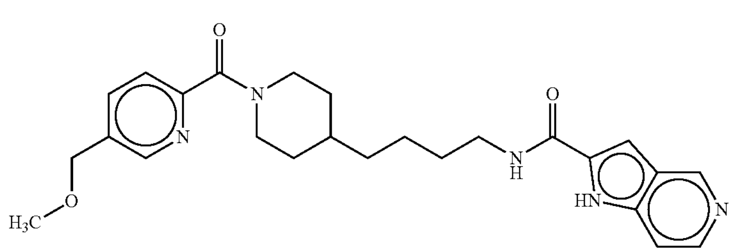 | N-[4-(1-{[5-(methoxymethyl)pyridin-2-yl]carbonyl}piperidin-4-yl)butyl]-1H-pyrrolo[3,2-c]pyridine-2-carboxamide |

TABLE 2-continued

| Structure | Chemical Name |
|---|---|
| 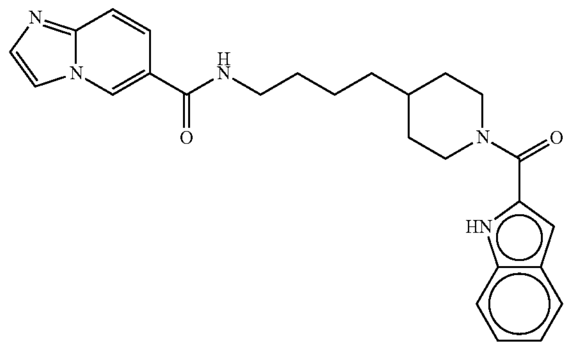 | N-(4-{1-[(1H-indol-2-yl)carbonyl]piperidin-4-yl}butyl)imidazo[1,2-a]pyridine-6-carboxamide |
| 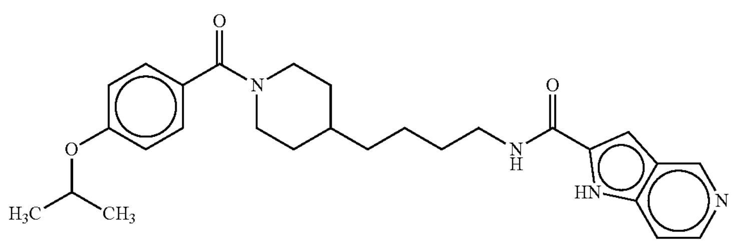 | N-[4-(1-{[4-(propan-2-yloxy)phenyl]carbonyl}piperidin-4-yl)butyl]-1H-pyrrolo[3,2-c]pyridine-2-carboxamide |
| 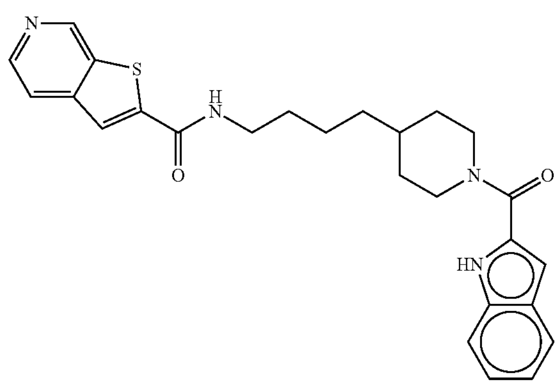 | N-(4-{1-[(1H-indol-2-yl)carbonyl]piperidin-4-yl}butyl)thieno[2,3-c]pyridine-2-carboxamide |
| 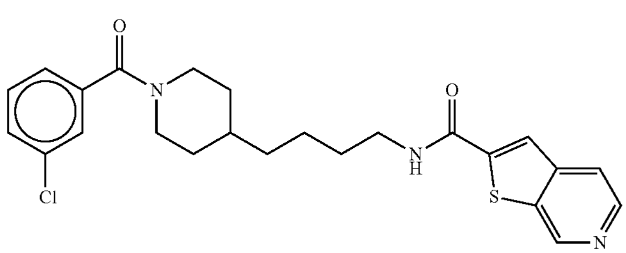 | N-(4-{1-[(3-chlorophenyl)carbonyl]piperidin-4-yl}butyl)thieno[2,3-c]pyridine-2-carboxamide |
| 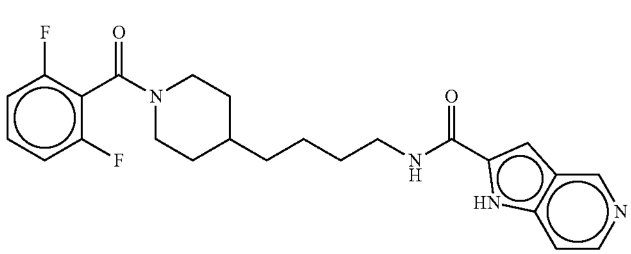 | N-(4-{1-[(2,6-difluorophenyl)carbonyl]piperidin-4-yl}butyl)-1H-pyrrolo[3,2-c]pyridine-2-carboxamide |

TABLE 2-continued

| Structure | Chemical Name |
|---|---|
| 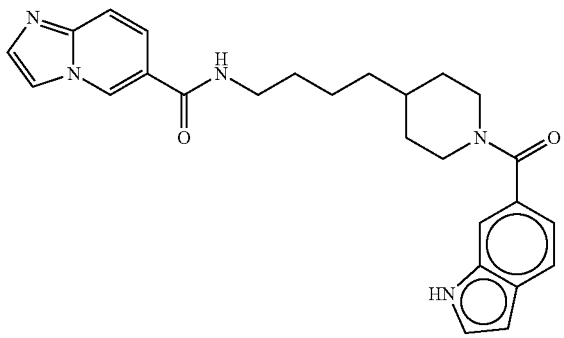 | N-(4-{1-[(1H-indol-6-yl)carbonyl]piperidin-4-yl}butyl)imidazo[1,2-a]pyridine-6-carboxamide |
| 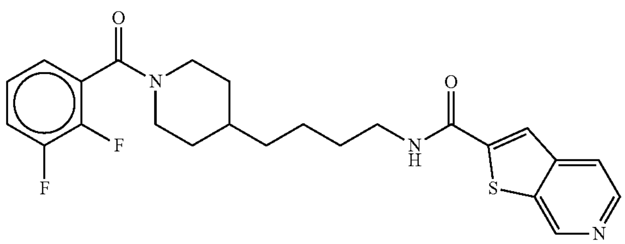 | N-(4-{1-[(2,3-difluorophenyl)carbonyl]piperidin-4-yl}butyl)thieno[2,3-c]pyridine-2-carboxamide |
| 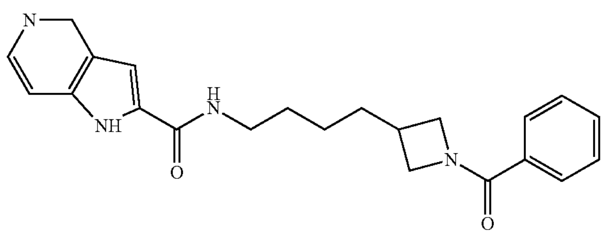 [SMILES: O=C(NCCCCC1CN(C(=O)c2ccccc2)C1)c1cc2c([nH]1)C=CNC2] | N-[4-(1-benzoylazetidin-3-yl)butyl]-1H-pyrrolo[3,2-c]pyridine-2-carboxamide |
| 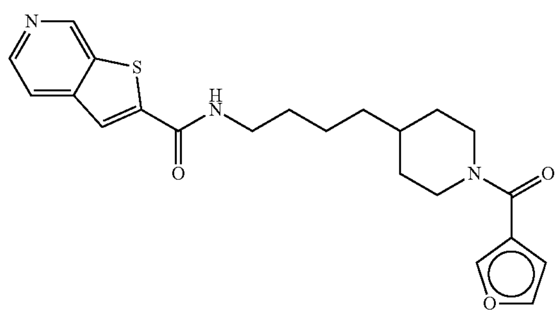 | N-(4-{1-[(furan-3-yl)carbonyl]piperidin-4-yl}butyl)thieno[2,3-c]pyridine-2-carboxamide |
| 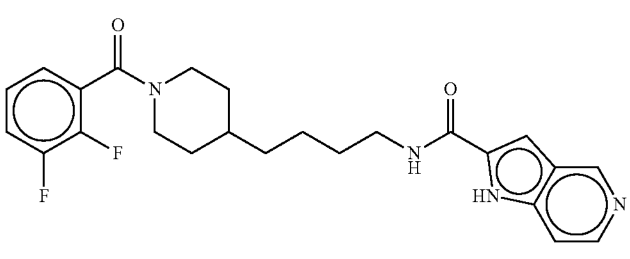 | N-(4-{1-[(2,3-difluorophenyl)carbonyl]piperidin-4-yl}butyl)-1H-pyrrolo[3,2-c]pyridine-2-carboxamide |
| 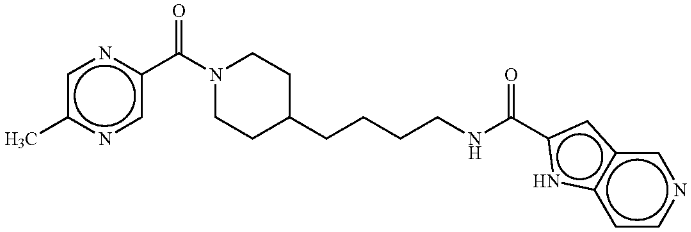 | N-(4-{1-[(5-methylpyrazin-2-yl)carbonyl]piperidin-4-yl}butyl)-1H-pyrrolo[3,2-c]pyridine-2-carboxamide |

TABLE 2-continued

| Structure | Chemical Name |
|---|---|
| 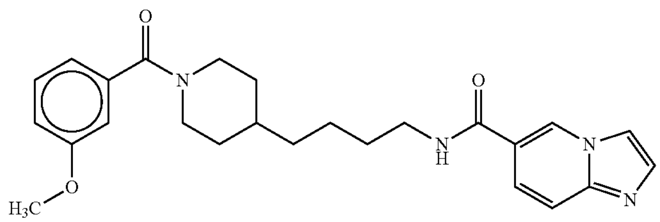 | N-(4-{1-[(3-methoxyphenyl)carbonyl]piperidin-4-yl}butyl)imidazo[1,2-a]pyridine-6-carboxamide |
| 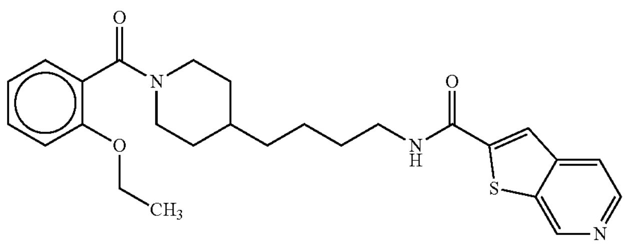 | N-(4-{1-[(2-ethoxyphenyl)carbonyl]piperidin-4-yl}butyl)thieno[2,3-c]pyridine-2-carboxamide |
| 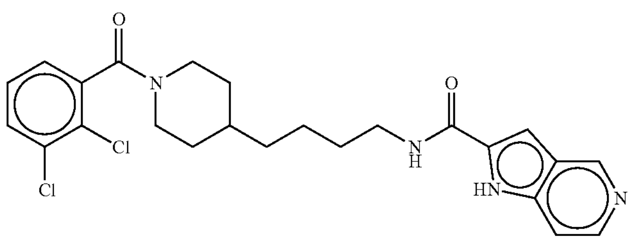 | N-(4-{1-[(2,3-dichlorophenyl)carbonyl]piperidin-4-yl}butyl)-1H-pyrrolo[3,2-c]pyridine-2-carboxamide |
| 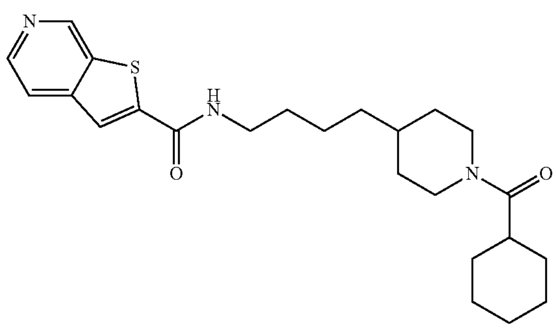 [SMILES: O=C(NCCCCC1CCN(C(=O)C2CCCCC2)CC1)c1cc2ccncc2s1] | N-[4-(1-cyclohexanecarbonylpiperidin-4-yl)butyl]thieno[2,3-c]pyridine-2-carboxamide |
| 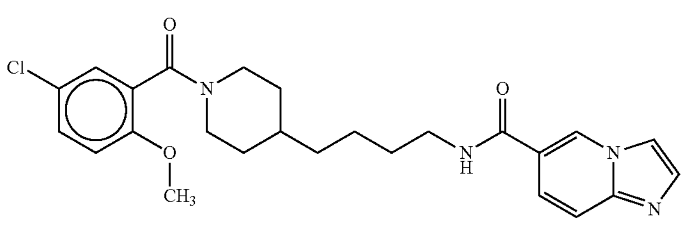 | N-(4-{1-[(5-chloro-2-methoxyphenyl)carbonyl]piperidin-4-yl}butyl)imidazo[1,2-a]pyridine-6-carboxamide |
| 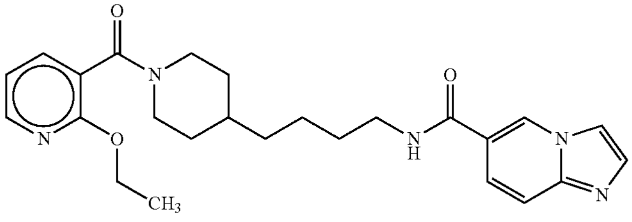 | N-(4-{1-[(2-ethoxypyridin-3-yl)carbonyl]piperidin-4-yl}butyl)imidazo[1,2-a]pyridine-6-carboxamide |

TABLE 2-continued

| Structure | Chemical Name |
|---|---|
| 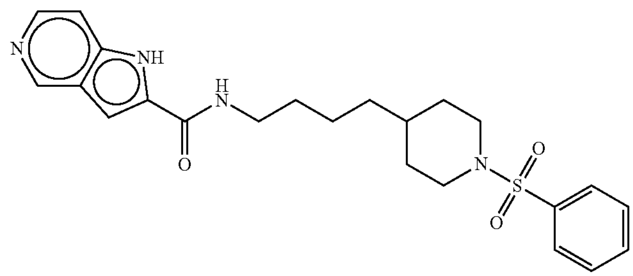 | N-{4-[1-(benzenesulfonyl)piperidin-4-yl]butyl}-1H-pyrrolo[3,2-c]pyridine-2-carboxamide |
| 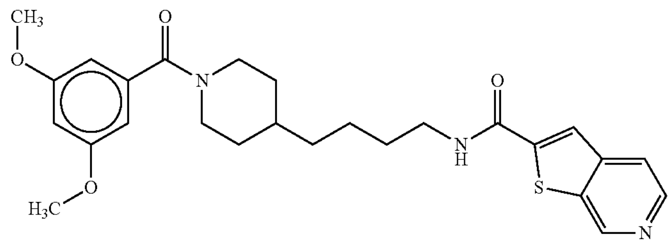 | N-(4-{1-[(3,5-dimethoxyphenyl)carbonyl]piperidin-4-yl}butyl)thieno[2,3-c]pyridine-2-carboxamide |
| 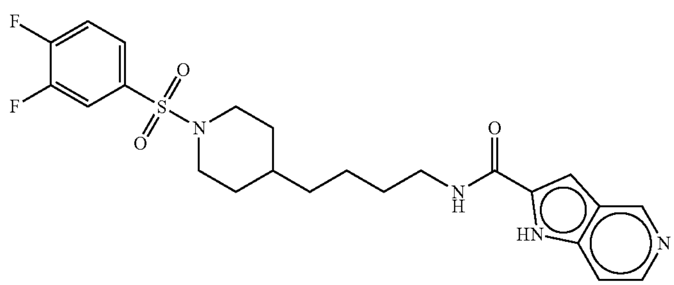 | N-(4-{1-[(3,4-difluorobenzene)sulfonyl]piperidin-4-yl}butyl)-1H-pyrrolo[3,2-c]pyridine-2-carboxamide |
| 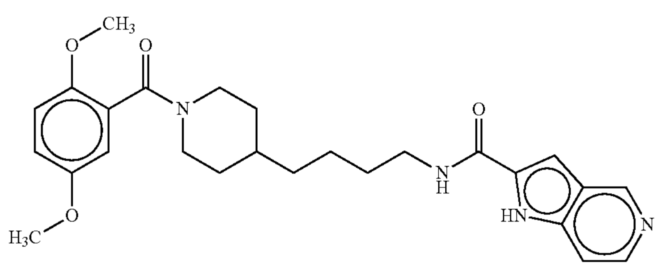 | N-(4-{1-[(2,5-dimethoxyphenyl)carbonyl]piperidin-4-yl}butyl)-1H-pyrrolo[3,2-c]pyridine-2-carboxamide |
| 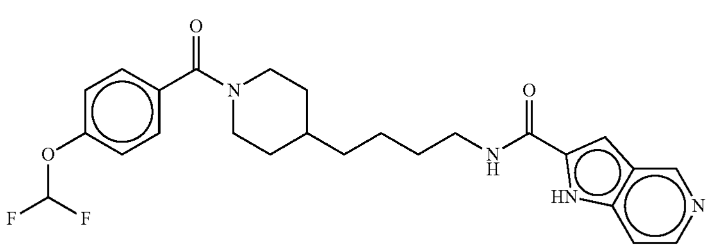 | N-[4-(1-{[4-(difluoromethoxy)phenyl]carbonyl}piperidin-4-yl)butyl]-1H-pyrrolo[3,2-c]pyridine-2-carboxamide |

TABLE 2-continued

| Structure | Chemical Name |
|---|---|
| 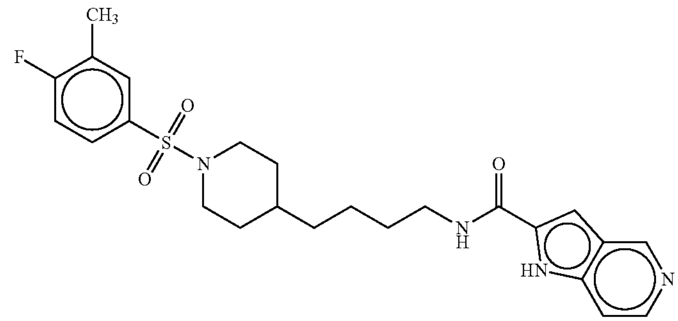 | N-(4-{1-[(4-fluoro-3-methylbenzene)sulfonyl]piperidin-4-yl}butyl)-1H-pyrrolo[3,2-c]pyridine-2-carboxamide |
| 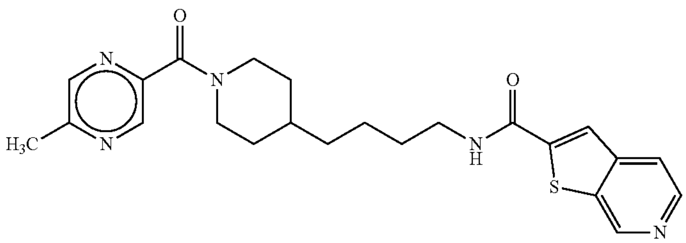 | N-(4-{1-[(5-methylpyrazin-2-yl)carbonyl]piperidin-4-yl}butyl)thieno[2,3-c]pyridine-2-carboxamide |
| 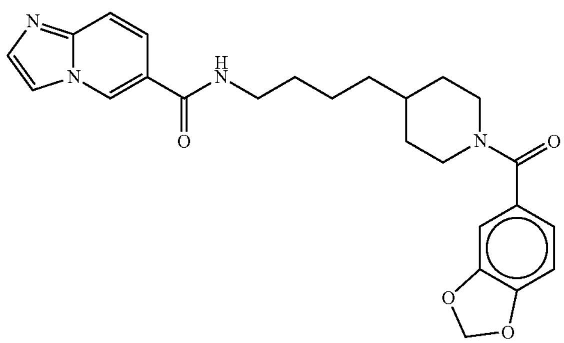 | N-(4-{1-[(2H-1,3-benzodioxol-5-yl)carbonyl]piperidin-4-yl}butyl)imidazo[1,2-a]pyridine-6-carboxamide |
| 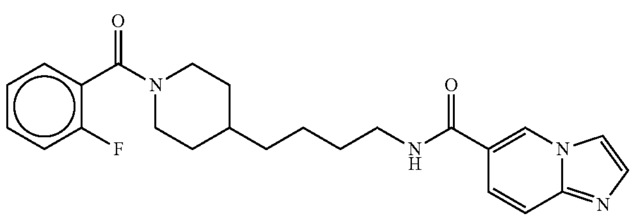 | N-(4-{1-[(2-fluorophenyl)carbonyl]piperidin-4-yl}butyl)imidazo[1,2-a]pyridine-6-carboxamide |
| 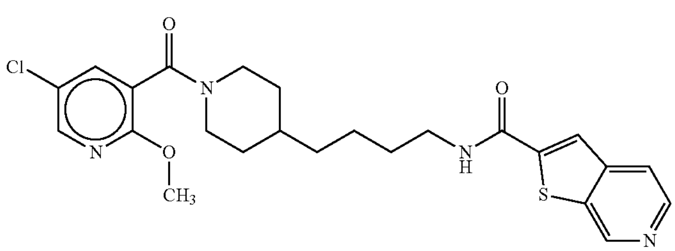 | N-(4-{1-[(5-chloro-2-methoxypyridin-3-yl)carbonyl]piperidin-4-yl}butyl)thieno[2,3-c]pyridine-2-carboxamide |
| 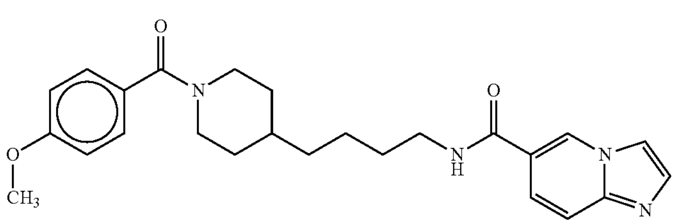 | N-(4-{1-[(4-methoxyphenyl)carbonyl]piperidin-4-yl}butyl)imidazo[1,2-a]pyridine-6-carboxamide |

TABLE 2-continued

| Structure | Chemical Name |
|---|---|
| 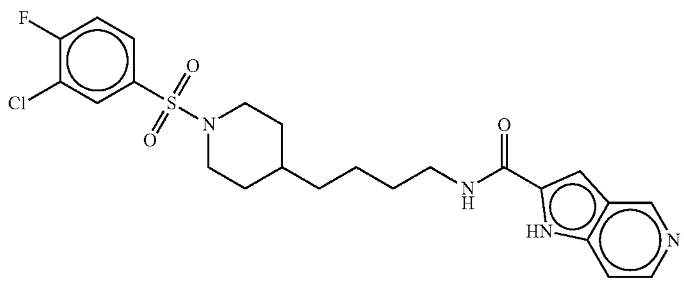 | N-(4-{1-[(3-chloro-4-fluorobenzene)sulfonyl]piperidin-4-yl}butyl)-1H-pyrrolo[3,2-c]pyridine-2-carboxamide |
| 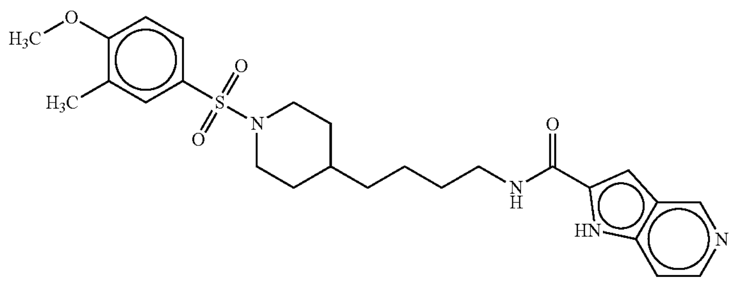 | N-(4-{1-[(4-methoxy-3-methylbenzene)sulfonyl]piperidin-4-yl}butyl)-1H-pyrrolo[3,2-c]pyridine-2-carboxamide |
| 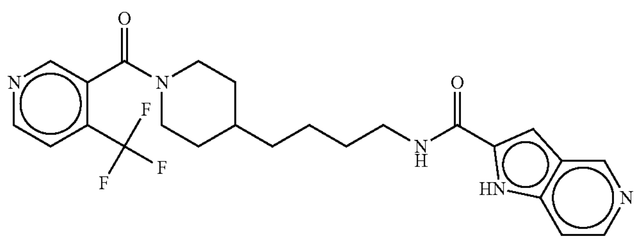 | N-[4-(1-{[4-(trifluoromethyl)pyridin-3-yl]carbonyl}piperidin-4-yl)butyl]-1H-pyrrolo[3,2-c]pyridine-2-carboxamide |
| 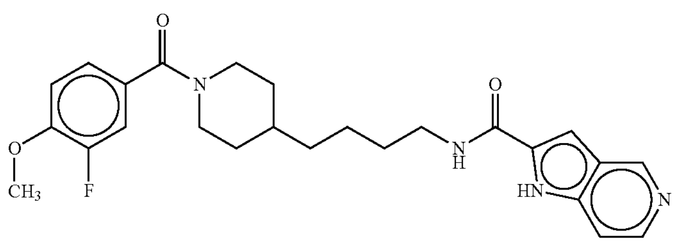 | N-(4-{1-[(3-fluoro-4-methoxyphenyl)carbonyl]piperidin-4-yl}butyl)-1H-pyrrolo[3,2-c]pyridine-2-carboxamide |
| 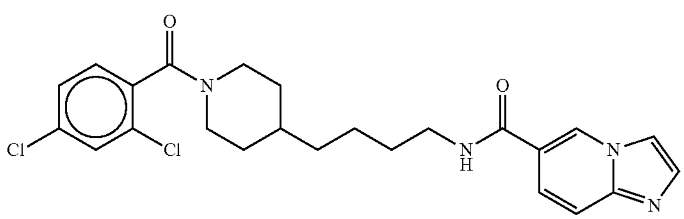 | N-(4-{1-[(2,4-dichlorophenyl)carbonyl]piperidin-4-yl}butyl)imidazo[1,2-a]pyridine-6-carboxamide |
| 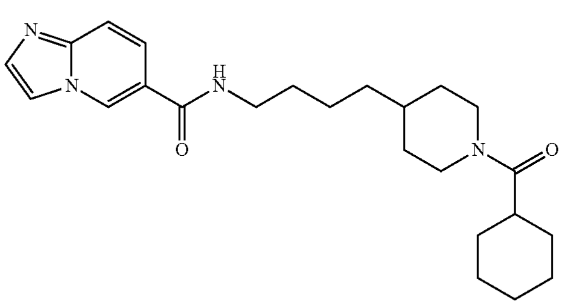 [SMILES: O=C(NCCCCC1CCN(C(=O)C2CCCCC2)CC1)c1ccc2nccn2c1] | N-[4-(1-cyclohexanecarbonylpiperidin-4-yl)butyl]imidazo[1,2-a]pyridine-6-carboxamide |

TABLE 2-continued

| Structure | Chemical Name |
| --- | --- |
| 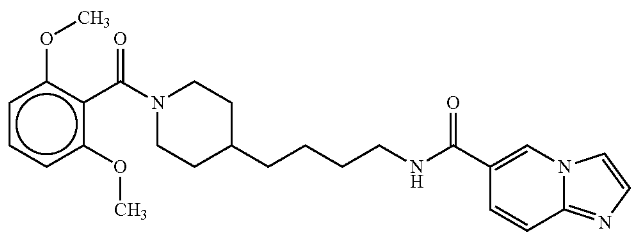 | N-(4-{1-[(2,6-dimethoxyphenyl)carbonyl]piperidin-4-yl}butyl)imidazo[1,2-a]pyridine-6-carboxamide |
| 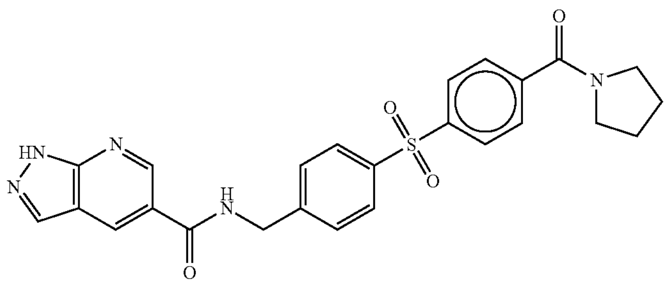 | N-{[4-({4-[(pyrrolidin-1-yl)carbonyl]benzene}sulfonyl)phenyl]methyl}-1H-pyrazolo[3,4-b]pyridine-5-carboxamide |
| 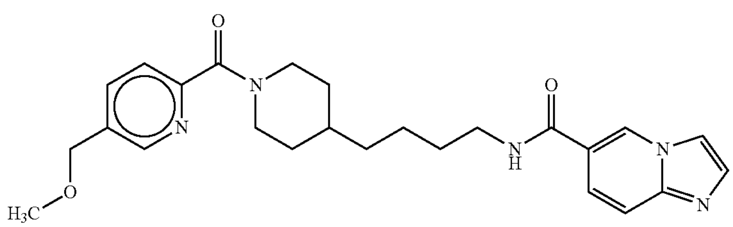 | N-[4-(1-{[5-(methoxymethyl)pyridin-2-yl]carbonyl}piperidin-4-yl)butyl]imidazo[1,2-a]pyridine-6-carboxamide |
| 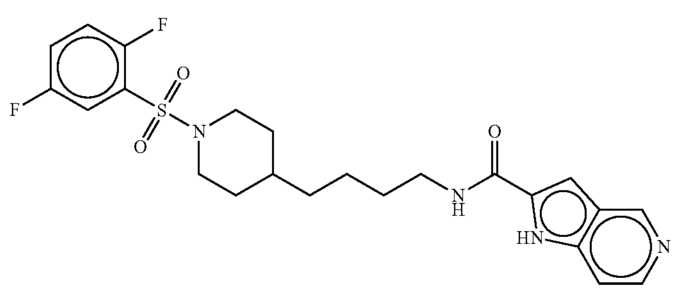 | N-(4-{1-[(2,5-difluorobenzene)sulfonyl]piperidin-4-yl}butyl)-1H-pyrrolo[3,2-c]pyridine-2-carboxamide |
| 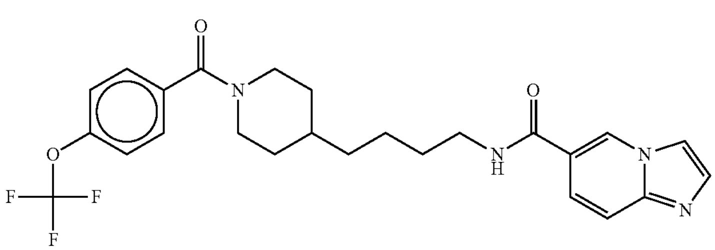 | N-[4-(1-{[4-(trifluoromethoxy)phenyl]carbonyl}piperidin-4-yl)butyl]imidazo[1,2-a]pyridine-6-carboxamide |
| 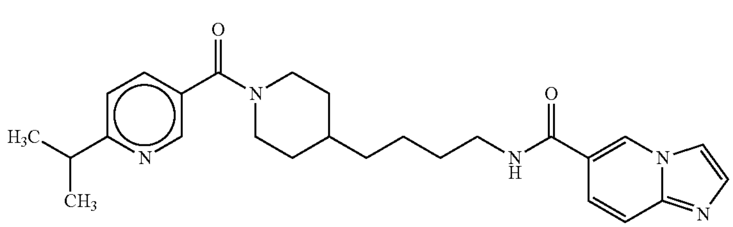 | N-[4-(1-{[6-(propan-2-yl)pyridin-3-yl]carbonyl}piperidin-4-yl)butyl]imidazo[1,2-a]pyridine-6-carboxamide |

TABLE 2-continued

| Structure | Chemical Name |
| --- | --- |
| 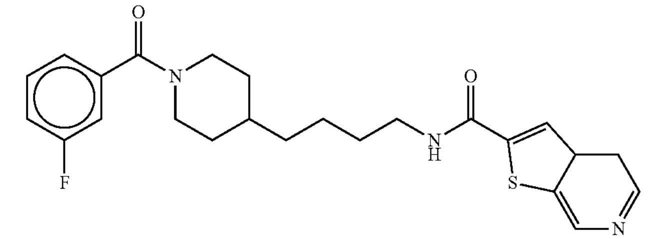 | N-(4-{1-[(3-fluorophenyl)carbonyl]piperidin-4-yl}butyl)thieno[2,3-c]pyridine-2-carboxamide |
| 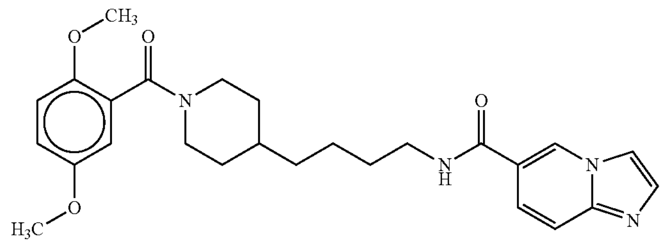 | N-(4-{1-[(2,5-dimethoxyphenyl)carbonyl]piperidin-4-yl}butyl)imidazo[1,2-a]pyridine-6-carboxamide |
| 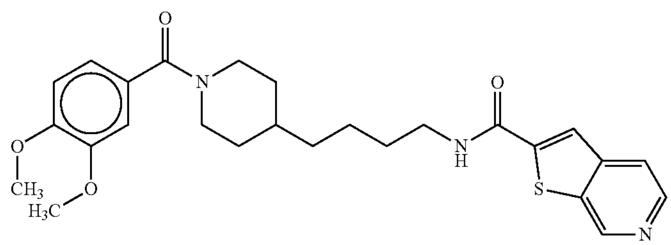 | N-(4-{1-[(3,4-dimethoxyphenyl)carbonyl]piperidin-4-yl}butyl)thieno[2,3-c]pyridine-2-carboxamide |
| 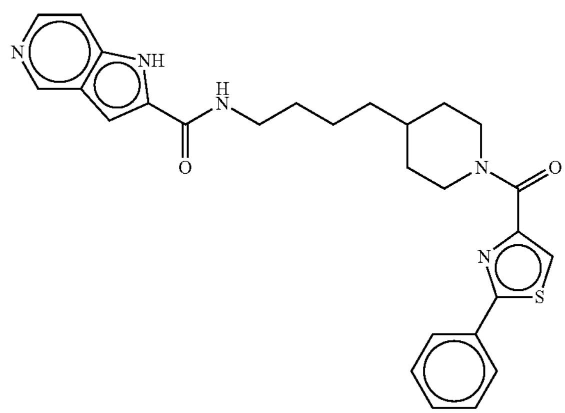 | N-(4-{1-[(2-phenyl-1,3-thiazol-4-yl)carbonyl]piperidin-4-yl}butyl)-1H-pyrrolo[3,2-c]pyridine-2-carboxamide |
| 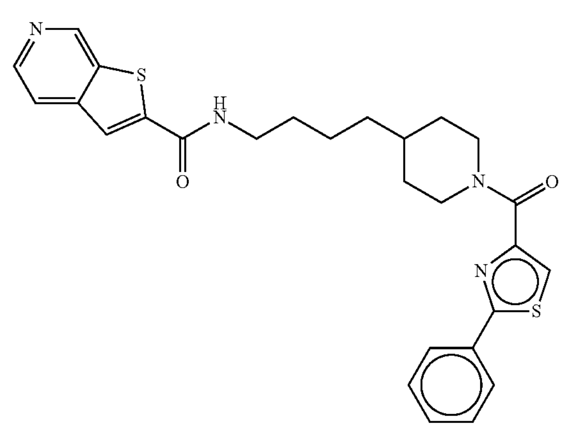 | N-(4-{1-[(2-phenyl-1,3-thiazol-4-yl)carbonyl]piperidin-4-yl}butyl)thieno[2,3-c]pyridine-2-carboxamide |

TABLE 2-continued

| Structure | Chemical Name |
|---|---|
| 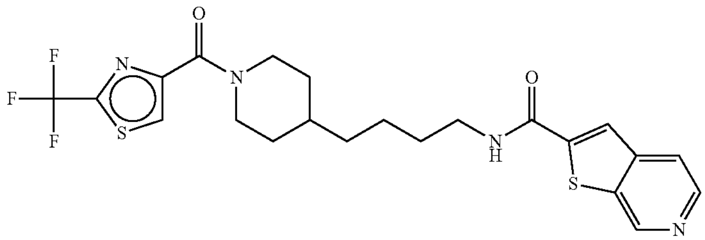 | N-[4-(1-{[2-(trifluoromethyl)-1,3-thiazol-4-yl]carbonyl}piperidin-4-yl)butyl]thieno[2,3-c]pyridine-2-carboxamide |
| 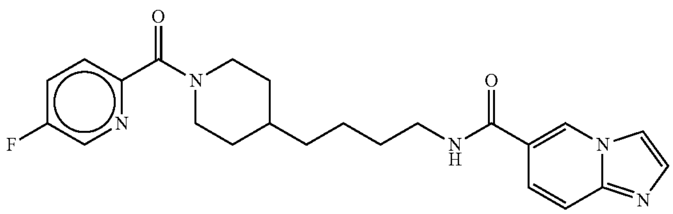 | N-(4-{1-[(5-fluoropyridin-2-yl)carbonyl]piperidin-4-yl}butyl)imidazo[1,2-a]pyridine-6-carboxamide |
| 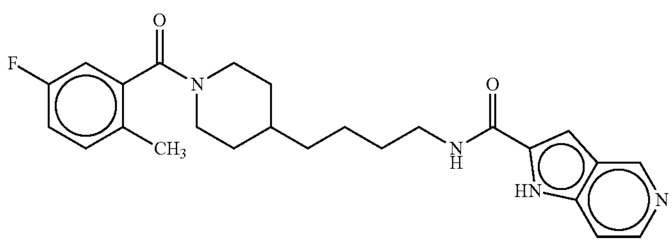 | N-(4-{1-[(5-fluoro-2-methylphenyl)carbonyl]piperidin-4-yl}butyl)-1H-pyrrolo[3,2-c]pyridine-2-carboxamide |
| 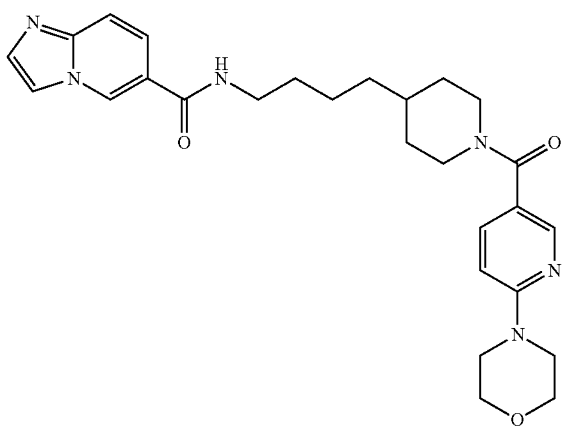 [SMILES: O=C(NCCCCC1CCN(C(=O)c2ccc(N3CCOCC3)nc2)CC1)c1ccc2nccn2c1] | N-[4-(1-{[6-(morpholin-4-yl)pyridin-3-yl]carbonyl}piperidin-4-yl)butyl]imidazo[1,2-a]pyridine-6-carboxamide |
| 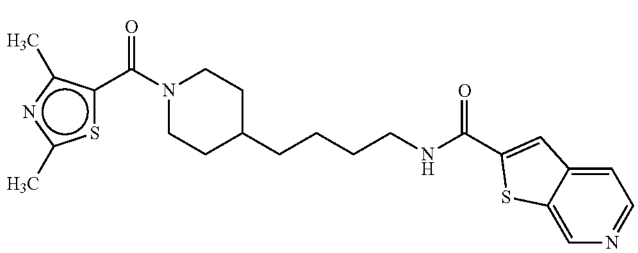 | N-(4-{1-[(dimethyl-1,3-thiazol-5-yl)carbonyl]piperidin-4-yl}butyl)thieno[2,3-c]pyridine-2-carboxamide |

TABLE 2-continued

| Structure | Chemical Name |
|---|---|
| 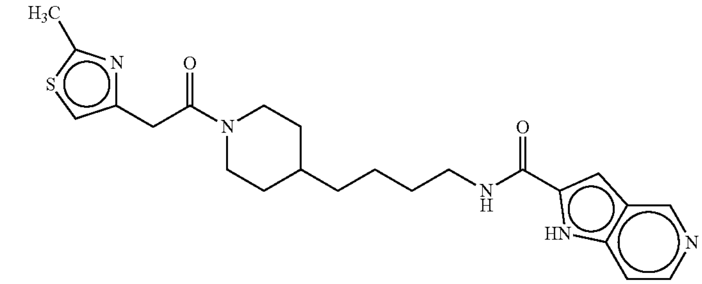 | N-(4-{1-[2-(2-methyl-1,3-thiazol-4-yl)acetyl]piperidin-4-yl}butyl)-1H-pyrrolo[3,2-c]pyridine-2-carboxamide |
| 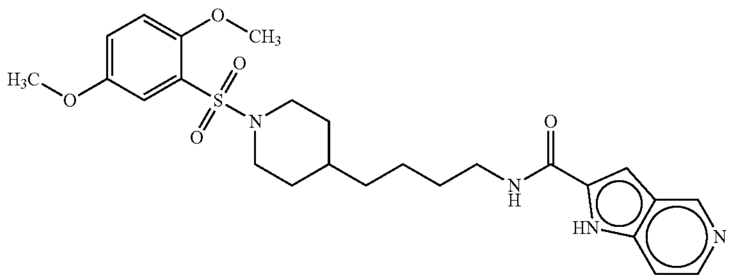 | N-(4-{1-[(2,5-dimethoxybenzene)sulfonyl]piperidin-4-yl}butyl)-1H-pyrrolo[3,2-c]pyridine-2-carboxamide |
| 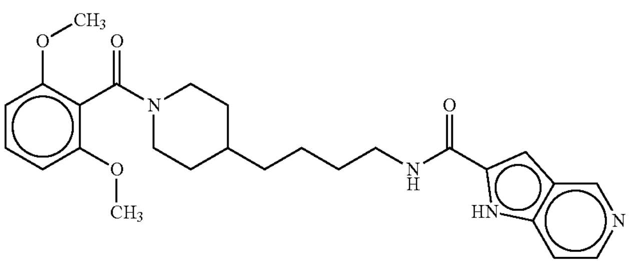 | N-(4-{1-[(2,6-dimethoxyphenyl)carbonyl]piperidin-4-yl}butyl)-1H-pyrrolo[3,2-c]pyridine-2-carboxamide |
| 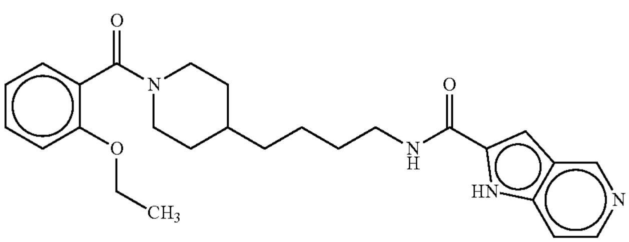 | N-(4-{1-[(2-ethoxyphenyl)carbonyl]piperidin-4-yl}butyl)-1H-pyrrolo[3,2-c]pyridine-2-carboxamide |
| 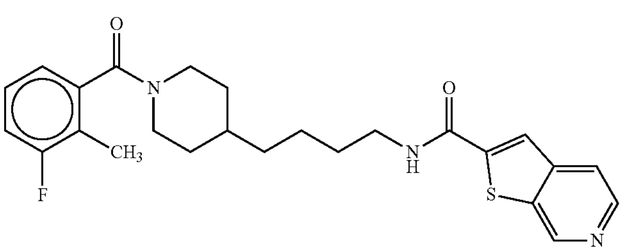 | N-(4-{1-[(3-fluoro-2-methylphenyl)carbonyl]piperidin-4-yl}butyl)thieno[2,3-c]pyridine-2-carboxamide |
| 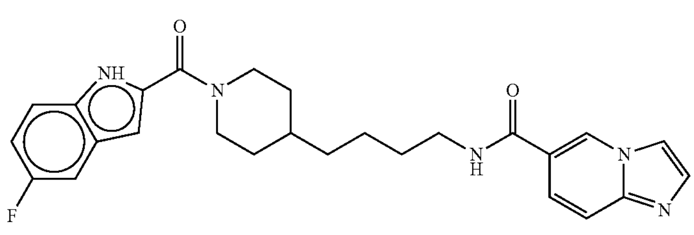 | N-(4-{1-[(5-fluoro-1H-indol-2-yl)carbonyl]piperidin-4-yl}butyl)imidazo[1,2-a]pyridine-6-carboxamide |

TABLE 2-continued

| Structure | Chemical Name |
|---|---|
| 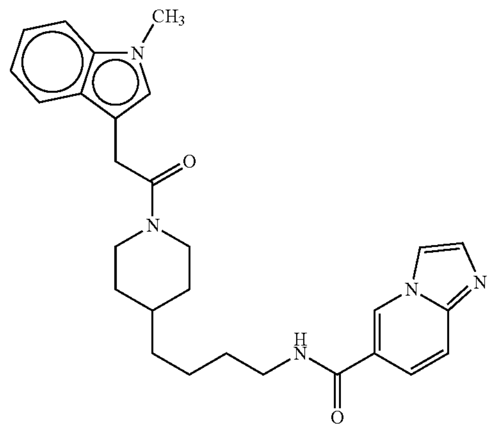 | N-(4-{1-[2-(1-methyl-1H-indol-3-yl)acetyl]piperidin-4-yl}butyl)imidazo[1,2-a]pyridine-6-carboxamide |
| 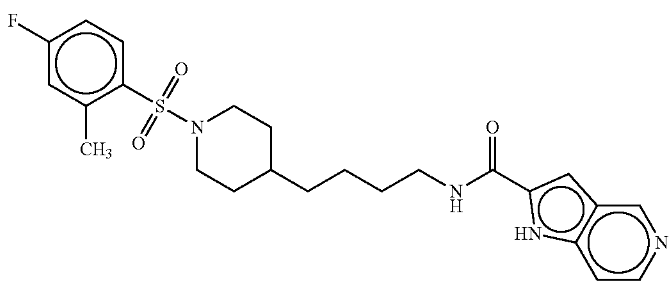 | N-(4-{1-[(4-fluoro-2-methylbenzene)sulfonyl]piperidin-4-yl}butyl)-1H-pyrrolo[3,2-c]pyridine-2-carboxamide |
| 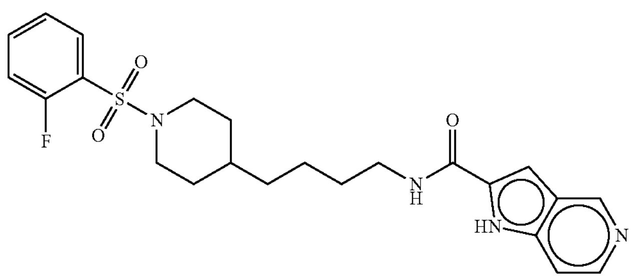 | N-(4-{1-[(2-fluorobenzene)sulfonyl]piperidin-4-yl}butyl)-1H-pyrrolo[3,2-c]pyridine-2-carboxamide |
| 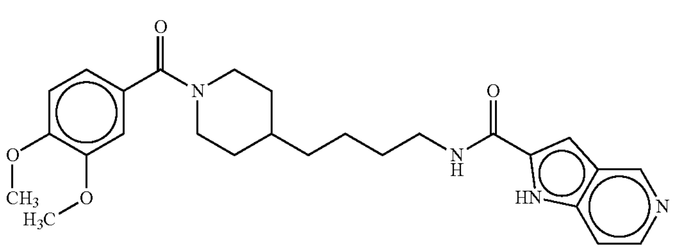 | N-(4-{1-[(3,4-dimethoxyphenyl)carbonyl]piperidin-4-yl}butyl)-1H-pyrrolo[3,2-c]pyridine-2-carboxamide |
| 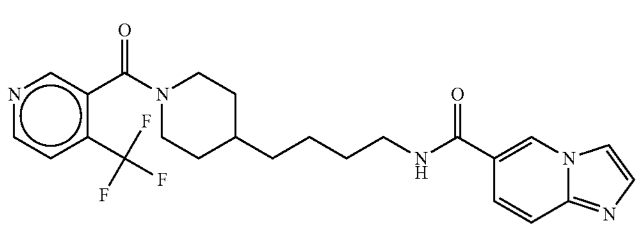 | N-[4-(1-{[4-(trifluoromethyl)pyridin-3-yl]carbonyl}piperidin-4-yl)butyl]imidazo[1,2-a]pyridine-6-carboxamide |

TABLE 2-continued

| Structure | Chemical Name |
|---|---|
| 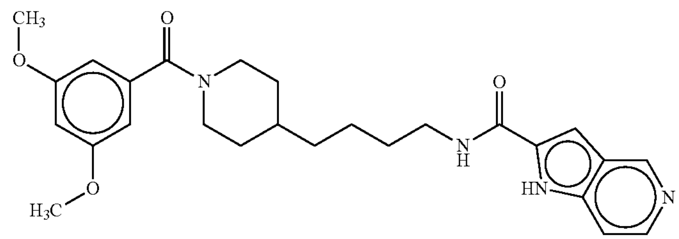 | N-(4-{1-[(3,5-dimethoxyphenyl)carbonyl]piperidin-4-yl}butyl)-1H-pyrrolo[3,2-c]pyridine-2-carboxamide |
| 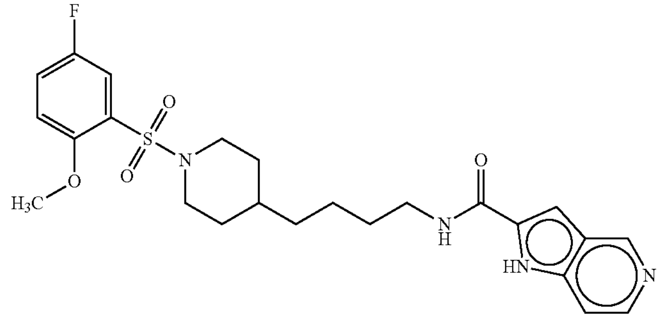 | N-(4-{1-[(5-fluoro-2-methoxybenzene)sulfonyl]piperidin-4-yl}butyl)-1H-pyrrolo[3,2-c]pyridine-2-carboxamide |
| 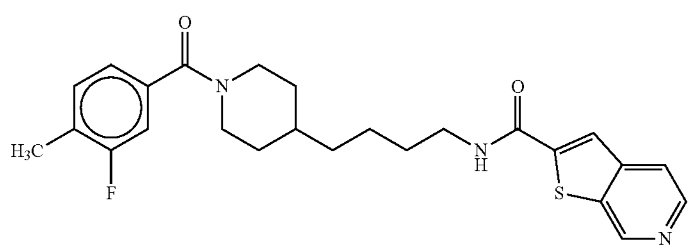 | N-(4-{1-[(3-fluoro-4-methylphenyl)carbonyl]piperidin-4-yl}butyl)thieno[2,3-c]pyridine-2-carboxamide |
| 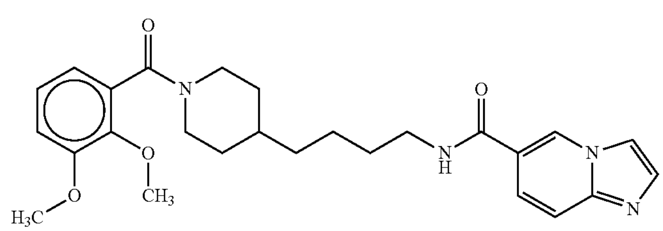 | N-(4-{1-[(2,3-dimethoxyphenyl)carbonyl]piperidin-4-yl}butyl)imidazo[1,2-a]pyridine-6-carboxamide |
| 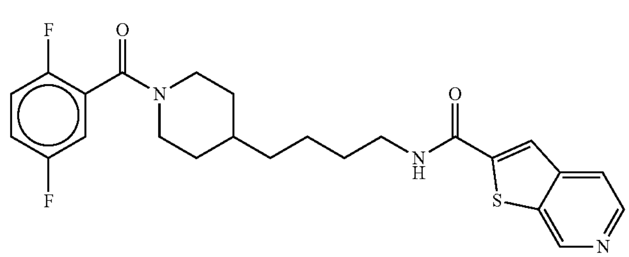 | N-(4-{1-[(2,5-difluorophenyl)carbonyl]piperidin-4-yl}butyl)thieno[2,3-c]pyridine-2-carboxamide |

TABLE 2-continued

| Structure | Chemical Name |
|---|---|
| 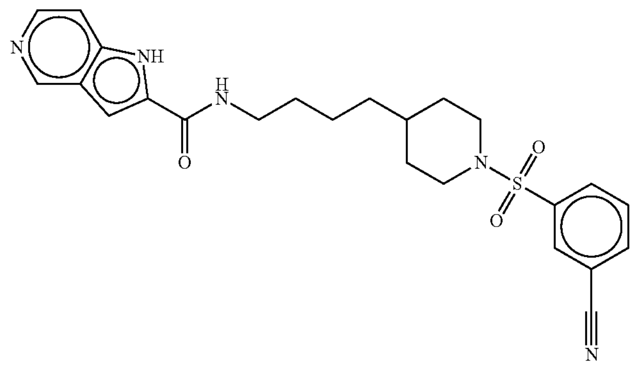 | N-(4-{1-[(3-cyanobenzene)sulfonyl]piperidin-4-yl}butyl)-1H-pyrrolo[3,2-c]pyridine-2-carboxamide |
| 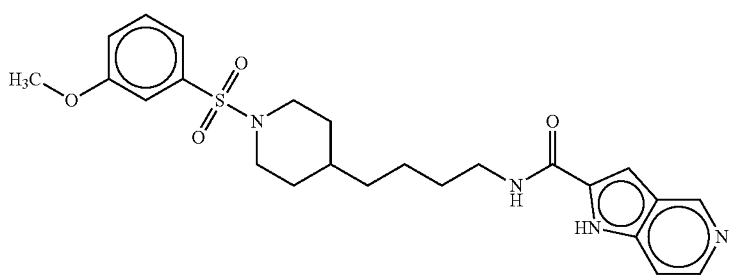 | N-(4-{1-[(3-methoxybenzene)sulfonyl]piperidin-4-yl}butyl)-1H-pyrrolo[3,2-c]pyridine-2-carboxamide |
| 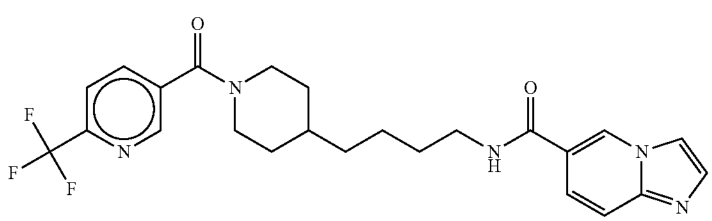 | N-[4-(1-{[6-(trifluoromethyl)pyridin-3-yl]carbonyl}piperidin-4-yl)butyl]imidazo[1,2-a]pyridine-6-carboxamide |
| 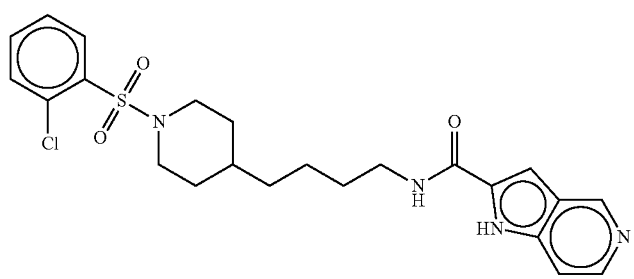 | N-(4-{1-[(2-chlorobenzene)sulfonyl]piperidin-4-yl}butyl)-1H-pyrrolo[3,2-c]pyridine-2-carboxamide |
| 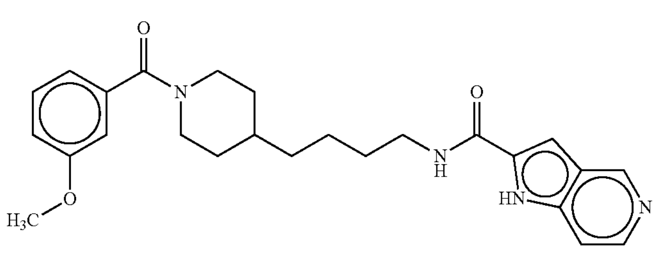 | N-(4-{1-[(3-methoxyphenyl)carbonyl]piperidin-4-yl}butyl)-1H-pyrrolo[3,2-c]pyridine-2-carboxamide |

TABLE 2-continued

| Structure | Chemical Name |
|---|---|
| 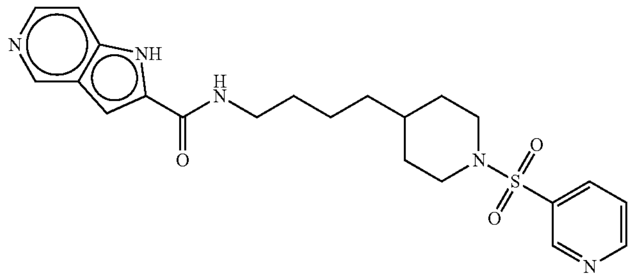 | N-{4-[1-(pyridine-3-sulfonyl)piperidin-4-yl]butyl}-1H-pyrrolo[3,2-c]pyridine-2-carboxamide |
| 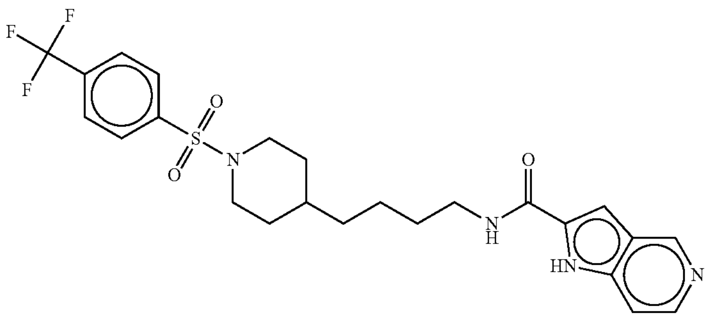 | N-[4-(1-{[4-(trifluoromethyl)benzene]sulfonyl}piperidin-4-yl)butyl]-1H-pyrrolo[3,2-c]pyridine-2-carboxamide |
| 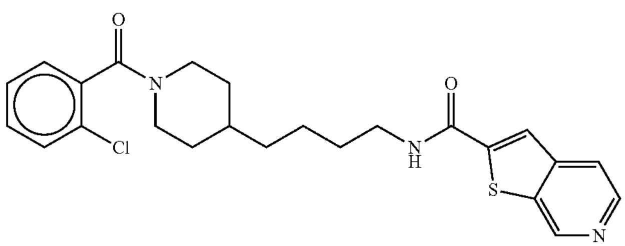 | N-(4-{1-[(2-chlorophenyl)carbonyl]piperidin-4-yl}butyl)thieno[2,3-c]pyridine-2-carboxamide |
| 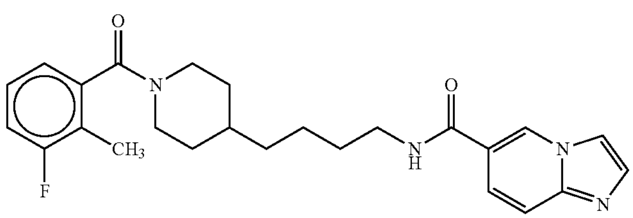 | N-(4-{1-[(3-fluoro-2-methylphenyl)carbonyl]piperidin-4-yl}butyl)imidazo[1,2-a]pyridine-6-carboxamide |
| 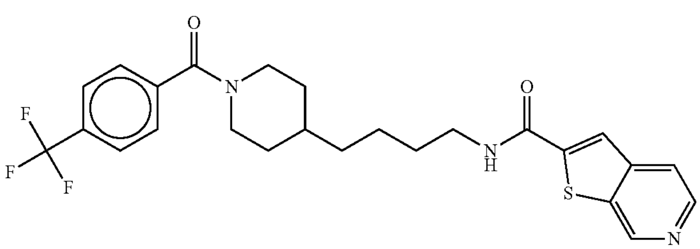 | N-[4-(1-{[4-(trifluoromethyl)phenyl]carbonyl}piperidin-4-yl)butyl]thieno[2,3-c]pyridine-2-carboxamide |
| 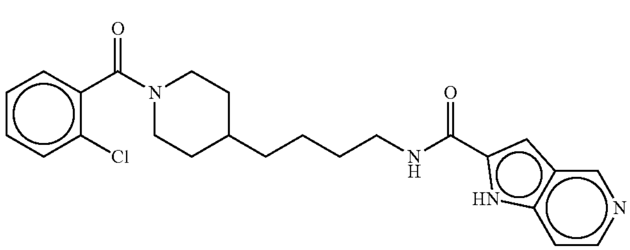 | N-(4-{1-[(2-chlorophenyl)carbonyl]piperidin-4-yl}butyl)-1H-pyrrolo[3,2-c]pyridine-2-carboxamide |

TABLE 2-continued

| Structure | Chemical Name |
|---|---|
| 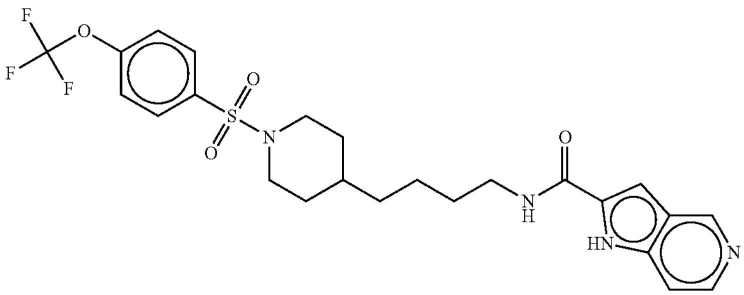 | N-[4-(1-{[4-(trifluoromethoxy)benzene]sulfonyl}piperidin-4-yl)butyl]-1H-pyrrolo[3,2-c]pyridine-2-carboxamide |
| 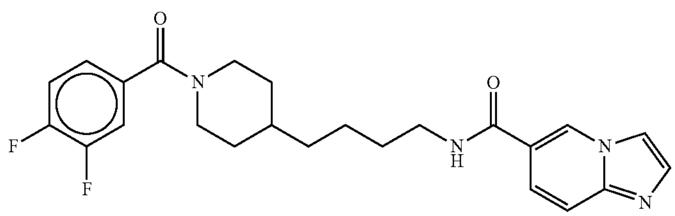 | N-(4-{1-[(3,4-difluorophenyl)carbonyl]piperidin-4-yl}butyl)imidazo[1,2-a]pyridine-6-carboxamide |
| 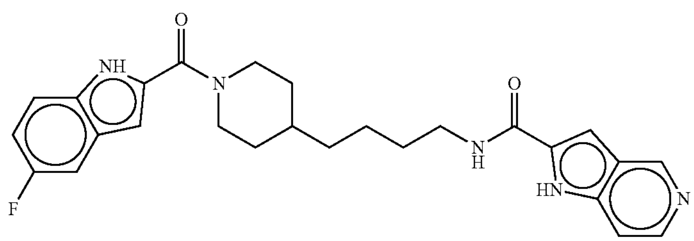 | N-(4-{1-[(5-fluoro-1H-indol-2-yl)carbonyl]piperidin-4-yl}butyl)-1H-pyrrolo[3,2-c]pyridine-2-carboxamide |
| 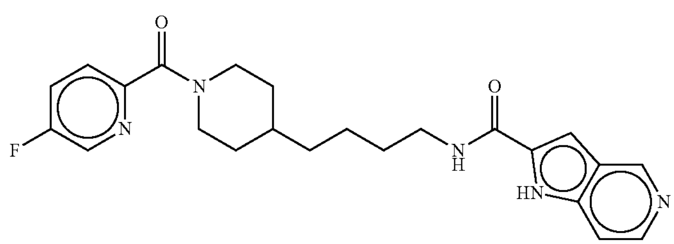 | N-(4-{1-[(5-fluoropyridin-2-yl)carbonyl]piperidin-4-yl}butyl)-1H-pyrrolo[3,2-c]pyridine-2-carboxamide |
| 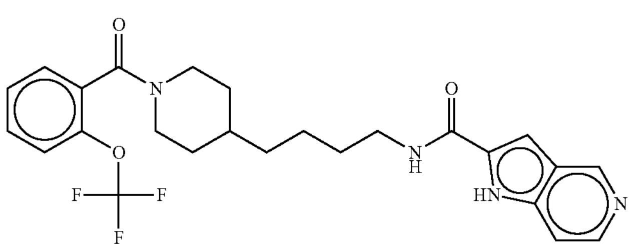 | N-[4-(1-{[2-(trifluoromethoxy)phenyl]carbonyl}piperidin-4-yl)butyl]-1H-pyrrolo[3,2-c]pyridine-2-carboxamide |
| 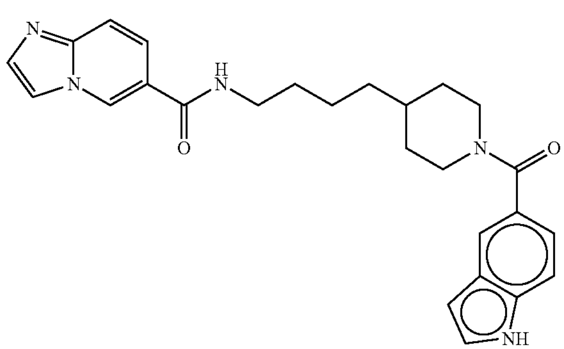 | N-(4-{1-[(1H-indol-5-yl)carbonyl]piperidin-4-yl}butyl)imidazo[1,2-a]pyridine-6-carboxamide |

TABLE 2-continued

| Structure | Chemical Name |
|---|---|
| 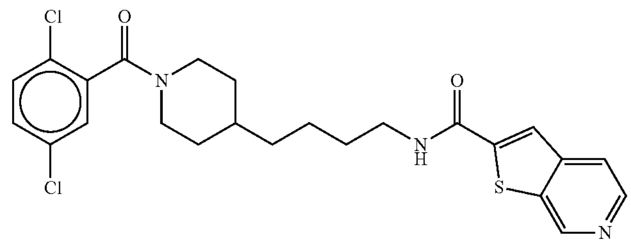 | N-(4-{1-[(2,5-dichlorophenyl)carbonyl]piperidin-4-yl}butyl)thieno[2,3-c]pyridine-2-carboxamide |
| 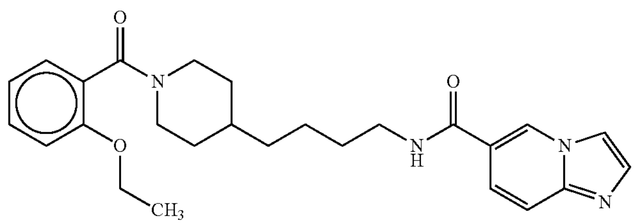 | N-(4-{1-[(2-ethoxyphenyl)carbonyl]piperidin-4-yl}butyl)imidazo[1,2-a]pyridine-6-carboxamide |
| 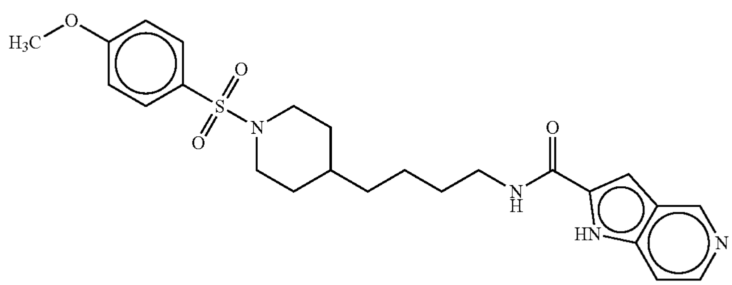 | N-(4-{1-[(4-methoxybenzene)sulfonyl]piperidin-4-yl}butyl)-1H-pyrrolo[3,2-c]pyridine-2-carboxamide |
| 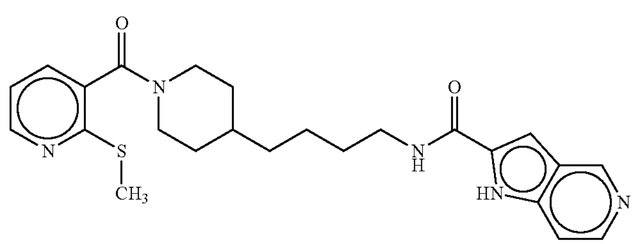 | N-[4-(1-{[2-(methylsulfanyl)pyridin-3-yl]carbonyl}piperidin-4-yl)butyl]-1H-pyrrolo[3,2-c]pyridine-2-carboxamide |
| 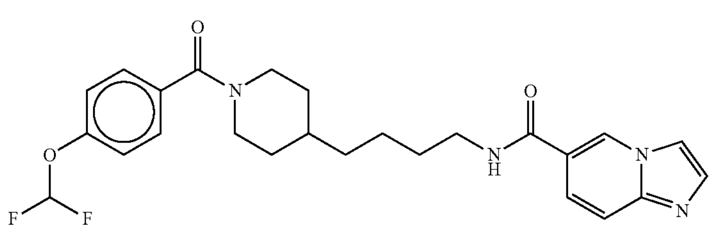 | N-[4-(1-{[4-(difluoromethoxy)phenyl]carbonyl}piperidin-4-yl)butyl]imidazo[1,2-a]pyridine-6-carboxamide |
| 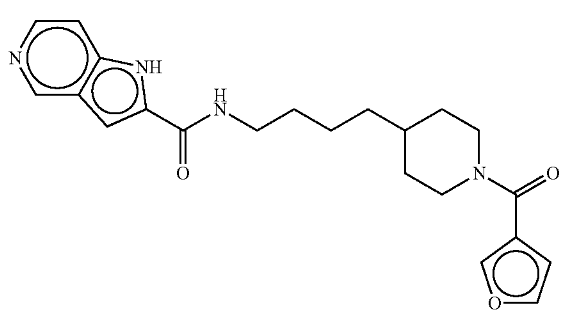 | N-(4-{1-[(furan-3-yl)carbonyl]piperidin-4-yl}butyl)-1H-pyrrolo[3,2-c]pyridine-2-carboxamide |

TABLE 2-continued

| Structure | Chemical Name |
|---|---|
| 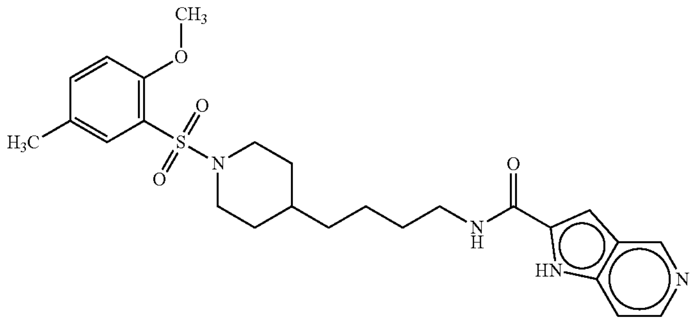 | N-(4-{1-[(2-methoxy-5-methylbenzene)sulfonyl]piperidin-4-yl}butyl)-1H-pyrrolo[3,2-c]pyridine-2-carboxamide |
| 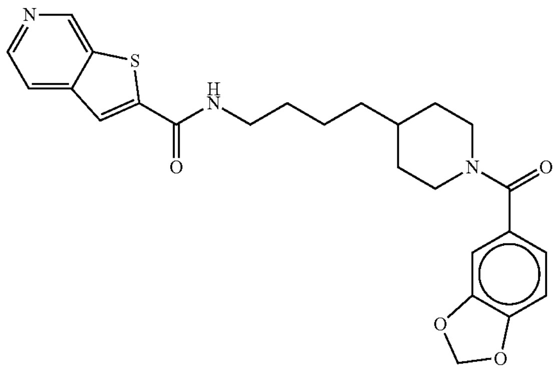 | N-(4-{1-[(2H-1,3-benzodioxol-5-yl)carbonyl]piperidin-4-yl}butyl)thieno[2,3-c]pyridine-2-carboxamide |
| 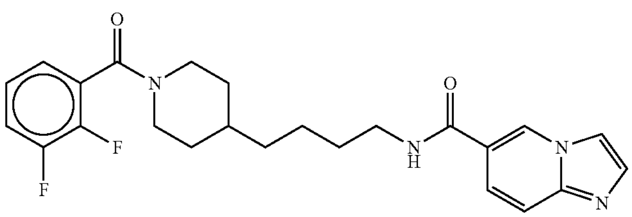 | N-(4-{1-[(2,3-difluorophenyl)carbonyl]piperidin-4-yl}butyl)imidazo[1,2-a]pyridine-6-carboxamide |
| 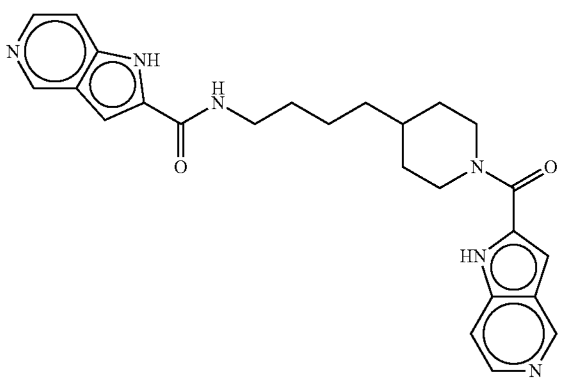 | N-{4-[1-({1H-pyrrolo[3,2-c]pyridin-2-yl}carbonyl)piperidin-4-yl]butyl}-1H-pyrrolo[3,2-c]pyridine-2-carboxamide |
| 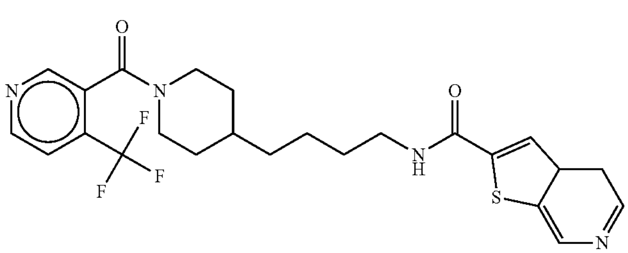 | N-[4-(1-{[4-(trifluoromethyl)pyridin-3-yl]carbonyl}piperidin-4-yl)butyl]thieno[2,3-c]pyridine-2-carboxamide |

TABLE 2-continued

| Structure | Chemical Name |
|---|---|
| 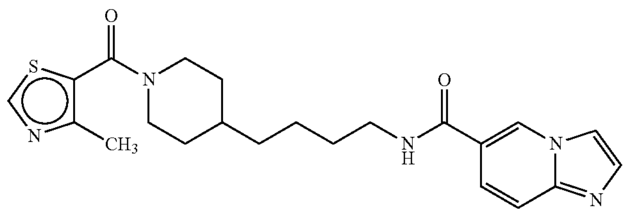 | N-(4-{1-[(4-methyl-1,3-thiazol-5-yl)carbonyl]piperidin-4-yl}butyl)imidazo[1,2-a]pyridine-6-carboxamide |
| 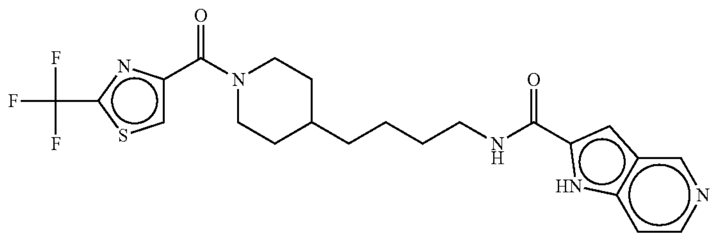 | N-[4-(1-{[2-(trifluoromethyl)-1,3-thiazol-4-yl]carbonyl}piperidin-4-yl)butyl]-1H-pyrrolo[3,2-c]pyridine-2-carboxamide |
| 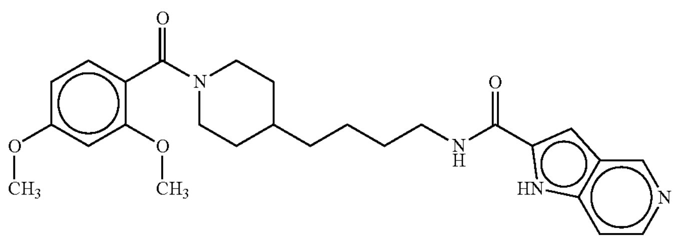 | N-(4-{1-[(2,4-dimethoxyphenyl)carbonyl]piperidin-4-yl}butyl)-1H-pyrrolo[3,2-c]pyridine-2-carboxamide |
| 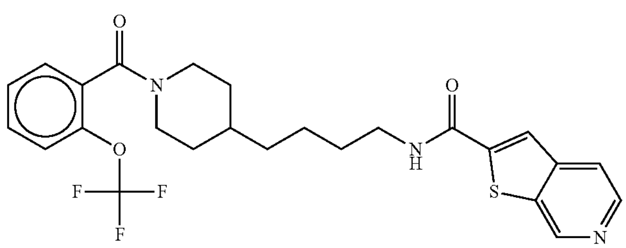 | N-[4-(1-{[2-(trifluoromethoxy)phenyl]carbonyl}piperidin-4-yl)butyl]thieno[2,3-c]pyridine-2-carboxamide |
| 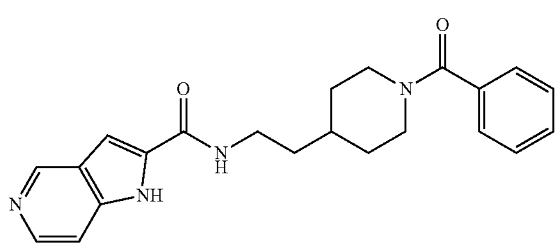 [SMILES: O=C(NCCC1CCN(C(=O)c2ccccc2)CC1)c1cc2cnccc2[nH]1] | N-[2-(1-benzoylpiperidin-4-yl)ethyl]-1H-pyrrolo[3,2-c]pyridine-2-carboxamide |
| 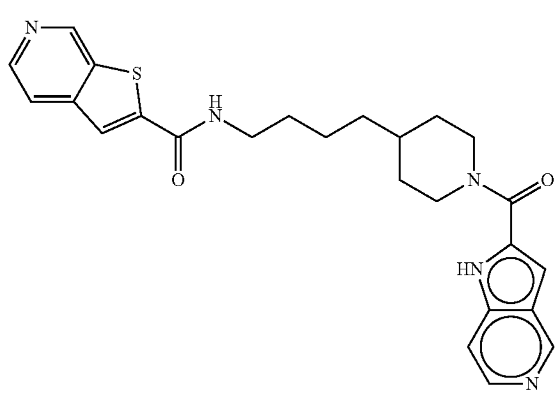 | N-{4-[1-({1H-pyrrolo[3,2-c]pyridin-2-yl}carbonyl)piperidin-4-yl]butyl}thieno[2,3-c]pyridine-2-carboxamide |

TABLE 2-continued

| Structure | Chemical Name |
|---|---|
| 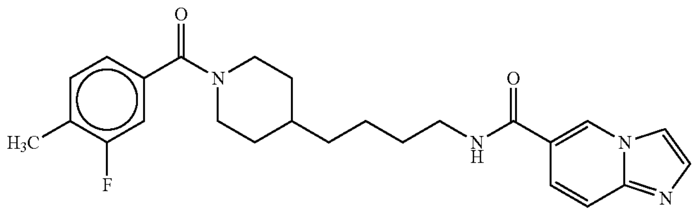 | N-(4-{1-[(3-fluoro-4-methylphenyl)carbonyl]piperidin-4-yl}butyl)imidazo[1,2-a]pyridine-6-carboxamide |
| 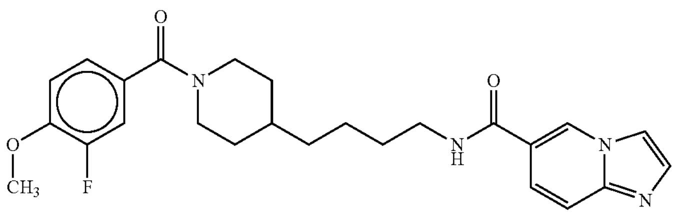 | N-(4-{1-[(3-fluoro-4-methoxyphenyl)carbonyl]piperidin-4-yl}butyl)imidazo[1,2-a]pyridine-6-carboxamide |
| 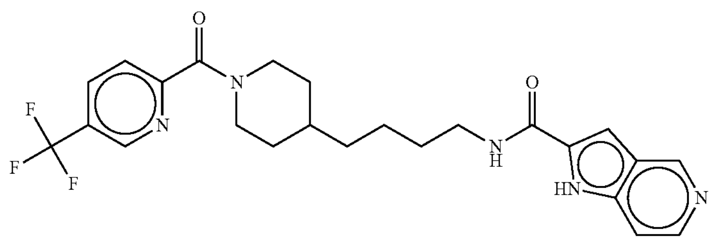 | N-[4-(1-{[5-(trifluoromethyl)pyridin-2-yl]carbonyl}piperidin-4-yl)butyl]-1H-pyrrolo[3,2-c]pyridine-2-carboxamide |
| 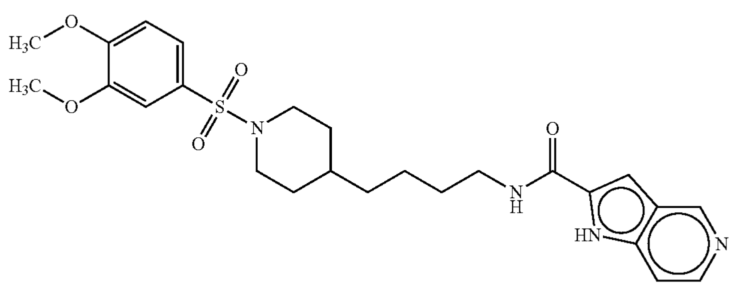 | N-(4-{1-[(3,4-dimethoxybenzene)sulfonyl]piperidin-4-yl}butyl)-1H-pyrrolo[3,2-c]pyridine-2-carboxamide |
| 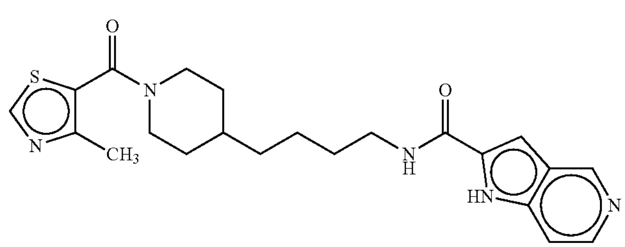 | N-(4-{1-[(4-methyl-1,3-thiazol-5-yl)carbonyl]piperidin-4-yl}butyl)-1H-pyrrolo[3,2-c]pyridine-2-carboxamide |
| 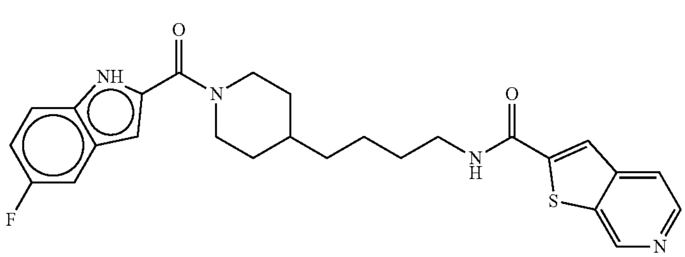 | N-(4-{1-[(5-fluoro-1H-indol-2-yl)carbonyl]piperidin-4-yl}butyl)thieno[2,3-c]pyridine-2-carboxamide |

TABLE 2-continued

| Structure | Chemical Name |
|---|---|
| 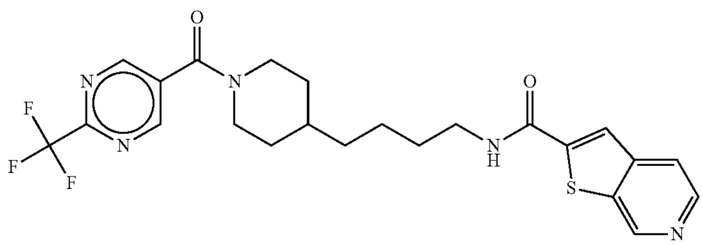 | N-[4-(1-{[2-(trifluoromethyl)pyrimidin-5-yl]carbonyl}piperidin-4-yl)butyl]thieno[2,3-c]pyridine-2-carboxamide |
| 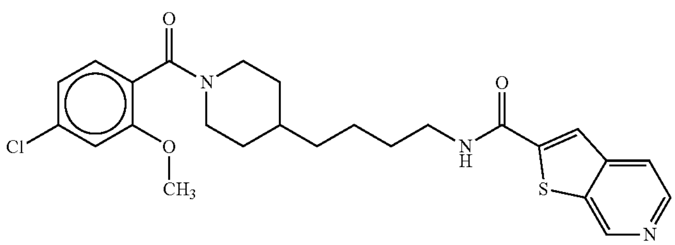 | N-(4-{1-[(4-chloro-2-methoxyphenyl)carbonyl]piperidin-4-yl}butyl)thieno[2,3-c]pyridine-2-carboxamide |
| 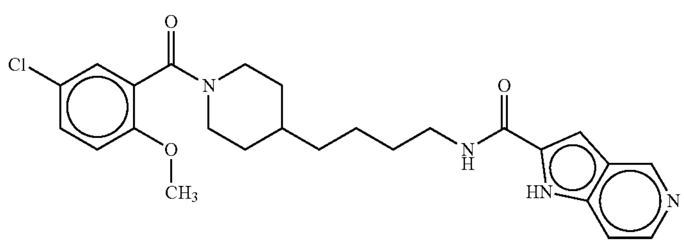 | N-(4-{1-[(5-chloro-2-methoxyphenyl)carbonyl]piperidin-4-yl}butyl)-1H-pyrrolo[3,2-c]pyridine-2-carboxamide |
| 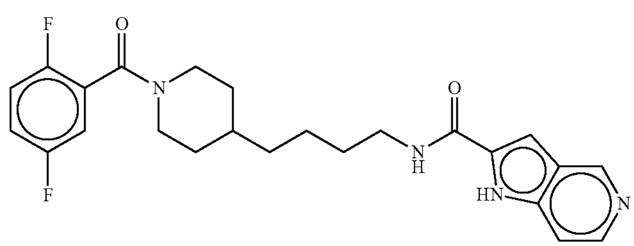 | N-(4-{1-[(2,5-difluorophenyl)carbonyl]piperidin-4-yl}butyl)-1H-pyrrolo[3,2-c]pyridine-2-carboxamide |
| 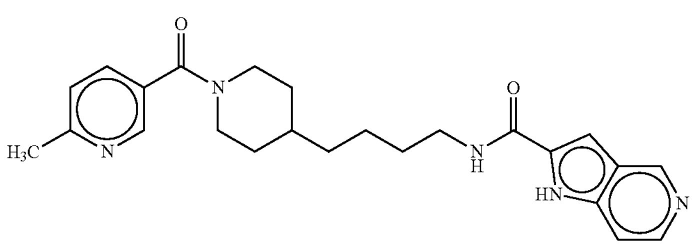 | N-(4-{1-[(6-methylpyridin-3-yl)carbonyl]piperidin-4-yl}butyl)-1H-pyrrolo[3,2-c]pyridine-2-carboxamide |
| 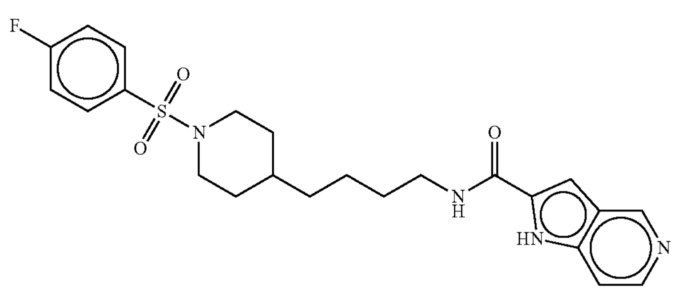 | N-(4-{1-[(4-fluorobenzene)sulfonyl]piperidin-4-yl}butyl)-1H-pyrrolo[3,2-c]pyridine-2-carboxamide |

TABLE 2-continued

| Structure | Chemical Name |
| --- | --- |
| 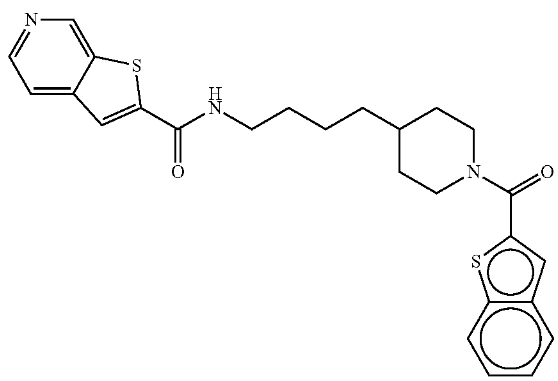 | N-(4-{1-[(1-benzothiophen-2-yl)carbonyl]piperidin-4-yl}butyl)thieno[2,3-c]pyridine-2-carboxamide |
| 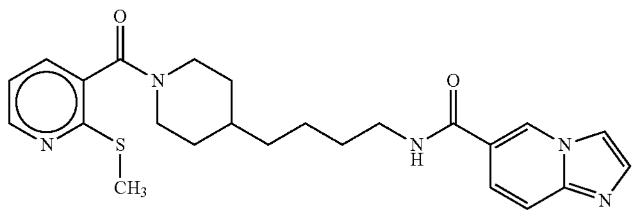 | N-[4-(1-{[2-(methylsulfanyl)pyridin-3-yl]carbonyl}piperidin-4-yl)butyl]imidazo[1,2-a]pyridine-6-carboxamide |
| 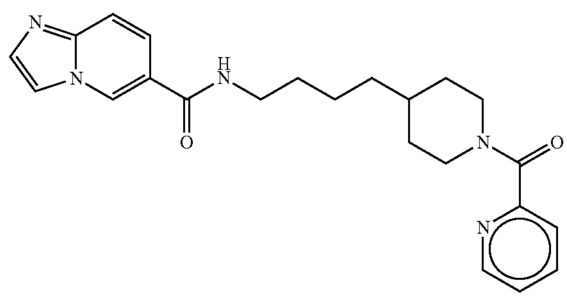 | N-(4-{1-[(pyridin-2-yl)carbonyl]piperidin-4-yl}butyl)imidazo[1,2-a]pyridine-6-carboxamide |
| 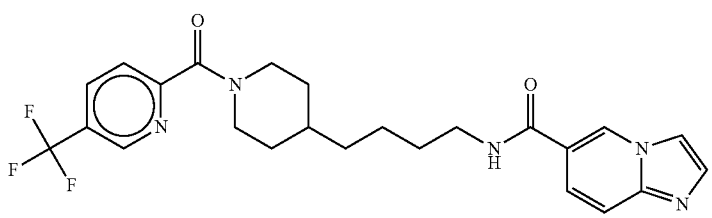 | N-[4-(1-{[5-(trifluoromethyl)pyridin-2-yl]carbonyl}piperidin-4-yl)butyl]imidazo[1,2-a]pyridine-6-carboxamide |
| 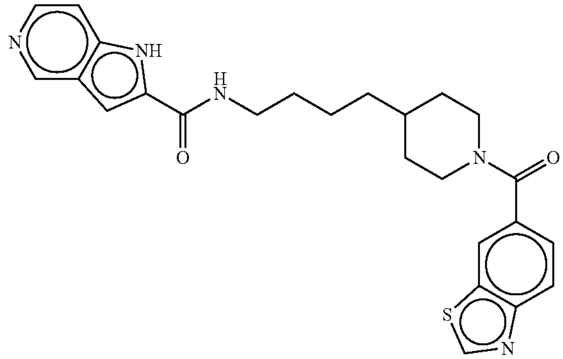 | N-(4-{1-[(1,3-benzothiazol-6-yl)carbonyl]piperidin-4-yl}butyl)-1H-pyrrolo[3,2-c]pyridine-2-carboxamide |

TABLE 2-continued

| Structure | Chemical Name |
|---|---|
| 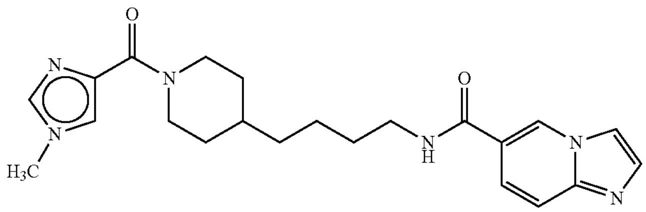 | N-(4-{1-[(1-methyl-1H-imidazol-4-yl)carbonyl]piperidin-4-yl}butyl)imidazo[1,2-a]pyridine-6-carboxamide |
| 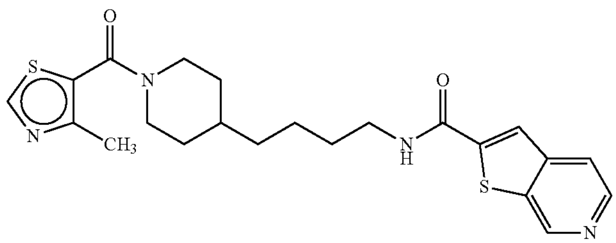 | N-(4-{1-[(4-methyl-1,3-thiazol-5-yl)carbonyl]piperidin-4-yl}butyl)thieno[2,3-c]pyridine-2-carboxamide |
| 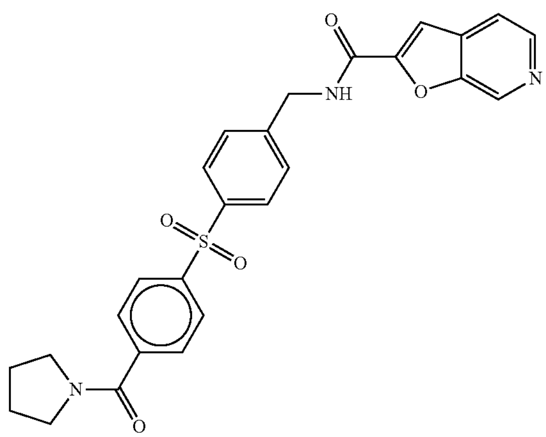 | N-{[4-({4-[(pyrrolidin-1-yl)carbonyl]benzene}sulfonyl)phenyl]methyl}furo[2,3-c]pyridine-2-carboxamide |
| 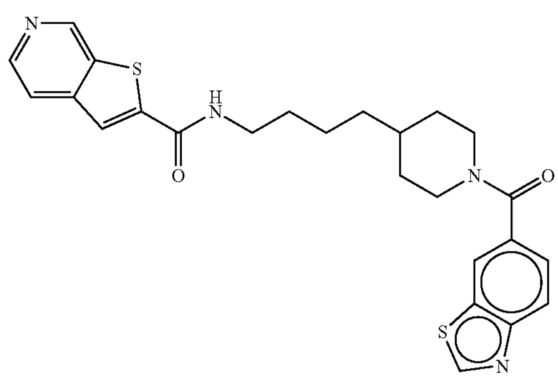 | N-(4-{1-[(1,3-benzothiazol-6-yl)carbonyl]piperidin-4-yl}butyl)thieno[2,3-c]pyridine-2-carboxamide |
| 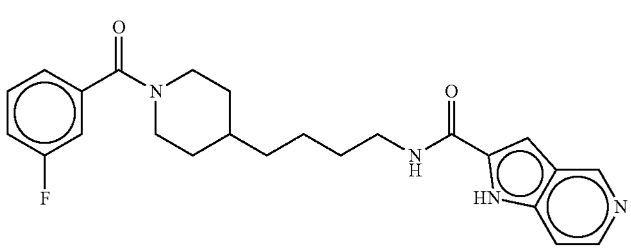 | N-(4-{1-[(3-fluorophenyl)carbonyl]piperidin-4-yl}butyl)-1H-pyrrolo[3,2-c]pyridine-2-carboxamide |

TABLE 2-continued

| Structure | Chemical Name |
|---|---|
| 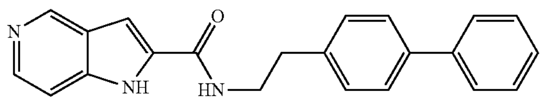 [SMILES: O=C(NCCc1ccc(-c2ccccc2)cc1)c1cc2cnccc2[nH]1] | N-[2-(4-phenylphenyl)ethyl]-1H-pyrrolo[3,2-c]pyridine-2-carboxamide |
| 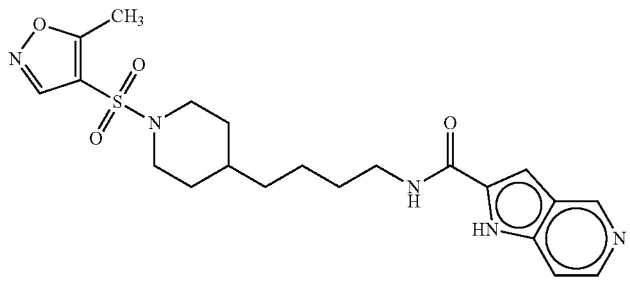 | N-{4-[1-(5-methyl-1,2-oxazole-4-sulfonyl)piperidin-4-yl]butyl}-1H-pyrrolo[3,2-c]pyridine-2-carboxamide |
| 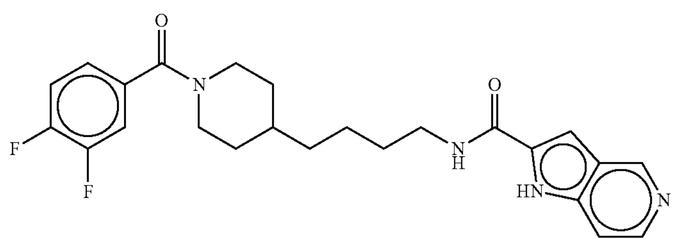 | N-(4-{1-[(3,4-difluorophenyl)carbonyl]piperidin-4-yl}butyl)-1H-pyrrolo[3,2-c]pyridine-2-carboxamide |
| 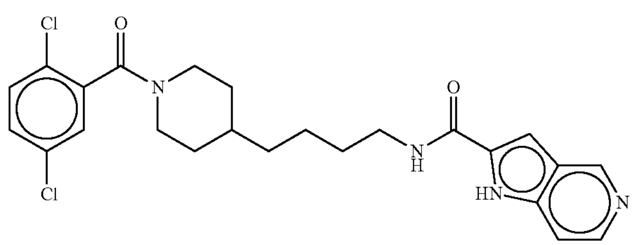 | N-(4-{1-[(2,5-dichlorophenyl)carbonyl]piperidin-4-yl}butyl)-1H-pyrrolo[3,2-c]pyridine-2-carboxamide |
| 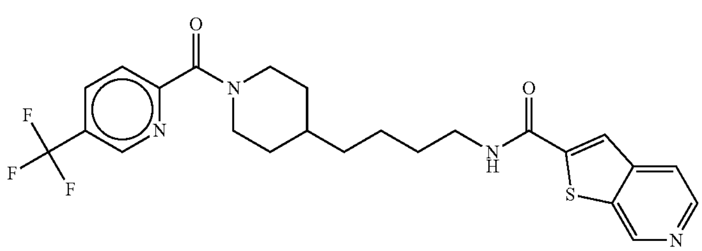 | N-[4-(1-{[5-(trifluoromethyl)pyridin-2-yl]carbonyl}piperidin-4-yl)butyl]thieno[2,3-c]pyridine-2-carboxamide |
| 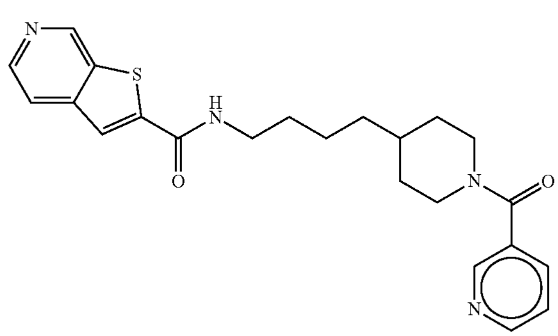 | N-(4-{1-[(pyridin-3-yl)carbonyl]piperidin-4-yl}butyl)thieno[2,3-c]pyridine-2-carboxamide |

TABLE 2-continued

| Structure | Chemical Name |
|---|---|
| 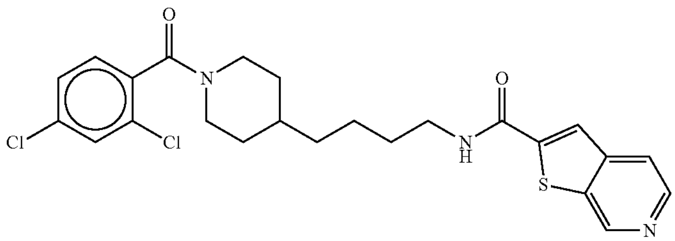 | N-(4-{1-[(2,4-dichlorophenyl)carbonyl]piperidin-4-yl}butyl)thieno[2,3-c]pyridine-2-carboxamide |
| 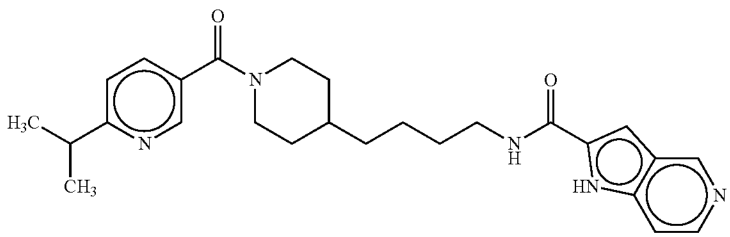 | N-[4-(1-{[6-(propan-2-yl)pyridin-3-yl]carbonyl}piperidin-4-yl)butyl]-1H-pyrrolo[3,2-c]pyridine-2-carboxamide |
| 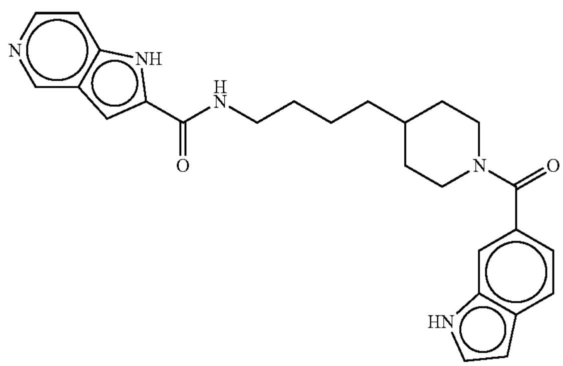 | N-(4-{1-[(1H-indol-6-yl)carbonyl]piperidin-4-yl}butyl)-1H-pyrrolo[3,2-c]pyridine-2-carboxamide |
| 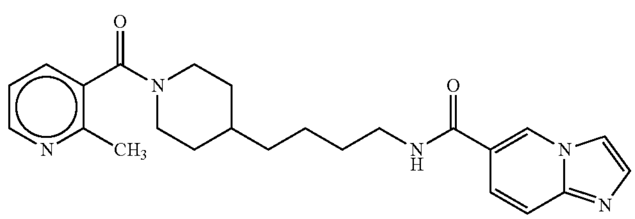 | N-(4-{1-[(2-methylpyridin-3-yl)carbonyl]piperidin-4-yl}butyl)imidazo[1,2-a]pyridine-6-carboxamide |
| 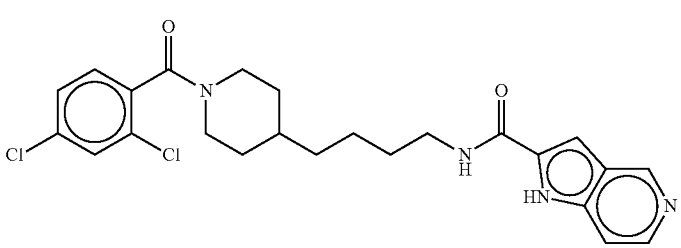 | N-(4-{1-[(2,4-dichlorophenyl)carbonyl]piperidin-4-yl}butyl)-1H-pyrrolo[3,2-c]pyridine-2-carboxamide |

TABLE 2-continued

| Structure | Chemical Name |
|---|---|
| 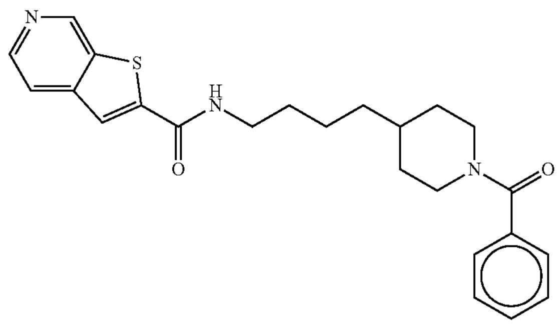 | N-[4-(1-benzoylpiperidin-4-yl)butyl]thieno[2,3-c]pyridine-2-carboxamide |
| 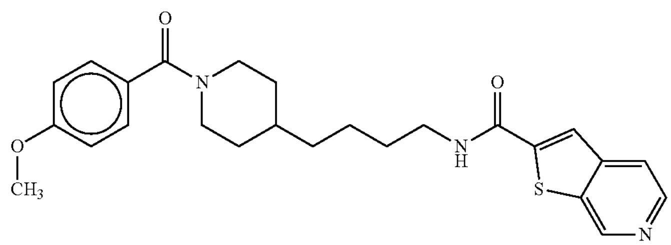 | N-(4-{1-[(4-methoxyphenyl)carbonyl]piperidin-4-yl}butyl)thieno[2,3-c]pyridine-2-carboxamide |
| 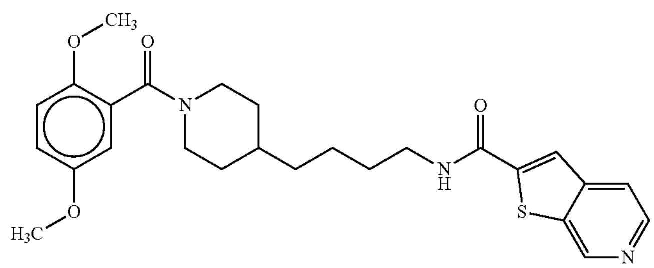 | N-(4-{1-[(2,5-dimethoxyphenyl)carbonyl]piperidin-4-yl}butyl)thieno[2,3-c]pyridine-2-carboxamide |
| 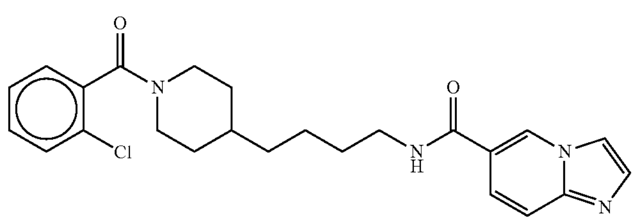 | N-(4-{1-[(2-chlorophenyl)carbonyl]piperidin-4-yl}butyl)imidazo[1,2-a]pyridine-6-carboxamide |
| 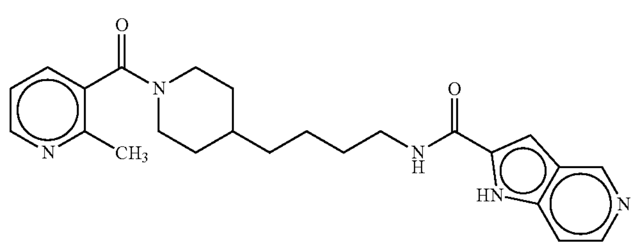 | N-(4-{1-[(2-methylpyridin-3-yl)carbonyl]piperidin-4-yl}butyl)-1H-pyrrolo[3,2-c]pyridine-2-carboxamide |
| 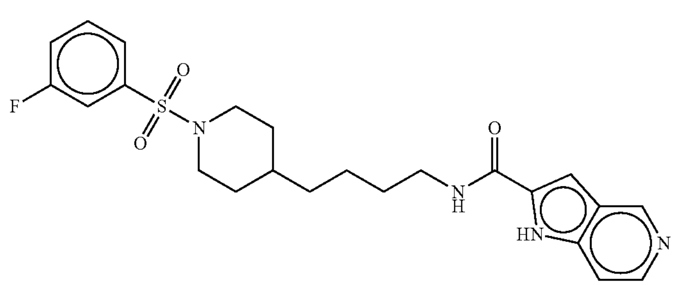 | N-(4-{1-[(3-fluorobenzene)sulfonyl]piperidin-4-yl}butyl)-1H-pyrrolo[3,2-c]pyridine-2-carboxamide |

TABLE 2-continued

| Structure | Chemical Name |
|---|---|
| 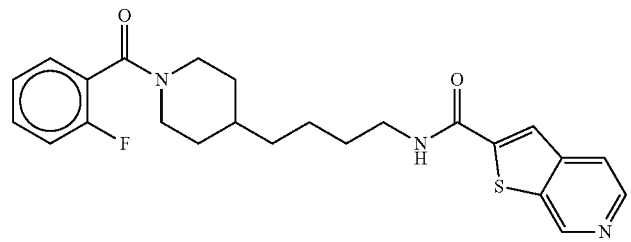 | N-(4-{1-[(2-fluorophenyl)carbonyl]piperidin-4-yl}butyl)thieno[2,3-c]pyridine-2-carboxamide |
| 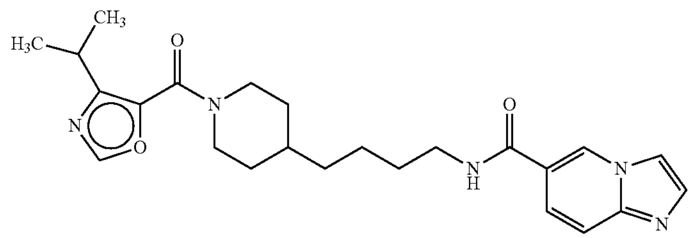 | N-[4-(1-{[4-(propan-2-yl)-1,3-oxazol-5-yl]carbonyl}piperidin-4-yl)butyl]imidazo[1,2-a]pyridine-6-carboxamide |
| 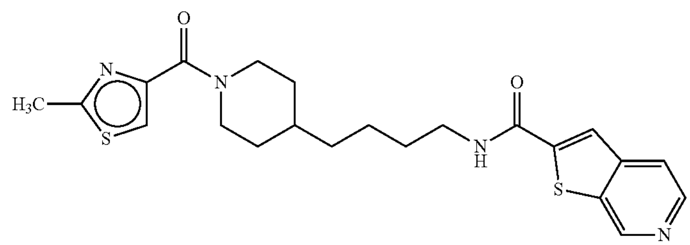 | N-(4-{1-[(2-methyl-1,3-thiazol-4-yl)carbonyl]piperidin-4-yl}butyl)thieno[2,3-c]pyridine-2-carboxamide |
| 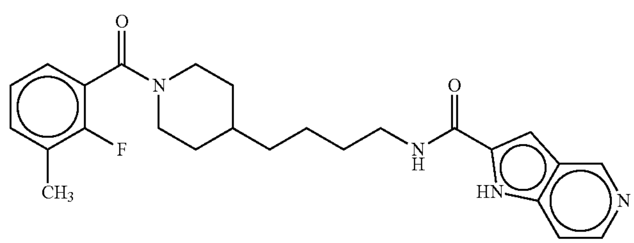 | N-(4-{1-[(2-fluoro-3-methylphenyl)carbonyl]piperidin-4-yl}butyl)-1H-pyrrolo[3,2-c]pyridine-2-carboxamide |
| 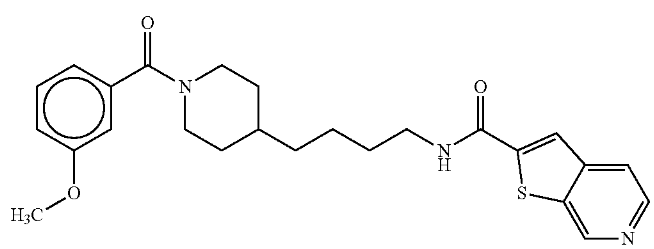 | N-(4-{1-[(3-methoxyphenyl)carbonyl]piperidin-4-yl}butyl)thieno[2,3-c]pyridine-2-carboxamide |
| 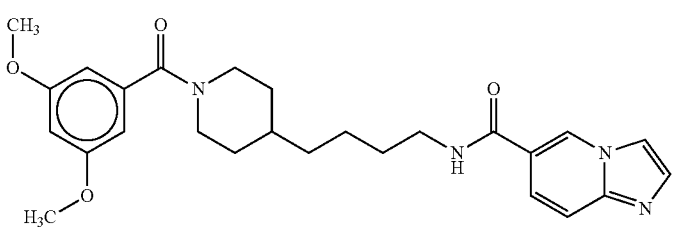 | N-(4-{1-[(3,5-dimethoxyphenyl)carbonyl]piperidin-4-yl}butyl)imidazo[1,2-a]pyridine-6-carboxamide |

TABLE 2-continued

| Structure | Chemical Name |
|---|---|
| 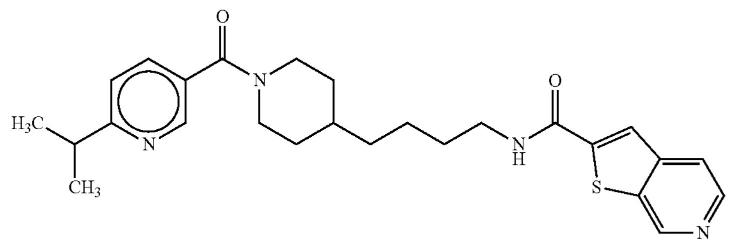 | N-[4-(1-{[6-(propan-2-yl)pyridin-3-yl]carbonyl}piperidin-4-yl)butyl]thieno[2,3-c]pyridine-2-carboxamide |
| 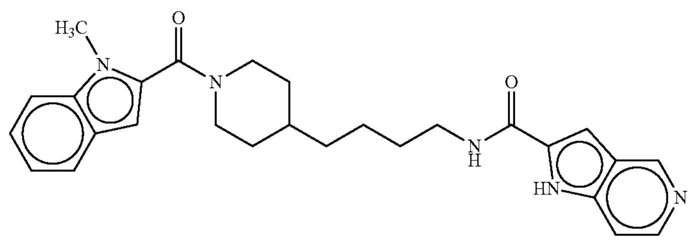 | N-(4-{1-[(1-methyl-1H-indol-2-yl)carbonyl]piperidin-4-yl}butyl)-1H-pyrrolo[3,2-c]pyridine-2-carboxamide |
| 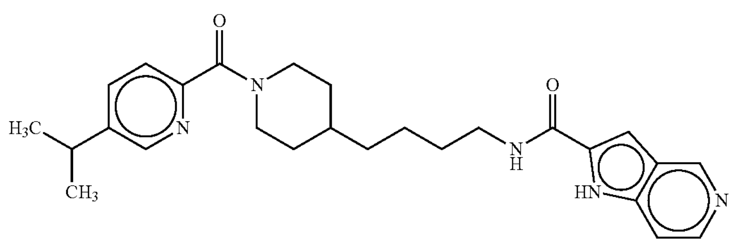 | N-[4-(1-{[5-(propan-2-yl)pyridin-2-yl]carbonyl}piperidin-4-yl)butyl]-1H-pyrrolo[3,2-c]pyridine-2-carboxamide |
| 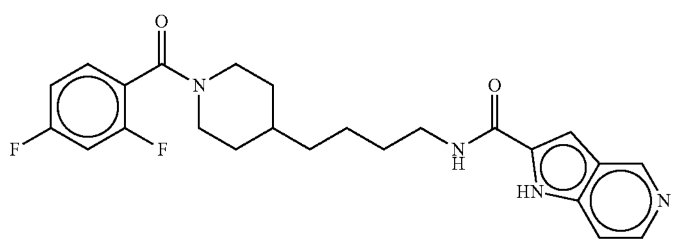 | N-(4-{1-[(2,4-difluorophenyl)carbonyl]piperidin-4-yl}butyl)-1H-pyrrolo[3,2-c]pyridine-2-carboxamide |
| 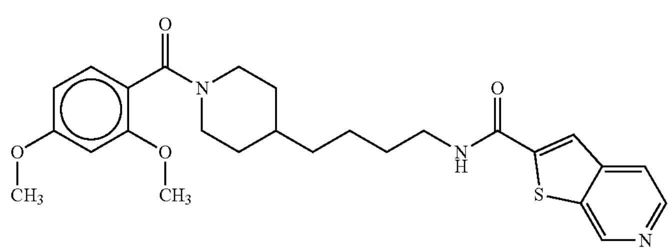 | N-(4-{1-[(2,4-dimethoxyphenyl)carbonyl]piperidin-4-yl}butyl)thieno[2,3-c]pyridine-2-carboxamide |
| 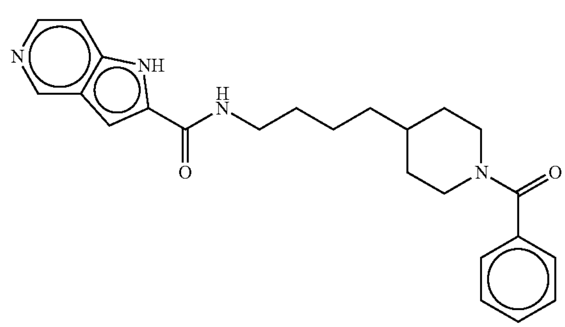 | N-[4-(1-benzoylpiperidin-4-yl)butyl]-1H-pyrrolo[3,2-c]pyridine-2-carboxamide |

TABLE 2-continued

| Structure | Chemical Name |
| --- | --- |
| 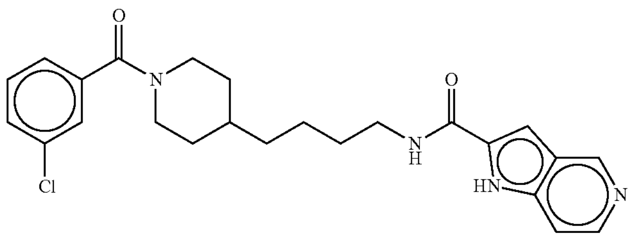 | N-(4-{1-[(3-chlorophenyl)carbonyl]piperidin-4-yl}butyl)-1H-pyrrolo[3,2-c]pyridine-2-carboxamide |
| 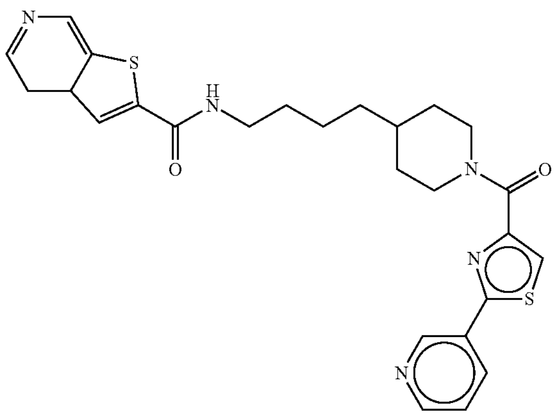 | N-[4-(1-{[2-(pyridin-3-yl)-1,3-thiazol-4-yl]carbonyl}piperidin-4-yl)butyl]thieno[2,3-c]pyridine-2-carboxamide |
| 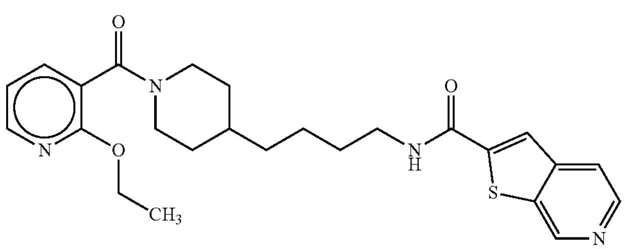 | N-(4-{1-[(2-ethoxypyridin-3-yl)carbonyl]piperidin-4-yl}butyl)thieno[2,3-c]pyridine-2-carboxamide |
| 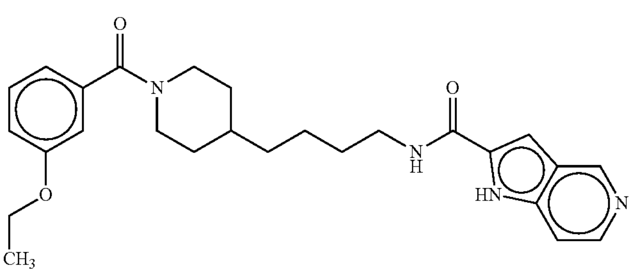 | N-(4-{1-[(3-ethoxyphenyl)carbonyl]piperidin-4-yl}butyl)-1H-pyrrolo[3,2-c]pyridine-2-carboxamide |
| 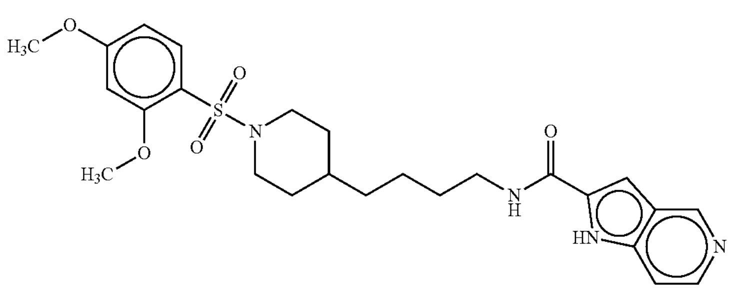 | N-(4-{1-[(2,4-dimethoxybenzene)sulfonyl]piperidin-4-yl}butyl)-1H-pyrrolo[3,2-c]pyridine-2-carboxamide |

TABLE 2-continued

| Structure | Chemical Name |
|---|---|
| 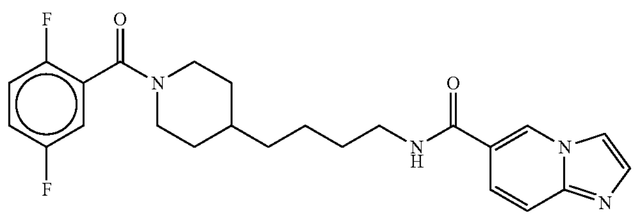 | N-(4-{1-[(2,5-difluorophenyl)carbonyl]piperidin-4-yl}butyl)imidazo[1,2-a]pyridine-6-carboxamide |
| 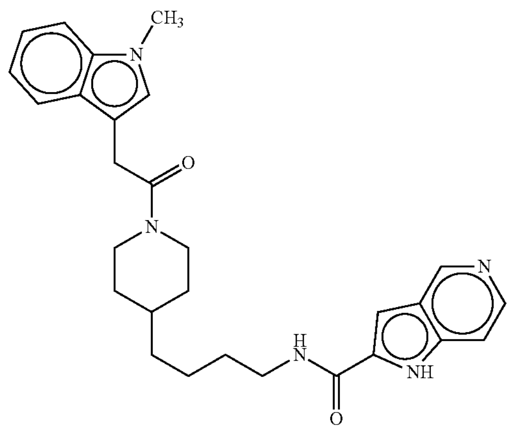 | N-(4-{1-[2-(1-methyl-1H-indol-3-yl)acetyl]piperidin-4-yl}butyl)-1H-pyrrolo[3,2-c]pyridine-2-carboxamide |
| 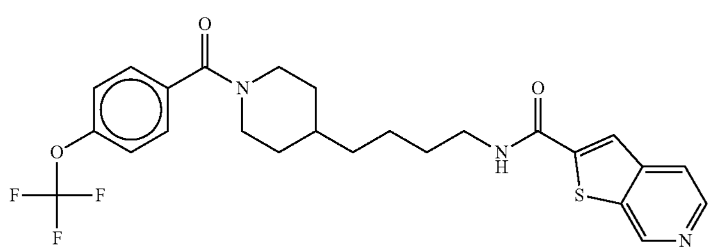 | N-[4-(1-{[4-(trifluoromethoxy)phenyl]carbonyl}piperidin-4-yl)butyl]thieno[2,3-c]pyridine-2-carboxamide |
| 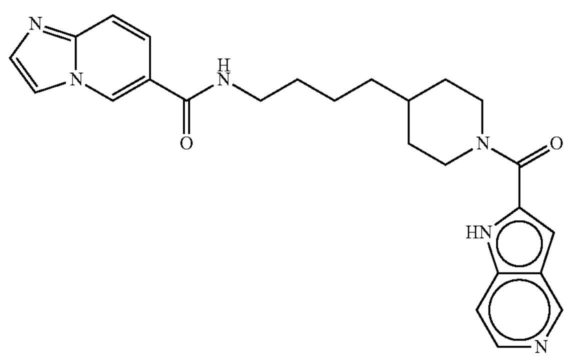 | N-{4--[1-({1H-pyrrolo[3,2-c]pyridin-2-yl}carbonyl)piperidin-4-yl]butyl}imidazo[1,2-a]pyridine-6-carboxamide |
| 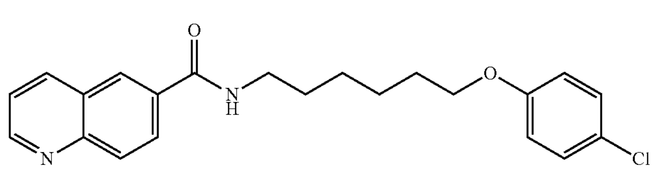 [SMILES: O=C(NCCCCCCOc1ccc(Cl)cc1)c1ccc2ncccc2c1] | N-[6-(4-chlorophenoxy)hexyl]quinoline-6-carboxamide |

TABLE 2-continued

| Structure | Chemical Name |
|---|---|
| 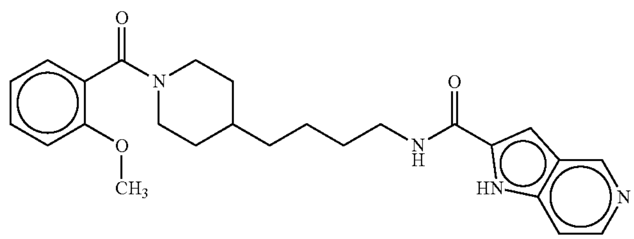 | N-(4-{1-[(2-methoxyphenyl)carbonyl]piperidin-4-yl}butyl)-1H-pyrrolo[3,2-c]pyridine-2-carboxamide |
| 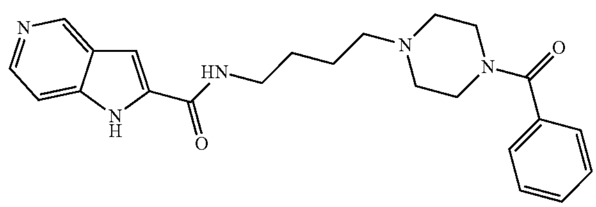 [SMILES: O=C(NCCCCN1CCN(C(=O)c2ccccc2)CC1)c1cc2cnccc2[nH]1] | N-[4-(4-benzoylpiperazin-1-yl)butyl]-1H-pyrrolo[3,2-c]pyridine-2-carboxamide |
| 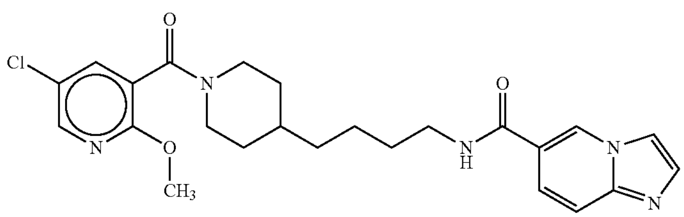 | N-(4-{1-[(5-chloro-2-methoxypyridin-3-yl)carbonyl]piperidin-4-yl}butyl)imidazo[1,2-a]pyridine-6-carboxamide |
| 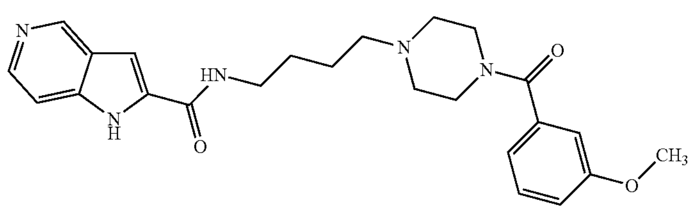 [SMILES: COc1cccc(C(=O)N2CCN(CCCCNC(=O)c3cc4cnccc4[nH]3)CC2)c1] | N-(4-{4-[(3-methoxyphenyl)carbonyl]piperazin-1-yl}butyl)-1H-pyrrolo[3,2-c]pyridine-2-carboxamide |
| 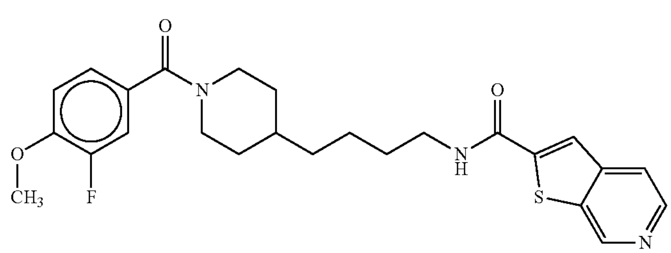 | N-(4-{1-[(3-fluoro-4-methoxyphenyl)carbonyl]piperidin-4-yl}butyl)thieno[2,3-c]pyridine-2-carboxamide |
| 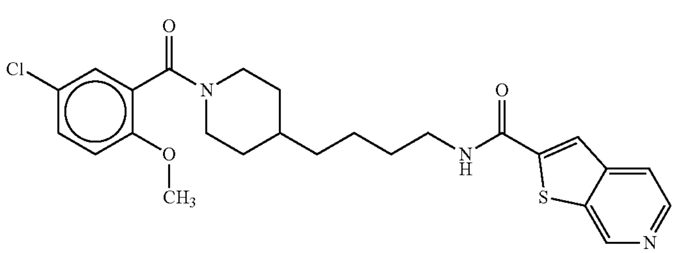 | N-(4-{1-[(5-chloro-2-methoxyphenyl)carbonyl]piperidin-4-yl}butyl)thieno[2,3-c]pyridine-2-carboxamide |

TABLE 2-continued

| Structure | Chemical Name |
|---|---|
| 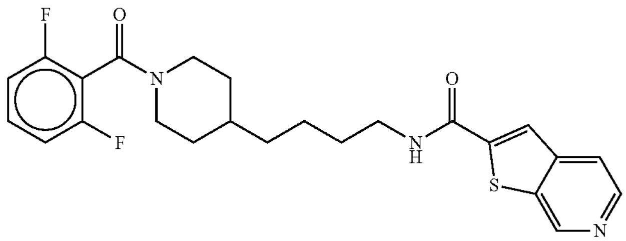 | N-(4-{1-[(2,6-difluorophenyl)carbonyl]piperidin-4-yl}butyl)thieno[2,3-c]pyridine-2-carboxamide |
| 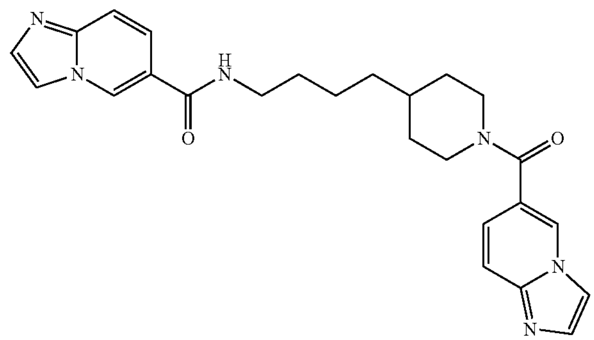 [SMILES: O=C(NCCCCC1CCN(C(=O)c2ccc3nccn3c2)CC1)c1ccc2nccn2c1] | N-{4-[1-({imidazo[1,2-a]pyridin-6-yl}carbonyl)piperidin-4-yl]butyl}imidazo[1,2-a]pyridine-6-carboxamide |
| 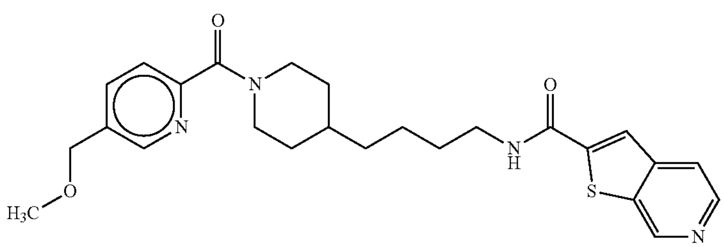 | N-[4-(1-{[5-(methoxymethyl)pyridin-2-yl]carbonyl}piperidin-4-yl)butyl]thieno[2,3-c]pyridine-2-carboxamide |
| 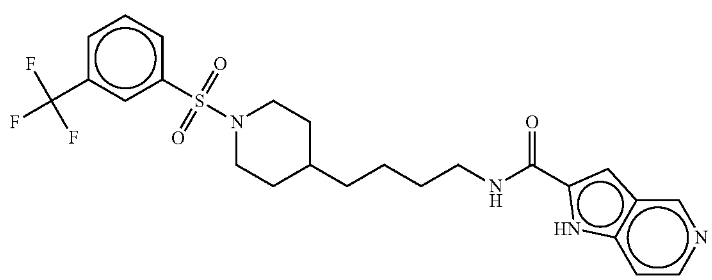 | N-[4-(1-{[3-(trifluoromethyl)benzene]sulfonyl}piperidin-4-yl)butyl]-1H-pyrrolo[3,2-c]pyridine-2-carboxamide |
| 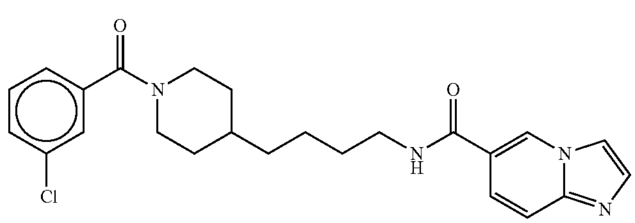 | N-(4-{1-[(3-chlorophenyl)carbonyl]piperidin-4-yl}butyl)imidazo[1,2-a]pyridine-6-carboxamide |
| 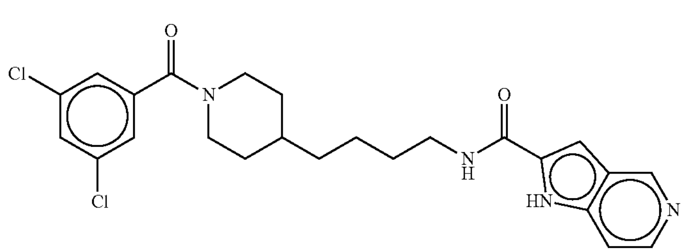 | N-(4-{1-[(3,5-dichlorophenyl)carbonyl]piperidin-4-yl}butyl)-1H-pyrrolo[3,2-c]pyridine-2-carboxamide |

TABLE 2-continued

| Structure | Chemical Name |
|---|---|
| 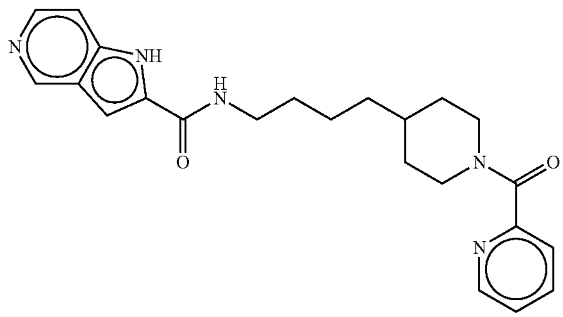 | N-(4-{1-[(pyridin-2-yl)carbonyl]piperidin-4-yl}butyl)-1H-pyrrolo[3,2-c]pyridine-2-carboxamide |
| 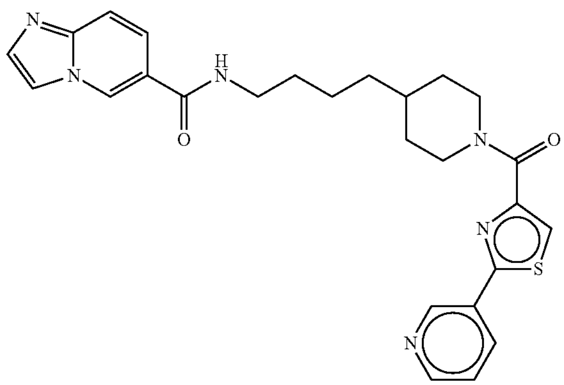 | N-[4-(1-{[2-(pyridin-3-yl)-1,3-thiazol-4-yl]carbonyl}piperidin-4-yl)butyl]imidazo[1,2-a]pyridine-6-carboxamide |
| 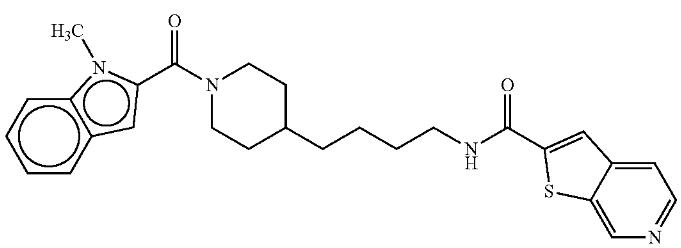 | N-(4-{1-[(1-methyl-1H-indol-2-yl)carbonyl]piperidin-4-yl}butyl)thieno[2,3-c]pyridine-2-carboxamide |
| 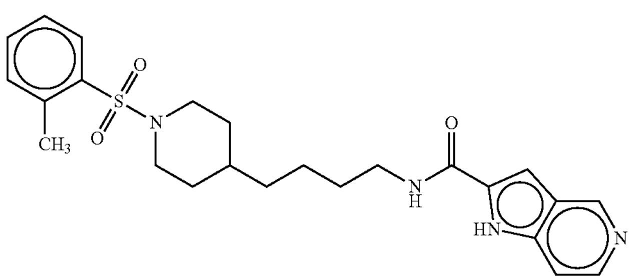 | N-(4-{1-[(2-methylbenzene)sulfonyl]piperidin-4-yl}butyl)-1H-pyrrolo[3,2-c]pyridine-2-carboxamide |
| 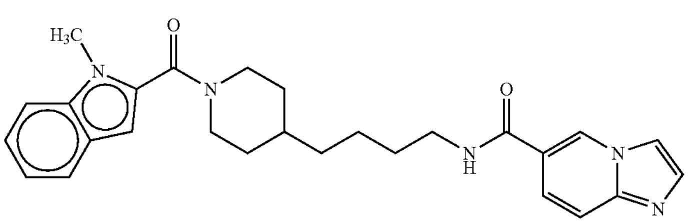 | N-(4-{1-[(1-rnethyl-1H-indol-2-yl)carbonyl]piperidin-4-yl}butyl)imidazo[1,2-a]pyridine-6-carboxamide |

TABLE 2-continued

| Structure | Chemical Name |
|---|---|
| 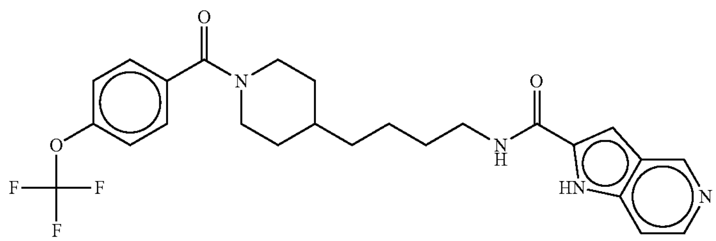 | N-[4-(1-{[4-(trifluoromethoxy)phenyl]carbonyl}piperidin-4-yl)butyl]-1H-pyrrolo[3,2-c]pyridine-2-carboxamide |
| 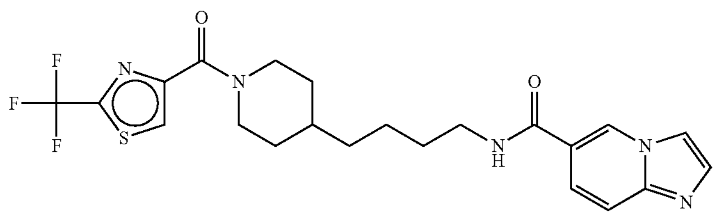 | N-[4-(1-{[2-(trifluoromethyl)-1,3-thiazol-4-yl]carbonyl}piperidin-4-yl)butyl]imidazo[1,2-a]pyridine-6-carboxamide |
| 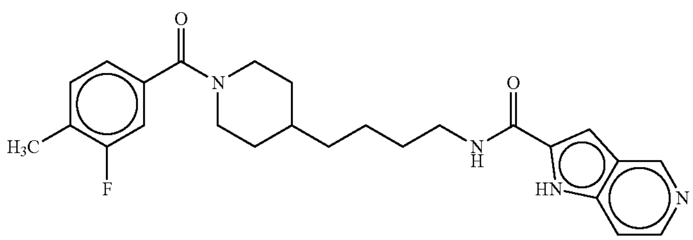 | N-(4-{1-[(3-fluoro-4-methylphenyl)carbonyl]piperidin-4-yl}butyl)-1H-pyrrolo[3,2-c]pyridine-2-carboxamide |
| 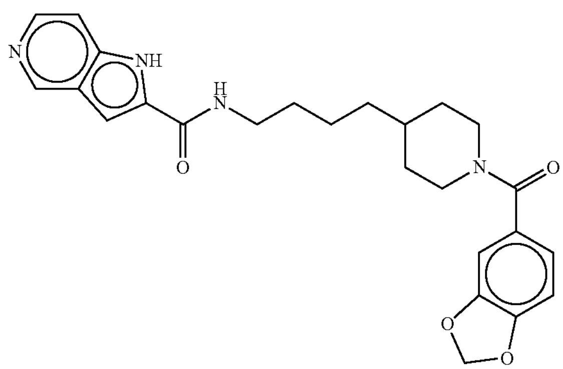 | N-(4-{1-[(2H-1,3-benzodioxol-5-yl)carbonyl]piperidin-4-yl}butyl)-1H-pyrrolol[3,2-c]pyridine-2-carboxamide |
| 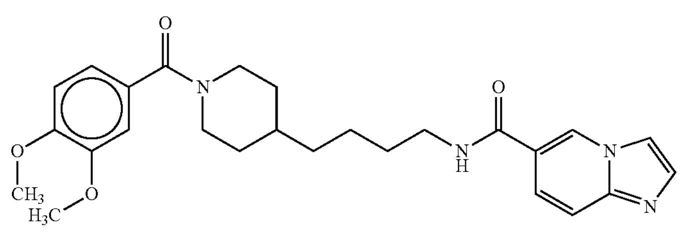 | N-(4-{1-[(3,4-dimethoxyphenyl)carbonyl]piperidin-4-yl}butyl)imidazo[1,2-a]pyridine-6-carboxamide |
| 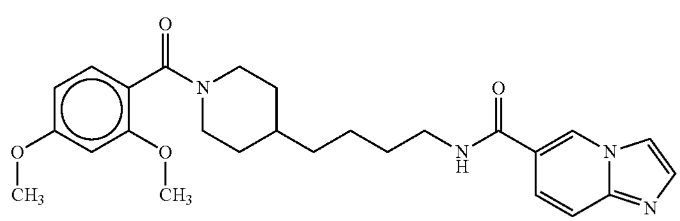 | N-(4-{1-[(2,4-dimethoxyphenyl)carbonyl]piperidin-4-yl}butyl)imidazo[1,2-a]pyridine-6-carboxamide |

TABLE 2-continued

| Structure | Chemical Name |
|---|---|
| 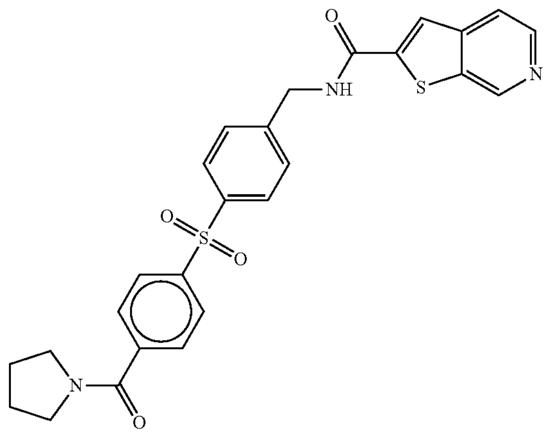 | N-{[4-({4-[(pyrrolidin-1-yl)carbonyl]benzene}sulfonyl)phenyl]methyl}thieno[2,3-c]pyridine-2-carboxamide |
| 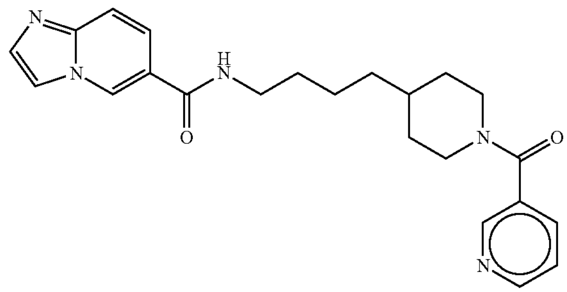 | N-(4-{1-[(pyridin-3-yl)carbonyl]piperidin-4-yl}butyl)imidazo[1,2-a]pyridine-6-carboxamide |
| 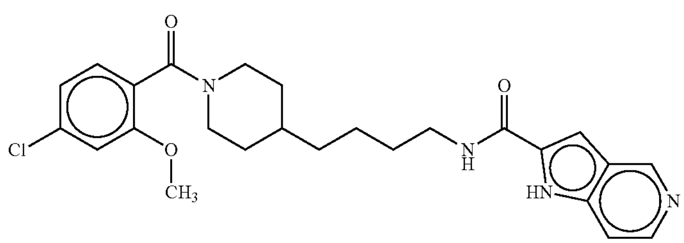 | N-(4-{1-[(4-chloro-2-methoxyphenyl)carbonyl]piperidin-4-yl}butyl)-1H-pyrrolo[3,2-c]pyridine-2-carboxamide |
| 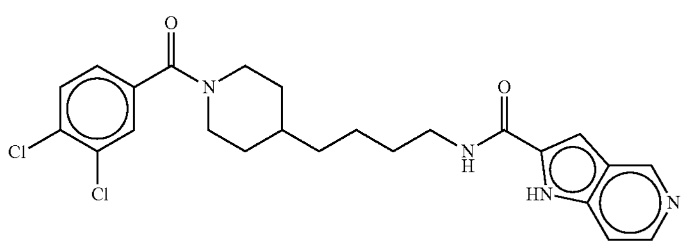 | N-(4-{1-[(3,4-dichlorophenyl)carbonyl]piperidin-4-yl}butyl)-1H-pyrrolo[3,2-c]pyridine-2-carboxamide |
| 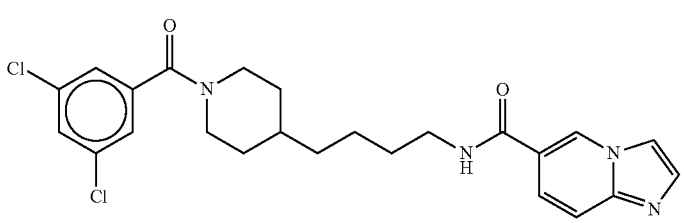 | N-(4-{1-[(3,5-dichlorophenyl)carbonyl]piperidin-4-yl}butyl)imidazo[1,2-a]pyridine-6-carboxamide |
| 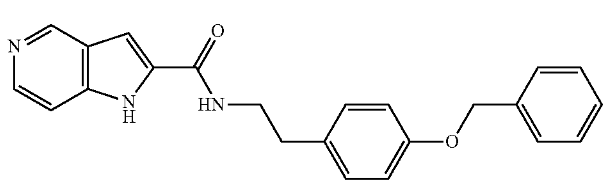 [SMILES: O=C(NCCc1ccc(OCc2ccccc2)cc1)c1cc2cnccc2[nH]1] | N-(4-(benzyloxy)phenethyl)-1H-pyrrolo[3,2-c]pyridine-2-carboxamide |

TABLE 2-continued

| Structure | Chemical Name |
|---|---|
| 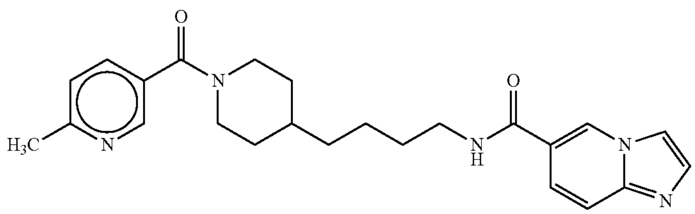 | N-(4-{1-[(6-methylpyridin-3-yl)carbonyl]piperidin-4-yl}butyl)imidazo[1,2-a]pyridine-6-carboxamide |
| 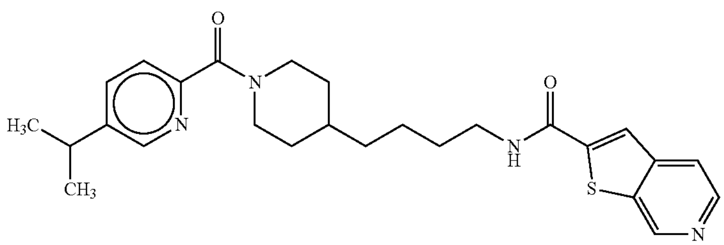 | N-[4-(1-{[5-(propan-2-yl)pyridin-2-yl]carbonyl}piperidin-4-yl)butyl]thieno[2,3-c]pyridine-2-carboxamide |
| 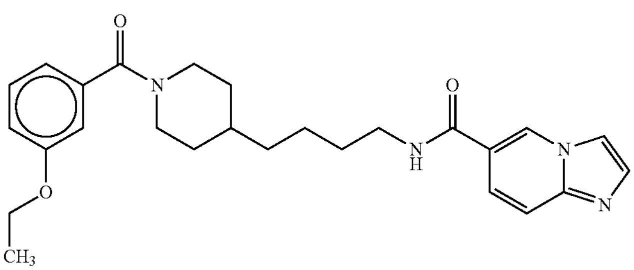 | N-(4-{1-[(3-ethoxyphenyl)carbonyl]piperidin-4-yl}butyl)imidazo[1,2-a]pyridine-6-carboxamide |
| 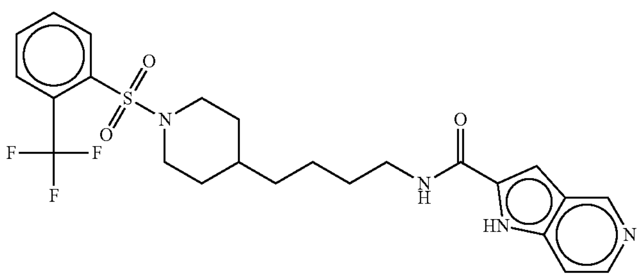 | N-[4-(1-{[2-(trifluoromethyl)benzene]sulfonyl}piperidin-4-yl)butyl]-1H-pyrrolo[3,2-c]pyridine-2-carboxamide |
| 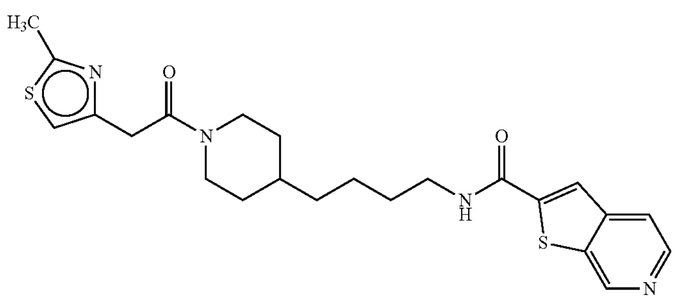 | N-(4-{1-[2-(2-methyl-1,3-thiazol-4-yl)acetyl]piperidin-4-yl}butyl)thieno[2,3-c]pyridine-2-carboxamide |
| 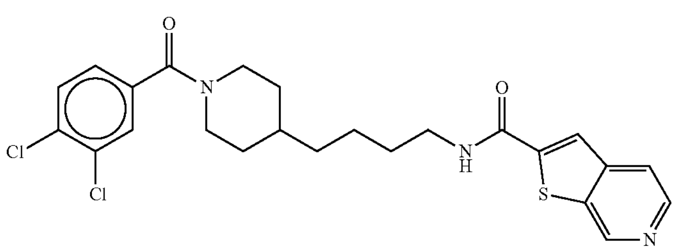 | N-(4-{1-[(3,4-dichlorophenyl)carbonyl]piperidin-4-yl}butyl)thieno[2,3-c]pyridine-2-carboxamide |

TABLE 2-continued

| Structure | Chemical Name |
|---|---|
| 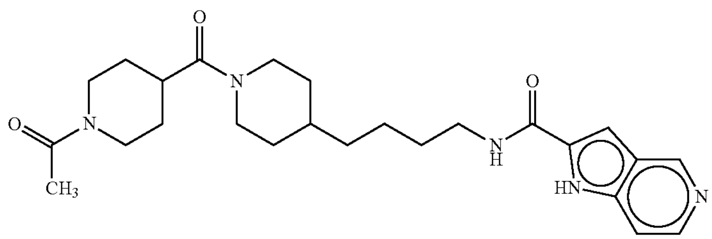 | N-(4-{1-[(1-acetylpiperidin-4-yl)carbonyl]piperidin-4-yl}butyl)-1H-pyrrolo[3,2-c]pyridine-2-carboxamide |
| 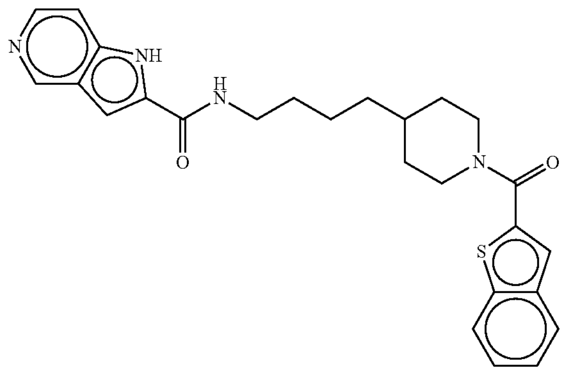 | N-(4-{1-[(1-benzothiophen-2-yl)carbonyl]piperidin-4-yl}butyl)-1H-pyrrolo[3,2-c]pyridine-2-carboxamide |
| 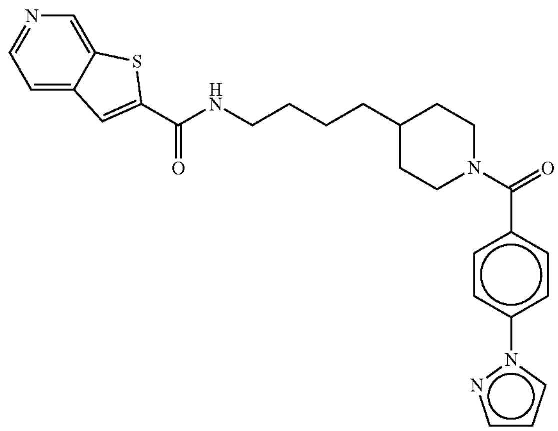 | N-[4-(1-{[4-(1H-pyrazol-1-yl)phenyl]carbonyl}piperidin-4-yl)butyl]thieno[2,3-c]pyridine-2-carboxamide |
| 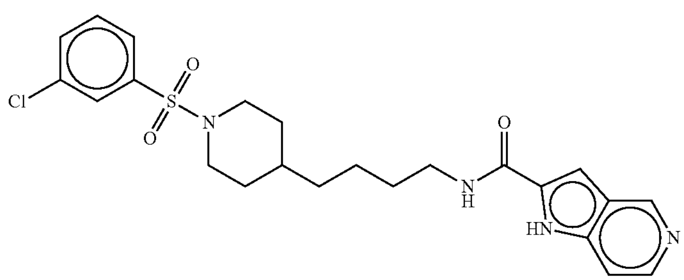 | N-(4-{1-[(3-chlorobenzene)sulfonyl]piperidin-4-yl}butyl)-1H-pyrrolo[3,2-c]pyridine-2-carboxamide |
| 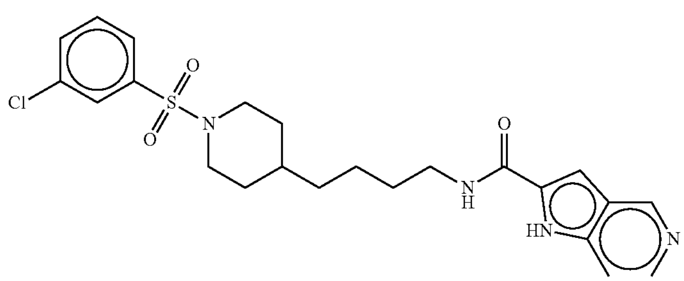 | N-[4-(1-{[6-(trifluoromethyl)pyridin-3-yl]carbonyl}piperidin-4-yl)butyl]thieno[2,3-c]pyridine-2-carboxamide |

TABLE 2-continued

| Structure | Chemical Name |
|---|---|
| 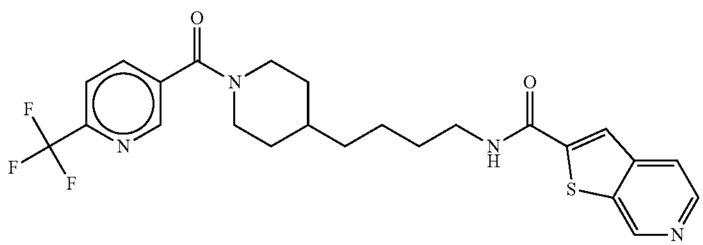 | N-(4-{1-[(2-methyl-1,3-thiazol-4-yl)carbonyl]piperidin-4-yl}butyl)-1H-pyrrolo[3,2-c]pyridine-2-carboxamide |
| 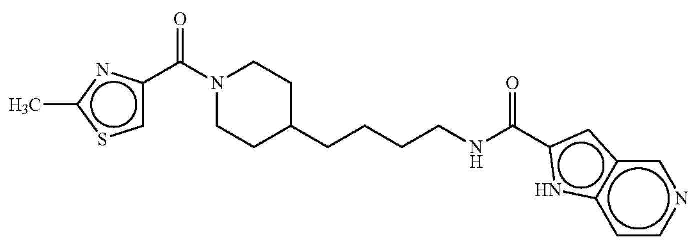 | N-[4-(1-{[5-(propan-2-yl)pyridin-2-yl]carbonyl}piperidin-4-yl)butyl]imidazo[1,2-a]pyridine-6-carboxamide |
| 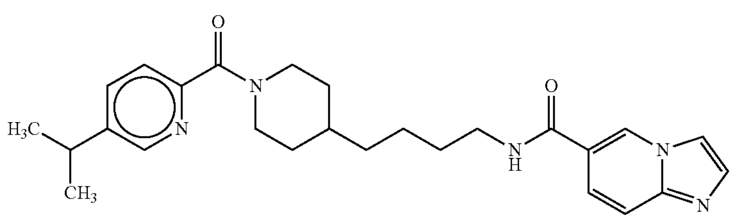 | N-(4-{1-[(4-methoxyphenyl)carbonyl]piperidin-4-yl}butyl)-1H-pyrrolo[3,2-c]pyridine-2-carboxamide |
| 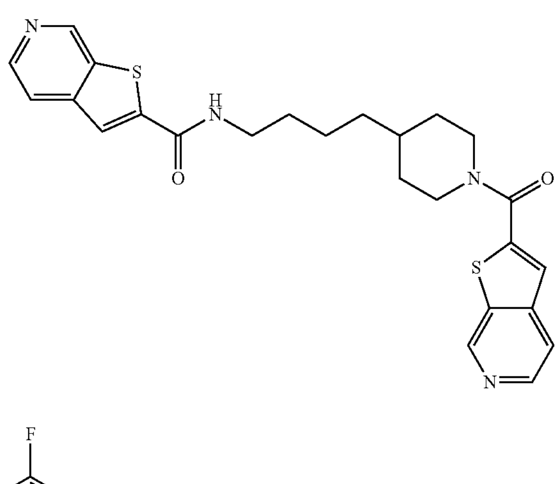 | N-{4-[1-({thieno[2,3-c]pyridin-2-yl}carbonyl)piperidin-4-yl]butyl}thieno[2,3-c]pyridine-2-carboxamide |
| 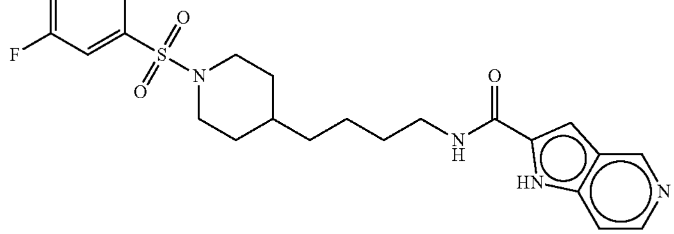 | N-(4-{1-[(3,5-difluorobenzene)sulfonyl]piperidin-4-yl}butyl)-1H-pyrrolo[3,2-c]pyridine-2-carboxamide |

TABLE 2-continued

| Structure | Chemical Name |
|---|---|
| 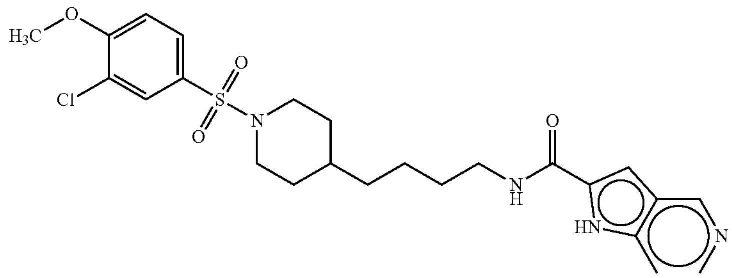 | N-(4-{1-[(3-chloro-4-methoxybenzene)sulfonyl]piperidin-4-yl}butyl)-1H-pyrrolo[3,2-c]pyridine-2-carboxamide |
| 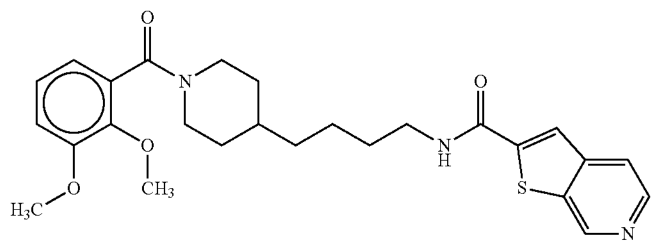 | N-(4-{1-[(2,3-dimethoxyphenyl)carbonyl]piperidin-4-yl}butyl)thieno[2,3-c]pyridine-2-carboxamide |
| 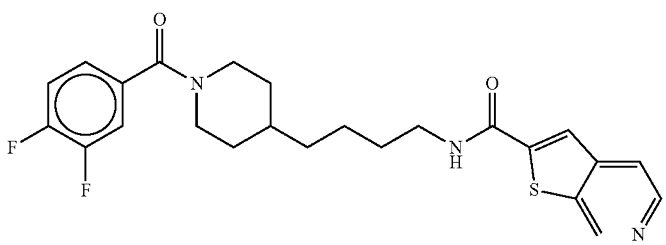 | N-(4-{1-[(3,4-difluorophenyl)carbonyl]piperidin-4-yl}butyl)thieno[2,3-c]pyridine-2-carboxamide |
| 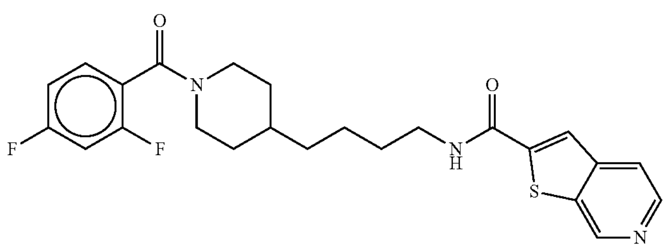 | N-(4-{1-[(2,4-difluorophenyl)carbonyl]piperidin-4-yl}butyl)thieno[2,3-c]pyridine-2-carboxamide |
| 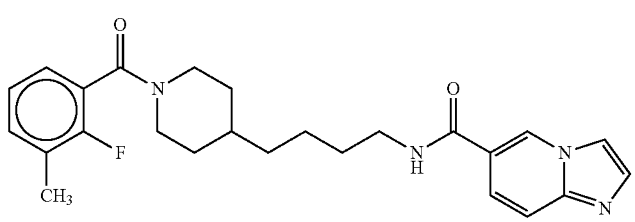 | N-(4-{1-[(2-fluoro-3-methylphenyl)carbonyl]piperidin-4-yl}butyl)imidazo[1,2-a]pyridine-6-carboxamide |
| 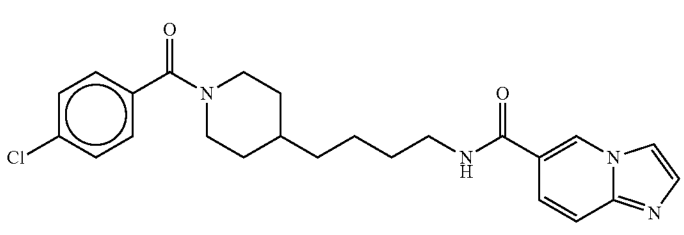 | N-(4-{1-[(4-chlorophenyl)carbonyl]piperidin-4-yl}butyl)imidazo[1,2-a]pyridine-6-carboxamide |

TABLE 2-continued

| Structure | Chemical Name |
|---|---|
| 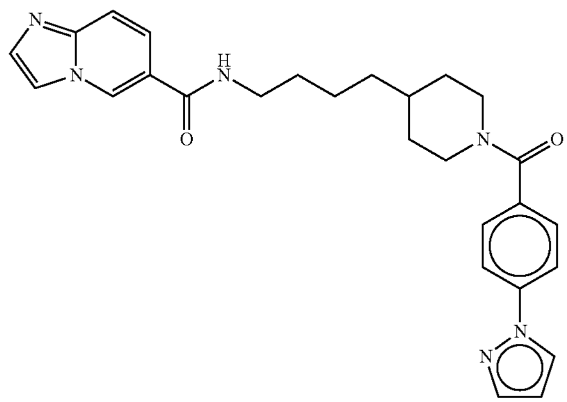 | N-[4-(1-{[4-(1H-pyrazol-1-yl)phenyl]carbonyl}piperidin-4-yl)butyl]imidazo[1,2-a]pyridine-6-carboxamide |
| 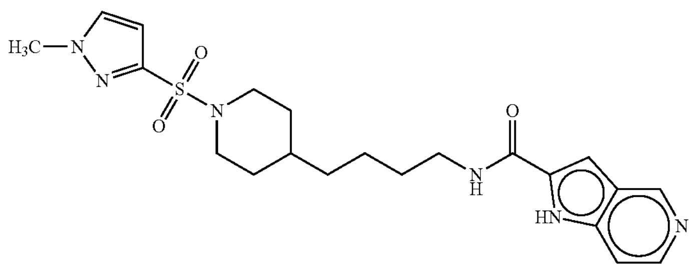 | N-{4-[1-(1-methyl-1H-pyrazole-3-sulfonyl)piperidin-4-yl]butyl}-1H-pyrrolo[3,2-c]pyridine-2-carboxamide |
| 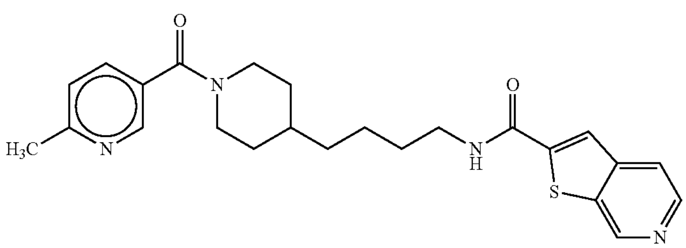 | N-(4-{1-[(6-methylpyridin-3-yl)carbonyl]piperidin-4-yl}butyl)thieno[2,3-c]pyridine-2-carboxamide |
| 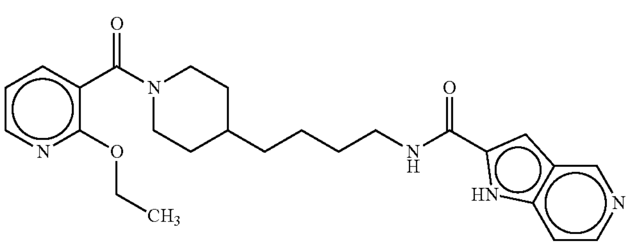 | N-(4-{1-[(2-ethoxypyridin-3-yl)carbonyl]piperidin-4-yl}butyl)-1H-pyrrolo[3,2-c]pyridine-2-carboxamide |
| 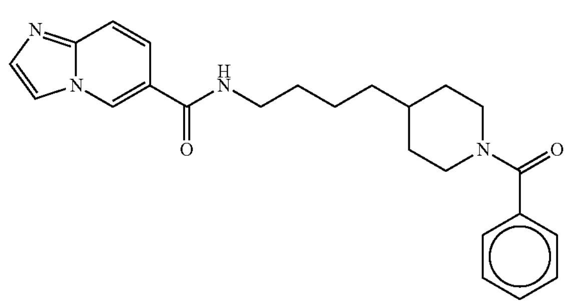 | N-[4-(1-benzoylpiperidin-4-yl)butyl]imidazo[1,2-a]pyridine-6-carboxamide |

TABLE 2-continued

| Structure | Chemical Name |
|---|---|
| 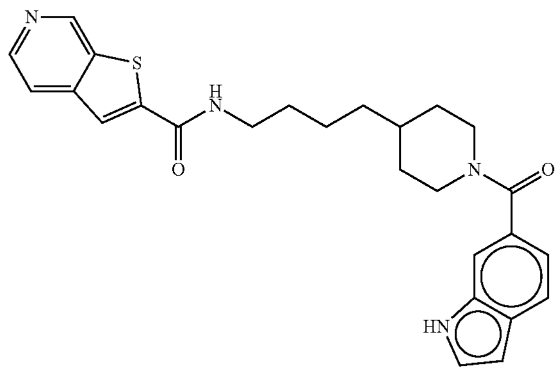 | N-(4-{1-[(1H-indol-6-yl)carbonyl]piperidin-4-yl}butyl)thieno[2,3-c]pyridine-2-carboxamide |
| 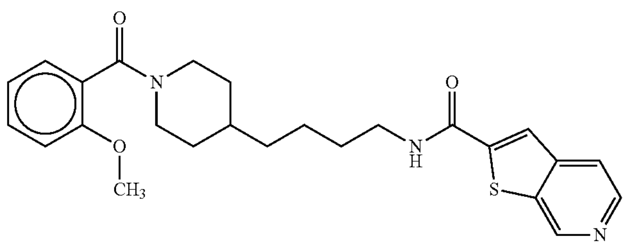 | N-(4-{1-[(2-methoxyphenyl)carbonyl]piperidin-4-yl}butyl)thieno[3,2-c]pyridine-2-carboxamide |
| 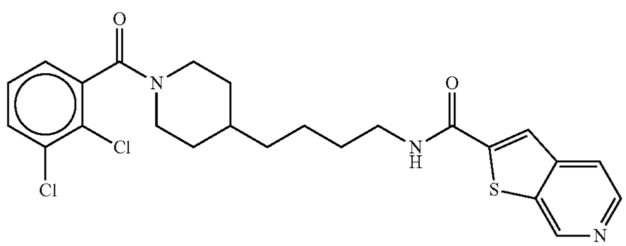 | N-(4-{1-[(2,3-dichlorophenyl)carbonyl]piperidin-4-yl}butyl)thieno[2,3-c]pyridine-2-carboxamide |
| 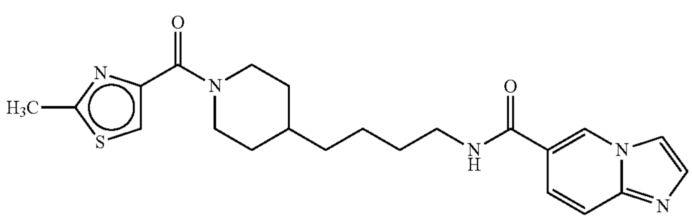 | N-(4-{1-[(2-methyl-1,3-thiazol-4-yl)carbonyl]piperidin-4-yl}butyl)imidazo[1,2-a]pyridine-6-carboxamide |
| 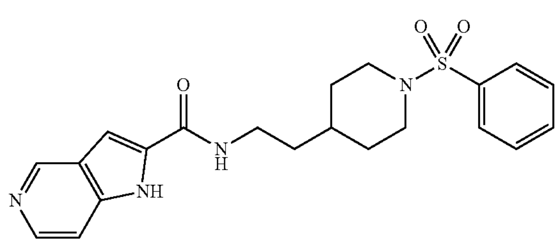 [SMILES: O=C(NCCC1CCN(S(=O)(=O)c2ccccc2)CC1)c1cc2cnccc2[nH]1] | N-{2-[1-(benzenesulfonyl)piperidin-4-yl]ethyl}-1H-pyrrolo[3,2-c]pyridine-2-carboxamide |
| 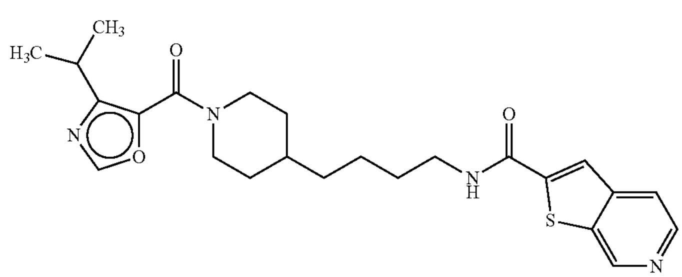 | N-[4-(1-{[4-(propan-2-yl)-1,3-oxazol-5-yl]carbonyl}piperidin-4-yl)butyl]thieno[2,3-c]pyridine-2-carboxamide |

TABLE 2-continued

| Structure | Chemical Name |
|---|---|
| 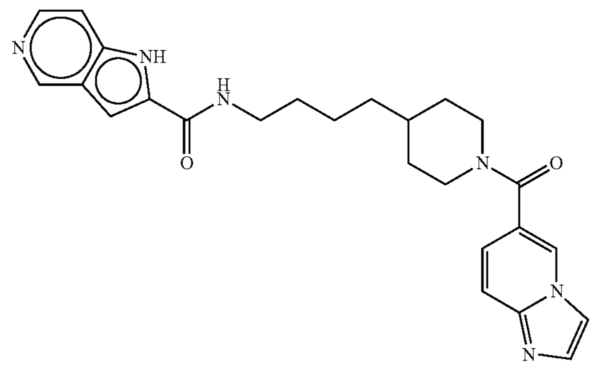 | N-{4-[1-({imidazo[1,2-a]pyridin-6-yl}carbonyl)piperidin-4-yl]butyl}-1H-pyrrolo[3,2-c]pyridine-2-carboxamide |
| 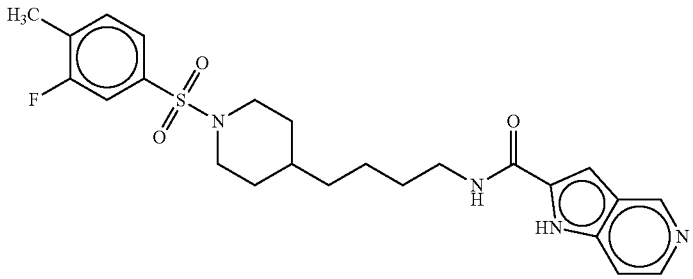 | N-(4-{1-[(3-fluoro-4-methylbenzene)sulfonyl]piperidin-4-yl}butyl)-1H-pyrrolo[3,2-c]pyridine-2-carboxamide |
| 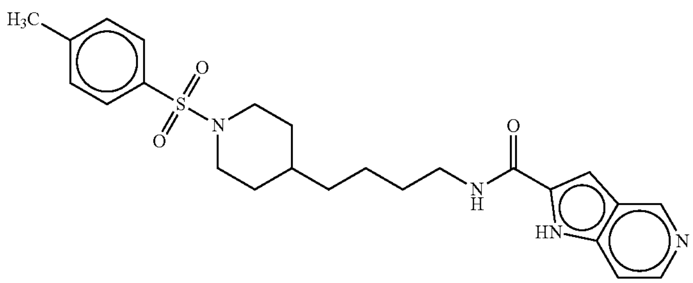 | N-(4-{1-[(4-methylbenzene)sulfonyl]piperidin-4-yl}butyl)-1H-pyrrolo[3,2-c]pyridine-2-carboxamide |
| 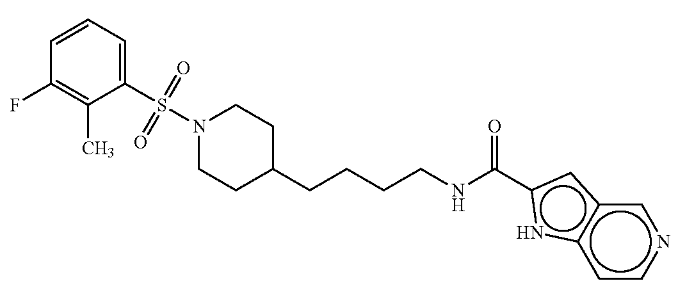 | N-(4-{1-[(3-fluoro-2-methylbenzene)sulfonyl]piperidin-4-yl}butyl)-1H-pyrrolo[3,2-c]pyridine-2-carboxamide |
| 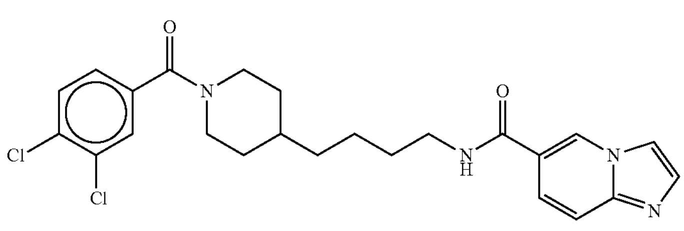 | N-(4-{1-[(3,4-dichlorophenyl)carbonyl]piperidin-4-yl}butyl)imidazo[1,2-a]pyridine-6-carboxamide |

TABLE 2-continued

| Structure | Chemical Name |
|---|---|
| 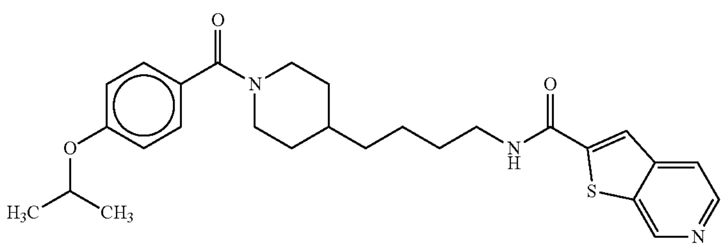 | N-[4-(1-{[4-(propan-2-yloxy)phenyl]carbonyl}piperidin-4-yl)butyl]thieno[2,3-c]pyridine-2-carboxamide |
| 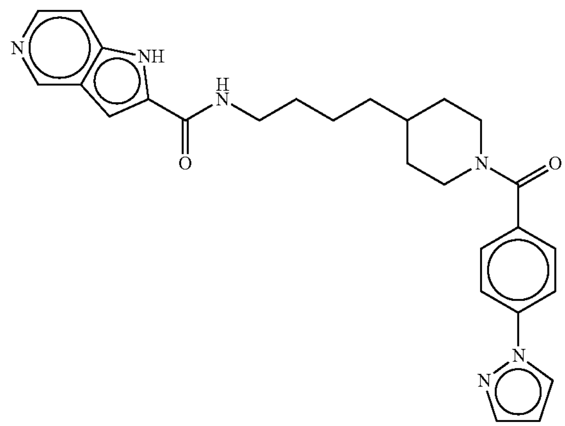 | N-[4-(1-{[4-(1H-pyrazol-1-yl)phenyl]carbonyl}piperidin-4-yl)butyl]-1H-pyrrolo[3,2-c]pyridine-2-carboxamide |
| 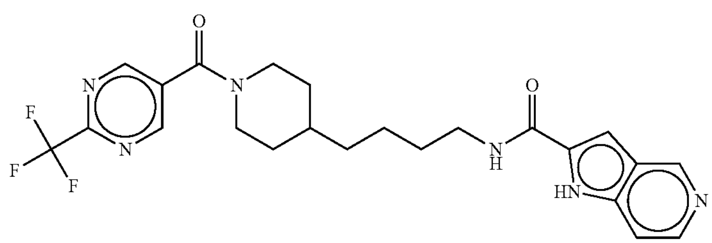 | N-[4-(1-{[2-(trifluoromethyl)pyrimidin-5-yl]carbonyl}piperidin-4-yl)butyl]-1H-pyrrolo[3,2-c]pyridine-2-carboxamide |
| 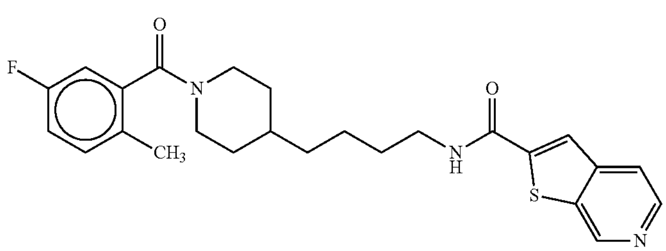 | N-(4-{1-[(5-fluoro-2-methylphenyl)carbonyl]piperidin-4-yl}butyl)thieno[2,3-c]pyridine-2-carboxamide |
| 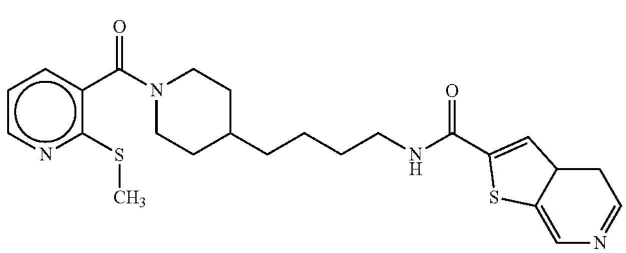 | N-[4-(1-{[2-(methylsulfanyl)pyridin-3-yl]carbonyl}piperidin-4-yl)butyl]thieno[2,3-c]pyridine-2-carboxamide |

TABLE 2-continued

| Structure | Chemical Name |
|---|---|
| 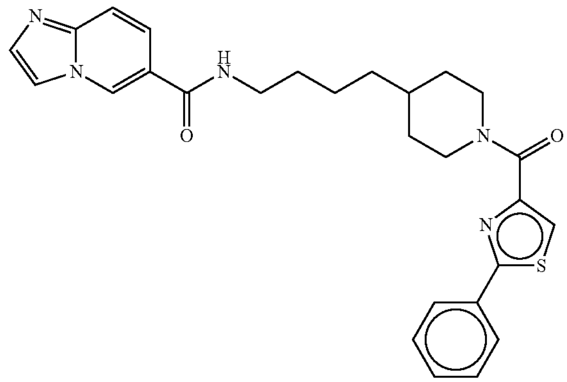 | N-(4-{1-[(2-phenyl-1,3-thiazol-4-yl)carbonyl]piperidin-4-yl}butyl)imidazo[1,2-a]pyridine-6-carboxamide |
| 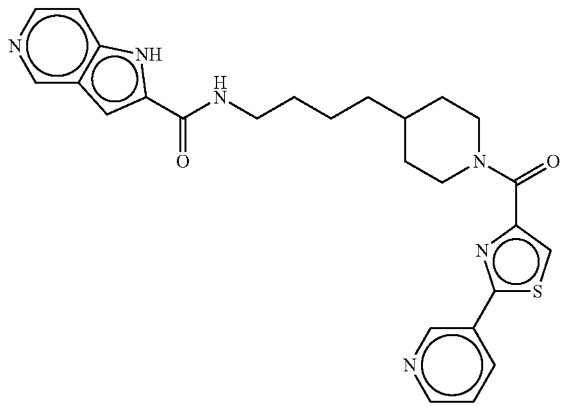 | N-[4-(1-{[2-(pyridin-3-yl)-1,3-thiazol-4-yl]carbonyl}piperidin-4-yl)butyl]-1H-pyrrolo[3,2-c]pyridine-2-carboxamide |
| 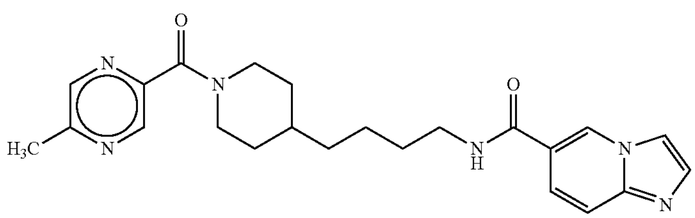 | N-(4-{1-[(5-methylpyrazin-2-yl)carbonyl]piperidin-4-yl}butyl)imidazo[1,2-a]pyridine-6-carboxamide |
| 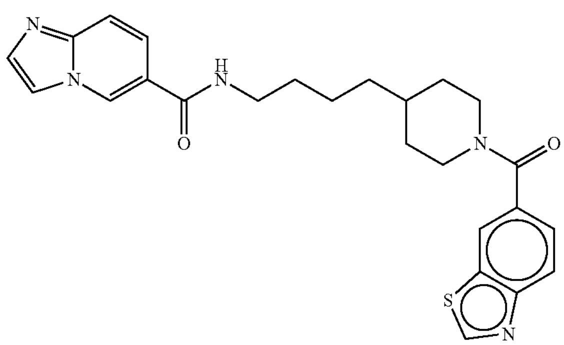 | N-(4-{1-[(1,3-benzothiazol-6-yl)carbonyl]piperidin-4-yl}butyl)imidazo[1,2-a]pyridine-6-carboxamide |
| 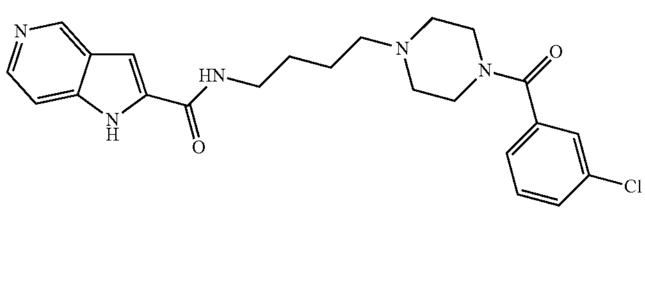 [SMILES: O=C(NCCCCN1CCN(C(=O)c2cccc(Cl)c2)CC1)c1cc2cnccc2[nH]1] | N-(4-{4-[(3-chlorophenyl)carbonyl]piperazin-1-yl}butyl)-1H-pyrrolo[3,2-c]pyridine-2-carboxamide |

TABLE 2-continued

| Structure | Chemical Name |
|---|---|
| 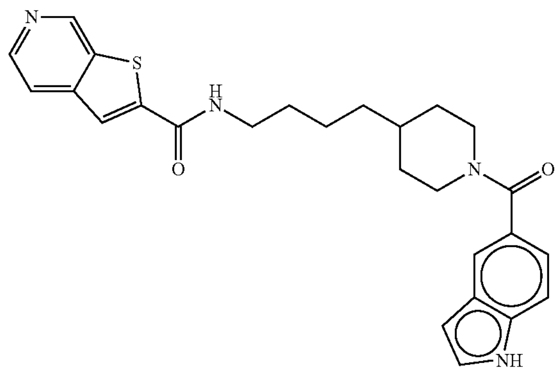 | N-(4-{1-[(1H-indol-5-yl)carbonyl]piperidin-4-yl}butyl)thieno[2,3-c]pyridine-2-carboxamide |
| 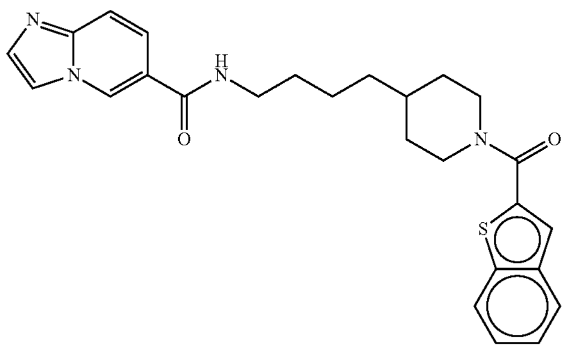 | N-(4-{1-[(1-benzothiophen-2-yl)carbonyl]piperidin-4-yl}butyl)imidazo[1,2-a]pyridine-6-carboxamide |
| 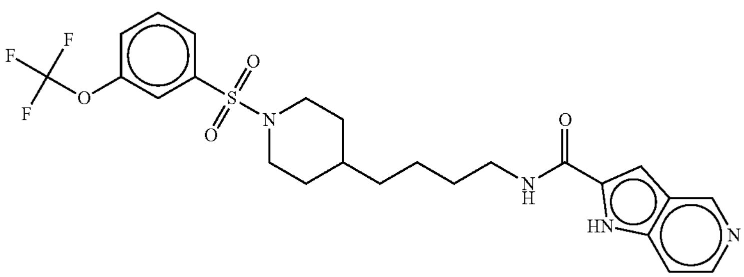 | N-[4-(1-{[3-(trifluoromethoxy)benzene]sulfonyl}piperidin-4-yl)butyl]-1H-pyrrolo[3,2-c]pyridine-2-carboxamide |
| 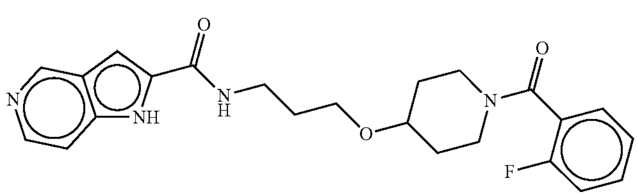 | N-(3-((1-(2-fluorobenzoyl)piperidin-4-yl)oxy)propyl)-1H-pyrrolo[3,2-c]pyridine-2-carboxamide |
| 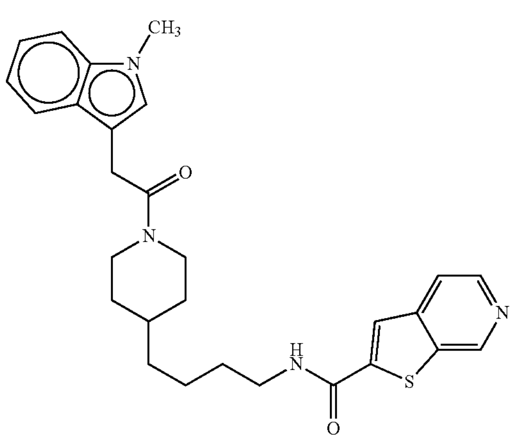 | N-(4-{1-[2-(1-methyl-1H-indol-3-yl)acetyl]piperidin-4-yl}butyl)thieno[2,3-c]pyridine-2-carboxamide |

TABLE 2-continued

| Structure | Chemical Name |
|---|---|
| 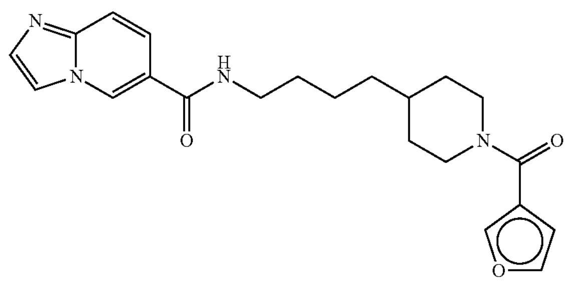 | N-(4-{1-[(furan-3-yl)carbonyl]piperidin-4-yl}butyl)imidazo[1,2-a]pyridine-6-carboxamide |
| 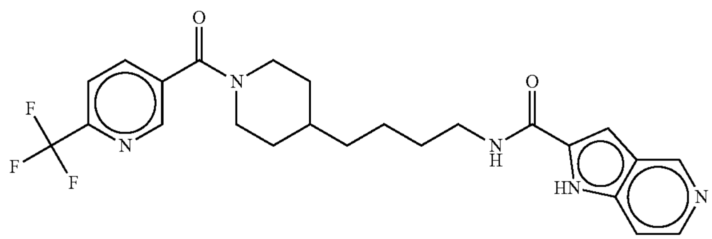 | N-[4-(1-{[6-(trifluoromethyl)pyridin-3-yl]carbonyl}piperidin-4-yl)butyl]-1H-pyrrolo[3,2-c]pyridine-2-carboxamide |
| 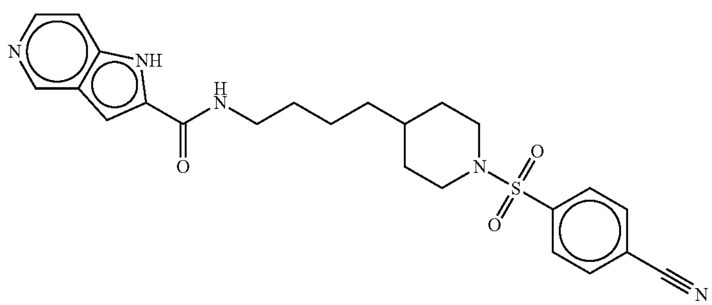 | N-(4-{1-[(4-cyanobenzene)sulfonyl]piperidin-4-yl}butyl)-1H-pyrrolo[3,2-c]pyridine-2-carboxamide |
| 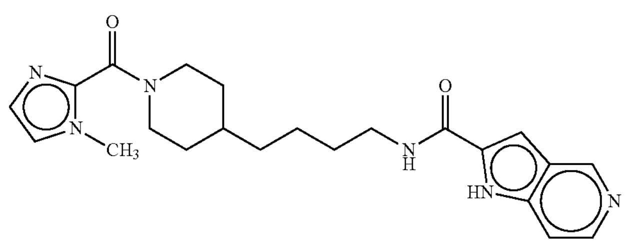 | N-(4-{1-[(1-methyl-1H-imidazol-2-yl)carbonyl]piperidin-4-yl}butyl)-1H-pyrrolo[3,2-c]pyridine-2-carboxamide |
| 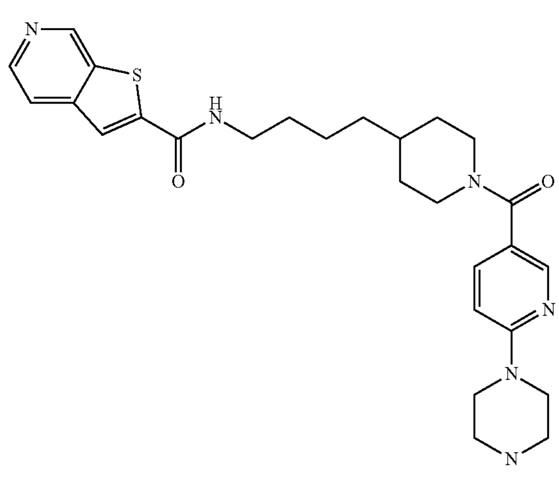 [SMILES: O=C(NCCCCC1CCN(C(=O)c2ccc(N3CCNCC3)nc2)CC1)c1cc2ccncc2s1] | N-[4-(1-{[6-(morpholin-4-yl)pyridin-3-yl]carbonyl}piperidin-4-yl)butyl]thieno[2,3-c]pyridine-2-carboxamide |

TABLE 2-continued

| Structure | Chemical Name |
|---|---|
| 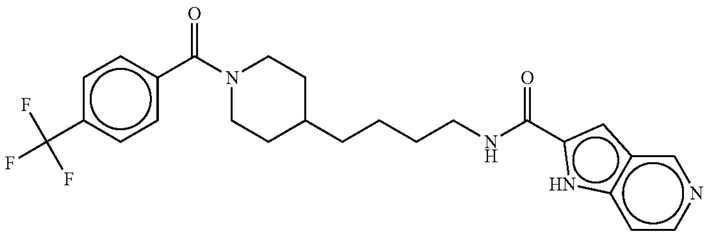 | N-[4-(1-{[4-(trifluoromethyl)phenyl]carbonyl}piperidin-4-yl)butyl]-1H-pyrrolo[3,2-c]pyridine-2-carboxamide |
| 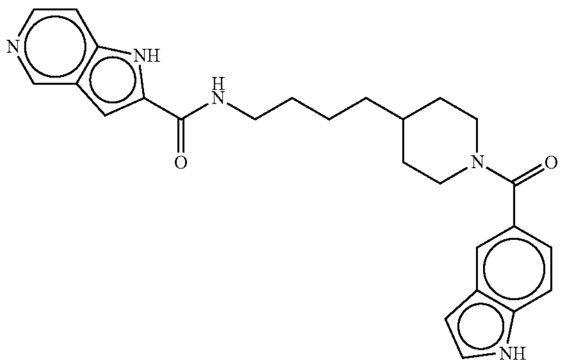 | N-(4-{1-[(1H-indol-5-yl)carbonyl]piperidin-4-yl}butyl)-1H-pyrrolo[3,2-c]pyridine-2-carboxamide |
| 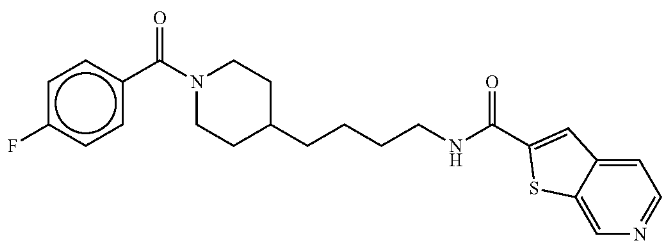 | N-(4-{1-[(4-fluorophenyl)carbonyl]piperidin-4-yl}butyl)thieno[2,3-c]pyridine-2-carboxamide |
| 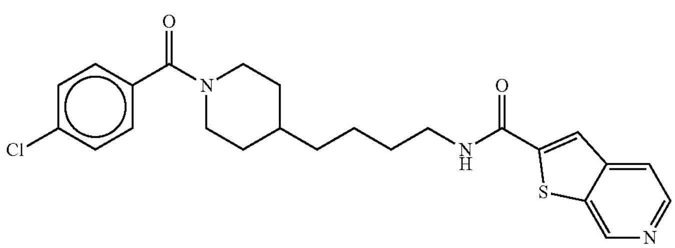 | N-(4-{1-[(4-chlorophenyl)carbonyl]piperidin-4-yl}butyl)thieno[2,3-c]pyridine-2-carboxamide |
| 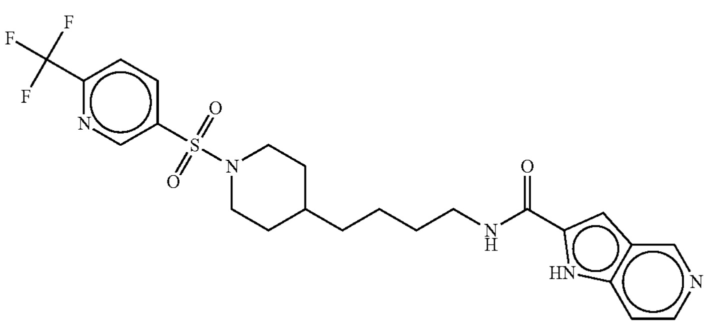 | N-(4-{1-[6-(trifluoromethyl)pyridine-3-sulfonyl]piperidin-4-yl}butyl)-1H-pyrrolo[3,2-c]pyridine-2-carboxamide |
| | N-(3-(1-benzoylpiperidin-4-yl)butyl)-1H-pyrrolo[3,2-c]pyridine-2-carboxamide |

TABLE 2-continued

| Structure | Chemical Name |
|---|---|
| 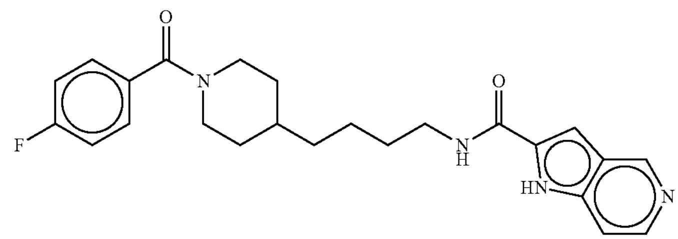 | N-(4-{1-[(4-fluorophenyl)carbonyl]piperidin-4-yl}butyl)-1H-pyrrolo[3,2-c]pyridine-2-carboxamide |
| 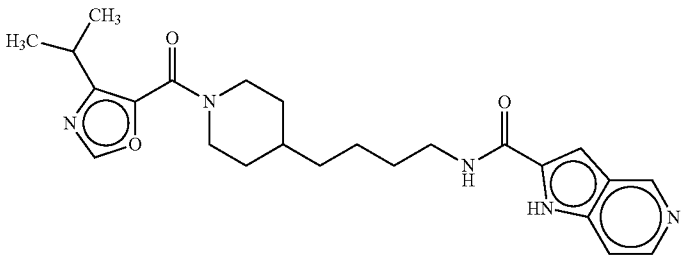 | N-[4-(1-{[4-(propan-2-yl)-1,3-oxazol-5-yl]carbonyl}piperidin-4-yl)butyl]-1H-pyrrolo[3,2-c]pyridine-2-carboxamide |
| 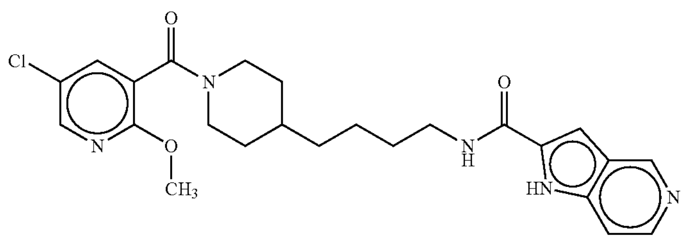 | N-(4-{1-[(5-chloro-2-methoxypyridin-3-yl)carbonyl]piperidin-4-yl}butyl)-1H-pyrrolo[3,2-c]pyridine-2-carboxamide |
| 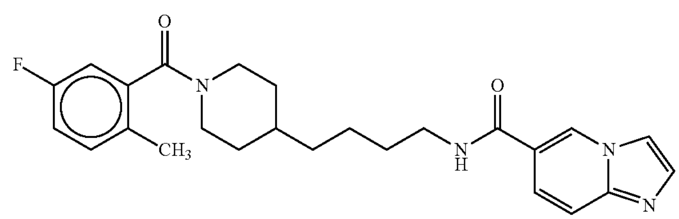 | N-(4-{1-[(5-fluoro-2-methylphenyl)carbonyl]piperidin-4-yl}butyl)imidazo[1,2-a]pyridine-6-carboxamide |

EXAMPLES

The following are illustrative, but non-limiting, examples of certain embodiments of the present invention.
Definitions used in the following Schemes and elsewhere herein are:
  BOP ammonium 4-(3-(pyridin-3-methyl)ureido)benzenesulfinate
  CDCl$_3$ deuterated chloroform
  δ chemical shift (ppm)
  DCM dichloromethane or methylene chloride
  DIEA N,N-diisopropylethylamine
  DMA N,N-dimethylacetamide
  DMF N,N-dimethylformamide
  DMSO dimethylsulfoxide
  DMSO-d$_6$ deuterated dimethylsulfoxide
  EDCI N1-((ethylimino)methylene)-N3,N3-dimethylpropane-1,3-diamine hydrochloride
  EtOAc ethyl acetate
  EtOH ethanol
  GF/F glass microfiber filter
  $^1$H NMR proton nuclear magnetic resonance
  HOAc acetic acid
  HATU 2-(3H-[1,2,3]triazolo[4,5-b]pyridin-3-yl)-1,1,3,3-tetramethylisouronium hexafluorophosphate
  HOBT 1H-benzo[d][1,2,3]triazol-1-ol hydrate
  HPLC high pressure liquid chromatography
  MHz megahertz
  KOAc potassium acetate
  i-PrOH isopropanol
  LC-MS liquid chromatography/mass spectrometry
  (M+1) mass+1
  m-CPBA m-chloroperbenzoic acid
  MeOH methanol
  N$_2$ nitrogen
  NaHCO$_3$ sodium bicarbonate
  MgSO$_4$ magnesium sulfate
  PTLC preparative thin layer chromatography
  TEA triethylamine
  THF tetrahydrofuran
  TLC thin layer chromatography
Preparation of Compounds
  The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Preferred methods include but are not limited to those methods described below. Compounds of the present invention amide-sulfonamide (III) can be synthesized by following the steps outlined in Scheme 1.

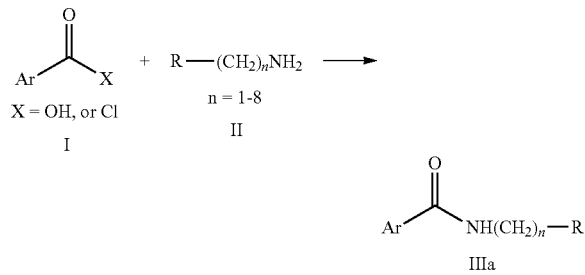

Compound III can be obtained by treating I with II (X=OH) in the presence of a coupling reagent such as EDCI, HATU, or HOBt, and a base (eg: $K_2CO_3$, $Cs_2CO_3$, $NR_1R_2R_3$, NaOR, KOR) in an inert solvent such as dichloromethane, N,N-dialkylformamide, N,N-dialkylacetamide, dialkylethers, cyclic ethers, DMSO, N-methyl-2-pyrrolidinone at temperatures ranging from −78° C. to 200° C. Alternatively, compound I can be treated with II (X=Cl) in the presence of base such as TEA in an inert solvent (such as dichloromethane) at temperatures ranging from −78° C. to 200° C.

Compounds (III) can also be synthesized by following the steps outlined in Scheme 2.

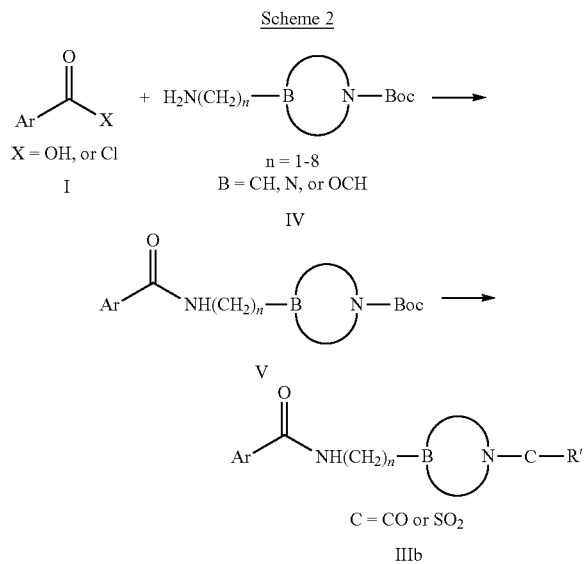

Compound V can be obtained by treating I with II (X=OH) in the presence of a coupling reagent such as EDCI, HATU, or HOBt, and a base (eg: $K_2CO_3$, $Cs_2CO_3$, $NR_1R_2R_3$, NaOR, KOR) in an inert solvent such as dichloromethane, N,N-dialkylformamide, N,N-dialkylacetamide, dialkylethers, cyclic ethers, DMSO, N-methyl-2-pyrrolidinone at temperatures ranging from −78° C. to 200° C. Alternatively, compound I can be treated with II (X=Cl) in the presence of base such as TEA in an inert solvent (such as dichloromethane) at temperatures ranging from −78° C. to 200° C. Removing the protecting group of compound V with acid such as TFA or HCl following with reacting with VI in the presence of base such as TEA in an inert solvent (such as dichloromethane) at temperatures ranging from −78° C. to 200° C. afford the desired compound III.

The disclosures in this application of all articles and references, including patents, are incorporated herein by reference.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. Unless otherwise specified, all reagents and solvents were of standard commercial grade and were used without further purification. In some cases, protection of certain reactive functionalities may be necessary to achieve some of the above transformations. In general, such need for protecting groups, as well as the conditions necessary to attach and remove such groups, will be apparent to those skilled in the art of organic synthesis.

Preparation of Representative Amide Analogues

These examples illustrate the preparation of representative substituted urea-sulfonamide analogues.

Example 1

N-(4-(1-benzoylpiperidin-4-yl)butyl)-1H-pyrrolo[3,2-c]pyridine-2-carboxamide

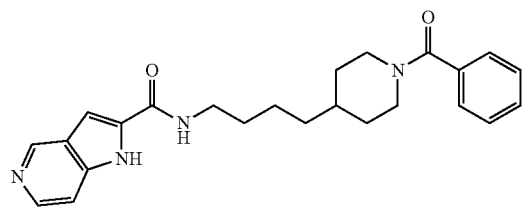 [SMILES: O=C(NCCCCC1CCN(C(=O)c2ccccc2)CC1)c1cc2cnccc2[nH]1]

In a 25 mL round-bottomed flask was added 1-H-pyrrolo[3,2-c]pyridine-2-carboxylic acid (100 mg, 0.617 mmol) and (4-(4-aminobutyl)piperidin-1-yl)(phenyl)methanone (161 mg, 0.617 mmol; prepared according to Galli U.; Ercolano, E.; Carraro, L.; Blasi Roman, C. R.; Sorba, G.; Canonico, P. L.; Genazzani, A. A.; Tron, G. C.; Billington, R. A. Synthesis and biological evaluation of isosteric analogues of FK866, an inhibitor of NAD salvage. ChemMedChem 2008, 3, 771-779) in dimethylformamide (5.0 ml) to give a light yellow suspension. O-(7-azabenzotriazol-1-yl)-N,N,N',N',-tetramethyluronium hexafluorphosphate (HATU) (220 mg, 0.577 mmol) and diisopropylethylamine (0.089 ml, 0.510 mmol) were added sequentially and the suspension was allowed to stir at room temperature overnight. The reaction was then poured in to a separatory funnel containing water and ethyl acetate. The aqueous phase was separated and extracted three times with ethyl acetate. The combined organic phase was dried over sodium sulfate, filtered and concentrated in vacuo. The resulting residue was purified by preparative HPLC to afford the title compound (76 mg, 31%).

1H NMR: (d6-DMSO, 300 MHz) δ$_H$ 11.94 (s, 1H), 8.88 (s, 1H), 8.59 (t, 1H), 8.19 (d, 2H), 7.39 (m, 3H), 7.31 (m, 3H), 7.20 (s, 1H), 4.43 (m, 1H), 3.51 (m, 1H), 3.26 (m, 2H), 2.96 (m, 1H), 2.70 (m, 1H), 1.70 (m, 2H), 1.51 (m, 3H) 1.29 (m, 4H) and 1.05 (m, 2H).

LCMS: 405.2 (MH$^+$)

Example 2

N-(4-(1-benzoylazetidin-3-yl)butyl)-1H-pyrrolo[3,2-c]pyridin-2-carboxamide

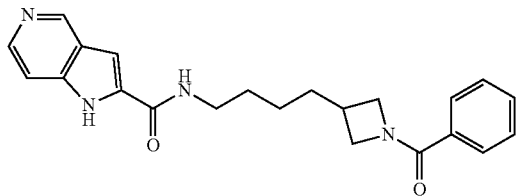 [SMILES: O=C(NCCCCC1CN(C(=O)c2ccccc2)C1)c1cc2cnccc2[nH]1]

A. tert-butyl 4-(1-benzoylazetidin-3-ylbutylcarbamate

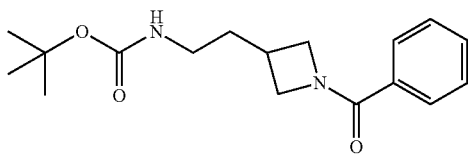 [SMILES: CC(C)(C)OC(=O)NCCC1CN(C(=O)c2ccccc2)C1]

In a 250 mL round-bottomed flask was added tert-butyl 4-(azetidin-3-yl)butylcarbamate (1 g, 4.38 mmol) and triethylamine (1.343 mL, 9.64 mmol) in dichloromethane (Volume: 50 mL) followed by dropwise addition of benzoyl chloride (0.508 mL, 4.38 mmol). The reaction was monitored by TLC and when complete, the reaction was diluted with methylene chloride and poured into a separatory funnel. The organic layer was washed with saturated, aqueous sodium bicarbonate, water, and saturated, aqueous sodium chloride. The organic was separated and concentrated under reduced pressure and purified on the Biotage to give 1.178 g of crude product. Material purified again on the Biotage to give 381 mg of product (26% yield).

$^1$H NMR (300 MHz, DMSO-d6): δ 7.59 (m, 2H), 7.45 (m, 3H), 6.77 (t, 1H), 4.43 (t, 1H), 4.09 (t, 1H), 3.89 (dd, 1H), 3.64 (dd, 1H), 2.89 (q, 2H), 2.58 (m, 11), 1.55 (m, 2H), 1.35 (m, 11H), 1.18 (m, 2H).

LC-MS (ESI): 355 (M+Na).

B. (3-(4-aminobutyl)azetidin-1-yl)(phenyl)methanone

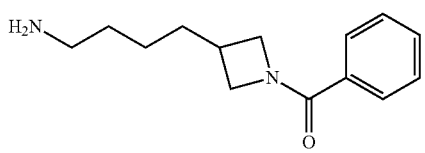 [SMILES: NCCCCC1CN(C(=O)c2ccccc2)C1]

In a 100 mL round-bottomed flask was added tert-butyl 4-(1-benzoylazetidin-3-yl)butylcarbamate (381 mg, 1.146 mmol) in dichloromethane (Ratio: 1.000, Volume: 12.00 mL)/TFA (Ratio: 1.000, Volume: 12.00 mL) which was stirred at room temperature overnight. The solvent was removed under vacuum and the residue re-diluted with methylene chloride and concentrated again. The residue was then diluted with methylene chloride and poured into a separatory funnel. The organic layer was washed with saturated, aqueous sodium bicarbonate and saturated, aqueous sodium chloride. The bottom was separated, dried with anhydrous magnesium sulfate, filtered and concentrated under reduced pressure to give 261 mg of crude product which was used without further purification (98% yield).

$^1$H NMR (300 MHz, DMSO-d6): δ 7.59 (m, 2H), 7.45 (m, 3H), 4.33 (t, 1H), 4.09 (t, 1H), 3.89 (dd, 1H), 3.64 (dd, 1H), 3.39 (br.s, 2H), 2.58 (m, 3H), 1.53 (m, 2H), 1.35 (m 4H).

LC-MS (ESI): 233 (M+1).

C. N-(4-(1-benzoylazetidin-3-yl)butyl)-1H-pyrrolo[3,2-c]pyridine-2-carboxamide

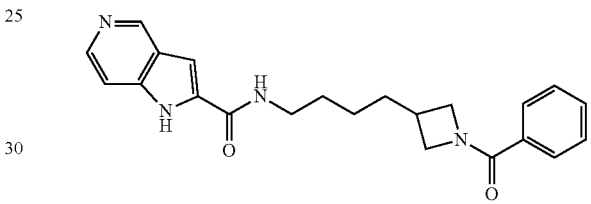

In a 100 mL round-bottomed flask was added (3-(4-aminobutyl)azetidin-1-yl)(phenyl)methanone (260 mg, 1.119 mmol), 1H-pyrrolo[3,2-c]pyridine-2-carboxylic acid (181 mg, 1.119 mmol) and HATU (638 mg, 1.679 mmol) in DMF (Volume: 10 mL) followed by DIEA (0.430 mL, 2.462 mmol). The reaction was stirred overnight at room temperature and then concentrated under reduced pressure. The residue was diluted with methylene chloride and poured into a separatory funnel. The organic layer was washed with aqueous 2M NaOH. The bottom was separated, concentrated under reduced pressure and purified on the Biotage to give 258.9 mg of product (62% yield).

$^1$H NMR (300 MHz, DMSO-d6): δ 12.01 (s, 1H), 8.94 (s, 1H), 8.63 (t, 1H), 8.22 (d, 1H), 7.62 (m, 2H), 7.44 (m, 4H), 7.25 (s, 1H), 4.35 (t, 1H), 4.12 (t, 1H), 3.90 (dd, 1H), 3.67 (dd, 1H), 3.30 (m, 2H), 2.60 (m, 1H), 1.59 (m, 4H), 1.28 (2H).

LC-MS (ESI): 377 (M+1).

Example 3

N(4-(1-benzoylpyrrolidin-3-ylbutyl)-1H-pyrrolo[3,2-c]pyridine-2-carboxamide

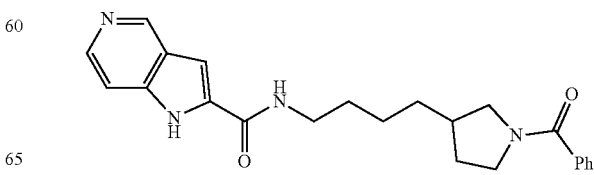

STEP A: To a solution of tert-butyl 4-(pyrrolidin-3-yl)butylcarbamate (0.993 g, 4.10 mmol) and triethylamine (1.343 mL, 9.64 mmol) in DCM (50 mL) at 0° C. was added dropwise benzoyl chloride (0.476 mL, 4.10 mmol). The reaction was allowed to warm slowly to ambient temperature over 16 h. The mixture was diluted with water and DCM and the layers separated. The organic layer was washed successively with saturated aqueous NaHCO$_3$ and brine, and dried over MgSO$_4$. The residue was purified by Biotage (EtOAc/hexane gradient) to afford tert-butyl (4-(1-benzoylpyrrolidin-3-yl)butyl)carbamate (474 mg, 33%) as a colorless oil.

STEP B: To a solution of tert-butyl 4-(1-benzoylpyrrolidin-3-yl)butylcarbamate (474 mg, 1.368 mmol) in DCM (10 mL) was added TFA (10 mL). The mixture was stirred at ambient temperature for 16 h, and then was concentrated under reduced pressure. The residue was diluted with methylene chloride and washed successively with saturated aqueous sodium bicarbonate and saturated aqueous sodium chloride. The organic layer was separated, dried with MgSO$_4$, filtered, and concentrated under reduced pressure to afford (3-(4-aminobutyl)pyrrolidin-1-yl)(phenyl)methanone (64 mg, 19%).

STEP C: To a mixture of (3-(4-aminobutyl)pyrrolidin-1-yl)(phenyl)methanone (64 mg, 0.260 mmol), 1H-pyrrolo[3,2-c]pyridine-2-carboxylic acid (42.1 mg, 0.260 mmol) and HATU (148 mg, 0.390 mmol) in DMF (5 mL) was added DIEA (0.100 mL, 0.572 mmol). The mixture was stirred for 16 hours at ambient temperature and was then concentrated under reduced pressure. The residue was diluted with ethyl acetate and washed with aqeuous 1N NaOH (2×) and dried (MgSO4). The crude mixture was purified by Biotage (DCM/MeOH gradient) to afford N-(4-(1-benzoylpyrrolidin-3-yl)butyl)-1H-pyrrolo[3,2-c]pyridine-2-carboxamide as a white solid (75 mg, 74%).

$^1$H NMR (DMSO-d$_6$): δ 12.05 (br s, 1H), 8.94 (d, 1H), 8.63 (dt, 1H), 8.21 (d, 1H), 7.49-7.36 (m, 6H), 7.25 (d, 1H), 3.68-3.21 (m, 5H), 3.08-2.99 (m, 1), 2.17-1.89 (m, 2H), 1.61-1.20 (m, 7H).

LC-MS (ESI): 391.17 (M+1).

Example 4

N-(6-(4-chlorophenoxy)hexyl)quinoline-6-carboxamide

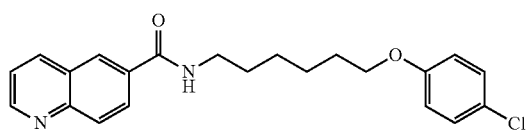 [SMILES: O=C(NCCCCCCOc1ccc(Cl)cc1)c1ccc2ncccc2c1]

In a 25 ml round-bottomed flask was added quinoline-6-carboxylic acid (100 mg, 0.577 mmol) and 6-(4-chlorophenoxy)hexan-1-amine (132 mg, 0.577 mmol) in dimethylformamide (5.8 ml) to give a light yellow suspension. O-(7-azabenzotriazol-1-yl)-N,N,N',N',-tetramethyluronium hexafluorphosphate (HATU) (220 mg, 0.577 mmol) and diisopropylethylamine (0.089 ml, 0.510 mmol) were added sequentially and the suspension was allowed to stir at room temperature overnight before being concentrated in vacuo. The resulting residue was purified by flash column chromatography (eluting with ethyl acetate) to afford the title compound (125 mg, 57%).

1H NMR: (d6-DMSO, 300 MHz) δ$_H$ 8.98 (d, 1H), 8.70 (t, 1H), 8.48 (m, 2H), 8.16 (dd, 1H), 8.07 (d, 1H), 7.61 (dd, 1H), 7.28 (d, 2H), 6.93 (d, 2H), 3.96 (t, 2H), 3.33 (m, 2H), 1.72 (m, 2H), 1.58 (m, 2H) and 1.42 (m, 4H).

LCMS: 383.0 (MH$^+$)

Example 5

N-(2-(biphenyl-4-ylethyl)-1H-pyrrolo[3,2-c]pyridine-2-carboxamide

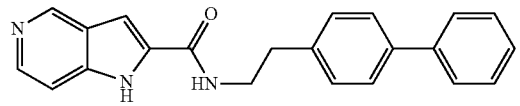 [SMILES: O=C(NCCc1ccc(-c2ccccc2)cc1)c1cc2cnccc2[nH]1]

In a 50 mL round-bottomed flask was added 1H-pyrrolo[3,2-c]pyridine-2-carboxylic acid (200 mg, 1.233 mmol), 2-(biphenyl-4-yl)ethanamine (243 mg, 1.233 mmol), and HATU (469 mg, 1.233 mmol) in DMF (Volume: 10 mL) along with DIEA (0.431 mL, 2.467 mmol). The reaction was stirred overnight, concentrated under reduced pressure and purified directly on the Biotage to give 273 mg of product with a small amount of impurities. Run through Biotage again to give 215.9 mg of product which was clean except for some DIEA salts. Diluted material in 10% MeOH/CH$_2$Cl$_2$ and washed with aq. sodium bicarbonate. Material formed emulsion. Drained methylene chloride and then added EtOAc. Emulsion again. Managed to separate organic layers and then combined and concentrated to give 159.6 mg of clean product (37% yield).

$^1$H NMR (DMSO-d6): δ 12.08 (br. s, 1H), 9.24 (t, 1H), 8.94 (s, 1H), 8.21 (d, 1H), 7.63 (m, 4H), 7.31-7.46 (m, 7H), 4.55 (d, 2H).

LC-MS (ESI): 328 (M+1).

Example 6

N-(4-(benzyloxy) phenethyl)-1H-pyrrolo [3, 2-c] pyridine-2-carboxamide

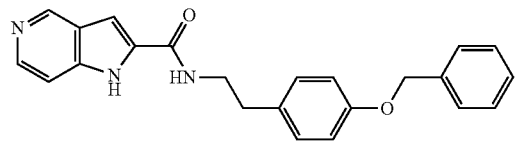 [SMILES: O=C(NCCc1ccc(OCc2ccccc2)cc1)c1cc2cnccc2[nH]1]

To a 100 ml flask as added 1H-pyrrolo[3,2-c]pyridine-2-carboxylic acid (100 mg and 0.617 mmol) 2-(4-(benzyloxy)phenyl)ethanamine HCl (195 mg, 0.740 mmol) in DMF (10 ml) to give a light yellow suspension. HATU (352 mg, 0.925 mmol) and DIEA (319 mg, 2.467 mmol) were added. The mixture was stirred at RT for 16 hours. Added water and extracted with ethyl acetate (3×20 mL). The organic layers were combined and washed with water (3×20 mL). The organic was separated, dried with anhydrous sodium sulfate, filtered and concentrated under reduced pressure The Biotage purification afforded 140 mg of the product (61%).

$^1$H NMR (DMSO-d$_6$). δ 13.00 (s, 1H), 9.30 (s, 1H), 9.00 (m, 1H), 8.37 (d, H), 7.78 (d, 1H), 7.52 (s, 1H), 7.30-7.47 (m,

5H), 7.18 (d, 2H), 6.90 (d, 2H), 5.02 (s, 2H), 3.37 (m, 2H0, 2.80 (m, 2H). LC-MS: 472.25 (M+1)

Example 7

N-(3-(1-benzoylpiperidin-4-yl)propyl)-1H-pyrrolo[3,2-c]pyridine-2-carboxamide

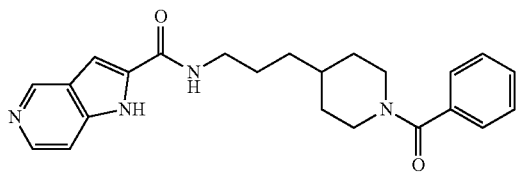 [SMILES: O=C(NCCCC1CCN(C(=O)c2ccccc2)CC1)c1cc2cnccc2[nH]1]

A. tert-butyl 4-(3-(1H-pyrrolo[3,2-c]pyridine-2-carboxamido)propyl)piperidine carboxylate

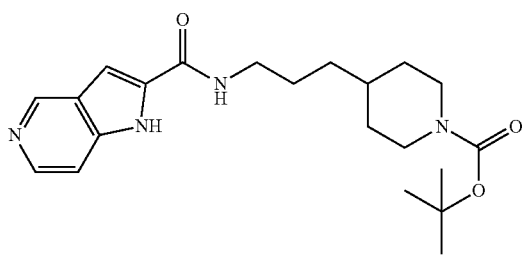 [SMILES: CC(C)(C)OC(=O)N1CCC(CCCNC(=O)c2cc3cnccc3[nH]2)CC1]

To a 100 ml of flask added tert-butyl 4-(3-aminopropyl)piperidine-1-carboxylate (250 mg, 1.032 mmol) and 1H-pyrrolo[3,2-c]pyridine-2-carboxylic acid (167 mg, 1.032 mmol) in DMF (10 ml). HATU (510 mg, 1.341 mmol) and DIPEA (0.721 ml, 4.13 mmol) were added. The mixture was stirred at RT for 16 hours. The mixture was diluted with water and extracted with ethyl acetate (3×20 mL).

The organic layers were combined and washed with water (3×20 mL). The organic was separated, dried with anhydrous sodium sulfate, filtered and concentrated under reduced pressure to give the crude product which was purified by the Biotage to afford 300 mg of product (75%).

$^1$H NMR (DMSO-d$_6$) δ: 12.35 (s, 1H), 9.08 (s, 1H), 8.75 (m, 1H), 3.87-3.91 (m, 2H), 3.23-3.30 (m, 4H), 1.49-1.63 (m, 5H), 1.32 (s, 9H), 1.20-1.24 (m, 2H), 0.90-0.98 (m, 2H).
LC-MS: 387.22 (M+1)

B. N-(3-(piperidin-4-yl)propyl)-1H-pyrrolo[3,2-c]pyridine-2-carboxamide, TFA salt

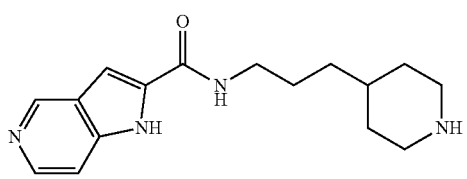 [SMILES: O=C(NCCCC1CCNCC1)c1cc2cnccc2[nH]1]

To a 100 ml flask was added tert-butyl 4-(3-(1H-pyrrolo[3,2-c]pyridine-2-carboxamido)propyl) piperidine-1-carboxylate (300 mg, 0.776 mmol) and 30 ml of 1:1 TFA/DCM.

The mixture was stirred at RT for overnight, removed solvent, added ether, filtered and dried to afford 300 mg of crude product (97%).

$^1$H NMR (DMSO-d$_6$). δ 13.27 (s, 1H), 9.44 (s, 1H), 9.05 (m, 1H), 8.45 (d, 1H), 7.88 (d, 1H), 7.64 (s, 1H), 3.21-3.33 (m, 4H), 2.83 (m, 2H), 1.78 (m, 2H), 1.54 (m, 3H), 1.26 (m, 4H).
LC-MS: 287.14 (M+1)

C. N-(3-(1-benzoylpiperidin-4-yl)propyl)-1H-pyrrolo[3,2-c]pyridine-2-carboxamide

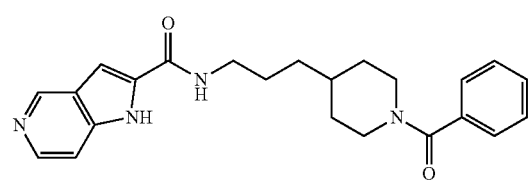 [SMILES: O=C(NCCCC1CCN(C(=O)c2ccccc2)CC1)c1cc2cnccc2[nH]1]

To a solution of N-(3-(piperidin-4-yl)propyl)-1H-pyrrolo[3,2-c]pyridine-2-carboxamide, TFA, and pyridine (20 mL) in 20 ml of DCM was added benzoyl chloride (211 mg. 1.499 mmol). The mixture was stirred at RT for overnight. Removed solvents, added EtOAc, washed with water, brine, dried and concentrated. The Biotage purification afforded 37 mg of product (13%).

$^1$H NMR (CDCl$_3$). δ 9.03 (s, 1H), 8.40 (d, 1H), 7.42 (d, 1H), 7.40 (s, 1H), 7.22 (m, 5H), 7.10 (s, 1H), 6.64 (s, 1H), 4.52 (m, 1H), 4.00 (m, 1H), 3.45 (m, 2H), 3.10 (m, 1H), 2.75 (m, 4H), 1.82 (m, 5H), 1.75 (m, 4H). LC-MS: 391.17 (M+1)

Example 8

N-(4-(4-Benzoylpiperazin-1-yl)butyl)-1H-pyrrolo[3,2-c]pyridine-2-carboxamide

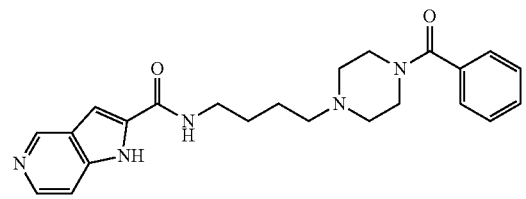 [SMILES: O=C(NCCCCN1CCN(C(=O)c2ccccc2)CC1)c1cc2cnccc2[nH]1]

A. tert-Butyl 4-(4-(1,3-dioxoisoindolin-2-yl)butyl)piperazine-1-carboxylate

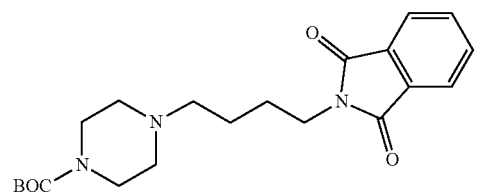 [SMILES: CC(C)(C)OC(=O)N1CCN(CCCCN2C(=O)c3ccccc3C2=O)CC1]

A mixture of 2-(4-bromobutyl)isoindoline-1,3-dione (3.33 g, 11.8 mmol), tert-butyl piperazine-1-carboxylate (2.2 g, 11.8 mmol) and Et$_3$N (4.9 nil, 35.4 mmol) in CH$_3$CN (50 mL) is heated at reflux for 16 h. The mixture is cooled and the solvent is evaporated. The residue is partitioned between EtOAc (70 mL) and water (70 mL). The organic layer is washed with brine (40 mL), dried ($Na_2SO_4$) and evaporated. The residue is purified by flash column with 1:1 Hexane/EtOAc gives colorless oil (3.91 g, 85%).

$^1$HNMR ($CDCl_3$) δ: 7.83 (dd, 2H), 7.71 (dd, 2H), 3.71 (t, 2H), 3.41 (t, 4H), 2.34-2.38 (m, 6H), 1.67-1.70 (m, 2H), 1.50-1.56 (m, 2H), 1.45 (s, 9H).

LC-MS M+1: 388.12;

B. tert-Butyl 4-(4-aminobutyl)piperazine-1-carboxylate

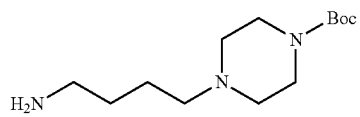

To a solution of tert-butyl 4-(4-(1,3-dioxoisoindolin-2-yl)butyl)piperazine-1-carboxylate (3.91 g, 10.1 mmol) in EtOH (60 mL) is added anhydrous hydrazine (3.23 mL, 100 mmol) and the mixture is stirred at ambient temperature for 24 h. The solvent is removed and to the solid is added EtOAc (40 mL) and Hexane (40 mL) and the suspension is stirred at RT for 2 h. The mixture is filtered and the solid is washed with 1:1 Hexane/EtOAc (20 mL). The filtrate is evaporated to gives a light yellow oil (2.41 g, 93%).

$^1$HNMR ($CDCl_3$, δ): 3.42 (t, 4H), 3.25 (s, 2H, broad), 2.69 (t, 2H), 2.32-2.38 (m, 6H), 1.41-1.48 (m, 13H). LC-MS M+1: 258.19.

C. tert-Butyl 4-(4-(1H-pyrrolo[3,2-c]pyridine-2-carboxamido)butyl)piperazine-1-carboxylate

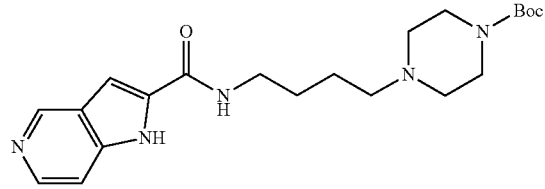 [SMILES: CC(C)(C)OC(=O)N1CCN(CCCCNC(=O)c2cc3cnccc3[nH]2)CC1]

To a solution of tert-butyl 4-(4-aminobutyl)piperazine-1-carboxylate (258 mg, 1 mol), $Et_3N$ (0.42 mL, 3 mol) and 1H-pyrrolo[3,2-c]pyridine-2-carboxylic acid (163 mg, 1 mmol) in DCM (20 mL) and DMSO (4 mL) is add HBTU (380 mg, 1 mmol). The mixture is stirred at ambient temperature overnight and the solvent is evaporated. To the residue is added $NaHCO_3$ (30 mL) and EtOAc (30 mL). The layers are separated and the organic layer is washed with water (30 mL), brine (30 mL) then dried and evaporated. The residue is purified by flash column with 100:8:0.8 DCM/MeOH/$NH_4OH$ to give the titled compounds as a white solid to give a light yellow solid (272 mg, 68%).

$^1$HNMR ($CDCl_3$, δ): 8.94 (s, 1H), 8.33 (d, 1H), 7.38 (d, 1H), 7.29 (t, 1H), 7.02 (s, 1H), 3.53 (q, 2H), 3.36-3.41 (m, 4H), 3.14 (q, 1H), 2.30-2.37 (m, 6H), 1.54-1.72 (m, 4H), 1.43 (s, 9H). LC-MS M+1: 402.22.

D. N-(4-(Piperazin-1-yl)butyl)-1H-pyrrolo[3,2-c]pyridine-2-carboxamide trihydrochloride

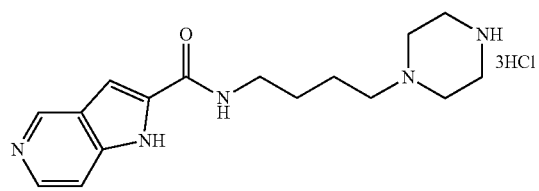 [SMILES: O=C(NCCCCN1CCNCC1)c1cc2cnccc2[nH]1]

To a solution of tert-butyl 4-(4-(1H-pyrrolo[3,2-c]pyridine-2-carboxamido)butyl)piperazine-1-carboxylate (272 mg, 0.68 mmol) in MeOH (10 mL) is added 4N HCl in dioxane (2 mL, 8 mmol) and the mixture is heated at 50° C. for 3 h then cooled to RT. The solvent is removed under vacuum and the residue is washed with ether to give a light yellow solid (216 mg, 94%). $^1$HNMR ($D_2O$, δ): 9.02 (s, 1H), 8.20 (d, 1H), 7.82 (d, 1H), 7.39 (s, 1H), 3.40-3.60 (m, 8H), 3.34 (t, 2H), 3.2 (t, 2H), 2.80 (s, 1H), 1.69-1.76 (m, 2H), 1.55-1.63 (m, 2H). LC-MS M+1: 302.24.

E. N-(4-(4-Benzoylpiperazin-1-yl)butyl)-1-pyrrolo[3,2-c]pyridine-2-carboxamide

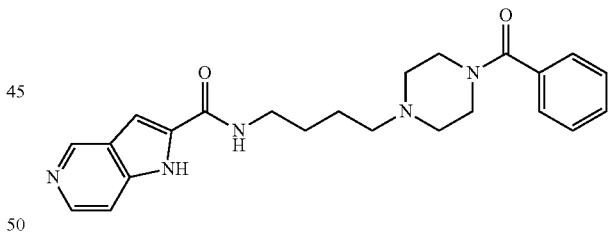

To a solution of N-(4-(piperazin-1-yl)butyl)-1H-pyrrolo[3,2-c]pyridine-2-carboxamide trihydrochloride (82 mg, 0.2 mmol), benzoic acid (25 mg, 0.2 mmol) and $Et_3N$ (0.14 ml, 1 mmol) in 5:1 dioxane and DMA (6 mL) is added HBTU (76 mg, 0.2 mmol) in $CH_3CN$ (2 ml) and the mixture is stirred at RT overnight. The solvent is removed under vacuum and the residue is partitioned between EtOAc (10 mL) and water (10 mL). The organic layer is dried ($Na_2SO_4$) then concentrated and the residue is purified by preparative TLC with 100:7:0.7 DCM/MeOH/$NH_4OH$ to give the titled compounds as a white solid (47 mg, 58%).

$^1$HNMR (DMSO-$d_6$, δ): 11.97 (s, broad, 1H), 8.90 (s, 1H), 8.61 (t, 1H), 8.19 (d, 1H), 7.33-7.43 (m, 5H), 7.23 (s, 1H), 3.26-3.58 (m, 9H), 2.30-2.38 (m, 5H), 1.48-1.55 (m, 3H). LC-MS M+1: 406.17.

Example 9

N-(4-(1-((4-Chlorophenyl)sulfonyl)piperidin-4-yl)butyl)-1H-pyrrolo[3,2-c]pyridine-2-carboxamide

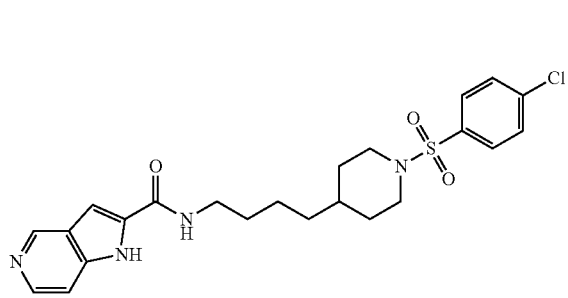 [SMILES: O=C(NCCCCC1CCN(S(=O)(=O)c2ccc(Cl)cc2)CC1)c1cc2cnccc2[nH]1]

A. tert-Butyl 4-(3-((methylsulfonyl)oxy)propyl)piperidine-1-carboxylate

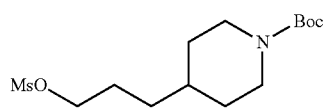 [SMILES: CC(C)(C)OC(=O)N1CCC(CCCOS(C)(=O)=O)CC1]

A solution of tert-butyl 4-(3-hydroxypropyl)piperidine-1-carboxylate (4.86 g, 20 mmol) and Et$_3$N (6.7 mL, 48 mmol) in DCM (80 mL) is cooled to 0° C. by an ice bath. MeSO$_2$Cl (2.75 g, 24 mmol) is added dropwise while maintaining the internal temperature below 10° C. The mixture is stirred at 0° C. for another 2 h then quenched with water (40 mL). The mixture is transferred to a separatory funnel and layers are separated. The organic layer is washed with NaHCO$_3$ (30 mL) and brine (30 mL) then dried (Na$_2$SO$_4$) and concentrated. The light yellow oil (6.17 g, 96%) is used to next step without further purification.

$^1$HNMR (CDCl$_3$, δ): 4.22 (t, 2H), 4.09 (t, 2H), 3.00 (s, 3H), 2.57 (t, 2H), 1.74-1.81 (m, 2H), 1.52-1.66 (m, 2H), 1.45 (s, 9H), 1.29-1.43 (m, 3H), 1.05-1.14 (m, 2H).

B. tert-Butyl 4-(3-cyanopropyl)piperidine-1-carboxylate

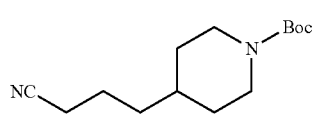 [SMILES: CC(C)(C)OC(=O)N1CCC(CCCC#N)CC1]

To a solution of tert-butyl 4-(3-((methylsulfonyl)oxy)propyl)piperidine-1-carboxylate (6.17 g, 19.2 mmol) in DMF (100 ml) is added solid KCN (1.56 g, 24 mmol) and the mixture is heated at 85° C. overnight. The solvent is removed under vacuum and the residue is partitioned between EtOAc (80 mL) and water (80 mL). The layers are separated and the organic layer is washed with water (40 mL) and brine (40 mL). The organic solution is dried over Na$_2$SO$_4$ and concentrated. The residue is purified by flash column with 1:1 EtOAc/hexane to give the titled compound as colorless oil (3.61 g, 74%).

$^1$HNMR (CDC$_3$, δ): 4.09 (m, 2H), 2.68 (t, 2H), 2.34 (t, 2H), 1.60-1.72 (m, 4H), 1.45 (s, 9H), 1.36-1.42 (m, 3H), 1.06-1.15 (m, 2H).

C. tert-Butyl 4-(4-aminobutyl)piperidine-1-carboxylate

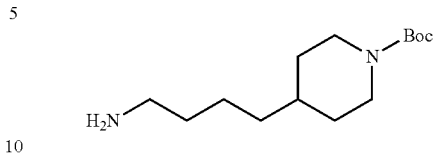

To a solution of tert-butyl 4-(3-cyanopropyl)piperidine-1-carboxylate (12 g, 4.76 mmol) in 2M NH3 in MeOH (30 mL) is add Raney Ni (0.5 mL, 50% in water). The mixture is hydrogenated at 50 psi for 4 h. The suspension is filtered through Celite and the filtrate is evaporated to give the titled compound as colorless oil (12 g, 100%).

$^1$HNMR (CDCl$_3$, δ: 4.07 (m, 2H), 2.66 (t, 2H), 1.58-1.72 (m, 4H), 1.45 (s, 9H), 1.22-1.44 (m, 7H), 1.01-1.15 (m, 2H). LC-MS M+1: 257.20

D. tert-Butyl 4-(4-(1H-pyrrolo[3,2-c]pyridine-2-carboxamido)butyl)piperidine-1-carboxylate

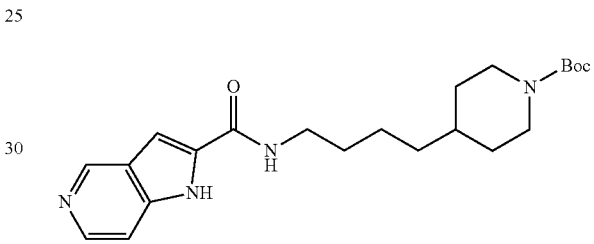

To a solution of tert-butyl 4-(4-aminobutyl)piperidine-1-carboxylate (677 mg, 2.64 mmol) in dioxane (12 ml) is added 1H-pyrrolo[3,2-c]pyridine-2-carboxylic acid (430 mg, 2.64 mmol) in 8:2 DMSO/Et$_3$N (6 mL) and the mixture is stirred at RT for 5 min. A solution of HBTU (1.0 g, 2.64 mmol) in CH$_3$CN (10 mL) is added slowly and the mixture is stirred at RT overnight. The solvent is removed under vacuum and the residue is partitioned between EtOAc (20 mL) and water (20 mL). The organic layer is concentrated and the residue is purified by flash column with 100:7:0.7 DCM/MeOH/NH4OH to give the titled compounds as a while solid (706 mg, 67%).

$^1$HNMR (CDCl$_3$, δ): 9.62 (s, broad, 1H), 9.00 (d, 1H), 8.39 (d, 1H), 7.36 (dd, 1H), 6.92 (s, 1H), 6.29 (s, broad, 1H), 4.06 (m, 2H), 3.51 (q, 2H), 2.66 (t, 2H), 1.61-1.68 (m, 4H), 1.45 (s, 9H), 1.25-1.44 (m, 5H), 1.02-1.12 (m, 2H). LC-MS M+1: 401.23.

E. N-(4-(Piperidin-4-yl)butyl)-1H-pyrrolo[3,2-c]pyridine-2-carboxamide dihydrochloride

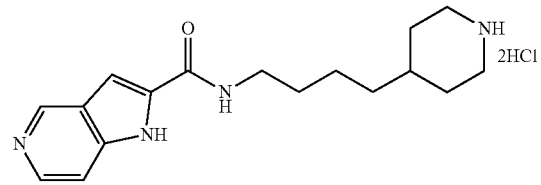 [SMILES: O=C(NCCCCC1CCNCC1)c1cc2cnccc2[nH]1]

To a solution of tert-butyl 4-(4-(1H-pyrrolo[3,2-c]pyridine-2-carboxamido)butyl)piperidine-1-carboxylate (706 mg, 1.76 mmol) in MeOH (12 mL) is added 4N HCl in dioxane (4.5 mL, 18 mmol) and the mixture is heated at 50° C. for 3 h then cooled to RT. The solvent is removed under vacuum and the residue is washed with ether to give a light yellow solid (580 mg, 98%).

¹HNMR (DMSO-$d_6$, δ): 9.46 (s, 1H), 9.17 (t, 1H), 8.97 (s, broad, 1H), 8.76 (s, broad, 1H), 8.43 (d, 1H), 7.87 (d, 1H), 7.71 (s, 1H), 4.35 (s, broad, 1H), 3.63-3.71 (m, 2H), 3.42-3.49 (m, 2H), 3.31 (q, 2H), 3.16-3.19 (m, 2H), 2.88 (s, broad, 1H), 2.77 (t, 2H), 1.74 (d, 2H), 1.48-1.56 (m, 2H), 1.22-1.33 (m, 3H). LC-MS M+1: 301.25.

F. N-(4-(1-((4-Chlorophenyl)sulfonyl)piperidin-4-yl)butyl)-1H-pyrrolo[3,2-c]pyridine-2-carboxamide

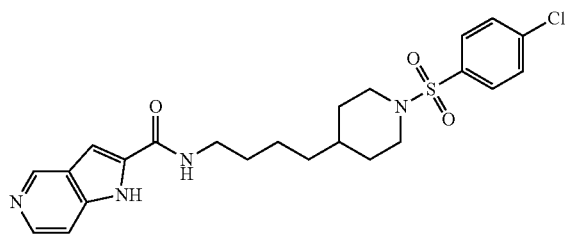 [SMILES: O=C(NCCCCC1CCN(S(=O)(=O)c2ccc(Cl)cc2)CC1)c1cc2cnccc2[nH]1]

To a solution of N-(4-(piperidin-4-yl)butyl)-1H-pyrrolo[3,2-c]pyridine-2-carboxamide dihydrochloride (75 mg, 0.2 mmol), and Et₃N (0.11 mL, 0.8 mmol) in 5:1 dioxane and DMA (6 mL) is added 4-chlorobenzenesulfonyl chloride (42 mg, 0.2 mmol) in DCM (2 mL) and the mixture is stirred at RT overnight. The solvent is removed under vacuum and the residue is partitioned between EtOAc (10 mL) and water (10 mL). The organic layer is dried (Na₂SO₄) then concentrated and the residue is purified by preparative TLC with 100:7:0.7 DCM/MeOH/NH4OH to give the titled compounds as a white solid (71 mg, 75%).

¹HNMR (DMSO-$d_6$, δ): 11.93 (s, broad, 1H), 8.88 (s, 1H), 8.56 (t, 1H), 8.18 (d, 1H), 7.70 (d, 4H), 7.32 (d, 1H), 7.19 (s, 1H), 3.59 (d, 2H), 3.24 (q, 2H), 2.18 (t, 2H), 1.68 (d, 2H), 1.47 (t, 2H), 1.08-1.27 (m, 7H). LC-MS M+1: 475.21.

Example 10

N-(3-((1-(2-fluorobenzoyl)piperidin-4-yl)oxy)propyl)-1H-pyrrolo[3,2-c]pyridine-2-carboxamide

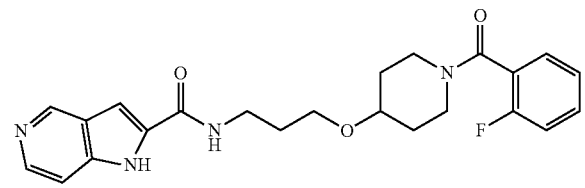 [SMILES: O=C(NCCCOC1CCN(C(=O)c2ccccc2F)CC1)c1cc2cnccc2[nH]1]

A: tert-butyl 4-(3-(1H-pyrrolo[3,2-c]pyridine-2-carboxamido)propoxy)piperidine-1-carboxylate

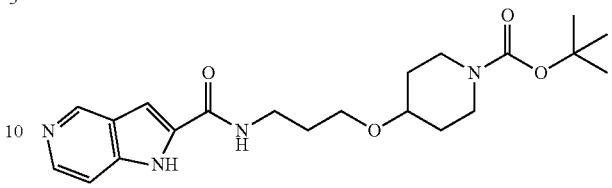

To a mixture of 1H-pyrrolo[3,2-c]pyridine-2-carboxylic acid (62.8 mg, 0.387 mmol), tert-butyl 4-(3-aminopropoxy)piperidine-1-carboxylate (100 mg, 0.387 mmol) in DMF (8 mL) was added BOP (188 mg, 0.426 mmol), followed by DIEA (0.081 mL, 0.464 mmol) to give a light yellow solution. The reaction was stirred at RT overnight. Crude LCMS shows major product (75%). Reaction mixture was concentrated in vacuo to remove the DMF. The residue was diluted with EtOAc and washed with 5% AcOH. The layers were separated. The aqueous layer was back-extracted with EtOAc. The combined EtOAc extracts were washed with saturated NaHCO₃, water, brine, dried over Na₂SO₄ and concentrated to afford off-white solids (200 mg, 86% yield, HPLC purity >95%). The crude was used for next reaction without further purification. LC-MS: 403.14 (M+H).

B: N-(3-(piperidin-4-yloxy)propyl)-1H-pyrrolo[3,2-c]pyridine-2-carboxamide 2,2,2-trifluoroacetate

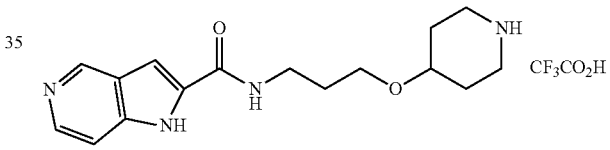

N-(3-(piperidin-4-yloxy)propyl)-1H-pyrrolo[3,2-c]pyridine-2-carboxamide 2,2,2-trifluoro-acetate (200 mg, 0.5 mmol) was dissolved in 8 mL of DCM, followed by addition of trifluoroacetic acid (2 mL). The reaction mixture was stirred for 3 h at room temperature. LC-MS analysis indicated that the reaction was completed. The solvent was removed via vacuo. The residual was taken up in a mixture of DCM/MeOH and continued to dry under reduced pressure to yield a desired product (235 mg).

¹H NMR (300 MHz, DMSO-$d_6$): δ 13.28 (s, 1H), 9.46 (s, 1H), 9.05 (s, 1H), 8.45 (d, 1H), 7.87 (d, 1H), 7.64 (s, 1H), 3.49-3.38 (m, 5H), 3.13 (s, 2H), 2.96 (s, 2H), 1.90-1.65 (m, 6H). LC-MS: 302.04 (M+H).

C: N-(3-((1-(2-fluorobenzoyl)piperidin-4-yl)oxy)propyl)-1H-pyrrolo[3,2-c]pyridine-2-carboxamide

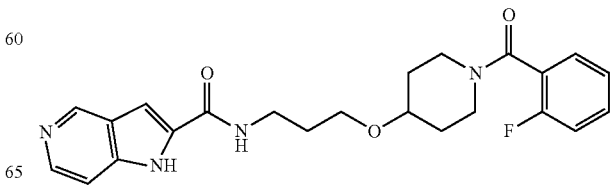

To a mixture of N-(3-(piperidin-4-yloxy)propyl)-1H-pyrrolo[3,2-c]pyridine-2-carboxamide, TFA salt (100 mg, 0.240 mmol) and triethylamine (0.134 mL, 0.961 mmol) in DCM (7 mL) was added 2-fluorobenzoyl chloride (38.1 mg, 0.240 mmol) to give a light yellow solution. The reaction mixture was stirred at RT overnight. LC-MS showed the major peak was the desired product. The reaction mixture was diluted with DCM and washed with only water and brine, then dried over $Na_2SO_4$, filtered and concentrated. The residue was dissolved in DMSO and purified on reversed phase HPLC to afford the desired product (12.2 mg, 12% yield)

$^1$H NMR (300 MHz, $CDCl_3$): δ 9.00 (s, 1H), 8.52 (s, 1H), 8.31 (d, 1H), 7.74 (s, 1H), 7.54 (d, 1H), 7.40-7.32 (m, 2H), 7.21-7.08 (m, 2H), 4.15 (s, 1H), 3.66-3.50 (m, 7H), 3.13 (s, 1H), 2.00-1.66 (m, 6H). LCMS: 425.16 (M+H).

Assays:

Assay Example 1

Biochemical Inhibition Assay
NAMPT Protein Purification

Recombinant His-tagged NAMPT was produced in *E. coli* cells, purified over a Ni column, and further purified over a size-exclusion column by XTAL Biostructures.

The NAMPT Enzymatic Reaction

The NAMPT enzymatic reactions were carried out in Buffer A (50 mM Hepes pH 7.5, 50 mM NaCl, 5 mM $MgCl_2$, and 1 mM THP) in 96-well V-bottom plates. The compound titrations were performed in a separate dilution plate by serially diluting the compounds in DMSO to make a 100× stock. Buffer A (89 µL) containing 33 nM of NAMPT protein was added to 1 µL of 100× compound plate containing controls (e.g. DMSO or blank). The compound and enzyme mix was incubated for 15 minutes at room temperature, then 10 µL of 10× substrate and co-factors in Buffer A were added to the test well to make a final concentration of 1 µM NAM, 100 µM 5-Phospho-D-ribose 1-diphosphate (PRPP), and 2.5 mM Adenosine 5'-triphosphate (ATP). The reaction was allowed to proceed for 30 minutes at room temperature, then was quenched with the addition of 11 µL of a solution of formic acid and 1-Cystathionine to make a final concentration of 1% formic acid and 10 µM L-Cystathionine. Background and signal strength was determined by addition (or non-addition) of a serial dilution of NMN to a pre-quenched enzyme and cofactor mix.

Quantification of NMN

A mass spectrometry-based assay was used to measure the Nampt reaction product (NMN) and the internal control (L-Cystathionine). NMN and L-Cystathionine were detected using the services of Biocius Lifesciences with the Rapid-Fire system. In short, the NMN and L-Cystathionine are bound to a graphitic carbon cartridge in 0.1% formic acid, eluted in 30% acetonitrile buffer, and injected into a Sciex 4000 mass spectrometer. The components of the sample were ionized with electrospray ionization and the positive ions were detected. The Q1 (parent ion) and Q3 (fragment ion) masses of NMN were 334.2 and 123.2, respectively. The Q1 and Q3 for L-Cystathionine were 223.1 and 134.1, respectively. The fragments are quantified and the analyzed by the following method.

% Inhibitions are Determined Using this Method.

First the NMN signal is normalized to the L-Cystathionine signal by dividing the NMN signal by the L-Cystathionine signal for each well. The signal from the background wells are averaged and subtracted from the test plates. The compound treated cells re then assayed for % inhibition by using this formula.

$$\% Inh = 100 - 100 * x/y$$

Wherein x denotes the average signal of the compound treated wells and y denotes the average signal of the DMSO treated wells.

IC50s are determined using Excel and this formula $$IC50 = 10^\wedge(LOG\ 10(X) + (((50 - \% Inh\ at\ Cmpd\ Concentration\ 1)/(XX - YY) * (LOG\ 10(X) - LOG\ 10(Y))))$$

Wherein X denotes the compound concentration 1, Y denotes the compound concentration 2, XX denotes the % inhibition at compound concentration 1 (X), and YY denotes the % inhibition at compound concentration 2 (Y). NAMPT inhibiting compounds of this invention have IC50 values below 1µ, more preferably below 0.1 µM and most preferably below 0.01 µM. Results for the compounds are provided in Table 3 below.

Assay Example 2

In-Vitro Cell Proliferation Assay

A2780 cells were seeded in 96-well plates at 1×10³ cells/well in 180 µL of culture medium (10% FBS, 1% Pen/Strep Amphoteericin B, RPMI-1640) with and without the addition of either β-nicotinamide mononucleotide (NMN) or nicotinamide (NAM). After overnight incubation at 37° C. and 5% $CO_2$, the compound titrations were performed in a separate dilution plate by serially diluting the compounds in DMSO to make a 1000× stock. The compounds were then further diluted to 10× final concentration in culture media, whereupon 20 µL of each dilution was added to the plated cells with controls (e.g. DMSO and blank) to make a final volume of 200 µL. The final DMSO concentration in each well was 0.1%. The plates were then incubated for 72 hours at 37° C. in a 5% $CO_2$ incubator. The number of viable cells was then assessed using sulforhodamine B (SRB) assay. Cells were fixed at 4° C. for 1 hour with the addition of 50 µL 30% trichloroacetic acid (TCA) to make a final concentration of 6% TCA. The plates were washed four times with $H_2O$ and allowed to dry for at least 1 hour, whereupon 100 µL of a 4% SRB in 1% acetic acid solution was added to each well and incubated at room temperature for at least 30 minutes. The plates were then washed three times with 1% acetic acid, dried, and treated with 100 µL of 10 mM Tris-Base solution. The plates were then read in a microplate reader at an absorbance of 570 nm. Background was generated on a separate plate with media only.

Method for Determining % Inhibition

First, the signals from the background plate are averaged, then the background was subtracted from the test plates. The compound-treated cells were then assayed for % inhibition by using the following formula:

$$\% Inh = 100 - 100 * x/y$$

wherein x denotes the average signal of the compound-treated cells and y denotes the average signal of the DMSO-treated cells.

Formula for determining $IC_{50}$ values:

$$IC50 = 10^\wedge(LOG\ 10(X) + (((50 - \% Inh\ at\ Cmpd\ Concentration\ 1)/(XX - YY) * (LOG\ 10(X) - LOG\ 10(Y))))$$

wherein X denotes the compound concentration 1, Y denotes the compound concentration 2, XX denotes the % inhibition at compound concentration 1 (X), and YY denotes the % inhibition at compound concentration 2 (Y).

Specificity of Cytotoxicity.

Inhibition of NAMPT could be reversed by the addition of NAM or NMN. The specificity of the compounds were determined via cell viability assay in the presence of the compound and either NAM or NMN. Percent inhibitions were determined using the method given above.

NAMPT-inhibiting compounds of this invention have IC50-values below 1 µM, preferably below 0.1 µM and most preferably below 0.01 µM. Results of for the compounds are provided below in Table 3.

TABLE 3

| IUPAC Name | Biochem IC50 uM | A2780 IC50 uM |
|---|---|---|
| N-[2-(4-phenylphenyl)ethyl]-1H-pyrrolo[3,2-c]pyridine-2-carboxamide | 0.126 | 3.98 |
| N-[2-(1-benzoylpiperidin-4-yl)ethyl]-1H-pyrrolo[3,2-c]pyridine-2-carboxamide | 10 | 20 |
| N-{2-[1-(benzenesulfonyl)piperidin-4-yl]ethyl}-1H-pyrrolo[3,2-c]pyridine-2-carboxamide | 0.0509 | 1.03 |
| N-[4-(1-benzoylpiperidin-4-yl)butyl]-1H-pyrrolo[3,2-c]pyridine-2-carboxamide | 0.0081 | 0.0014 |
| N-[6-(4-chlorophenoxy)hexyl]quinoline-6-carboxamide | 0.0259 | 9.89 |
| N-(4-{4-[(3-methoxyphenyl)carbonyl]piperazin-1-yl}butyl)-1H-pyrrolo[3,2-c]pyridine-2-carboxamide | 0.436 | 0.855 |
| N-[4-(1-cyclohexanecarbonylpiperidin-4-yl)butyl]-1H-pyrrolo[3,2-c]pyridine-2-carboxamide | 0.18 | 0.0155 |
| N-(4-{4-[(3-chlorophenyl)carbonyl]piperazin-1-yl}butyl)-1H-pyrrolo[3,2-c]pyridine-2-carboxamide | 0.106 | 0.347 |
| N-(4-(1-{[2-(pyridin-3-yl)-1,3-thiazol-4-yl]carbonyl}piperidin-4-yl)butyl]-1H-pyrrolo[3,2-c]pyridine-2-carboxamide | 0.0811 | 0.0149 |
| N-[4-(4-benzoylpiperazin-1-yl)butyl]-1H-pyrrolo[3,2-c]pyridine-2-carboxamide | 0.016 | 0.0947 |
| N-{4-[1-({1H-pyrrolo[3,2-c]pyridin-2-yl}carbonyl)piperidin-4-yl]butyl}-1H-pyrrolo[3,2-c]pyridine-2-carboxamide | 0.0209 | 0.0113 |
| N-(4-{1-[(4-methoxyphenyl)carbonyl]piperidin-4-yl}butyl)-1H-pyrrolo[3,2-c]pyridine-2-carboxamide | 0.0797 | 0.0163 |
| N-(4-{1-[(4-fluorophenyl)carbonyl]piperidin-4-yl}butyl)-1H-pyrrolo[3,2-c]pyridine-2-carboxamide | 0.0598 | 0.0147 |
| N-[4-(1-{[4-(difluoromethoxy)phenyl]carbonyl}piperidin-4-yl)butyl]-1H-pyrrolo[3,2-c]pyridine-2-carboxamide | 0.183 | 0.0314 |
| N-(4-{1-[(2H-1,3-benzodioxol-5-yl)carbonyl]piperidin-4-yl}butyl)-1H-pyrrolo[3,2-c]pyridine-2-carboxamide | 0.0783 | 0.014 |
| N-(4-{1-[(2,5-difluorophenyl)carbonyl]piperidin-4-yl}butyl)-1H-pyrrolo[3,2-c]pyridine-2-carboxamide | 0.0103 | 0.0015 |
| N-(4-{1-[(2-methoxyphenyl)carbonyl]piperidin-4-yl}butyl)-1H-pyrrolo[3,2-c]pyridine-2-carboxamide | 0.0144 | 0.0019 |
| N-(4-{1-[(pyridin-4-yl)carbonyl]piperidin-4-yl}butyl)-1H-pyrrolo[3,2-c]pyridine-2-carboxamide | 0.0097 | 0.0044 |
| N-[4-(1-{[6-(morpholin-4-yl)pyridin-3-yl]carbonyl}piperidin-4-yl)butyl]-1H-pyrrolo[3,2-c]pyridine-2-carboxamide | 0.0647 | 0.0034 |
| N-[4-(1-{[5-(propan-2-yl)pyridin-2-yl]carbonyl}piperidin-4-yl)butyl]-1H-pyrrolo[3,2-c]pyridine-2-carboxamide | 0.163 | 0.0141 |
| N-(4-{1-[(1H-indol-2-yl)carbonyl]piperidin-4-yl}butyl)-1H-pyrrolo[3,2-c]pyridine-2-carboxamide | 0.125 | 0.0603 |
| N-(4-{1-[(2-methyl-1,3-thiazol-4-yl)carbonyl]piperidin-4-yl}butyl)-1H-pyrrolo[3,2-c]pyridine-2-carboxamide | 0.0695 | 0.025 |
| N-(4-{1-[(1-acetylpiperidin-4-yl)carbonyl]piperidin-4-yl}butyl)-1H-pyrrolo[3,2-c]pyridine-2-carboxamide | 0.134 | 0.0239 |
| N-(4-{1-[(3-methoxyphenyl)carbonyl]piperidin-4-yl}butyl)-1H-pyrrolo[3,2-c]pyridine-2-carboxamide | 0.0248 | 0.0038 |
| N-[4-(1-{[4-(difluoromethoxy)phenyl]carbonyl}piperidin-4-yl)butyl]-1H-pyrrolo[3,2-c]pyridine-2-carboxamide | 0.183 | 0.0314 |
| N-[4-(1-{[4-(trifluoromethyl)phenyl]carbonyl}piperidin-4-yl)butyl]-1H-pyrrolo[3,2-c]pyridine-2-carboxamide | 0.164 | 0.0381 |
| N-(4-{1-[(3-ethoxyphenyl)carbonyl]piperidin-4-yl}butyl)-1H-pyrrolo[3,2-c]pyridine-2-carboxamide | 0.0851 | 0.011 |
| N-(4-{1-[(1H-indol-5-yl)carbonyl]piperidin-4-yl}butyl)-1H-pyrrolo[3,2-c]pyridine-2-carboxamide | 0.0394 | 0.0135 |
| N-(4-{1-[(3-fluoro-4-methoxyphenyl)carbonyl]piperidin-4-yl}butyl)-1H-pyrrolo[3,2-c]pyridine-2-carboxamide | 0.0631 | 0.021 |
| N-[4-(1-{[4-(trifluoromethoxy)phenyl]carbonyl}piperidin-4-yl)butyl]-1H-pyrrolo[3,2-c]pyridine-2-carboxamide | 0.145 | 0.0127 |
| N-(4-{1-[(3,4-dimethoxyphenyl)carbonyl]piperidin-4-yl}butyl)-1H-pyrrolo[3,2-c]pyridine-2-carboxamide | 0.0686 | 0.003 |
| N-[4-(1-{[4-(propan-2-yloxy)phenyl]carbonyl}piperidin-4-yl)butyl]-1H-pyrrolo[3,2-c]pyridine-2-carboxamide | 0.0937 | 0.0131 |

TABLE 3-continued

| IUPAC Name | Biochem IC50 uM | A2780 IC50 uM |
|---|---|---|
| N-(4-{1-[(3,5-dimethoxyphenyl)carbonyl]piperidin-4-yl}butyl)-1H-pyrrolo[3,2-c]pyridine-2-carboxamide | 0.0741 | 0.0026 |
| N-(4-{1-[(3-fluorophenyl)carbonyl]piperidin-4-yl}butyl)-1H-pyrrolo[3,2-c]pyridine-2-carboxamide | 0.0164 | 0.0033 |
| N-(4-{1-[(2-fluorophenyl)carbonyl]piperidin-4-yl}butyl)-1H-pyrrolo[3,2-c]pyridine-2-carboxamide | 0.0075 | 0.0005 |
| N-(4-{1-[(3-chlorophenyl)carbonyl]piperidin-4-yl}butyl)-1H-pyrrolo[3,2-c]pyridine-2-carboxamide | 0.0217 | 0.0119 |
| N-(4-{1-[(4-chlorophenyl)carbonyl]piperidin-4-yl}butyl)-1H-pyrrolo[3,2-c]pyridine-2-carboxamide | 0.114 | 0.0657 |
| N-(4-{1-[(2-fluoro-3-methylphenyl)carbonyl]piperidin-4-yl}butyl)-1H-pyrrolo[3,2-c]pyridine-2-carboxamide | 0.0475 | 0.0069 |
| N-(4-{1-[(2,6-difluorophenyl)carbonyl]piperidin-4-yl}butyl)-1H-pyrrolo[3,2-c]pyridine-2-carboxamide | 0.0073 | 0.0014 |
| N-(4-{1-[(3,4-difluorophenyl)carbonyl]piperidin-4-yl}butyl)-1H-pyrrolo[3,2-c]pyridine-2-carboxamide | 0.056 | 0.0206 |
| N-(4-{1-[(2,4-difluorophenyl)carbonyl]piperidin-4-yl}butyl)-1H-pyrrolo[3,2-c]pyridine-2-carboxamide | 0.0393 | 0.0081 |
| N-(4-{1-[(3,4-dichlorophenyl)carbonyl]piperidin-4-yl}butyl)-1H-pyrrolo[3,2-c]pyridine-2-carboxamide | 0.093 | 0.058 |
| N-(4-{1-[(1-benzothiophen-2-yl)carbonyl]piperidin-4-yl}butyl)-1H-pyrrolo[3,2-c]pyridine-2-carboxamide | 0.124 | 0.0699 |
| N-(4-{1-[(3,5-dichlorophenyl)carbonyl]piperidin-4-yl}butyl)-1H-pyrrolo[3,2-c]pyridine-2-carboxamide | 0.0813 | 0.013 |
| N-[4-(1-{[2-(trifluoromethoxy)phenyl]carbonyl}piperidin-4-yl)butyl]-1H-pyrrolo[3,2-c]pyridine-2-carboxamide | 0.0205 | 0.0013 |
| N-(4-{1-[(5-chloro-2-methoxyphenyl)carbonyl]piperidin-4-yl}butyl)-1H-pyrrolo[3,2-c]pyridine-2-carboxamide | 0.0338 | 0.0033 |
| N-(4-{1-[(2,6-dimethoxyphenyl)carbonyl]piperidin-4-yl}butyl)-1H-pyrrolo[3,2-c]pyridine-2-carboxamide | 0.0215 | 0.0014 |
| N-[4-(1-{[4-(trifluoromethyl)pyridin-3-yl]carbonyl}piperidin-4-yl)butyl]-1H-pyrrolo[3,2-c]pyridine-2-carboxamide | 0.0398 | 0.0029 |
| N-(4-{1-[(2,3-dimethoxyphenyl)carbonyl]piperidin-4-yl}butyl)-1H-pyrrolo[3,2-c]pyridine-2-carboxamide | 0.0208 | 0.0019 |
| N-(4-{1-[(2,5-dimethoxyphenyl)carbonyl]piperidin-4-yl}butyl)-1H-pyrrolo[3,2-c]pyridine-2-carboxamide | 0.0155 | 0.0022 |
| N-(4-{1-[(2,4-dimethoxyphenyl)carbonyl]piperidin-4-yl}butyl)-1H-pyrrolo[3,2-c]pyridine-2-carboxamide | 0.0671 | 0.0033 |
| N-(4-{1-[(2-chlorophenyl)carbonyl]piperidin-4-yl}butyl)-1H-pyrrolo[3,2-c]pyridine-2-carboxamide | 0.0158 | 0.0015 |
| N-(4-{1-[(2,3-dichlorophenyl)carbonyl]piperidin-4-yl}butyl)-1H-pyrrolo[3,2-c]pyridine-2-carboxamide | 0.0312 | 0.0032 |
| N-(4-{1-[(4-methoxyphenyl)carbonyl]piperidin-4-yl}butyl)thieno[2,3-c]pyridine-2-carboxamide | 0.0522 | 0.0803 |
| N-(4-{1-[(2,5-dichlorophenyl)carbonyl]piperidin-4-yl}butyl)-1H-pyrrolo[3,2-c]pyridine-2-carboxamide | 0.0513 | 0.0061 |
| N-(4-{1-[(1-methyl-1H-indol-2-yl)carbonyl]piperidin-4-yl}butyl)-1H-pyrrolo[3,2-c]pyridine-2-carboxamide | 0.134 | 0.0238 |
| N-[4-(1-{[5-(trifluoromethyl)pyridin-2-yl]carbonyl}piperidin-4-yl)butyl]-1H-pyrrolo[3,2-c]pyridine-2-carboxamide | 0.137 | 0.0596 |
| N-(4-{1-[(4-chloro-2-methoxyphenyl)carbonyl]piperidin-4-yl}butyl)-1H-pyrrolo[3,2-c]pyridine-2-carboxamide | 0.0621 | 0.0061 |
| N-(4-{1-[(pyridin-3-yl)carbonyl]piperidin-4-yl}butyl)-1H-pyrrolo[3,2-c]pyridine-2-carboxamide | 0.0986 | 0.0231 |
| N-(4-{1-[(2-methylpyridin-3-yl)carbonyl]piperidin-4-yl}butyl)-1H-pyrrolo[3,2-c]pyridine-2-carboxamide | 0.0215 | 0.0017 |
| N-(4-{1-[(5-methylpyrazin-2-yl)carbonyl]piperidin-4-yl}butyl)-1H-pyrrolo[3,2-c]pyridine-2-carboxamide | 0.115 | 0.0238 |
| N-(4-{1-[(pyridin-2-yl)carbonyl]piperidin-4-yl}butyl)-1H-pyrrolo[3,2-c]pyridine-2-carboxamide | 0.0306 | 0.0063 |
| N-(4-{1-[(dimethyl-1,3-thiazol-5-yl)carbonyl]piperidin-4-yl}butyl)-1H-pyrrolo[3,2-c]pyridine-2-carboxamide | 0.0621 | 0.0057 |
| N-[4-(1-{[2-(methylsulfanyl)pyridin-3-yl]carbonyl}piperidin-4-yl)butyl]-1H-pyrrolo[3,2-c]pyridine-2-carboxamide | 0.0083 | 0.0007 |
| N-(4-{1-[(2-ethoxypyridin-3-yl)carbonyl]piperidin-4-yl}butyl)-1H-pyrrolo[3,2-c]pyridine-2-carboxamide | 0.0206 | 0.0006 |
| N-(4-{1-[(5-chloro-2-methoxypyridin-3-yl)carbonyl]piperidin-4-yl}butyl)-1H-pyrrolo[3,2-c]pyridine-2-carboxamide | 0.0303 | 0.0033 |
| N-(4-{1-[(1-methyl-1H-imidazol-4-yl)carbonyl]piperidin-4-yl}butyl)-1H-pyrrolo[3,2-c]pyridine-2-carboxamide | 0.0937 | 0.055 |
| N-(4-{1-[(2-ethoxyphenyl)carbonyl]piperidin-4-yl}butyl)-1H-pyrrolo[3,2-c]pyridine-2-carboxamide | 0.0305 | 0.0005 |
| N-(4-{1-[(4-methyl-1,3-thiazol-5-yl)carbonyl]piperidin-4-yl}butyl)-1H-pyrrolo[3,2-c]pyridine-2-carboxamide | 0.0054 | 0.001 |

TABLE 3-continued

| IUPAC Name | Biochem IC50 uM | A2780 IC50 uM |
|---|---|---|
| N-(4-{1-[(1H-indol-6-yl)carbonyl]piperidin-4-yl}butyl)-1H-pyrrolo[3,2-c]pyridine-2-carboxamide | 0.0529 | 0.0134 |
| N-[4-(1-{[2-(trifluoromethyl)-1,3-thiazol-4-yl]carbonyl}piperidin-4-yl)butyl]-1H-pyrrolo[3,2-c]pyridine-2-carboxamide | 0.0685 | 0.0222 |
| N-[4-(1-{[6-(trifluoromethyl)pyridin-3-yl]carbonyl}piperidin-4-yl)butyl]-1H-pyrrolo[3,2-c]pyridine-2-carboxamide | 0.278 | 0.0476 |
| N-[4-{1-[(6-methylpyridin-3-yl)carbonyl]piperidin-4-yl}butyl)-1H-pyrrolo[3,2-c]pyridine-2-carboxamide | 0.0651 | 0.0213 |
| N-[4-(1-{[2-(trifluoromethyl)pyrimidin-5-yl]carbonyl}piperidin-4-yl)butyl]-1H-pyrrolo[3,2-c]pyridine-2-carboxamide | 0.242 | 0.1-1 |
| N-[4-(1-{[5-(methoxymethyl)pyridin-2-yl]carbonyl}piperidin-4-yl)butyl]-1H-pyrrolo[3,2-c]pyridine-2-carboxamide | 0.0311 | 0.0142 |
| N-(4-{1-[(5-fluoropyridin-2-yl)carbonyl]piperidin-4-yl}butyl)-1H-pyrrolo[3,2-c]pyridine-2-carboxamide | 0.0572 | 0.014 |
| N-(4-{1-[(5-fluoro-2-methylphenyl)carbonyl]piperidin-4-yl}butyl)-1H-pyrrolo[3,2-c]pyridine-2-carboxamide | 0.0142 | 0.0023 |
| N-(4-{1-[2-(2-methyl-1,3-thiazol-4-yl)acetyl]piperidin-4-yl}butyl)-1H-pyrrolo[3,2-c]pyridine-2-carboxamide | 0.0494 | 0.0139 |
| N-(4-{1-[(5-fluoro-1H-indol-2-yl)carbonyl]piperidin-4-yl}butyl)-1H-pyrrolo[3,2-c]pyridine-2-carboxamide | 0.0971 | 0.1-1 |
| N-(4-{1-[2-(1-methyl-1H-indol-3-yl)acetyl]piperidin-4-yl}butyl)-1H-pyrrolo[3,2-c]pyridine-2-carboxamide | 0.0091 | 0.0112 |
| N-[4-(1-{[4-(propan-2-yl)-1,3-oxazol-5-yl]carbonyl}piperidin-4-yl)butyl]-1H-pyrrolo[3,2-c]pyridine-2-carboxamide | 0.0304 | 0.0053 |
| N-(4-{1-[(2-phenyl-1,3-thiazol-4-yl)carbonyl]piperidin-4-yl}butyl)-1H-pyrrolo[3,2-c]pyridine-2-carboxamide | 0.11 | 0.0725 |
| N-(4-{1-[(3-fluoro-4-methylphenyl)carbonyl]piperidin-4-yl}butyl)-1H-pyrrolo[3,2-c]pyridine-2-carboxamide | 0.0771 | 0.0224 |
| N-(4-{1-[(3-fluoro-2-methylphenyl)carbonyl]piperidin-4-yl}butyl)-1H-pyrrolo[3,2-c]pyridine-2-carboxamide | 0.0205 | 0.0031 |
| N-(4-{1-[(1,3-benzothiazol-6-yl)carbonyl]piperidin-4-yl}butyl)-1H-pyrrolo[3,2-c]pyridine-2-carboxamide | 0.0727 | 0.0126 |
| N-(4-{1-[(2,3-difluorophenyl)carbonyl]piperidin-4-yl}butyl)-1H-pyrrolo[3,2-c]pyridine-2-carboxamide | 0.0121 | 0.0034 |
| N-{4-[1-({imidazo[1,2-a]pyridin-6-yl}carbonyl)piperidin-4-yl]butyl}-1H-pyrrolo[3,2-c]pyridine-2-carboxamide | 0.0077 | 0.0138 |
| N-(4-{1-[(furan-3-yl)carbonyl]piperidin-4-yl}butyl)-1H-pyrrolo[3,2-c]pyridine-2-carboxamide | 0.0091 | 0.0101 |
| N-[4-(1-benzoylpiperidin-4-yl)butyl]thieno[2,3-c]pyridine-2-carboxamide | 0.0063 | 0.0012 |
| N-[4-(1-{[2-(pyridin-3-yl)-1,3-thiazol-4-yl]carbonyl}piperidin-4-yl)butyl]thieno[2,3-c]pyridine-2-carboxamide | 0.0706 | 0.0853 |
| N-{4-[1-({1H-pyrrolo[3,2-c]pyridin-2-yl}carbonyl)piperidin-4-yl]butyl}thieno[2,3-c]pyridine-2-carboxamide | 0.0069 | 0.0137 |
| N-[4-(1-cyclohexanecarbonylpiperidin-4-yl)butyl]thieno[2,3-c]pyridine-2-carboxamide | 0.0779 | 0.0727 |
| N-[4-(1-{[4-(1H-pyrazol-1-yl)phenyl]carbonyl}piperidin-4-yl)butyl]-1H-pyrrolo[3,2-c]pyridine-2-carboxamide | 0.0507 | 0.0136 |
| N-(4-{1-[(4-fluorophenyl)carbonyl]piperidin-4-yl}butyl)thieno[2,3-c]pyridine-2-carboxamide | 0.0518 | 0.1-1 |
| N-[4-(1-{[4-(trifluoromethyl)phenyl]carbonyl}piperidin-4-yl)butyl]thieno[2,3-c]pyridine-2-carboxamide | 0.305 | 1 |
| N-(4-{1-[(2H-1,3-benzodioxol-5-yl)carbonyl]piperidin-4-yl}butyl)thieno[2,3-c]pyridine-2-carboxamide | 0.0211 | 0.1-1 |
| N-(4-{1-[(2-methoxyphenyl)carbonyl]piperidin-4-yl}butyl)thieno[2,3-c]pyridine-2-carboxamide | 0.0077 | 0.0033 |
| N-(4-{1-{[6-(morpholin-4-yl)pyridin-3-yl]carbonyl}piperidin-4-yl)butyl]thieno[2,3-c]pyridine-2-carboxamide | 0.0301 | 0.0131 |
| N-(4-{1-[(2-methyl-1,3-thiazol-4-yl)carbonyl]piperidin-4-yl}butyl)thieno[2,3-c]pyridine-2-carboxamide | 0.0224 | 0.1-1 |
| N-(4-{1-[(2,5-dichlorophenyl)carbonyl]piperidin-4-yl}butyl)thieno[2,3-c]pyridine-2-carboxamide | 0.016 | 0.0071 |
| N-[4-(1-{[6-(propan-2-yl)pyridin-3-yl]carbonyl}piperidin-4-yl)butyl]thieno[2,3-c]pyridine-2-carboxamide | 0.138 | 0.1-1 |
| N-(4-{1-[(1H-indol-2-yl)carbonyl]piperidin-4-yl}butyl)thieno[2,3-c]pyridine-2-carboxamide | 0.0335 | 0.1-1 |
| N-(4-{1-[(3-methoxyphenyl)carbonyl]piperidin-4-yl}butyl)thieno[2,3-c]pyridine-2-carboxamide | 0.0261 | 0.011 |
| N-[4-(1-{[4-(difluoromethoxy)phenyl]carbonyl}piperidin-4-yl)butyl]thieno[2,3-c]pyridine-2-carboxamide | 0.0774 | 0.1-1 |

TABLE 3-continued

| IUPAC Name | Biochem IC50 uM | A2780 IC50 uM |
|---|---|---|
| N-(4-{1-[(3-ethoxyphenyl)carbonyl]piperidin-4-yl}butyl)thieno[2,3-c]pyridine-2-carboxamide | 0.0391 | 0.0765 |
| N-(4-{1-[(1H-indol-5-yl)carbonyl]piperidin-4-yl}butyl)thieno[2,3-c]pyridine-2-carboxamide | 0.0427 | 0.0711 |
| N-(4-{1-[(3-fluoro-4-methoxyphenyl)carbonyl]piperidin-4-yl}butyl)thieno[2,3-c]pyridine-2-carboxamide | 0.0714 | 0.1-1 |
| N-(4-{1-[(2,5-difluorophenyl)carbonyl]piperidin-4-yl}butyl)thieno[2,3-c]pyridine-2-carboxamide | 0.0076 | 0.0016 |
| N-[4-(1-{[4-(trifluoromethoxy)phenyl]carbonyl}piperidin-4-yl)butyl]thieno[2,3-c]pyridine-2-carboxamide | 0.166 | 0.1-1 |
| N-(4-{1-[(3,4-dimethoxyphenyl)carbonyl]piperidin-4-yl}butyl)thieno[2,3-c]pyridine-2-carboxamide | 0.0326 | 0.0069 |
| N-[4-(1-{[4-(propan-2-yloxy)phenyl]carbonyl}piperidin-4-yl)butyl]thieno[2,3-c]pyridine-2-carboxamide | 0.04 | 0.1-1 |
| N-(4-{1-[(3,5-dimethoxyphenyl)carbonyl]piperidin-4-yl}butyl)thieno[2,3-c]pyridine-2-carboxamide | 0.0571 | 0.0202 |
| N-(4-{1-[(3-fluorophenyl)carbonyl]piperidin-4-yl}butyl)thieno[2,3-c]pyridine-2-carboxamide | 0.0077 | 0.0074 |
| N-(4-{1-[(2-fluorophenyl)carbonyl]piperidin-4-yl}butyl)thieno[2,3-c]pyridine-2-carboxamide | 0.0088 | 0.0006 |
| N-(4-{1-[(3-chlorophenyl)carbonyl]piperidin-4-yl}butyl)thieno[2,3-c]pyridine-2-carboxamide | 0.0334 | 0.0455 |
| N-(4-{1-[(4-chlorophenyl)carbonyl]piperidin-4-yl}butyl)thieno[2,3-c]pyridine-2-carboxamide | 0.0228 | 1-10 |
| N-(4-{1-[(1-methyl-1H-imidazol-2-yl)carbonyl]piperidin-4-yl}butyl)-1H-pyrrolo[3,2-c]pyridine-2-carboxamide | 0.0765 | 0.0236 |
| N-(4-{1-[(2-fluoro-3-methylphenyl)carbonyl]piperidin-4-yl}butyl)thieno[2,3-c]pyridine-2-carboxamide | 0.0212 | 0.0126 |
| N-(4-{1-[(2,6-difluorophenyl)carbonyl]piperidin-4-yl}butyl)thieno[2,3-c]pyridine-2-carboxamide | 0.0043 | 0.0008 |
| N-(4-{1-[(3,4-difluorophenyl)carbonyl]piperidin-4-yl}butyl)thieno[2,3-c]pyridine-2-carboxamide | 0.0229 | 0.1-1 |
| N-(4-{1-[(2,4-difluorophenyl)carbonyl]piperidin-4-yl}butyl)thieno[2,3-c]pyridine-2-carboxamide | 0.0128 | 0.0135 |
| N-(4-{1-[(2,6-dimethoxyphenyl)carbonyl]piperidin-4-yl}butyl)thieno[2,3-c]pyridine-2-carboxamide | 0.0056 | 0.0012 |
| N-(4-{1-[(3,4-dichlorophenyl)carbonyl]piperidin-4-yl}butyl)thieno[2,3-c]pyridine-2-carboxamide | 0.0345 | 0.1-1 |
| N-(4-{1-[(1-benzothiophen-2-yl)carbonyl]piperidin-4-yl}butyl)thieno[2,3-c]pyridine-2-carboxamide | 0.0177 | 0.1-1 |
| N-(4-{1-[(3,5-dichlorophenyl)carbonyl]piperidin-4-yl}butyl)thieno[2,3-c]pyridine-2-carboxamide | 0.03 | 0.0513 |
| N-[4-(1-{[2-(trifluoromethoxy)phenyl]carbonyl}piperidin-4-yl)butyl]thieno[2,3-c]pyridine-2-carboxamide | 0.0104 | 0.0031 |
| N-(4-{1-[(2-ethoxyphenyl)carbonyl]piperidin-4-yl}butyl)thieno[2,3-c]pyridine-2-carboxamide | 0.004 | 0.0006 |
| N-(4-{1-[(5-chloro-2-methoxyphenyl)carbonyl]piperidin-4-yl}butyl)thieno[2,3-c]pyridine-2-carboxamide | 0.0141 | 0.0033 |
| N-(4-{1-[(4-chloro-2-methoxyphenyl)carbonyl]piperidin-4-yl}butyl)thieno[2,3-c]pyridine-2-carboxamide | 0.0155 | 0.013 |
| N-(4-{1-[(2,5-dimethoxyphenyl)carbonyl]piperidin-4-yl}butyl)thieno[2,3-c]pyridine-2-carboxamide | 0.0055 | 0.0029 |
| N-[4-(1-{[6-(trifluoromethyl)pyridin-3-yl]carbonyl}piperidin-4-yl)butyl]thieno[2,3-c]pyridine-2-carboxamide | 0.0903 | 0.414 |
| N-(4-{1-[(2,4-dimethoxyphenyl)carbonyl]piperidin-4-yl}butyl)thieno[2,3-c]pyridine-2-carboxamide | 0.0157 | 0.0069 |
| N-(4-{1-[(2-chlorophenyl)carbonyl]piperidin-4-yl}butyl)thieno[2,3-c]pyridine-2-carboxamide | 0.0083 | 0.0017 |
| N-(4-{1-[(2,3-dichlorophenyl)carbonyl]piperidin-4-yl}butyl)thieno[2,3-c]pyridine-2-carboxamide | 0.0201 | 0.0067 |
| N-(4-{1-[(2,4-dichlorophenyl)carbonyl]piperidin-4-yl}butyl)thieno[2,3-c]pyridine-2-carboxamide | 0.041 | 0.0861 |
| N-(4-{1-[(1-methyl-1H-indol-2-yl)carbonyl]piperidin-4-yl}butyl)thieno[2,3-c]pyridine-2-carboxamide | 0.065 | 0.1-1 |
| N-(4-{1-[(2,4-dichlorophenyl)carbonyl]piperidin-4-yl}butyl)-1H-pyrrolo[3,2-c]pyridine-2-carboxamide | 0.07 | 0.012 |
| N-[4-(1-{[4-(trifluoromethyl)pyridin-3-yl]carbonyl}piperidin-4-yl)butyl]thieno[2,3-c]pyridine-2-carboxamide | 0.0099 | 0.0069 |
| N-(4-{1-[(pyridin-3-yl)carbonyl]piperidin-4-yl}butyl)thieno[2,3-c]pyridine-2-carboxamide | 0.0111 | 0.0274 |
| N-(4-{1-[(5-methylpyrazin-2-yl)carbonyl]piperidin-4-yl}butyl)thieno[2,3-c]pyridine-2-carboxamide | 0.0685 | 0.1-1 |
| N-(4-{1-[(dimethyl-1,3-thiazol-5-yl)carbonyl]piperidin-4-yl}butyl)thieno[2,3-c]pyridine-2-carboxamide | 0.0355 | 0.013 |

TABLE 3-continued

| IUPAC Name | Biochem IC50 uM | A2780 IC50 uM |
|---|---|---|
| N-[4-(1-{[2-(methylsulfanyl)pyridin-3-yl]carbonyl}piperidin-4-yl)butyl]thieno[2,3-c]pyridine-2-carboxamide | 0.0101 | 0.0014 |
| N-(4-{1-[(2-ethoxypyridin-3-yl)carbonyl]piperidin-4-yl}butyl)thieno[2,3-c]pyridine-2-carboxamide | 0.0056 | 0.0015 |
| N-(4-{1-[(5-chloro-2-methoxypyridin-3-yl)carbonyl]piperidin-4-yl}butyl)thieno[2,3-c]pyridine-2-carboxamide | 0.017 | 0.0071 |
| N-(4-{1-[(4-methyl-1,3-thiazol-5-yl)carbonyl]piperidin-4-yl}butyl)thieno[2,3-c]pyridine-2-carboxamide | 0.0053 | 0.0008 |
| N-[4-(1-{[4-(1H-pyrazol-1-yl)phenyl]carbonyl}piperidin-4-yl)butyl]thieno[2,3-c]pyridine-2-carboxamide | 0.0481 | 0.1-1 |
| N-(4-{1-[(1H-indol-6-yl)carbonyl]piperidin-4-yl}butyl)thieno[2,3-c]pyridine-2-carboxamide | 0.0361 | 0.0703 |
| N-[4-(1-{[2-(trifluoromethyl)-1,3-thiazol-4-yl]carbonyl}piperidin-4-yl)butyl]thieno[2,3-c]pyridine-2-carboxamide | 0.094 | 0.1-1 |
| N-(4-{1-[(6-methylpyridin-3-yl)carbonyl]piperidin-4-yl}butyl)thieno[2,3-c]pyridine-2-carboxamide | 0.0697 | 0.1-1 |
| N-[4-(1-{[5-(trifluoromethyl)pyridin-2-yl]carbonyl}piperidin-4-yl)butyl]thieno[2,3-c]pyridine-2-carboxamide | 0.0918 | 0.1-1 |
| N-[4-(1-{[2-(trifluoromethyl)pyrimidin-5-yl]carbonyl}piperidin-4-yl)butyl]thieno[2,3-c]pyridine-2-carboxamide | 0.158 | 0.1-1 |
| N-[4-(1-{[5-(methoxymethyl)pyridin-2-yl]carbonyl}piperidin-4-yl)butyl]thieno[2,3-c]pyridine-2-carboxamide | 0.0183 | 0.0302 |
| N-(4-{1-[(5-fluoropyridin-2-yl)carbonyl]piperidin-4-yl}butyl)thieno[2,3-c]pyridine-2-carboxamide | 0.0265 | 0.1-1 |
| N-(4-{1-[2-(2-methyl-1,3-thiazol-4-yl)acetyl]piperidin-4-yl}butyl)thieno[2,3-c]pyridine-2-carboxamide | 0.0135 | 0.0282 |
| N-[4-(1-{[5-(propan-2-yl)pyridin-2-yl]carbonyl}piperidin-4-yl)butyl]thieno[2,3-c]pyridine-2-carboxamide | 0.0898 | 0.1-1 |
| N-(4-{1-[(5-fluoro-1H-indol-2-yl)carbonyl]piperidin-4-yl}butyl)thieno[2,3-c]pyridine-2-carboxamide | 0.0304 | 1-10 |
| N-(4-{1-[2-(1-methyl-1H-indol-3-yl)acetyl]piperidin-4-yl}butyl)thieno[2,3-c]pyridine-2-carboxamide | 0.0116 | 0.024 |
| N-[4-(1-{[4-(propan-2-yl)-1,3-oxazol-5-yl]carbonyl}piperidin-4-yl)butyl]thieno[2,3-c]pyridine-2-carboxamide | 0.0074 | 0.0076 |
| N-(4-{1-[(2-phenyl-1,3-thiazol-4-yl)carbonyl]piperidin-4-yl}butyl)thieno[2,3-c]pyridine-2-carboxamide | 0.0131 | 0.0762 |
| N-(4-{1-[(3-fluoro-4-methylphenyl)carbonyl]piperidin-4-yl}butyl)thieno[2,3-c]pyridine-2-carboxamide | 0.0417 | 0.1-1 |
| N-(4-{1-[(5-fluoro-2-methylphenyl)carbonyl]piperidin-4-yl}butyl)thieno[2,3-c]pyridine-2-carboxamide | 0.0045 | 0.0018 |
| N-(4-{1-[(1,3-benzothiazol-6-yl)carbonyl]piperidin-4-yl}butyl)thieno[2,3-c]pyridine-2-carboxamide | 0.0323 | 0.0354 |
| N-(4-{1-[(2,3-difluorophenyl)carbonyl]piperidin-4-yl}butyl)thieno[2,3-c]pyridine-2-carboxamide | 0.0068 | 0.0045 |
| N-{4-[1-({thieno[2,3-c]pyridin-2-yl}carbonyl)piperidin-4-yl]butyl}thieno[2,3-c]pyridine-2-carboxamide | 0.0152 | 0.1-1 |
| N-(4-{1-[(furan-3-yl)carbonyl]piperidin-4-yl}butyl)thieno[2,3-c]pyridine-2-carboxamide | 0.004 | 0.006 |
| N-[4-(1-benzoylpiperidin-4-yl)butyl]imidazo[1,2-a]pyridine-6-carboxamide | 0.0055 | 0.0057 |
| N-[4-(1-{[2-(pyridin-3-yl)-1,3-thiazol-4-yl]carbonyl}piperidin-4-yl)butyl]imidazo[1,2-a]pyridine-6-carboxamide | 0.0611 | 0.067 |
| N-(4-{1-[(2,3-dimethoxyphenyl)carbonyl]piperidin-4-yl}butyl)thieno[2,3-c]pyridine-2-carboxamide | 0.0169 | 0.0056 |
| N-{4-[1-({1H-pyrrolo[3,2-c]pyridin-2-yl}carbonyl)piperidin-4-yl]butyl}imidazo[1,2-a]pyridine-6-carboxamide | 0.0086 | 0.0131 |
| N-[4-(1-{[4-(trifluoromethyl)phenyl]carbonyl}piperidin-4-yl)butyl]imidazo[1,2-a]pyridine-6-carboxamide | 0.152 | 0.1-1 |
| N-[4-(1-cyclohexanecarbonylpiperidin-4-yl)butyl]imidazo[1,2-a]pyridine-6-carboxamide | 0.0181 | 0.0009 |
| N-(4-{1-[(3,4-difluorophenyl)carbonyl]piperidin-4-yl}butyl)imidazo[1,2-a]pyridine-6-carboxamide | 0.019 | 0.0662 |
| N-(4-{1-[(4-methoxyphenyl)carbonyl]piperidin-4-yl}butyl)imidazo[1,2-a]pyridine-6-carboxamide | 0.0232 | 0.0576 |
| N-(4-{1-[(4-fluorophenyl)carbonyl]piperidin-4-yl}butyl)imidazo[1,2-a]pyridine-6-carboxamide | 0.012 | 0.0262 |
| N-(4-{1-[(2H-1,3-benzodioxol-5-yl)carbonyl]piperidin-4-yl}butyl)imidazo[1,2-a]pyridine-6-carboxamide | 0.0213 | 0.0292 |
| N-[4-(1-{[6-(morpholin-4-yl)pyridin-3-yl]carbonyl}piperidin-4-yl)butyl]imidazo[1,2-a]pyridine-6-carboxamide | 0.0129 | 0.0059 |
| N-(4-{1-[(2-methyl-1,3-thiazol-4-yl)carbonyl]piperidin-4-yl}butyl)imidazo[1,2-a]pyridine-6-carboxamide | 0.0314 | 0.0611 |

TABLE 3-continued

| IUPAC Name | Biochem IC50 uM | A2780 IC50 uM |
|---|---|---|
| N-[4-(1-{[5-(propan-2-yl)pyridin-2-yl]carbonyl}piperidin-4-yl)butyl]imidazo[1,2-a]pyridine-6-carboxamide | 0.0567 | 0.0529 |
| N-[4-(1-{[6-(propan-2-yl)pyridin-3-yl]carbonyl}piperidin-4-yl)butyl]imidazo[1,2-a]pyridine-6-carboxamide | 0.0387 | 0.0261 |
| N-(4-{1-[(1H-indol-2-yl)carbonyl]piperidin-4-yl}butyl)imidazo[1,2-a]pyridine-6-carboxamide | 0.0616 | 0.1-1 |
| N-(4-{1-[(1-acetylpiperidin-4-yl)carbonyl]piperidin-4-yl}butyl)imidazo[1,2-a]pyridine-6-carboxamide | 0.0396 | 0.0278 |
| N-(4-{1-[(3-methoxyphenyl)carbonyl]piperidin-4-yl}butyl)imidazo[1,2-a]pyridine-6-carboxamide | 0.0212 | 0.0066 |
| N-[4-(1-{[4-(difluoromethoxy)phenyl]carbonyl}piperidin-4-yl)butyl]imidazo[1,2-a]pyridine-6-carboxamide | 0.0427 | 0.101 |
| N-(4-{1-[(3-ethoxyphenyl)carbonyl]piperidin-4-yl}butyl)imidazo[1,2-a]pyridine-6-carboxamide | 0.0102 | 0.0132 |
| N-(4-{1-[(1H-indol-5-yl)carbonyl]piperidin-4-yl}butyl)imidazo[1,2-a]pyridine-6-carboxamide | 0.0195 | 0.0185 |
| N-(4-{1-[(3-fluoro-4-methoxyphenyl)carbonyl]piperidin-4-yl}butyl)imidazo[1,2-a]pyridine-6-carboxamide | 0.0202 | 0.0652 |
| N-[4-(1-{[4-(trifluoromethoxy)phenyl]carbonyl}piperidin-4-yl)butyl]imidazo[1,2-a]pyridine-6-carboxamide | 0.091 | 0.1-1 |
| N-(4-{1-[(3,4-dimethoxyphenyl)carbonyl]piperidin-4-yl}butyl)imidazo[1,2-a]pyridine-6-carboxamide | 0.0385 | 0.0029 |
| N-[4-(1-{[4-(propan-2-yloxy)phenyl]carbonyl}piperidin-4-yl)butyl]imidazo[1,2-a]pyridine-6-carboxamide | 0.0552 | 0.0209 |
| N-(4-{1-[(3-fluorophenyl)carbonyl]piperidin-4-yl}butyl)imidazo[1,2-a]pyridine-6-carboxamide | 0.0092 | 0.0103 |
| N-(3-(1-benzoylpiperidin-4-yl)butyl)-1H-pyrrolo[3,2-c]pyridine-2-carboxamide | 0.028 | 0.0175 |
| N-(4-{1-[(2-fluorophenyl)carbonyl]piperidin-4-yl}butyl)imidazo[1,2-a]pyridine-6-carboxamide | 0.0038 | 0.0005 |
| N-(4-{1-[(3-chlorophenyl)carbonyl]piperidin-4-yl}butyl)imidazo[1,2-a]pyridine-6-carboxamide | 0.0171 | 0.0223 |
| N-(4-{1-[(4-chlorophenyl)carbonyl]piperidin-4-yl}butyl)imidazo[1,2-a]pyridine-6-carboxamide | 0.0846 | 0.1-1 |
| N-(4-{1-[(3-fluoro-2-methylphenyl)carbonyl]piperidin-4-yl}butyl)thieno[2,3-c]pyridine-2-carboxamide | 0.0068 | 0.0032 |
| N-(4-{1-[(2-fluoro-3-methylphenyl)carbonyl]piperidin-4-yl}butyl)imidazo[1,2-a]pyridine-6-carboxamide | 0.0226 | 0.0127 |
| N-(4-{1-[(2,6-difluorophenyl)carbonyl]piperidin-4-yl}butyl)imidazo[1,2-a]pyridine-6-carboxamide | 0.0047 | 0.0012 |
| N-(4-{1-[(2,4-difluorophenyl)carbonyl]piperidin-4-yl}butyl)imidazo[1,2-a]pyridine-6-carboxamide | 0.0071 | 0.0256 |
| N-(4-{1-[(3,4-dichlorophenyl)carbonyl]piperidin-4-yl}butyl)imidazo[1,2-a]pyridine-6-carboxamide | 0.049 | 0.1-1 |
| N-(4-{1-[(2,3-dimethoxyphenyl)carbonyl]piperidin-4-yl}butyl)imidazo[1,2-a]pyridine-6-carboxamide | 0.0191 | 0.0029 |
| N-[4-(1-{[6-(propan-2-yl)pyridin-3-yl]carbonyl}piperidin-4-yl)butyl]-1H-pyrrolo[3,2-c]pyridine-2-carboxamide | 0.0867 | 0.0132 |
| N-(4-{1-[(1-benzothiophen-2-yl)carbonyl]piperidin-4-yl}butyl)imidazo[1,2-a]pyridine-6-carboxamide | 0.0258 | 0.0718 |
| N-(4-{1-[(3,5-dichlorophenyl)carbonyl]piperidin-4-yl}butyl)imidazo[1,2-a]pyridine-6-carboxamide | 0.0616 | 0.0329 |
| N-[4-(1-{[2-(trifluoromethoxy)phenyl]carbonyl}piperidin-4-yl)butyl]imidazo[1,2-a]pyridine-6-carboxamide | 0.0025 | 0.0019 |
| N-(4-{1-[(2-ethoxyphenyl)carbonyl]piperidin-4-yl}butyl)imidazo[1,2-a]pyridine-6-carboxamide | 0.0052 | 0.0007 |
| N-(4-{1-[(5-chloro-2-methoxyphenyl)carbonyl]piperidin-4-yl}butyl)imidazo[1,2-a]pyridine-6-carboxamide | 0.0105 | 0.0031 |
| N-(4-{1-[(4-chloro-2-methoxyphenyl)carbonyl]piperidin-4-yl}butyl)imidazo[1,2-a]pyridine-6-carboxamide | 0.0806 | 0.027 |
| N-(4-{1-[(2,6-dimethoxyphenyl)carbonyl]piperidin-4-yl}butyl)imidazo[1,2-a]pyridine-6-carboxamide | 0.0286 | 0.001 |
| N-(4-{1-[(2,5-dimethoxyphenyl)carbonyl]piperidin-4-yl}butyl)imidazo[1,2-a]pyridine-6-carboxamide | 0.0429 | 0.0019 |
| N-(4-{1-[(2,4-dimethoxyphenyl)carbonyl]piperidin-4-yl}butyl)imidazo[1,2-a]pyridine-6-carboxamide | 0.0222 | 0.0033 |
| N-(4-{1-[(2-chlorophenyl)carbonyl]piperidin-4-yl}butyl)imidazo[1,2-a]pyridine-6-carboxamide | 0.005 | 0.0015 |
| N-(4-{1-[(2,4-dichlorophenyl)carbonyl]piperidin-4-yl}butyl)imidazo[1,2-a]pyridine-6-carboxamide | 0.0357 | 0.0144 |
| N-(4-{1-[(3,5-dimethoxyphenyl)carbonyl]piperidin-4-yl}butyl)imidazo[1,2-a]pyridine-6-carboxamide | 0.0225 | 0.0028 |
| N-(4-{1-[(1-methyl-1H-indol-2-yl)carbonyl]piperidin-4-yl}butyl)imidazo[1,2-a]pyridine-6-carboxamide | 0.124 | 0.0551 |

TABLE 3-continued

| IUPAC Name | Biochem IC50 uM | A2780 IC50 uM |
|---|---|---|
| N-[4-(1-{[4-(trifluoromethyl)pyridin-3-yl]carbonyl}piperidin-4-yl)butyl]imidazo[1,2-a]pyridine-6-carboxamide | 0.0156 | 0.0038 |
| N-(4-{1-[(pyridin-3-yl)carbonyl]piperidin-4-yl}butyl)imidazo[1,2-a]pyridine-6-carboxamide | 0.0127 | 0.0274 |
| N-(4-{1-[(3-fluoro-4-methylphenyl)carbonyl]piperidin-4-yl}butyl)imidazo[1,2-a]pyridine-6-carboxamide | 0.0394 | |
| N-(4-{1-[(2-methylpyridin-3-yl)carbonyl]piperidin-4-yl}butyl)imidazo[1,2-a]pyridine-6-carboxamide | 0.0098 | 0.0018 |
| N-[4-(1-{[6-(trifluoromethyl)pyridin-3-yl]carbonyl}piperidin-4-yl)butyl]imidazo[1,2-a]pyridine-6-carboxamide | 0.0919 | 0.093 |
| N-(4-{1-[(5-methylpyrazin-2-yl)carbonyl]piperidin-4-yl}butyl)imidazo[1,2-a]pyridine-6-carboxamide | 0.0109 | 0.0667 |
| N-(4-{1-[(pyridin-2-yl)carbonyl]piperidin-4-yl}butyl)imidazo[1,2-a]pyridine-6-carboxamide | 0.0364 | 0.0135 |
| N-(4-{1-[(dimethyl-1,3-thiazol-5-yl)carbonyl]piperidin-4-yl}butyl)imidazo[1,2-a]pyridine-6-carboxamide | 0.0241 | 0.0066 |
| N-[4-(1-{[2-(methylsulfanyl)pyridin-3-yl]carbonyl}piperidin-4-yl)butyl]imidazo[1,2-a]pyridine-6-carboxamide | 0.0055 | 0.0007 |
| N-(4-{1-[(2-ethoxypyridin-3-yl)carbonyl]piperidin-4-yl}butyl)imidazo[1,2-a]pyridine-6-carboxamide | 0.0092 | 0.0005 |
| N-(4-{1-[(5-chloro-2-methoxypyridin-3-yl)carbonyl]piperidin-4-yl}butyl)imidazo[1,2-a]pyridine-6-carboxamide | 0.0123 | 0.0033 |
| N-(4-{1-[(2,5-dichlorophenyl)carbonyl]piperidin-4-yl}butyl)imidazo[1,2-a]pyridine-6-carboxamide | 0.0102 | 0.0055 |
| N-(4-{1-[(1-methyl-1H-imidazol-4-yl)carbonyl]piperidin-4-yl}butyl)imidazo[1,2-a]pyridine-6-carboxamide | 0.0567 | 0.107 |
| N-(4-{1-[(4-methyl-1,3-thiazol-5-yl)carbonyl]piperidin-4-yl}butyl)imidazo[1,2-a]pyridine-6-carboxamide | 0.0029 | 0.0008 |
| N-[4-(1-{[4-(1H-pyrazol-1-yl)phenyl]carbonyl}piperidin-4-yl)butyl]imidazo[1,2-a]pyridine-6-carboxamide | 0.0307 | 0.0671 |
| N-(4-{1-[(2,5-difluorophenyl)carbonyl]piperidin-4-yl}butyl)imidazo[1,2-a]pyridine-6-carboxamide | 0.005 | 0.005 |
| N-(4-{1-[(1H-indol-6-yl)carbonyl]piperidin-4-yl}butyl)imidazo[1,2-a]pyridine-6-carboxamide | 0.0298 | 0.0149 |
| N-[4-(1-{[2-(trifluoromethyl)-1,3-thiazol-4-yl]carbonyl}piperidin-4-yl)butyl]imidazo[1,2-a]pyridine-6-carboxamide | 0.0743 | 0.074 |
| N-(4-{1-[(6-methylpyridin-3-yl)carbonyl]piperidin-4-yl}butyl)imidazo[1,2-a]pyridine-6-carboxamide | 0.0238 | 0.0736 |
| N-[4-(1-{[5-(trifluoromethyl)pyridin-2-yl]carbonyl}piperidin-4-yl)butyl]imidazo[1,2-a]pyridine-6-carboxamide | 0.0823 | |
| N-[4-(1-{[5-(methoxymethyl)pyridin-2-yl]carbonyl}piperidin-4-yl)butyl]imidazo[1,2-a]pyridine-6-carboxamide | 0.0574 | 0.0671 |
| N-(4-{1-[(5-fluoropyridin-2-yl)carbonyl]piperidin-4-yl}butyl)imidazo[1,2-a]pyridine-6-carboxamide | 0.074 | 0.0679 |
| N-(4-{1-[2-(2-methyl-1,3-thiazol-4-yl)acetyl]piperidin-4-yl}butyl)imidazo[1,2-a]pyridine-6-carboxamide | 0.0189 | 0.028 |
| N-(4-{1-[(5-fluoro-1H-indol-2-yl)carbonyl]piperidin-4-yl}butyl)imidazo[1,2-a]pyridine-6-carboxamide | 0.0713 | |
| N-(4-{1-[2-(1-methyl-1H-indol-3-yl)acetyl]piperidin-4-yl}butyl)imidazo[1,2-a]pyridine-6-carboxamide | 0.0295 | 0.0213 |
| N-[4-(1-{[4-(propan-2-yl)-1,3-oxazol-5-yl]carbonyl}piperidin-4-yl)butyl]imidazo[1,2-a]pyridine-6-carboxamide | 0.0275 | 0.0082 |
| N-(4-{1-[(2-phenyl-1,3-thiazol-4-yl)carbonyl]piperidin-4-yl}butyl)imidazo[1,2-a]pyridine-6-carboxamide | 0.0523 | |
| N-(3-(1-benzoylpiperidin-4-yl)propyl)-1H-pyrrolo[3,2-c]pyridine-2-carboxamide | 0.126 | 0.4316 |
| N-(4-{1-[(3-fluoro-2-methylphenyl)carbonyl]piperidin-4-yl}butyl)imidazo[1,2-a]pyridine-6-carboxamide | 0.0131 | 0.0035 |
| N-(4-{1-[(4-fluoro-3-methylbenzene)sulfonyl]piperidin-4-yl}butyl)-1H-pyrrolo[3,2-c]pyridine-2-carboxamide | 0.0696 | 0.0147 |
| N-(4-{1-[(1,3-benzothiazol-6-yl)carbonyl]piperidin-4-yl}butyl)imidazo[1,2-a]pyridine-6-carboxamide | 0.0237 | 0.0393 |
| N-(4-{1-[(2,3-difluorophenyl)carbonyl]piperidin-4-yl}butyl)imidazo[1,2-a]pyridine-6-carboxamide | 0.0079 | 0.0101 |
| N-{4-[1-({imidazo[1,2-a]pyridin-6-yl}carbonyl)piperidin-4-yl]butyl}imidazo[1,2-a]pyridine-6-carboxamide | 0.0085 | |
| N-(4-{1-[(furan-3-yl)carbonyl]piperidin-4-yl}butyl)imidazo[1,2-a]pyridine-6-carboxamide | 0.0062 | 0.0256 |
| N-(4-{1-[(3,4-dimethoxybenzene)sulfonyl]piperidin-4-yl}butyl)-1H-pyrrolo[3,2-c]pyridine-2-carboxamide | 0.0276 | 0.0032 |
| N-(4-{1-[(2-fluorobenzene)sulfonyl]piperidin-4-yl}butyl)-1H-pyrrolo[3,2-c]pyridine-2-carboxamide | 0.0076 | 0.0063 |
| N-{4-[1-(benzenesulfonyl)piperidin-4-yl]butyl}-1H-pyrrolo[3,2-c]pyridine-2-carboxamide | 0.0249 | 0.0067 |
| N-{4-[1-(5-methyl-1,2-oxazole-4-sulfonyl)piperidin-4-yl]butyl}-1H-pyrrolo[3,2-c]pyridine-2-carboxamide | 0.0367 | |

TABLE 3-continued

| IUPAC Name | Biochem IC50 uM | A2780 IC50 uM |
|---|---|---|
| N-{4-[1-(1-methyl-1H-pyrazole-3-sulfonyl)piperidin-4-yl]butyl}-1H-pyrrolo[3,2-c]pyridine-2-carboxamide | 0.0495 | 0.0068 |
| N-{4-[1-(pyridine-3-sulfonyl)piperidin-4-yl]butyl}-1H-pyrrolo[3,2-c]pyridine-2-carboxamide | 0.0161 | 0.0139 |
| N-(4-{1-[(5-fluoro-2-methylphenyl)carbonyl]piperidin-4-yl}butyl)imidazo[1,2-a]pyridine-6-carboxamide | 0.0109 | 0.0039 |
| N-(4-{1-[(2,5-dimethoxybenzene)sulfonyl]piperidin-4-yl}butyl)-1H-pyrrolo[3,2-c]pyridine-2-carboxamide | 0.0284 | 0.0018 |
| N-(4-{1-[(4-cyanobenzene)sulfonyl]piperidin-4-yl}butyl)-1H-pyrrolo[3,2-c]pyridine-2-carboxamide | 0.0496 | 0.0127 |
| N-(4-{1-[(4-fluorobenzene)sulfonyl]piperidin-4-yl}butyl)-1H-pyrrolo[3,2-c]pyridine-2-carboxamide | 0.0489 | 0.0176 |
| N-(4-{1-[(2-methylbenzene)sulfonyl]piperidin-4-yl}butyl)-1H-pyrrolo[3,2-c]pyridine-2-carboxamide | 0.036 | 0.0067 |
| N-(4-{1-[(4-chlorobenzene)sulfonyl]piperidin-4-yl}butyl)-1H-pyrrolo[3,2-c]pyridine-2-carboxamide | 0.0499 | 0.0275 |
| N-(4-{1-[(4-methoxybenzene)sulfonyl]piperidin-4-yl}butyl)-1H-pyrrolo[3,2-c]pyridine-2-carboxamide | 0.0338 | 0.0071 |
| N-[4-(1-{[4-(trifluoromethyl)benzene]sulfonyl}piperidin-4-yl)butyl]-1H-pyrrolo[3,2-c]pyridine-2-carboxamide | 0.0748 | 0.0233 |
| N-[4-(1-{[4-(trifluoromethoxy)benzene]sulfonyl}piperidin-4-yl)butyl]-1H-pyrrolo[3,2-c]pyridine-2-carboxamide | 0.076 | 0.0272 |
| N-[4-(1-{[4-(propan-2-yloxy)benzene]sulfonyl}piperidin-4-yl)butyl]-1H-pyrrolo[3,2-c]pyridine-2-carboxamide | 0.0193 | 0.0019 |
| N-(4-{1-[(4-methylbenzene)sulfonyl]piperidin-4-yl}butyl)-1H-pyrrolo[3,2-c]pyridine-2-carboxamide | 0.0302 | 0.0099 |
| N-[4-(1-{[2-(trifluoromethyl)benzene]sulfonyl}piperidin-4-yl)butyl]-1H-pyrrolo[3,2-c]pyridine-2-carboxamide | 0.0245 | 0.005 |
| N-(3-(((1-(2-fluorobenzoyl)piperidin-4-yl)oxy)propyl)-1H-pyrrolo[3,2-c]pyridine-2-carboxamide | 0.035 | 0.1771 |
| N-[4-(1-{[2-(trifluoromethoxy)benzene]sulfonyl}piperidin-4-yl)butyl]-1H-pyrrolo[3,2-c]pyridine-2-carboxamide | 0.0226 | 0.0033 |
| N-(4-{1-[(3-cyanobenzene)sulfonyl]piperidin-4-yl}butyl)-1H-pyrrolo[3,2-c]pyridine-2-carboxamide | 0.015 | 0.0276 |
| N-(4-{1-[(4-fluoro-2-methylbenzene)sulfonyl]piperidin-4-yl}butyl)-1H-pyrrolo[3,2-c]pyridine-2-carboxamide | 0.0152 | 0.0076 |
| N-(4-{1-[(3-methoxybenzene)sulfonyl]piperidin-4-yl}butyl)-1H-pyrrolo[3,2-c]pyridine-2-carboxamide | 0.0353 | 0.0107 |
| N-(4-{1-[(3-chlorobenzene)sulfonyl]piperidin-4-yl}butyl)-1H-pyrrolo[3,2-c]pyridine-2-carboxamide | 0.0388 | 0.0277 |
| N-[4-(1-{[3-(trifluoromethyl)benzene]sulfonyl}piperidin-4-yl)butyl]-1H-pyrrolo[3,2-c]pyridine-2-carboxamide | 0.0769 | 0.0623 |
| N-[4-(1-{[3-(trifluoromethoxy)benzene]sulfonyl}piperidin-4-yl)butyl]-1H-pyrrolo[3,2-c]pyridine-2-carboxamide | 0.0778 | 0.0187 |
| N-(4-{1-[(3-fluorobenzene)sulfonyl]piperidin-4-yl}butyl)-1H-pyrrolo[3,2-c]pyridine-2-carboxamide | 0.0217 | 0.0129 |
| N-(4-{1-[(2,5-difluorobenzene)sulfonyl]piperidin-4-yl}butyl)-1H-pyrrolo[3,2-c]pyridine-2-carboxamide | 0.0111 | 0.0058 |
| N-(4-{1-[(2-fluoro-5-methylbenzene)sulfonyl]piperidin-4-yl}butyl)-1H-pyrrolo[3,2-c]pyridine-2-carboxamide | 0.0268 | 0.0067 |
| N-(4-{1-[(2,4-dimethoxybenzene)sulfonyl]piperidin-4-yl}butyl)-1H-pyrrolo[3,2-c]pyridine-2-carboxamide | 0.0191 | 0.0017 |
| N-(4-{1-[(3-fluoro-4-methylbenzene)sulfonyl]piperidin-4-yl}butyl)-1H-pyrrolo[3,2-c]pyridine-2-carboxamide | 0.0307 | 0.0156 |
| N-(4-{1-[(3-chloro-4-fluorobenzene)sulfonyl]piperidin-4-yl}butyl)-1H-pyrrolo[3,2-c]pyridine-2-carboxamide | 0.0598 | 0.0685 |
| N-(4-{1-[(3-fluoro-4-methoxybenzene)sulfonyl]piperidin-4-yl}butyl)-1H-pyrrolo[3,2-c]pyridine-2-carboxamide | 0.0248 | 0.0075 |
| N-(4-{1-[(2-methoxy-5-methylbenzene)sulfonyl]piperidin-4-yl}butyl)-1H-pyrrolo[3,2-c]pyridine-2-carboxamide | 0.0273 | 0.0017 |
| N-(4-{1-[(3,5-difluorobenzene)sulfonyl]piperidin-4-yl}butyl)-1H-pyrrolo[3,2-c]pyridine-2-carboxamide | 0.0225 | 0.0069 |
| N-{[4-({4-[(pyrrolidin-1-yl)carbonyl]benzene}sulfonyl)phenyl]methyl}furo[2,3-c]pyridine-2-carboxamide | 0.0015 | 0.0014 |
| N-(4-{1-[(5-fluoro-2-methoxybenzene)sulfonyl]piperidin-4-yl}butyl)-1H-pyrrolo[3,2-c]pyridine-2-carboxamide | 0.0232 | 0.0015 |
| N-(4-{1-[(3-chloro-4-methoxybenzene)sulfonyl]piperidin-4-yl}butyl)-1H-pyrrolo[3,2-c]pyridine-2-carboxamide | 0.0293 | 0.0137 |
| N-(4-{1-[6-(trifluoromethyl)pyridine-3-sulfonyl]piperidin-4-yl}butyl)-1H-pyrrolo[3,2-c]pyridine-2-carboxamide | 0.0815 | 0.0298 |
| N-(4-{1-[(3-fluoro-2-methylbenzene)sulfonyl]piperidin-4-yl}butyl)-1H-pyrrolo[3,2-c]pyridine-2-carboxamide | 0.0255 | 0.0129 |
| N-(4-{1-[(2-chlorobenzene)sulfonyl]piperidin-4-yl}butyl)-1H-pyrrolo[3,2-c]pyridine-2-carboxamide | 0.0212 | 0.0071 |
| N-{4-[1-(propane-2-sulfonyl)piperidin-4-yl]butyl}-1H-pyrrolo[3,2-c]pyridine-2-carboxamide | 0.0306 | 0.023 |

TABLE 3-continued

| IUPAC Name | Biochem IC50 uM | A2780 IC50 uM |
|---|---|---|
| N-(4-{1-[(3,4-difluorobenzene)sulfonyl]piperidin-4-yl}butyl)-1H-pyrrolo[3,2-c]pyridine-2-carboxamide | 0.0346 | 0.0228 |
| N-(4-{1-[(4-methoxy-3-methylbenzene)sulfonyl]piperidin-4-yl}butyl)-1H-pyrrolo[3,2-c]pyridine-2-carboxamide | 0.0216 | 0.007 |
| N-{[4-({4-[(pyrrolidin-1-yl)carbonyl]benzene}sulfonyl)phenyl]methyl}thieno[2,3-c]pyridine-2-carboxamide | 0.0037 | 0.0017 |
| N-{[4-({4-[(pyrrolidin-1-yl)carbonyl]benzene}sulfonyl)phenyl]methyl}-1H-pyrazolo[3,4-b]pyridine-5-carboxamide | 0.0158 | 0.0093 |
| N-(4-(benzyloxy) phenethyl)-1H-pyrrolo [3,2-c] pyridine-2-carboxamide | | 2.0 |
| N-[4-(1-benzoylazetidin-3-yl)butyl]-1H-pyrrolo[3,2-c]pyridine-2-carboxamide | 0.0232 | 0.0769 |

We claim:

1. A process for preparing a compound of Formula II:

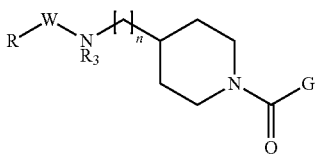

or a pharmaceutically acceptable salt thereof,
wherein:
W is —C(O)—;
R is aryl or bicyclic heteroaryl;
  wherein said heteroaryl contains 1, 2, or 3 heteroatoms independently selected from N, S, and O, with the proviso that no two adjacent ring heteroatoms are both S or both O; and
  each of said aryl or heteroaryl is optionally substituted with one or more substituents which can be the same or different and are independently selected from the group consisting of deuterium, halo, cyano, amino, aminoalkyl, (amino)alkoxy, —CONH$_2$, —C(O)NH(alkyl), —C(O)N(alkyl)$_2$, —C(O)NH(aryl), —C(O)N(aryl)$_2$, —CF$_3$, —CHF$_2$, —CH$_2$F, -alkyl, alkoxy, hydroxyl, hydroxyalkyl, (alkoxyalkyl) amino, —N(R$^3$)—C(O)-alkyl, —N(R$^3$)—C(O)-aryl, cycloalkyl, heterocycloalkyl, aryl, and heteroaryl, with the proviso that no two adjacent ring heteroatoms are both S or both O;
G is aryl, heteroaryl, cycloalkyl, heterocycloalkyl, or —NR$^1$R$^2$;
  wherein each of said aryl, heteroaryl, heterocycloalkyl and cycloalkyl is either unsubstituted or substituted with 1, 2, 3, or 4 substituents which can be the same or different and are independently selected from the group consisting of deuterium, halo, cyano, amino, aminoalkyl, (amino)alkoxy, —CONH$_2$, —C(O)NH(alkyl), —C(O)N(alkyl)$_2$, —C(O)NH(aryl), —C(O)N(aryl)$_2$, —CF$_3$, —CHF$_2$, —CH$_2$F, alkyl, alkenyl, alkynyl, alkoxy, hydroxyl, hydroxyalkyl, aryloxy, (alkoxyalkyl)amino, —N(R$^3$)—C(O)-alkyl, —N(R$^3$)—C(O)-aryl, cycloalkyl, heterocycloalkyl, aryl, and heteroaryl;
R$^1$ and R$^2$ are the same or they are different, and are independently selected from H, C$_1$ to C$_7$ alkyl, C$_1$ to C$_7$ alkoxy, C$_1$ to C$_4$ hydroxyalkyl, aryl, heteroaryl, heterocycloalkyl and cycloalkyl, and
  wherein heteroatoms of said heteroaryl and heterocycloalkyl are independently selected from one or more of N, O and S, with the proviso that no two adjacent ring heteroatoms are both S or both O; and
  wherein R$^1$ and R$^2$ are each unsubstituted or substituted with one or more substituents which can be the same or different and are independently selected from the group consisting of deuterium, halo, cyano, amino, aminoalkyl, (amino)alkoxy, —CONH$_2$, —C(O)NH(alkyl), —C(O)N(alkyl)$_2$, —C(O)NH(aryl), —C(O)N(aryl)$_2$, —CF$_3$, —CHF$_2$, —CH$_2$F, alkyl, hydroxyalkyl, alkoxy, hydroxyl, hydroxyalkyl, carboxy, (alkoxyalkyl)amino, alkylamine, aminocarbonyl, —CHO, —N(R$^3$)—C(O)-alkyl, —N(R$^3$)—C(O)-aryl, cycloalkyl, heterocycloalkyl, aryl, and heteroaryl;
R$^3$ is H; and
n is 4, 5, or 6;
wherein the process comprises a step of treating an acid:

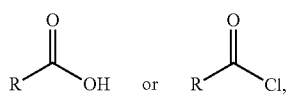

with an amine:

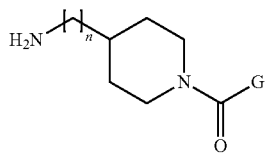

in the presence of a base.

2. The process of claim 1, wherein the acid is:

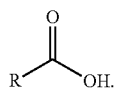

3. The process of claim 2, wherein the process of obtaining the compound of Formula II further comprises addition of a coupling agent.

4. The process of claim 3, wherein the coupling agent is EDCI, HATU, or HOBt.
5. The process of claim 3, wherein the base is $K_2CO_3$, $Cs_2CO_3$, DIEA, NaOH, or KOH.
6. The process of claim 1, wherein the acid is:
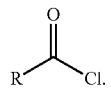
7. The process of claim 6, wherein the base is TEA.
* * * * *